(12) United States Patent
Stoks et al.

(10) Patent No.: US 10,974,015 B2
(45) Date of Patent: Apr. 13, 2021

(54) RESPIRATORY GAS HUMIDIFICATION SYSTEM

(71) Applicant: Fisher & Paykel Healthcare Limited, Auckland (NZ)

(72) Inventors: Elmo Benson Stoks, Auckland (NZ); Charles Christopher North, Auckland (NZ); Hamish Adrian Osborne, Auckland (NZ); Abhishek Vadnerkar, Remuera (CA); James Owen Kehoe, Auckland (NZ); Po-Yen Liu, Auckland (NZ); John James Jackson, Auckland (NZ); Igor Yevgeniiovich Shvarchuck, Auckland (NZ); Mahran Maumoon Sujau, Auckland (NZ); Sanjay Parag Patel, Auckland (NZ); Man Kit Jacky Cheung, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 267 days.

(21) Appl. No.: 15/936,309

(22) Filed: Mar. 26, 2018

(65) Prior Publication Data

US 2018/0214660 A1 Aug. 2, 2018

Related U.S. Application Data

(63) Continuation of application No. 14/485,608, filed on Sep. 12, 2014, now Pat. No. 9,987,455, which is a
(Continued)

(51) Int. Cl.
*A61M 16/16* (2006.01)
*A61M 16/08* (2006.01)
(Continued)

(52) U.S. Cl.
CPC ........ *A61M 16/161* (2014.02); *A61M 16/024* (2017.08); *A61M 16/0816* (2013.01);
(Continued)

(58) Field of Classification Search
CPC .................... A61M 16/161; A61M 2205/3368
See application file for complete search history.

(56) References Cited

U.S. PATENT DOCUMENTS 2,073,335 A 3/1937 Connell
2,510,125 A * 6/1950 Meakin ................ F16L 37/127
174/47

(Continued)

FOREIGN PATENT DOCUMENTS

AU 2000071791 3/2001
AU 2002244571 9/2002
(Continued)

OTHER PUBLICATIONS

Chinese Examination Report for Application No. 201580038988.3 dated Aug. 30, 2018.
(Continued)

*Primary Examiner* — John Fitzgerald
(74) *Attorney, Agent, or Firm* — Knobbe, Martens, Olson & Bear, LLP

(57) ABSTRACT

A humidification system comprises a first sensor and a second sensor. The first and second sensors are adapted to sense flow characteristics within the system. The first and second sensors are isolated from the flow by barriers formed by respective first and second sealing members. The sealing members extend through apertures formed in the system and have a portion that contacts the sensing elements of the respective first and second sensors. A cartridge can hold the sensors and provide repeatable penetration depths into a flow passage of the system. A medical tube has a composite
(Continued)

structure made of two or more distinct components that are spirally wound to form an elongate tube. One component can be a spirally wound elongate hollow body; the other component can be an elongate structural component spirally wound between turns of the spirally wound hollow body.

24 Claims, 82 Drawing Sheets

Related U.S. Application Data continuation of application No. PCT/NZ2013/000042, filed on Mar. 15, 2013.

(60) Provisional application No. 61/611,331, filed on Mar. 15, 2012, provisional application No. 61/722,659, filed on Nov. 5, 2012, provisional application No. 61/733,359, filed on Dec. 4, 2012, provisional application No. 61/733,360, filed on Dec. 4, 2012.

(51) Int. Cl.
*A61M 16/10* (2006.01)
*A61M 16/00* (2006.01)
*G01F 1/69* (2006.01)
*G01F 23/26* (2006.01)

(52) U.S. Cl.
CPC .... *A61M 16/0841* (2014.02); *A61M 16/0875* (2013.01); *A61M 16/109* (2014.02); *A61M 16/1095* (2014.02); *A61M 16/16* (2013.01); *G01F 1/69* (2013.01); *G01F 23/26* (2013.01); *A61M 16/0066* (2013.01); *A61M 2016/0039* (2013.01); *A61M 2205/3368* (2013.01); *A61M 2205/3379* (2013.01); *A61M 2205/502* (2013.01)

(56) References Cited

U.S. PATENT DOCUMENTS

| | | | |
|---|---|---|---|
| 2,516,864 A | 8/1950 | Gilmore et al. | |
| 2,745,074 A | 1/1951 | Darling | |
| 2,590,797 A | 3/1952 | Siciliano | |
| 2,621,875 A * | 12/1952 | Darling | A62B 9/04 |
| | | | 244/122 A |
| 2,634,311 A | 4/1953 | Darling | |
| 3,117,596 A | 1/1964 | Kahn | |
| 3,163,707 A | 12/1964 | Darling | |
| 3,283,580 A | 11/1966 | Jacob et al. | |
| 3,394,954 A | 7/1968 | Sarns | |
| 3,485,237 A | 12/1969 | Bedford | |
| 3,495,628 A | 2/1970 | Boender | |
| 3,582,094 A | 6/1971 | Whittaker | |
| 3,588,859 A | 6/1971 | Petree | |
| 3,623,511 A | 11/1971 | Levin | |
| 3,638,926 A | 2/1972 | Melville et al. | |
| 3,659,604 A | 5/1972 | Melville et al. | |
| 3,703,892 A | 11/1972 | Meyers | |
| 3,777,298 A | 12/1973 | Newman | |
| 3,903,742 A | 9/1975 | Colton | |
| 3,954,920 A | 5/1976 | Heath | |
| 3,987,133 A | 10/1976 | Andra | |
| 3,990,727 A | 11/1976 | Gallagher | |
| 4,028,444 A | 6/1977 | Brown | |
| 4,038,519 A | 7/1977 | Foucras | |
| 4,060,576 A | 11/1977 | Grant | |
| 4,111,197 A | 9/1978 | Warncke et al. | |
| 4,139,762 A | 2/1979 | Pohrer et al. | |
| 4,160,466 A | 7/1979 | Jousson | |
| 4,172,709 A | 10/1979 | Kippel et al. | |
| 4,183,248 A | 1/1980 | West | |
| 4,192,836 A | 3/1980 | Bartscher | |
| 4,301,200 A | 11/1981 | Langenfeld et al. | |
| 4,333,451 A | 6/1982 | Paluch | |
| 4,428,403 A | 1/1984 | Lee | |
| 4,463,593 A | 8/1984 | Parker | |
| 4,473,923 A | 10/1984 | Neroni et al. | |
| 4,529,867 A | 7/1985 | Velnosky et al. | |
| 4,531,551 A | 7/1985 | Eichelberger et al. | |
| 4,545,290 A | 10/1985 | Lieberman | |
| 4,564,748 A | 1/1986 | Gupton | |
| 4,588,425 A | 5/1986 | Usry et al. | |
| 4,621,632 A | 11/1986 | Bartels et al. | |
| 4,676,237 A | 6/1987 | Wood et al. | |
| 4,686,354 A | 8/1987 | Makin | |
| 4,708,831 A | 11/1987 | Elsworth et al. | |
| 4,714,078 A | 12/1987 | Paluch | |
| 4,774,032 A | 9/1988 | Coates et al. | |
| 4,809,698 A | 3/1989 | Kogo | |
| 4,813,280 A | 3/1989 | Miller et al. | |
| 4,830,515 A | 5/1989 | Cortes | |
| 4,844,512 A | 7/1989 | Gahwiler | |
| 4,942,877 A | 7/1990 | Sakai et al. | |
| 4,944,310 A | 7/1990 | Sullivan | |
| 4,967,744 A | 11/1990 | Chua | |
| 5,017,875 A * | 5/1991 | Hori | G01N 27/18 |
| | | | 219/505 |
| 5,031,612 A | 7/1991 | Clementi | |
| 5,054,819 A | 10/1991 | Grunwald | |
| 5,058,588 A | 10/1991 | Kaestle | |
| 5,060,506 A | 10/1991 | Douglas | |
| 5,062,145 A | 10/1991 | Zwaan | |
| 5,117,819 A | 6/1992 | Servidio et al. | |
| 5,127,442 A | 7/1992 | Blomqvist | |
| 5,134,996 A | 8/1992 | Bell | |
| 5,148,801 A | 9/1992 | Douwens et al. | |
| 5,213,138 A | 5/1993 | Presz, Jr. | |
| 5,213,376 A | 5/1993 | Szabo | |
| 5,303,701 A | 4/1994 | Heins et al. | |
| RE34,599 E | 5/1994 | Suszynk et al. | |
| 5,342,126 A | 8/1994 | Heston | |
| 5,357,948 A | 10/1994 | Eilentropp | |
| 5,367,604 A * | 11/1994 | Murray | A61M 16/1075 |
| | | | 392/394 |
| 5,392,770 A | 2/1995 | Clawson et al. | |
| 5,396,884 A | 3/1995 | Bagwell et al. | |
| 5,454,061 A | 9/1995 | Carlson | |
| 5,454,479 A | 10/1995 | Kraus | |
| 5,483,616 A | 1/1996 | Chiu et al. | |
| 5,484,223 A * | 1/1996 | Saito | H01R 13/4368 |
| | | | 403/13 |
| 5,488,447 A | 1/1996 | Patton | |
| 5,495,872 A | 3/1996 | Gallagher et al. | |
| 5,499,737 A | 3/1996 | Kraus | |
| 5,529,093 A | 6/1996 | Gallagher et al. | |
| 5,537,996 A | 7/1996 | McPhee | |
| 5,548,879 A * | 8/1996 | Wu | A44B 11/263 |
| | | | 24/616 |
| 5,551,883 A | 9/1996 | Davis | |
| 5,558,084 A * | 9/1996 | Daniell | A61M 16/1075 |
| | | | 128/203.12 |
| 5,600,752 A | 2/1997 | Lopatinsky | |
| 5,630,806 A | 5/1997 | Inagaki et al. | |
| 5,637,006 A * | 6/1997 | Almeras | H01R 13/005 |
| | | | 439/191 |
| 5,640,951 A | 6/1997 | Huddart et al. | |
| 5,660,567 A | 8/1997 | Nierlich et al. | |
| 5,667,306 A | 9/1997 | Montreuil | |
| 5,720,293 A | 2/1998 | Quinn et al. | |
| 5,778,872 A | 7/1998 | Fukunaga et al. | |
| 5,829,880 A * | 11/1998 | Diedrich | G01K 13/02 |
| | | | 374/208 |
| 5,881,393 A | 3/1999 | Marchello | |
| 5,906,201 A | 5/1999 | Nilson | |
| 5,943,473 A | 8/1999 | Levine | |
| D419,522 S | 1/2000 | Kamagai | |
| 6,024,694 A | 2/2000 | Godlberg | |
| 6,039,696 A * | 3/2000 | Bell | A61M 16/08 |
| | | | 128/204.21 |
| 6,050,260 A | 4/2000 | Daniell | |

(56) References Cited

U.S. PATENT DOCUMENTS

| | | | |
|---|---|---|---|
| 6,053,482 A | 4/2000 | Glenn et al. |
| 6,058,977 A | 5/2000 | Hotta |
| 6,078,729 A | 6/2000 | Kopel |
| 6,078,730 A | 6/2000 | Huddart et al. |
| 6,102,037 A | 8/2000 | Koch |
| 6,105,970 A | 8/2000 | Siegrist et al. |
| 6,126,610 A | 10/2000 | Rich et al. |
| 6,138,674 A | 10/2000 | Gull et al. |
| 6,190,480 B1 | 2/2001 | Carlson |
| 6,196,980 B1 | 3/2001 | Akerfeldt et al. |
| 6,201,983 B1 | 3/2001 | Haumann et al. |
| 6,208,514 B1 | 3/2001 | Stark |
| 6,226,451 B1 | 5/2001 | Wong |
| 6,272,933 B1 | 8/2001 | Gradon et al. |
| 6,347,646 B2 | 2/2002 | Fukui |
| 6,349,722 B1 | 2/2002 | Gradon et al. |
| 6,349,724 B1 | 2/2002 | Burton et al. |
| 6,360,741 B2 | 3/2002 | Truschel |
| 6,367,974 B1 | 4/2002 | Lin |
| 6,374,864 B1 | 4/2002 | Philp |
| 6,394,145 B1 | 5/2002 | Gessil |
| 6,397,841 B1 | 6/2002 | Kenyon et al. |
| 6,402,207 B1 | 6/2002 | Segal et al. |
| 6,435,180 B1 | 8/2002 | Hewson et al. |
| 6,467,477 B1 | 10/2002 | Frank et al. |
| 6,508,249 B2 | 1/2003 | Hoenig |
| 6,511,075 B1 | 1/2003 | Schmidt |
| 6,540,734 B1 | 4/2003 | Chiu |
| 6,551,143 B2 | 4/2003 | Tanaka et al. |
| 6,554,260 B1 | 4/2003 | Lipscombe et al. |
| 6,591,061 B2 | 7/2003 | Wang |
| 6,598,604 B1 | 7/2003 | Seakins |
| 6,612,624 B1 | 9/2003 | Segal et al. |
| 6,631,718 B1 | 10/2003 | Lovell |
| 6,648,669 B1 | 11/2003 | Kim et al. |
| 6,668,828 B1 | 12/2003 | Figley et al. |
| 6,685,491 B2 | 2/2004 | Gergek |
| 6,698,966 B2 * | 3/2004 | Hilton ................ F16B 21/08 24/616 |
| 6,824,180 B2 * | 11/2004 | Tomchak ............ A01B 1/22 294/57 |
| 6,827,084 B2 | 12/2004 | Grubb, Jr. |
| 6,874,771 B2 | 4/2005 | Birdsell et al. |
| 6,895,803 B2 | 5/2005 | Seakins et al. |
| 6,915,705 B1 | 7/2005 | Truitt |
| 6,918,389 B2 | 7/2005 | Seakins et al. |
| 6,935,337 B2 | 8/2005 | Virr et al. |
| 6,943,566 B2 | 9/2005 | Florin et al. |
| 6,953,354 B2 | 10/2005 | Edirisuriya et al. |
| 7,043,979 B2 | 5/2006 | Smith et al. |
| 7,063,668 B2 | 6/2006 | Cardelius et al. |
| 7,086,422 B2 | 8/2006 | Huber et al. |
| 7,090,541 B1 | 8/2006 | Ho |
| 7,096,864 B1 | 8/2006 | Mayer et al. |
| 7,120,354 B2 | 10/2006 | Mackie et al. |
| 7,137,654 B2 | 11/2006 | Segal et al. |
| 7,140,367 B2 | 11/2006 | White et al. |
| 7,157,035 B2 | 1/2007 | Edirisuriya et al. |
| 7,191,780 B2 | 3/2007 | Faram |
| 7,225,809 B1 | 6/2007 | Bowen et al. |
| 7,284,554 B2 | 10/2007 | Shaw |
| 7,316,769 B2 | 1/2008 | Aldridge |
| 7,327,547 B1 | 2/2008 | Epstein |
| 7,327,949 B1 | 2/2008 | Cheng et al. |
| 7,334,587 B2 | 2/2008 | Lake |
| 7,364,436 B2 | 4/2008 | Yen |
| 7,396,995 B2 | 7/2008 | Laurent et al. |
| 7,448,383 B2 | 11/2008 | Delache et al. |
| 7,469,586 B2 * | 12/2008 | Wild ................ G01N 27/4062 73/431 |
| 7,478,635 B2 | 1/2009 | Wixey et al. |
| 7,525,663 B2 | 4/2009 | Kwok et al. |
| 7,637,288 B2 | 12/2009 | Kressierer/Huber et al. |
| 7,677,246 B2 | 3/2010 | Kepler et al. |
| 7,743,767 B2 | 6/2010 | Ging et al. |
| 7,766,050 B2 | 8/2010 | Patel |
| 7,794,426 B2 | 9/2010 | Briones et al. |
| 7,814,907 B2 | 10/2010 | Bremner et al. |
| 7,816,888 B2 * | 10/2010 | Rejman ................ B25F 5/02 320/114 |
| D628,288 S | 11/2010 | Row et al. |
| 7,827,981 B2 | 11/2010 | Barnford |
| 7,870,857 B2 | 1/2011 | Dhuper et al. |
| 7,874,291 B2 | 1/2011 | Ging et al. |
| 7,900,528 B2 * | 3/2011 | Vincent ................ G01D 11/245 73/866.5 |
| 7,913,689 B2 | 3/2011 | Henry et al. |
| 7,942,380 B2 | 5/2011 | Bertinetti et al. |
| 7,942,389 B2 | 5/2011 | Koch et al. |
| 7,965,930 B2 | 6/2011 | Carlson et al. |
| 7,983,542 B2 | 7/2011 | McGhin et al. |
| 7,987,847 B2 | 8/2011 | Wickham |
| 7,992,554 B2 | 8/2011 | Radomski et al. |
| 7,997,267 B2 | 8/2011 | Ging et al. |
| 8,025,849 B2 | 9/2011 | Baldwin et al. |
| 8,059,947 B2 | 11/2011 | Bradley et al. |
| 8,063,343 B2 | 11/2011 | McGhin et al. |
| 8,078,040 B2 | 12/2011 | Forrester |
| 8,100,124 B2 | 1/2012 | Becker et al. |
| 8,122,882 B2 | 2/2012 | McGhin et al. |
| 8,136,521 B2 | 3/2012 | Matthews et al. |
| 8,137,082 B2 | 3/2012 | Campbell |
| 8,181,940 B2 | 5/2012 | Payne et al. |
| 8,182,144 B2 | 5/2012 | Koch |
| 8,186,345 B2 | 5/2012 | Payton et al. |
| 8,186,352 B2 | 5/2012 | Gunaratnam et al. |
| 8,197,123 B2 | 6/2012 | Snyder et al. |
| 8,206,337 B2 | 6/2012 | Blackhurst et al. |
| 8,221,530 B2 | 7/2012 | Peter et al. |
| 8,226,293 B2 | 7/2012 | Farles |
| 8,245,709 B2 | 8/2012 | Rossen et al. |
| 8,245,710 B2 | 8/2012 | Makinson et al. |
| 8,253,076 B2 | 8/2012 | Andel et al. |
| 8,257,286 B2 | 9/2012 | Meyer et al. |
| 8,267,084 B2 | 9/2012 | Kwok |
| 8,267,614 B2 * | 9/2012 | Khoe ................ F16B 5/0016 403/326 |
| 8,282,427 B2 * | 10/2012 | Yamazaki ........ H01R 13/4368 439/595 |
| 8,287,517 B2 | 10/2012 | Hanlon et al. |
| 8,316,848 B2 | 11/2012 | Kwok et al. |
| 8,333,194 B2 | 12/2012 | Lewis et al. |
| 8,333,195 B2 | 12/2012 | Cortez, Jr. et al. |
| 8,333,199 B2 | 12/2012 | Landis et al. |
| 8,355,753 B2 | 1/2013 | Bochenko et al. |
| 8,360,059 B2 | 1/2013 | Koulechov et al. |
| 8,365,726 B2 | 2/2013 | Snow et al. |
| 8,381,724 B2 | 2/2013 | Bowen et al. |
| 8,424,514 B2 | 4/2013 | Oates et al. |
| 8,453,641 B2 | 6/2013 | Payton et al. |
| 8,453,643 B2 | 6/2013 | Sanchez et al. |
| 8,469,025 B2 | 6/2013 | Mayer et al. |
| 8,490,621 B2 | 7/2013 | Radomski et al. |
| 8,496,001 B2 | 7/2013 | Schermeier et al. |
| RE44,453 E | 8/2013 | Virr et al. |
| 8,511,305 B2 | 8/2013 | Liu et al. |
| 8,511,651 B2 | 8/2013 | Fridberg et al. |
| 8,516,911 B2 | 8/2013 | Inoue |
| 8,522,782 B2 | 9/2013 | Lewis et al. |
| 8,528,552 B2 | 9/2013 | von Blumenthal |
| 8,544,465 B2 | 10/2013 | Smith et al. |
| 8,545,096 B2 | 10/2013 | Reiter |
| 8,550,072 B2 | 10/2013 | Thudor et al. |
| 8,631,789 B2 | 1/2014 | Virr et al. |
| 8,640,560 B2 * | 2/2014 | Burke ................ C12M 29/00 73/866.5 |
| 8,640,696 B2 | 2/2014 | Pujol et al. |
| 8,651,800 B2 | 2/2014 | Li |
| 8,733,348 B2 | 5/2014 | Korneff et al. |
| 8,733,349 B2 | 5/2014 | Bath et al. |
| 8,783,252 B2 | 7/2014 | Pierro et al. |
| 8,800,970 B2 | 8/2014 | Heine et al. |
| 8,770,190 B2 | 9/2014 | McCarthy |

(56) References Cited

U.S. PATENT DOCUMENTS

| | | | |
|---|---|---|---|
| 8,844,388 B2* | 9/2014 | Burke | C12M 37/02 |
| | | | 73/866.5 |
| 8,844,521 B2 | 9/2014 | McCarthy | |
| 8,851,071 B2 | 10/2014 | Kuo et al. | |
| 8,905,023 B2 | 12/2014 | Niland et al. | |
| 8,915,250 B2 | 12/2014 | Dugan et al. | |
| 8,931,481 B2 | 1/2015 | Jones et al. | |
| 8,939,147 B2 | 1/2015 | Henry et al. | |
| 8,985,105 B2 | 3/2015 | Burton et al. | |
| 9,022,946 B2 | 5/2015 | Haque | |
| 9,039,277 B2* | 5/2015 | Le Bouquin | G01K 1/16 |
| | | | 374/144 |
| 9,067,036 B2 | 6/2015 | Korneff et al. | |
| 9,095,668 B2* | 8/2015 | Blackhurst | A61B 1/00154 |
| 9,119,933 B2 | 9/2015 | Bedford et al. | |
| 9,132,252 B2 | 9/2015 | Barlow et al. | |
| 9,162,035 B2 | 10/2015 | Kwok | |
| 9,186,477 B2 | 11/2015 | Hunt et al. | |
| 9,205,220 B2 | 12/2015 | Korneff et al. | |
| 9,212,673 B2 | 12/2015 | Korneff et al. | |
| 9,242,064 B2 | 1/2016 | Rustad et al. | |
| 9,254,368 B2 | 2/2016 | Blumenthal et al. | |
| 9,289,572 B2 | 3/2016 | Korneff et al. | |
| RE46,079 E | 7/2016 | Virr et al. | |
| 9,381,317 B2 | 7/2016 | Landis et al. | |
| 9,387,299 B2 | 7/2016 | Zwolinsky et al. | |
| 9,427,547 B2 | 8/2016 | Landis et al. | |
| 9,446,210 B2 | 9/2016 | Orr et al. | |
| 9,512,856 B2 | 12/2016 | Nibu | |
| 9,517,321 B2 | 12/2016 | Buechi et al. | |
| 9,545,493 B2 | 1/2017 | Mayer et al. | |
| 9,566,409 B2 | 2/2017 | Gründler et al. | |
| 9,572,949 B2 | 2/2017 | Vos et al. | |
| 9,572,951 B2 | 2/2017 | Barker et al. | |
| 9,586,019 B2 | 3/2017 | Heine et al. | |
| 9,642,979 B2 | 5/2017 | Korneff et al. | |
| 9,838,759 B2 | 12/2017 | Kirmse et al. | |
| 9,861,778 B2 | 1/2018 | Roderick et al. | |
| 9,937,314 B2 | 4/2018 | Buechi et al. | |
| 9,937,316 B2 | 4/2018 | Buechi et al. | |
| 9,974,921 B2 | 5/2018 | Klenner et al. | |
| 9,987,455 B2* | 6/2018 | Stoks | G01F 1/69 |
| 10,046,136 B2 | 8/2018 | Pujol | |
| 10,245,407 B2 | 4/2019 | Osborne et al. | |
| 10,449,319 B2 | 10/2019 | Osborne et al. | |
| 2001/0017134 A1 | 8/2001 | Bahr | |
| 2001/0017880 A1 | 8/2001 | Beerwerth et al. | |
| 2001/0050080 A1 | 12/2001 | Seakins et al. | |
| 2002/0100320 A1* | 8/2002 | Smith | A61M 16/1095 |
| | | | 73/431 |
| 2002/0132511 A1* | 9/2002 | Groebe | H01R 12/725 |
| | | | 439/357 |
| 2002/0153011 A1 | 10/2002 | Tanhehco | |
| 2003/0066526 A1 | 4/2003 | Thurdor et al. | |
| 2003/0066530 A1 | 4/2003 | Shahbazpour et al. | |
| 2003/0107325 A1 | 6/2003 | Birkhead | |
| 2003/0127096 A1 | 7/2003 | McAuliffe | |
| 2003/0148664 A1 | 8/2003 | Cheng | |
| 2003/0183294 A1 | 10/2003 | Carlson | |
| 2003/0200727 A1 | 10/2003 | Kim | |
| 2003/0236015 A1 | 12/2003 | Edirisuriya et al. | |
| 2004/0013162 A1 | 1/2004 | Beerwerth et al. | |
| 2004/0055597 A1 | 3/2004 | Virr et al. | |
| 2004/0074493 A1 | 4/2004 | Seakins et al. | |
| 2004/0079371 A1 | 4/2004 | Gray | |
| 2004/0087213 A1 | 5/2004 | Kao | |
| 2004/0099268 A1 | 5/2004 | Smith et al. | |
| 2004/0101026 A1 | 5/2004 | Nitta et al. | |
| 2004/0149284 A1 | 8/2004 | Smith et al. | |
| 2004/0168530 A1* | 9/2004 | Adolfs | A61B 5/0215 |
| | | | 73/866.5 |
| 2004/0182392 A1 | 9/2004 | Gerder et al. | |
| 2004/0221843 A1 | 11/2004 | Baecke | |
| 2004/0234254 A1 | 11/2004 | Czupich et al. | |
| 2004/0239001 A1 | 12/2004 | Edirisuriya et al. | |
| 2004/0244858 A1 | 12/2004 | Jeong | |
| 2005/0039809 A1 | 2/2005 | Speldrich | |
| 2005/0059957 A1 | 3/2005 | Campbell et al. | |
| 2005/0152733 A1 | 7/2005 | Patel | |
| 2006/0030191 A1 | 2/2006 | Tuin et al. | |
| 2006/0118113 A1 | 6/2006 | Bremner et al. | |
| 2006/0137445 A1* | 6/2006 | Smith | A61M 16/1095 |
| | | | 73/204.22 |
| 2006/0150712 A1 | 7/2006 | Berstis et al. | |
| 2006/0165829 A1 | 7/2006 | Smith et al. | |
| 2006/0196510 A1 | 9/2006 | McDonald | |
| 2006/0237012 A1 | 10/2006 | Thudor et al. | |
| 2006/0249160 A1 | 11/2006 | Scarberry | |
| 2006/0283450 A1 | 12/2006 | Shissler et al. | |
| 2007/0039374 A1 | 2/2007 | Borali | |
| 2007/0079982 A1 | 4/2007 | Laurent et al. | |
| 2007/0107737 A1 | 5/2007 | Landis et al. | |
| 2007/0110124 A1 | 5/2007 | Shiraki et al. | |
| 2007/0144519 A1 | 6/2007 | Henry et al. | |
| 2007/0157928 A1 | 7/2007 | Pujol et al. | |
| 2007/0169776 A1 | 7/2007 | Kepler et al. | |
| 2007/0175473 A1 | 8/2007 | Lewis et al. | |
| 2007/0248934 A1 | 10/2007 | Mosimann | |
| 2007/0284361 A1 | 12/2007 | Nadjafizadeh et al. | |
| 2008/0000474 A1 | 1/2008 | Jochle et al. | |
| 2008/0015257 A1 | 1/2008 | Grosskreutz et al. | |
| 2008/0051674 A1 | 2/2008 | Davenport et al. | |
| 2008/0066751 A1 | 3/2008 | Polacsek | |
| 2008/0072900 A1 | 3/2008 | Kenyon et al. | |
| 2008/0105257 A1 | 5/2008 | Klasek et al. | |
| 2008/0142019 A1 | 6/2008 | Lewis et al. | |
| 2008/0196716 A1 | 8/2008 | Wachter | |
| 2008/0202512 A1 | 8/2008 | Kressierer/ Huber | |
| 2008/0205481 A1 | 8/2008 | Faries | |
| 2008/0205979 A1* | 8/2008 | Gombert | F16B 5/0216 |
| | | | 403/326 |
| 2008/0207028 A1* | 8/2008 | Schutz | A61B 1/00114 |
| | | | 439/191 |
| 2008/0251073 A1 | 10/2008 | Jassell | |
| 2008/0264413 A1 | 10/2008 | Doherty et al. | |
| 2008/0302362 A1 | 12/2008 | Kwok | |
| 2008/0308169 A1 | 12/2008 | Nielsen et al. | |
| 2009/0041080 A1 | 2/2009 | Koch | |
| 2009/0044808 A1 | 2/2009 | Guney et al. | |
| 2009/0050150 A1 | 2/2009 | Rossen et al. | |
| 2009/0056712 A1 | 3/2009 | Cortez, Jr. et al. | |
| 2009/0056713 A1 | 3/2009 | Cortez, Jr. et al. | |
| 2009/0078259 A1 | 3/2009 | Kooji et al. | |
| 2009/0087259 A1 | 3/2009 | Kooji et al. | |
| 2009/0107493 A1 | 4/2009 | Liu et al. | |
| 2009/0107496 A1 | 4/2009 | McGhin et al. | |
| 2009/0107501 A1 | 4/2009 | Krieger | |
| 2009/0107981 A1 | 4/2009 | Andel et al. | |
| 2009/0110022 A1 | 4/2009 | Snyder et al. | |
| 2009/0110378 A1* | 4/2009 | Bradley | A61M 16/16 |
| | | | 392/441 |
| 2009/0174092 A1 | 7/2009 | Kwok et al. | |
| 2009/0180829 A1* | 7/2009 | Rejman | B25F 5/02 |
| | | | 403/331 |
| 2009/0223514 A1 | 9/2009 | Smith et al. | |
| 2009/0247989 A1 | 10/2009 | Burke | |
| 2009/0301482 A1 | 12/2009 | Burton et al. | |
| 2009/0320840 A1 | 12/2009 | Klasek et al. | |
| 2010/0015830 A1* | 1/2010 | Simeon | H01R 13/642 |
| | | | 439/191 |
| 2010/0083965 A1 | 4/2010 | Virr et al. | |
| 2010/0102799 A1 | 4/2010 | Schnidrig | |
| 2010/0116272 A1 | 5/2010 | Row et al. | |
| 2010/0147301 A1 | 6/2010 | Kwok | |
| 2010/0154796 A1 | 6/2010 | Smith et al. | |
| 2010/0204602 A1 | 8/2010 | Addington et al. | |
| 2010/0242963 A1 | 9/2010 | Brieger et al. | |
| 2010/0272507 A1* | 10/2010 | Khoe | F16B 5/0016 |
| | | | 403/354 |
| 2011/0017212 A1 | 1/2011 | Kenyon et al. | |
| 2011/0023874 A1 | 2/2011 | Bath et al. | |
| 2011/0046433 A1 | 2/2011 | Khodak | |
| 2011/0046494 A1 | 2/2011 | Balji et al. | |

(56) References Cited

U.S. PATENT DOCUMENTS

| | | |
|---|---|---|
| 2011/0078109 A1 | 3/2011 | Mayer et al. |
| 2011/0088693 A1 | 4/2011 | Somervell et al. |
| 2011/0108031 A1 | 5/2011 | Korneff et al. |
| 2011/0114093 A1 | 5/2011 | Patil et al. |
| 2011/0155132 A1 | 6/2011 | Virr et al. |
| 2011/0180068 A1 | 7/2011 | Kenyon et al. |
| 2011/0186048 A1 | 8/2011 | Casse et al. |
| 2011/0247623 A1 | 10/2011 | McCarthy |
| 2011/0253136 A1 | 10/2011 | Sweeney et al. |
| 2011/0283999 A2 | 11/2011 | Smith et al. |
| 2011/0308518 A1 | 12/2011 | McGroary et al. |
| 2011/0313689 A1 | 12/2011 | Holley et al. |
| 2011/0316562 A1 | 12/2011 | Cefai et al. |
| 2012/0060838 A1 | 3/2012 | Lapoint et al. |
| 2012/0073573 A1 | 3/2012 | Thurdor et al. |
| 2012/0125333 A1 | 5/2012 | Bedford et al. |
| 2012/0125334 A1 | 5/2012 | Korneff et al. |
| 2012/0146251 A1 | 6/2012 | Heine et al. |
| 2012/0174924 A1 | 7/2012 | Smith et al. |
| 2012/0215125 A1 | 8/2012 | Orr et al. |
| 2012/0227738 A1 | 9/2012 | Virr et al. |
| 2012/0255758 A1 | 10/2012 | Lee |
| 2012/0266880 A1 | 10/2012 | Young |
| 2012/0285448 A1 | 11/2012 | Dugan et al. |
| 2013/0008158 A1 | 1/2013 | Hon |
| 2013/0042867 A1 | 2/2013 | Kwok et al. |
| 2013/0043677 A1 | 2/2013 | Gibson |
| 2013/0079667 A1 | 3/2013 | Berkcan et al. |
| 2013/0087143 A1 | 4/2013 | Pujol |
| 2013/0104888 A1 | 5/2013 | Landis et al. |
| 2013/0104901 A1 | 5/2013 | Landis et al. |
| 2013/0112201 A1 | 5/2013 | Graham et al. |
| 2013/0112202 A1 | 5/2013 | Fogelbrink |
| 2013/0174839 A1 | 7/2013 | Ging et al. |
| 2013/0206140 A1 | 8/2013 | Kepler et al. |
| 2013/0237781 A1 | 9/2013 | Gyrn |
| 2013/0239960 A1 | 9/2013 | Bertinetti et al. |
| 2013/0239966 A1 | 9/2013 | Klasek et al. |
| 2013/0247905 A1 | 9/2013 | Miller et al. |
| 2013/0248044 A1 | 9/2013 | Shiga et al. |
| 2013/0255677 A1 | 10/2013 | Varga |
| 2013/0333701 A1 | 12/2013 | Herron |
| 2013/0340752 A1 | 12/2013 | Landis et al. |
| 2014/0020684 A1 | 1/2014 | Klasek et al. |
| 2014/0048065 A1 | 2/2014 | Haroutunian |
| 2014/0090649 A1 | 4/2014 | Groll et al. |
| 2014/0116433 A1 | 5/2014 | Ghalib et al. |
| 2014/0130802 A1 | 5/2014 | Virr et al. |
| 2014/0202460 A1 | 7/2014 | Bath et al. |
| 2014/0202462 A1 | 7/2014 | Stoks |
| 2014/0202463 A1 | 7/2014 | Ging et al. |
| 2014/0216446 A1 | 8/2014 | Wruck |
| 2014/0251322 A1 | 9/2014 | Miller |
| 2014/0251331 A1 | 9/2014 | Korneff et al. |
| 2014/0283829 A1 | 9/2014 | Miller |
| 2014/0311489 A1 | 10/2014 | Heine et al. |
| 2014/0318536 A1 | 10/2014 | Landis et al. |
| 2014/0331786 A1* | 11/2014 | Romano ........... A61M 16/0051 73/861.52 |
| 2014/0338666 A1 | 11/2014 | Visveshwara et al. |
| 2014/0345614 A1 | 11/2014 | Kwok |
| 2014/0366876 A1 | 12/2014 | Huby et al. |
| 2015/0040897 A1 | 2/2015 | Buechi |
| 2015/0048530 A1 | 2/2015 | Cheung et al. |
| 2015/0083126 A1 | 3/2015 | Rogers |
| 2015/0083132 A1 | 3/2015 | Jones et al. |
| 2015/0090260 A1 | 4/2015 | Seakins et al. |
| 2015/0096560 A1 | 4/2015 | Klenner et al. |
| 2015/0107588 A1 | 4/2015 | Cheung et al. |
| 2015/0144130 A1 | 5/2015 | O'Donnell et al. |
| 2015/0196725 A1 | 7/2015 | Oates et al. |
| 2015/0359990 A1 | 12/2015 | Barker et al. |
| 2016/0008560 A1 | 1/2016 | Kwok |
| 2016/0015927 A1 | 1/2016 | Winski et al. |
| 2016/0022954 A1 | 1/2016 | Bath et al. |
| 2016/0051789 A1 | 2/2016 | Korneff et al. |
| 2016/0089510 A1 | 3/2016 | Korneff et al. |
| 2016/0101258 A1 | 4/2016 | Rustad et al. |
| 2016/0199612 A1 | 7/2016 | Foote et al. |
| 2016/0256642 A1 | 9/2016 | Soysa et al. |
| 2016/0256657 A1 | 9/2016 | Klasek et al. |
| 2016/0296721 A1 | 10/2016 | Landis et al. |
| 2016/0310691 A1 | 10/2016 | Bath et al. |
| 2016/0367776 A1 | 12/2016 | Landis et al. |
| 2016/0367779 A1 | 12/2016 | Landis et al. |
| 2017/0000968 A1 | 1/2017 | Harrington et al. |
| 2017/0095635 A1 | 4/2017 | Huby |
| 2017/0136198 A1 | 5/2017 | Delangre et al. |
| 2017/0161461 A1 | 6/2017 | Delangre et al. |
| 2017/0173293 A1 | 6/2017 | Osborne et al. |
| 2017/0197057 A1 | 7/2017 | Osborne et al. |
| 2017/0239432 A1 | 8/2017 | Delangre et al. |
| 2017/0326320 A1 | 11/2017 | Baigent et al. |
| 2018/0078730 A1 | 3/2018 | Bath et al. |
| 2018/0169361 A1 | 6/2018 | Dennis et al. |
| 2018/0250491 A1 | 9/2018 | Row et al. |
| 2018/0296791 A1 | 10/2018 | Klenner et al. |
| 2019/0255278 A1 | 8/2019 | Osborne et al. |
| 2020/0101253 A1 | 4/2020 | Osborne et al. |

FOREIGN PATENT DOCUMENTS

| | | |
|---|---|---|
| AU | 2007317198 | 5/2008 |
| AU | 2010206053 | 2/2011 |
| CA | 2464530 | 5/2003 |
| CA | 2495451 | 3/2004 |
| CA | 2852215 | 4/2013 |
| CN | 2243015 Y | 12/1996 |
| CN | 1598510 | 3/2005 |
| CN | 1688358 | 10/2005 |
| CN | 101666664 | 3/2010 |
| CN | 102844645 A | 12/2012 |
| CN | 201672170 | 12/2015 |
| DE | 3110903 | 9/1982 |
| DE | 36 18 614 | 12/1987 |
| DE | 3618614 | 12/1987 |
| DE | 4020522 | 1/1992 |
| DE | 4102223 | 7/1992 |
| DE | 19647548 | 5/1998 |
| DE | 19958296 | 9/2001 |
| DE | 20 2004 006 484.7 | 9/2005 |
| DE | 102004030747 | 1/2006 |
| DE | 20 2005 008 152.3 | 10/2006 |
| DE | 20 2005 008 156.6 | 10/2006 |
| DE | 203 21 468.4 | 8/2007 |
| DE | 203 21 469.2 | 8/2007 |
| DE | 203 21 470.6 | 8/2007 |
| DE | 203 21 471.4 | 8/2007 |
| DE | 203 21 472.2 | 8/2007 |
| DE | 20 2006 007 397.3 | 9/2007 |
| DE | 20 2004 021 759.7 | 10/2007 |
| DE | 20 2006 011 754.7 | 12/2007 |
| DE | 201 22 844.0 | 5/2008 |
| DE | 102007003454 | 7/2008 |
| DE | 102007003455 | 8/2008 |
| DE | 102007039391 | 2/2009 |
| DE | 102008001022 | 10/2009 |
| DE | 20 2004 021 757.0 | 9/2010 |
| DE | 20 2004 021 758.9 | 9/2010 |
| DE | 201 22 937.4 | 9/2010 |
| DE | 20 2004 021 756.2 | 10/2010 |
| DE | 20 2004 021 774.0 | 11/2010 |
| DE | 20 2004 021 777.5 | 12/2010 |
| DE | 20 2004 021 794.5 | 2/2011 |
| DE | 20 2004 021 795.3 | 2/2011 |
| DE | 20 2004 021 796.1 | 2/2011 |
| DE | 20 2004 021 798.8 | 2/2011 |
| DE | 20 2006 020 951.4 | 2/2011 |
| DE | 20 2006 020 952.4 | 2/2011 |
| DE | 20 2004 021829.1 | 5/2011 |
| DE | 201 22 943.9 | 5/2011 |
| DE | 201 22 944.7 | 5/2011 |
| DE | 201 22 945.5 | 5/2011 |
| DE | 20 2005 021 927.4 | 6/2011 |

(56) References Cited

FOREIGN PATENT DOCUMENTS

| | | |
|---|---|---|
| DE | 20 2006 021 019.9 | 11/2011 |
| DE | 203 21 882.5 | 12/2011 |
| DE | 20 2004 021876.3 | 1/2012 |
| DE | 20 2007 019350.5 | 1/2012 |
| DE | 20 2011 107 902.7 | 1/2012 |
| DE | 20 2010 016 037.5 | 3/2012 |
| DE | 20 2012 007 229.3 | 10/2012 |
| EP | 0 111 248 | 6/1984 |
| EP | 0201985 | 11/1986 |
| EP | 0291921 | 11/1988 |
| EP | 0535952 | 4/1993 |
| EP | 0567158 | 10/1993 |
| EP | 0 232 864 | 5/1994 |
| EP | 0885623 | 12/1998 |
| EP | 1262208 | 12/2002 |
| EP | 1352670 | 10/2003 |
| EP | 1 396 277 | 3/2004 |
| EP | 1 535 722 | 6/2005 |
| EP | 1646910 | 4/2006 |
| EP | 1669098 | 6/2006 |
| EP | 1683066 | 7/2006 |
| EP | 1457223 B1 | 10/2006 |
| EP | 1741462 | 1/2007 |
| EP | 1837640 A2 | 9/2007 |
| EP | 1924311 | 5/2008 |
| EP | 1933914 | 6/2008 |
| EP | 1979030 | 10/2008 |
| EP | 2079505 | 7/2009 |
| EP | 2089086 | 8/2009 |
| EP | 2101851 | 9/2009 |
| EP | 2195061 | 6/2010 |
| EP | 2236167 | 10/2010 |
| EP | 2282795 | 2/2011 |
| EP | 2307082 | 4/2011 |
| EP | 2335761 | 6/2011 |
| EP | 2 340 867 | 7/2011 |
| EP | 2340867 | 7/2011 |
| EP | 2355881 | 8/2011 |
| EP | 2 133 611 | 9/2011 |
| EP | 2415445 | 2/2012 |
| EP | 2471568 | 7/2012 |
| EP | 2498854 | 9/2012 |
| EP | 2514478 | 10/2012 |
| EP | 2575944 | 4/2013 |
| EP | 2640451 | 9/2013 |
| EP | 2651481 | 10/2013 |
| EP | 2654869 | 10/2013 |
| EP | 2667919 | 12/2013 |
| EP | 2703034 A2 | 3/2014 |
| EP | 2760516 | 8/2014 |
| EP | 2830695 | 2/2015 |
| EP | 2877224 | 6/2015 |
| EP | 2968829 | 1/2016 |
| EP | 3013402 | 5/2016 |
| EP | 3053623 | 8/2016 |
| EP | 3148418 | 4/2017 |
| EP | 3149696 | 4/2017 |
| EP | 3082920 | 10/2017 |
| EP | 3148419 | 1/2018 |
| GB | 1310949 | 3/1973 |
| GB | 1 364 127 | 8/1974 |
| GB | 1364127 | 8/1974 |
| GB | 2176313 | 12/1986 |
| GB | 2504284 A | 1/2014 |
| JP | 59-113392 | 6/1984 |
| JP | H0623051 | 2/1994 |
| JP | 11-033119 | 2/1999 |
| JP | 11-286058 | 10/1999 |
| JP | 2001095920 | 4/2001 |
| JP | 2001-129091 A | 5/2001 |
| JP | 2001-511507 | 8/2001 |
| JP | 2003-139276 | 5/2003 |
| JP | 03194747 | 7/2003 |
| JP | 2003275312 | 9/2003 |
| JP | 4242816 | 3/2009 |
| JP | 44-022293 | 2/2010 |
| JP | 11248076 | 12/2011 |
| NZ | 564886 | 2/2011 |
| NZ | 587113 | 12/2011 |
| NZ | 586325 | 1/2012 |
| NZ | 583968 | 10/2012 |
| NZ | 597020 | 6/2013 |
| NZ | 600986 | 8/2013 |
| NZ | 604137 | 6/2014 |
| NZ | 610299 | 11/2014 |
| NZ | 630762 | 2/2016 |
| NZ | 625605 | 4/2016 |
| NZ | 710078 | 1/2017 |
| NZ | 710351 | 1/2017 |
| NZ | 631374 | 4/2017 |
| NZ | 631008 | 7/2017 |
| NZ | 733931 | 2/2019 |
| WO | WO 1996/020748 | 7/1996 |
| WO | WO 97/18001 | 5/1997 |
| WO | WO 1997/042475 A1 | 11/1997 |
| WO | WO 2000/029057 | 5/2000 |
| WO | WO 2001/032069 | 5/2001 |
| WO | WO 01/97894 | 12/2001 |
| WO | WO 02/066106 | 8/2002 |
| WO | WO 02/066107 | 8/2002 |
| WO | WO 2003/026721 | 4/2003 |
| WO | WO 2004/011072 | 2/2004 |
| WO | WO 2004/024429 | 3/2004 |
| WO | WO 2004/037330 | 5/2004 |
| WO | WO 2005/011785 | 2/2005 |
| WO | WO 2005/021076 | 3/2005 |
| WO | WO 2005/079670 A1 | 9/2005 |
| WO | WO 2006/017350 | 2/2006 |
| WO | WO 2006/019323 | 2/2006 |
| WO | WO 2007/051230 | 5/2007 |
| WO | WO 2008/055308 | 5/2008 |
| WO | WO 2008/056993 | 5/2008 |
| WO | WO 2008/058328 | 5/2008 |
| WO | WO 2008/060046 | 5/2008 |
| WO | WO 2008/060295 | 5/2008 |
| WO | WO 2008/076230 | 6/2008 |
| WO | WO 2009/002004 | 12/2008 |
| WO | WO 2009/022004 | 2/2009 |
| WO | WO 2009/127192 | 10/2009 |
| WO | WO 2010/031125 | 3/2010 |
| WO | WO 2010/031126 | 3/2010 |
| WO | WO 2010/091259 | 8/2010 |
| WO | WO 2011/030251 A1 | 3/2011 |
| WO | WO 2012/053910 | 4/2012 |
| WO | WO 2012/065999 | 5/2012 |
| WO | WO 2012/154883 | 11/2012 |
| WO | WO 2012/164407 | 12/2012 |
| WO | WO 2013/022356 A1 | 2/2013 |
| WO | WO 2013/026901 | 2/2013 |
| WO | WO 2013/045572 | 4/2013 |
| WO | WO 2013/045575 | 4/2013 |
| WO | WO 2013/045586 | 4/2013 |
| WO | WO 2013/049660 | 4/2013 |
| WO | WO 2013/050907 | 4/2013 |
| WO | WO 2013/050907 A1 | 4/2013 |
| WO | WO 2013/088351 | 6/2013 |
| WO | WO 2013/127474 | 9/2013 |
| WO | WO 2013/137753 A1 | 9/2013 |
| WO | WO 2013/151447 | 10/2013 |
| WO | WO 2013/162386 | 10/2013 |
| WO | WO 2014/055407 | 4/2014 |
| WO | WO 2014/077706 | 5/2014 |
| WO | WO 2014/205513 | 12/2014 |
| WO | WO 2015/038013 A1 | 3/2015 |
| WO | WO 2015/060729 | 4/2015 |
| WO | WO 2015/119515 A1 | 8/2015 |
| WO | WO 2015/160268 | 10/2015 |
| WO | WO 2016/042522 | 3/2016 |
| WO | WO 2016/089224 | 6/2016 |
| WO | WO 2016/139645 | 6/2016 |

(56) References Cited

FOREIGN PATENT DOCUMENTS

WO  WO 2017/027906  2/2017
WO  WO 2017/126980  7/2017

OTHER PUBLICATIONS

Extended European Search Report for Application No. 15803457.9, dated Nov. 28, 2017, 8 pages.
ISR for Inernational App No. PCT/NZ2015/050011; dated Mar. 19, 2015, 4 pages.
ISR for International App No. PCT/NZ2014/000201, dated Jan. 13, 2015, 21 pages.
ISR for International App. No. PCT/NZ2015/050069, dated Sep. 4, 2015.
ISR for International App. No. PCT/NZ2017/050157, dated May 9, 2018, 10 pages.
ISR from International App No. PCT/NZ2013/000075 dated Jun. 24, 2013.
Sawyer, Dick, et al. "An introduction to human factors in medical devices." US Department of Health and Human Services, Public Health Service, Food and Drug Administration, Center for Devices and Radiological Health (1996).
The Pacific Energy Association Reporter, Summer Issue, 1992, vol. II, pp. 13-17.
Jul. 9, 2013 International Search Report and Written Opinion for International Application No. PCT/NZ2013/000042 filed on Mar. 15, 2013.
International Preliminary Report on Patentability; Application No. PCT/IB2012/001786; Filed May 30, 2012.
International Search Report; PCT/IB2012/001786; dated Nov. 21, 2012.
International Preliminary Report on Patentability dated Jun. 9, 2015 for PCT Application No. PCT/NZ2013/000222 filed on Dec. 4, 2013.
U.S. Appl. No. 11/54259, filed Sep. 21, 1915, Light.

* cited by examiner

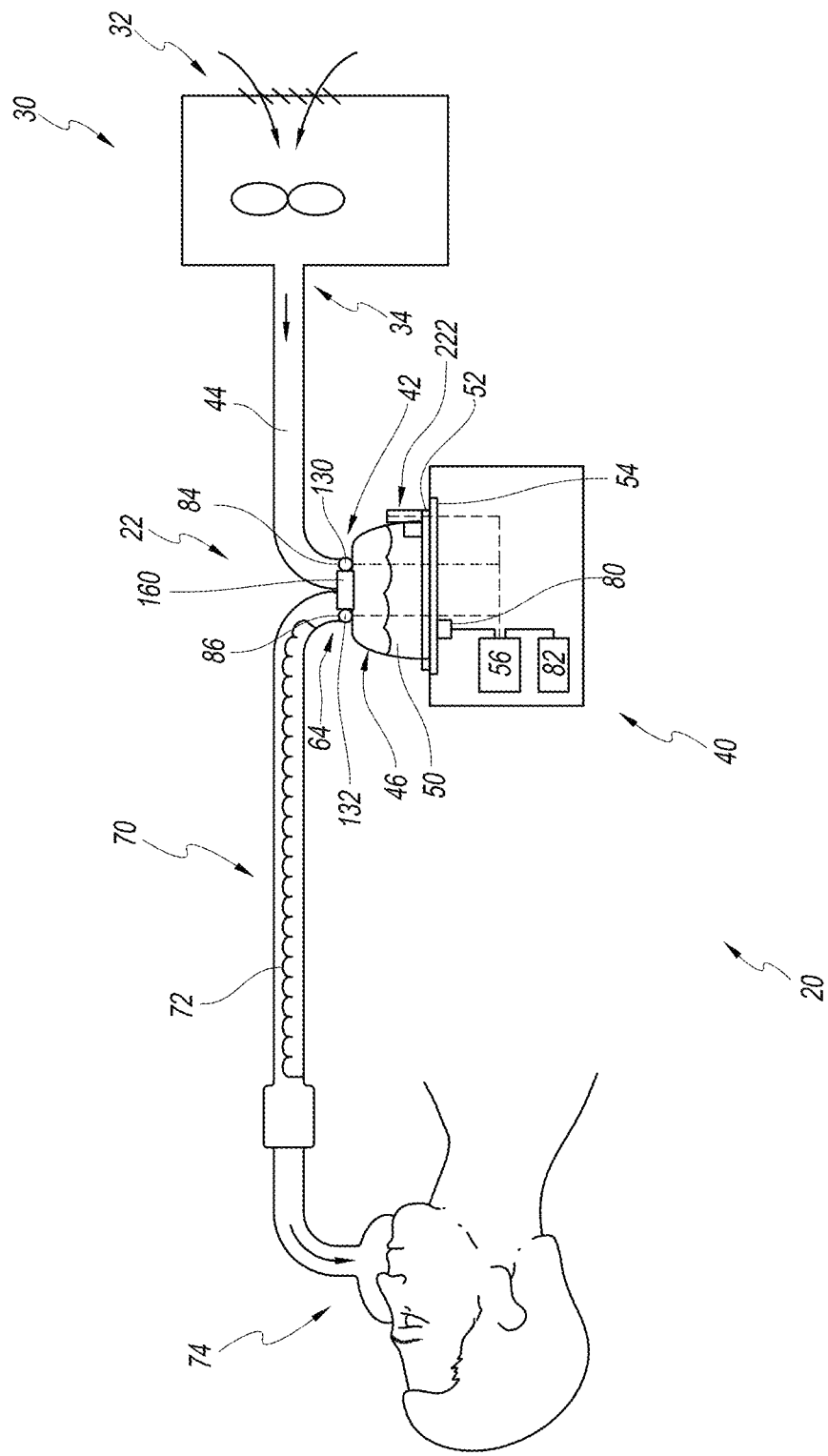

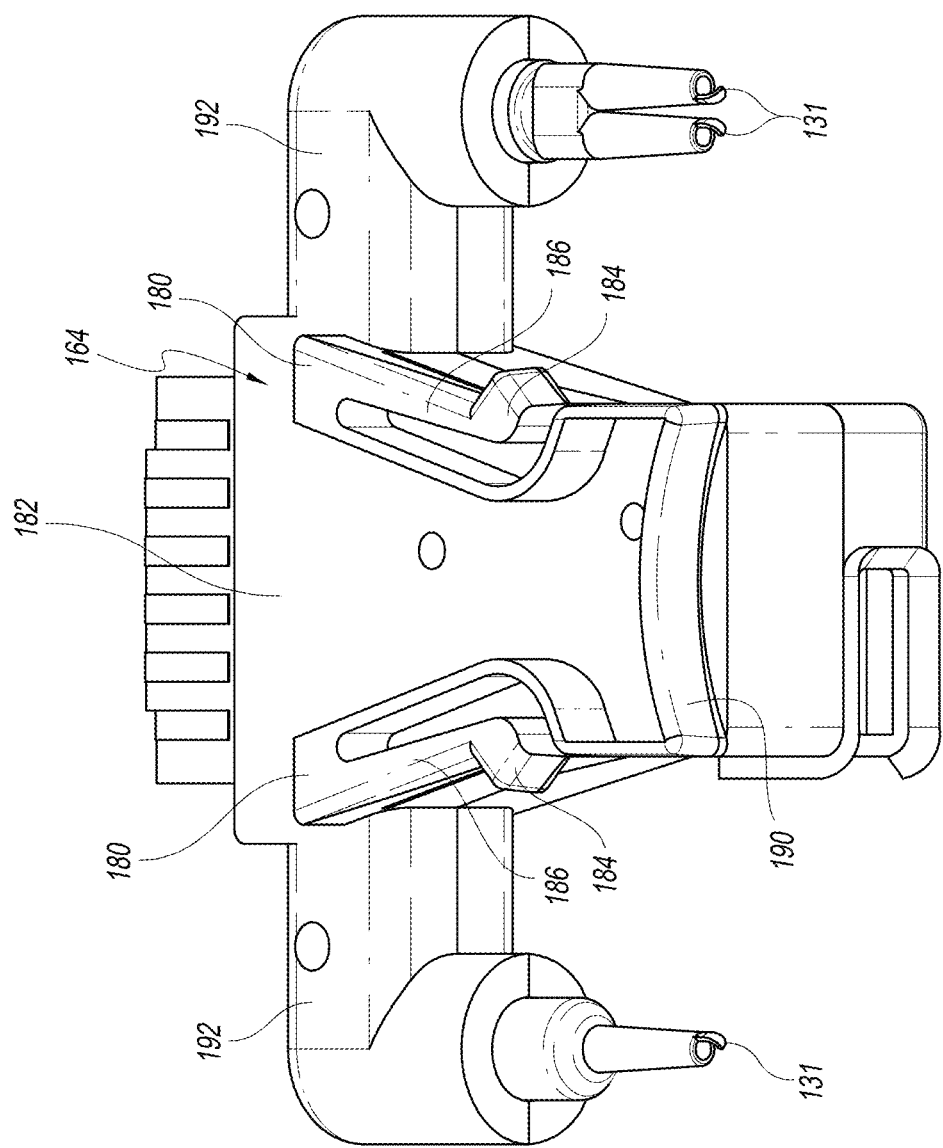

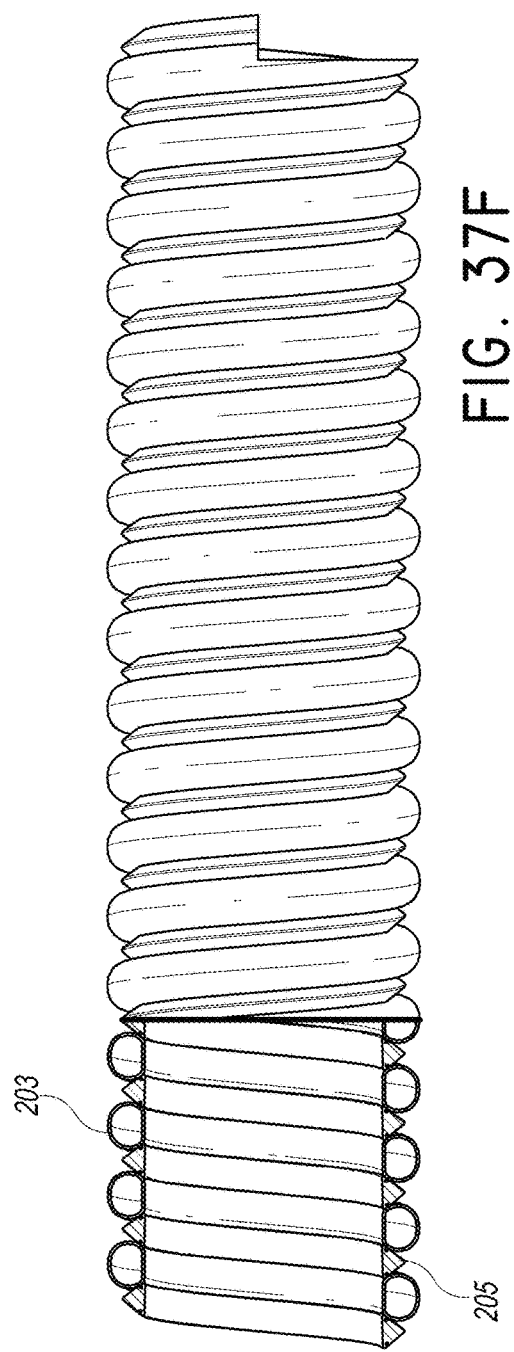
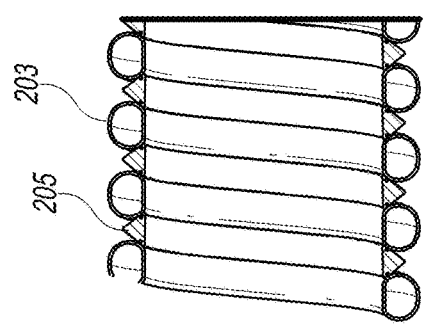
FIG. 37F
FIG. 37G

RELAXED STATE

1.

2.

3.

4.

5.

STRETCHED STATE

1.

2.

3.

4.

5.

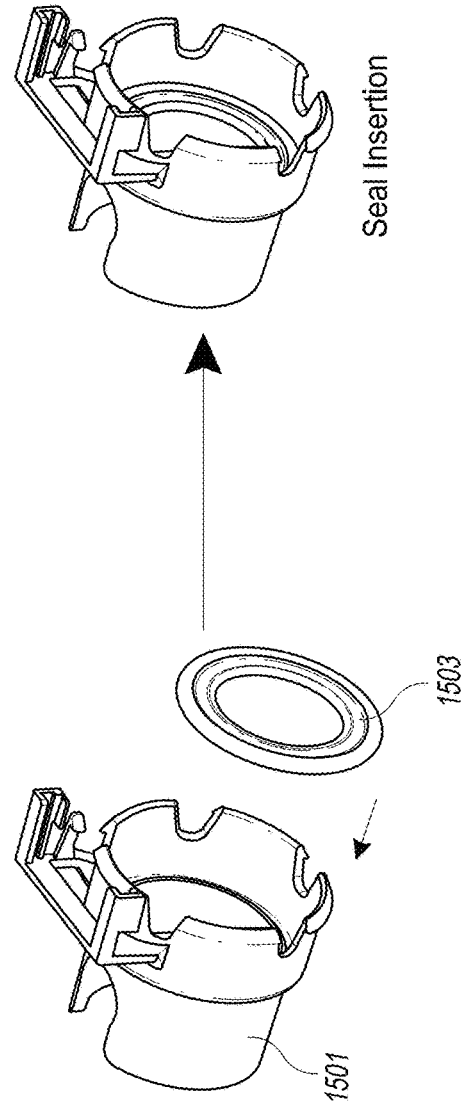
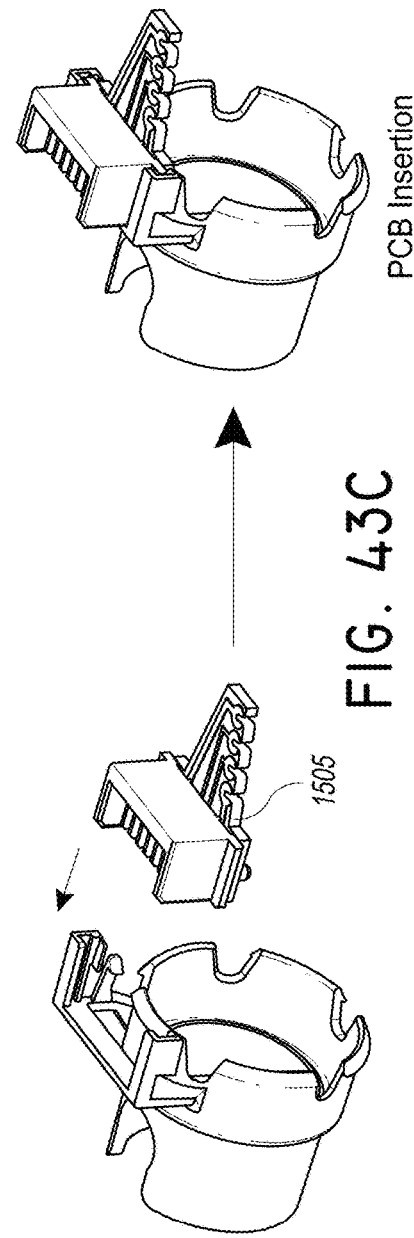

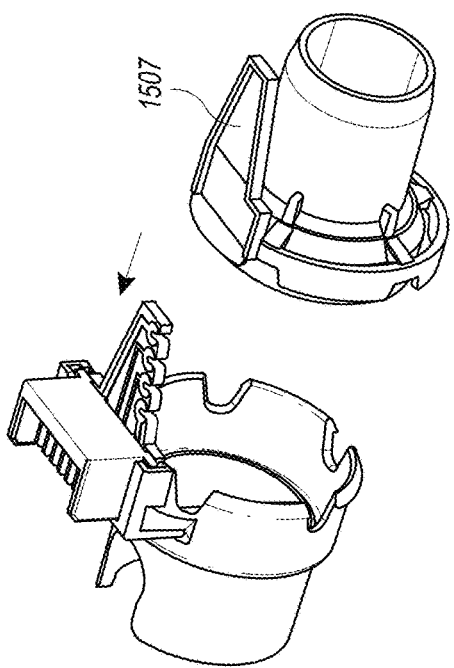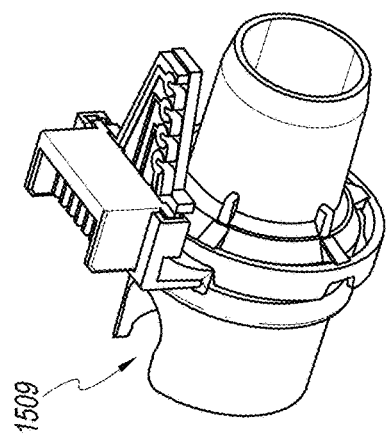
FIG. 43D
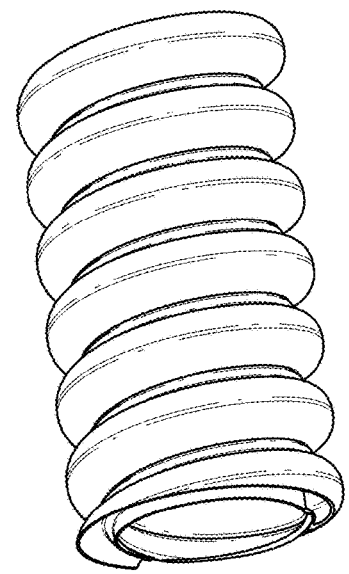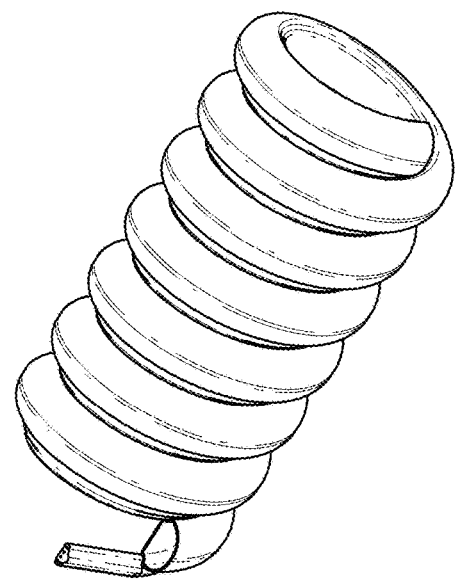
FIG. 43E

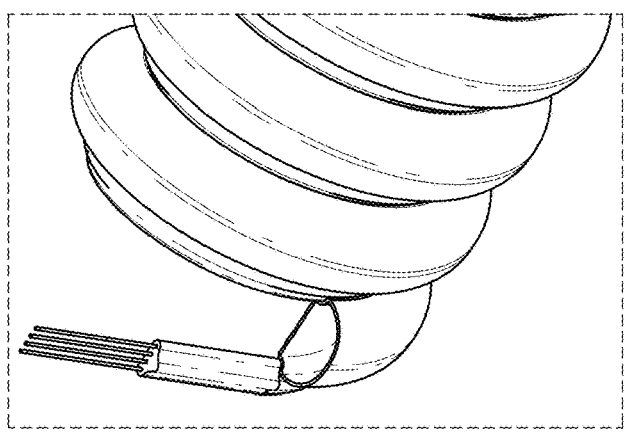
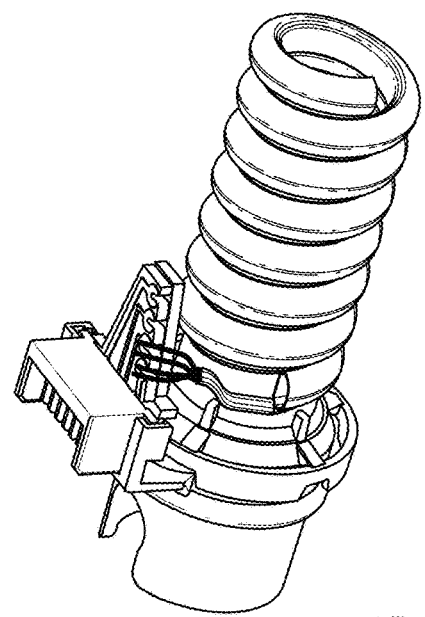
FIG. 43F
FIG. 43G
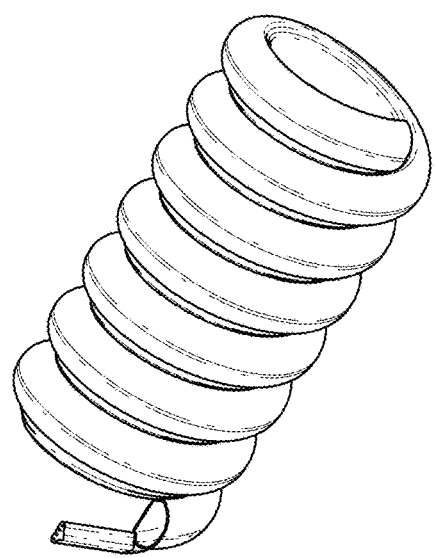
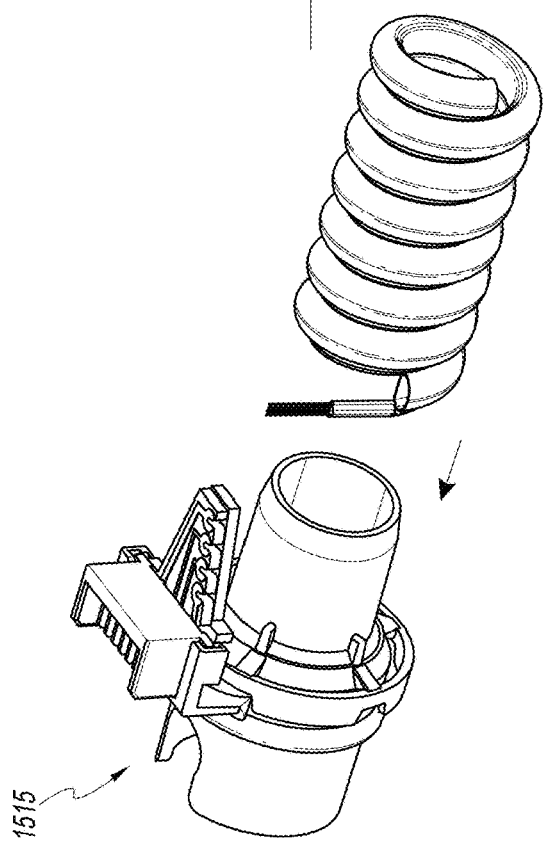

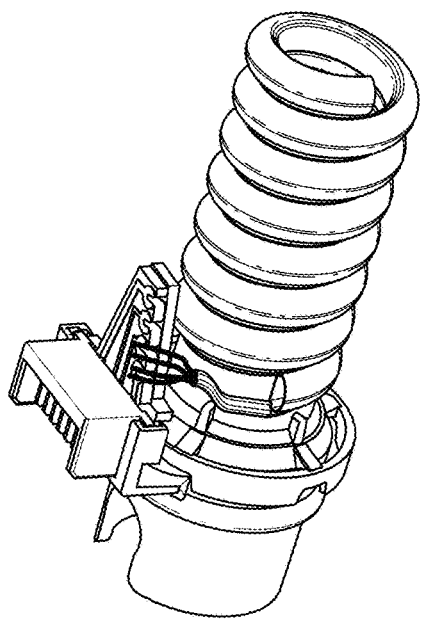
FIG. 43H
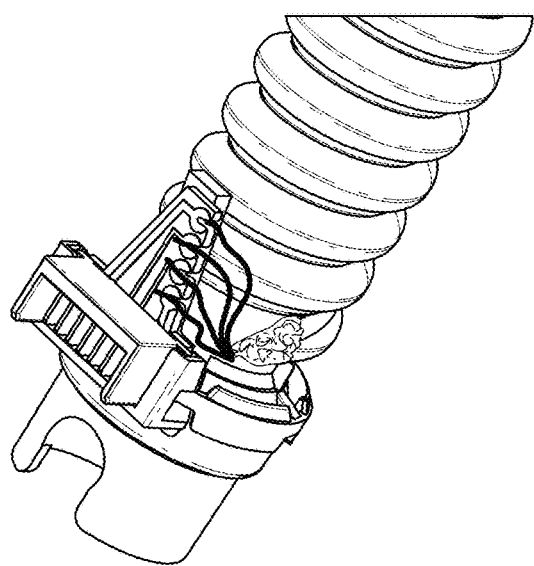
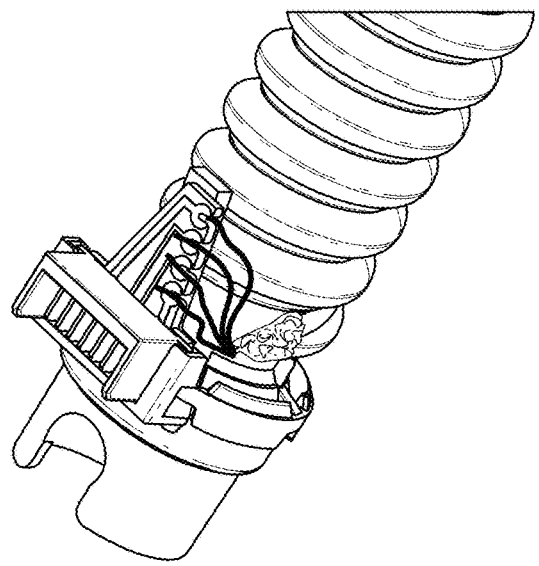
FIG. 43I
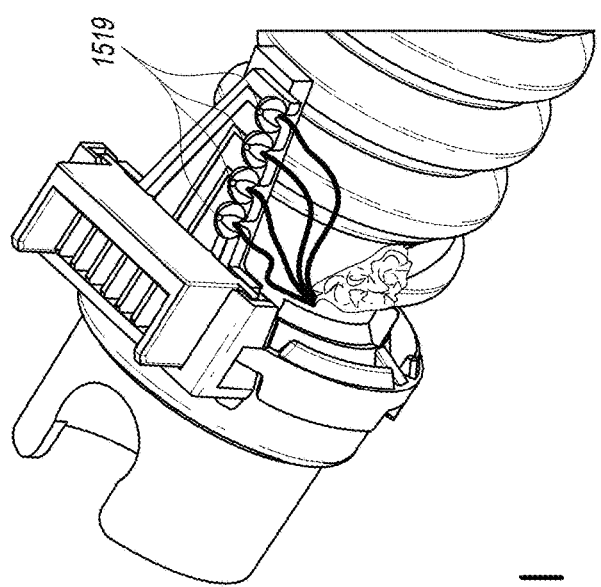

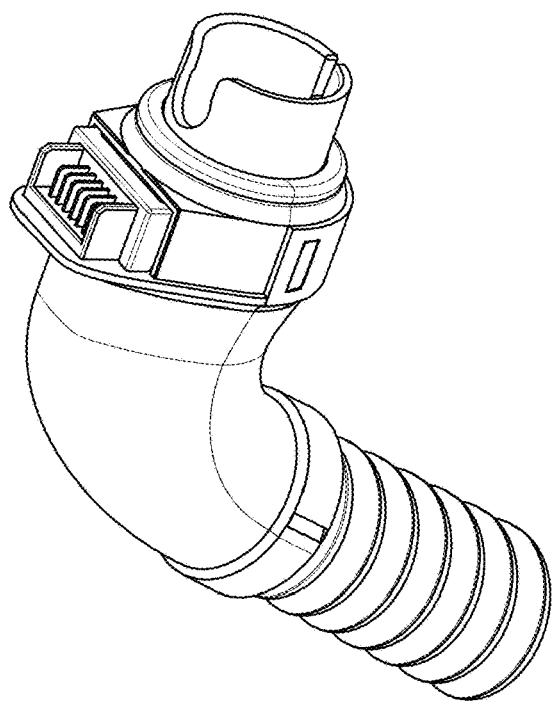
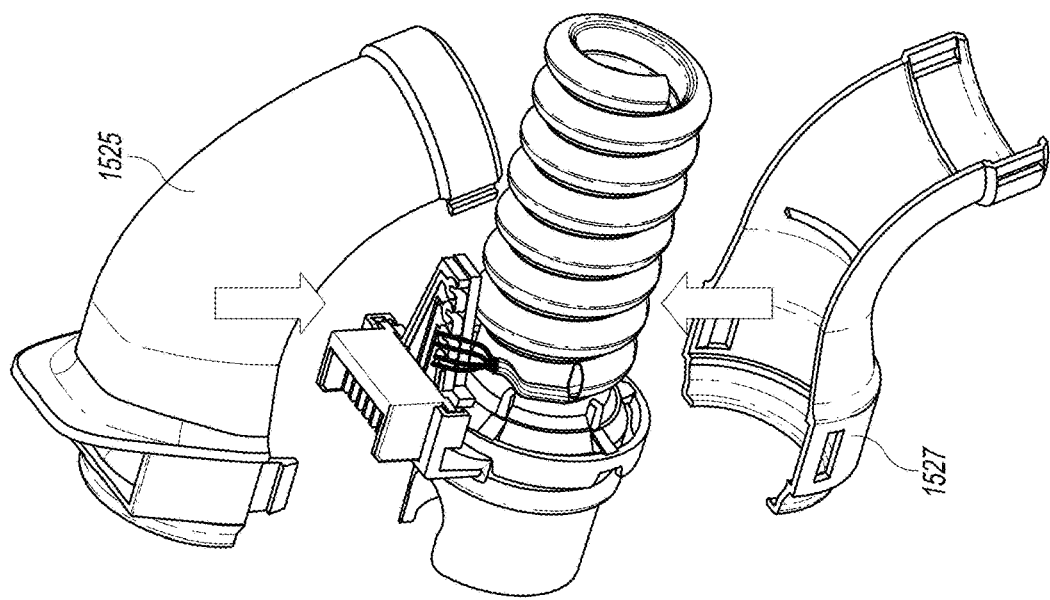
FIG. 43K

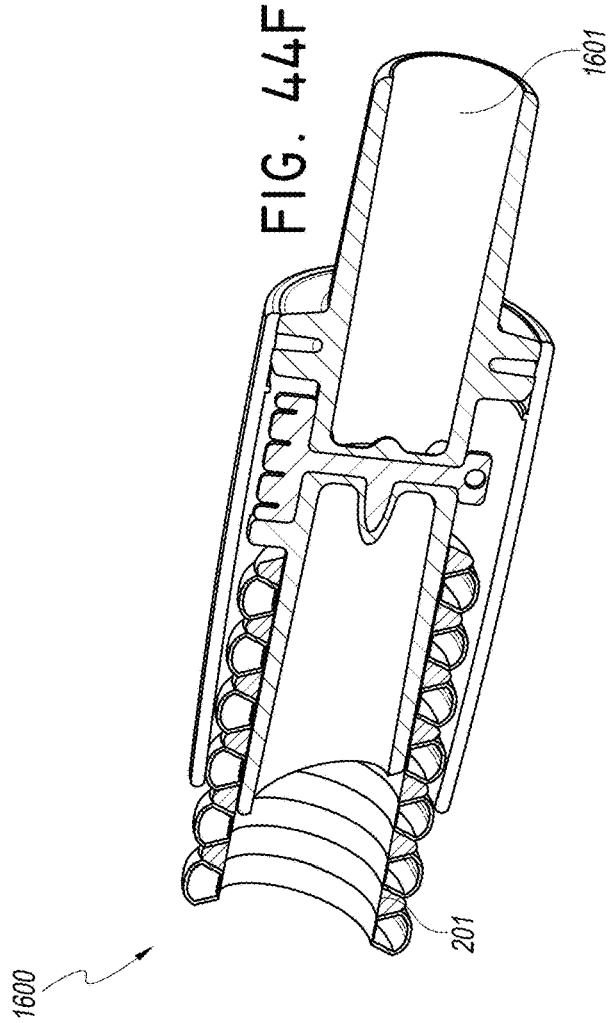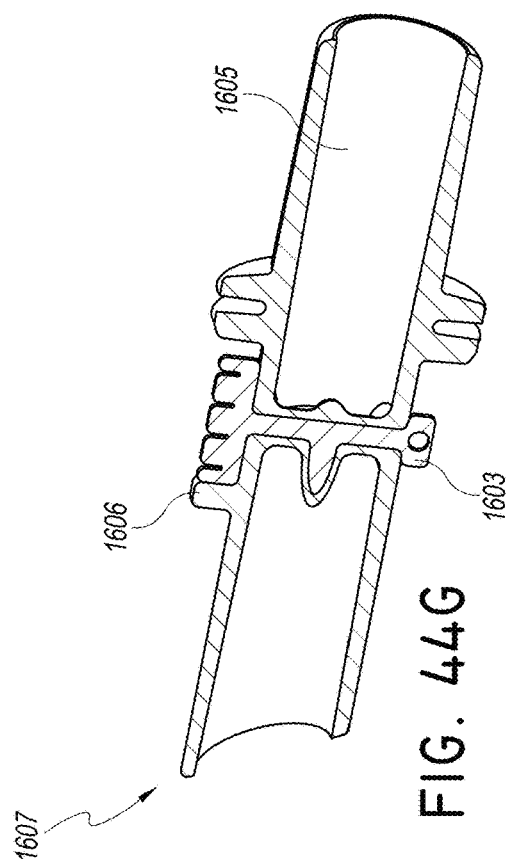

RESPIRATORY GAS HUMIDIFICATION SYSTEM

CROSS-REFERENCE TO RELATED APPLICATIONS

The present application is a continuation of U.S. application Ser. No. 14/485,608, filed Sep. 12, 2014, which is a continuation of PCT International Application No. PCT/NZ2013/000042, filed Mar. 15, 2013, issued as U.S. Pat. No. 9,987,455, which claims priority to U.S. Provisional Application Nos. 61/733,360, filed Dec. 4, 2012; 61/733,359, filed Dec. 4, 2012; 61/611,331, filed Mar. 15, 2012; and 61/722,659, filed Nov. 5, 2012, the entirety of each of which is hereby incorporated by reference herein.

BACKGROUND OF THE INVENTION

Field of the Invention

The present invention generally relates to respiratory methods or devices and methods and devices for providing heated and humidified gases to a user. More particularly, the present invention relates to techniques for measuring flow characteristics within such devices and tubes for use in medical circuits suitable for providing gases to and/or removing gases from a patient, such as in positive airway pressure (PAP), respirator, anaesthesia, ventilator, and insufflation systems.

Description of the Related Art

Many gas humidification systems deliver heated and humidified gases for various medical procedures, including respiratory treatment, laparoscopy and the like. These systems can be configured to control temperature, humidity and flow rates.

To provide a desired level of control, sensors must be used to detect flow characteristics. These sensors often are inserted directly into the flow and, because the sensors are not isolated from the fluid exchanges with the patient, the sensors must be cleaned or discarded. In other words, the sensors cannot be reused immediately after disconnection from the first patient. Such systems are described, for example, in U.S. Pat. No. 6,584,972, which is hereby incorporated by reference in its entirety.

Gas humidification systems also include medical circuits including various components to transport the heated and/or humidified gases to and from patients. For example, in some breathing circuits such as PAP or assisted breathing circuits, gases inhaled by a patient are delivered from a heater-humidifier through an inspiratory tube. As another example, tubes can deliver humidified gas (commonly $CO_2$) into the abdominal cavity in insufflation circuits. This can help prevent "drying out" of the patient's internal organs, and can decrease the amount of time needed for recovery from surgery. Unheated tubing allows significant heat loss to ambient cooling. This cooling may result in unwanted condensation or "rainout" along the length of the tubing transporting warm, humidified air. A need remains for tubing that insulates against heat loss and, for example, allows for improved temperature and/or humidity control in medical circuits. Accordingly, it is an object of certain features, aspects and advantages of the invention to overcome or ameliorate one or more of the disadvantages of the prior art or to at least provide the public with a useful choice.

SUMMARY OF THE INVENTION

Thus, humidification apparatuses are described herein that will facilitate sensing of liquid level in a humidification chamber and flow characteristics in a fluid flow while reducing waste and facilitating moderate reuse of certain components. Medical tubes and methods of manufacturing medical tubes are also disclosed herein in various embodiments. Certain features, aspects and advantages of the present invention go some way to overcoming the above-described disadvantages and/or at least provide the public with a useful choice.

In some configurations, a humidification apparatus comprises a pressurized gas source. The pressurized gas source comprises an outlet. The outlet of the pressurized gas source is connected to an inlet to a humidification unit. The humidification unit comprises an outlet. The outlet of the humidification unit is connected to a delivery component. A flow passage is defined between the pressurized gas source and the delivery component. A sensor is adapted to sense a flow characteristic within the flow passage. The flow passage comprises an aperture. The sensor extends through the aperture into the flow passage. The sensor comprises a sensing portion. A barrier is positioned between the flow passage and the sensor. The barrier contacts the sensing portion of the sensor with the barrier comprising a substantially constant thickness in the region contacting the sensing portion.

In some configurations, the humidification unit comprises a humidification chamber with the humidification chamber comprising a port and the aperture extending through a wall that defines at least a portion of the port.

In some configurations, the sensor comprises a first thermistor and a second thermistor. The barrier comprises a first sleeve that receives the first thermistor and a second sleeve that receives the second thermistor. In some configurations, two thermistors can be positioned within a single barrier.

In some configurations, the first thermistor is heated and the second thermistor is non-heated.

In some configurations, the barrier comprises a mounting portion, a first thickness and a second thickness that is less than the first thickness. The second thickness is located adjacent to the sensing portion of the sensor. A region having the first thickness is positioned between the mounting portion and the portion having the second thickness.

In some configurations, the barrier comprises a tip portion and a mounting portion. The mounting portion secures the barrier within the aperture and the tip portion comprises a reduced thickness.

In some configurations, the barrier pneumatically seals the aperture and receives at least a portion of the sensor such that the sensing portion can be positioned within the flow passage and a mounting portion is positioned outside of the flow passage.

In some configurations, the sensor is supported by a cartridge. The humidification unit comprises a humidification chamber. The cartridge and the humidification chamber are removably attached and comprise an interlocking connector.

In some configurations, the cartridge comprises a connector that is adapted to make electrical connection with the humidification unit when the cartridge is mounted to the humidification chamber and the humidification chamber is mounted to the humidification unit.

In some configurations, the cartridge supports the sensor in a repeatable manner relative to a portion of the flow passage through the humidification chamber such that the sensing portion of the sensor is consistently positioned with repeated removal and replacement of the cartridge from the humidification chamber.

In some configurations, the barrier comprises a generally cylindrical base and a generally bell-shaped head.

In some configurations, the generally bell-shaped head comprises a plurality of deflectable ribs.

In some configurations, the plurality of ribs are triangular and positioned around a perimeter of the bell-shaped head.

In some configurations, one or more of the plurality of ribs has a width of rib to width of separation ratio of about 3.7.

In some configurations, a humidification chamber comprises an outer body defining a chamber. An inlet port comprises a wall defining a passage into the chamber. An outlet port comprises a wall defining a passage out of the chamber. The wall of the inlet port comprises a first aperture. The first aperture receives a first sealing member. The first sealing member pneumatically seals the first aperture that extends through the wall of the inlet port. The wall of the outlet port comprises a second aperture. The second aperture receives a second sealing member. The second sealing member pneumatically seals the second aperture that extends through the wall of the outlet port. A cartridge is removably attachable to the outer body of the chamber with an interlocking structure. The cartridge supports a first sensor that is receivable within the first seal and that extends through the first aperture. The cartridge supports a second sensor that is receivable within the second seal and that extends through the second aperture.

In some configurations, the first sensor comprises a first sensing component and a second sensing component. The first sealing member separates the first sensing component from the second sensing component.

In some configurations, the first sensing component is a first thermistor and the second sensing component is a second thermistor.

In some configurations, the first sealing member and the second sealing member are removable.

In some configurations, the first sealing member has a contact portion that is adapted to contact a sensing portion of the first sensor with the contact portion having a reduced thickness.

In some configurations, the first sealing member has a contact portion that is adapted to contact a sensing portion of the first sensor with the contact portion having a substantially contact thickness.

In some configurations, the cartridge comprises an electrical connector with the electrical connector being electrically connected to the first sensor and the second sensor.

In some configurations, the interlocking structure comprises a recess defined on the outer body of the chamber and a boss defined on the cartridge.

Some embodiments provide for a chamber having a liquid level sensing system and being adapted to hold a conductive liquid. The chamber includes a body comprising a non-conductive wall having an interior surface and an exterior surface, and a conductive base affixed to the non-conductive wall to form a container adapted to hold liquids. The chamber includes a sensor electrode positioned on the exterior surface of the non-conducting wall. The chamber includes a base electrode electrically coupled to the conductive base and positioned on an exterior surface of the conductive base. The chamber includes a conductive bridge attached to the interior surface of the non-conducting wall. The chamber includes a voltage source and a detection system electrically coupled to the sensor electrode. The conductive bridge and the sensor electrode are capacitively coupled to one another in the chamber and the conductive bridge and the base electrode are conductively coupled to one another when the conductive liquid contacts both the bridge and the base electrode. To determine a liquid level in the chamber, the voltage source is configured to supply a varying voltage to the sensor electrode, and the detection system is configured to determine a capacitance of the sensor electrode.

Some embodiments provide for a chamber having a liquid level sensing system and being adapted to hold a non-conductive liquid. The chamber includes a body comprising a non-conductive wall having an interior surface and an exterior surface, and a conductive base affixed to the non-conductive wall to form a container adapted to hold liquids. The chamber includes a sensor electrode positioned on the exterior surface of the non-conducting wall. The chamber includes a base electrode electrically coupled to the conductive base and positioned on an exterior surface of the conductive base. The chamber includes a conductive bridge attached to the interior surface of the non-conducting wall. The chamber includes a voltage source and a detection system electrically coupled to the sensor electrode. The conductive bridge and the sensor electrode are capacitively coupled to one another in the chamber and the conductive bridge and the base electrode are capacitively coupled to one another. To determine a liquid level in the chamber, the voltage source is configured to supply a varying voltage to the sensor electrode, and the detection system is configured to determine a capacitance of the sensor electrode.

Some embodiments provide for a chamber having a liquid level sensing system and being adapted to hold a conductive liquid. The chamber includes a body comprising a non-conductive wall having an interior surface and an exterior surface; a wicking material attached to the interior surface of the non-conducting wall, the wicking material being configured to allow the conductive liquid to move up the non-conductive wall through the wicking material; and a conductive base affixed to the non-conductive wall to form a container adapted to hold liquids. The chamber includes a sensor electrode positioned on the exterior surface of the non-conducting wall. The chamber includes a voltage source and a detection system electrically coupled to the sensor electrode. The sensor electrode and the conductive liquid are capacitively coupled to one another. To determine a liquid level in the chamber, the voltage source is configured to supply a varying voltage to the sensor electrode, and the detection system is configured to determine a capacitance of the sensor electrode.

In some configurations a composite tube usable in various medical circuits includes a first elongate member comprising a spirally wound elongate hollow body and a second elongate member comprising an elongate structural component spirally wound between turns of the spirally wound hollow body. The first elongate member can form in longitudinal cross-section a plurality of bubbles with a flattened surface at the lumen. Adjacent bubbles can be separated by a gap above the second elongate member, or may not be directly connected to each other. The bubbles can have perforations. In some configurations, a "double bubble" tube includes a plurality of bubbles, for example, two adjacent wraps of the first elongate member, between wraps of the second elongate member. The second elongate member can have a longitudinal cross-section that is wider proximal the lumen and narrower at a radial distance from the lumen. Specifically, the second elongate member can have a longitudinal cross-section that is generally triangular, generally T-shaped, or generally Y-shaped. One or more conductive filaments can be embedded or encapsulated in the second elongate member. The one or more conductive filaments can be heating filaments (or more specifically, resistance heating filaments) and/or sensing filaments. The tube can comprise pairs of conductive filaments, such as two or four conductive filaments. Pairs of conductive filaments can be formed into a connecting loop at one end of the composite tube. The one or more conductive filaments can be spaced from the lumen wall. In at least one embodiment, the second elongate member can have a longitudinal cross-section that is generally triangular, generally T-shaped, or generally Y-shaped, and one or more conductive filaments can be embedded or encapsulated in the second elongate member on opposite sides of the triangle, T-shape, or Y-shape.

In some configurations, a humidification apparatus comprises a pressurized gas source comprising an outlet. An outlet of the pressurized gas source is connected to an inlet to a humidification unit. The humidification unit comprises an outlet. The outlet of the humidification unit is connected to a delivery component. A flow passage is defined between the pressurized gas source and the delivery component. A sensor is adapted to sense a flow characteristic within the flow passage. The flow passage comprises an aperture. The sensor extends through the aperture into the flow passage. The sensor comprises a sensing portion. A barrier is positioned between the flow passage and the sensor. The barrier contacts the sensing portion of the sensor with the barrier comprising a substantially constant thickness in the region contacting the sensing portion.

In some configurations, the humidification unit comprises a humidification chamber. The humidification chamber comprises a port and the aperture extends through a wall that defines at least a portion of the port.

In some configurations, the sensor comprises a first thermistor and a second thermistor. The barrier comprises a first sleeve that receives the first thermistor and a second sleeve that receives the second thermistor.

In some configurations, the first thermistor is heated and the second thermistor is non-heated.

In some configurations, the barrier comprises a mounting portion, a first thickness and a second thickness that is less than the first thickness. The second thickness is located adjacent to the sensing portion of the sensor and a region having the first thickness is positioned between the mounting portion and the portion having the second thickness.

In some configurations, the barrier comprises a tip portion and a mounting portion. The mounting portion secures the barrier within the aperture and the tip portion comprises a reduced thickness.

In some configurations, the barrier pneumatically seals the aperture and receives at least a portion of the sensor such that the sensing portion can be positioned within the flow passage and a mounting portion can be positioned outside of the flow passage.

In some configurations, the sensor is supported by a cartridge. The humidification unit comprises a humidification chamber. The cartridge and the humidification chamber can be removably attached and can comprise an interlocking connector.

In some configurations, the cartridge comprises a connector that is adapted to make electrical connection with the humidification unit when the cartridge is mounted to the humidification chamber and the humidification chamber is mounted to the humidification unit.

In some configurations, the cartridge supports the sensor in a repeatable manner relative to a portion of the flow passage through the humidification chamber such that the sensing portion of the sensor is consistently positioned with repeated removal and replacement of the cartridge from the humidification chamber.

In some configurations, a humidification chamber comprises an outer body defining a chamber. An inlet port comprises a wall that defines a passage into the chamber. An outlet port comprises a wall that defines a passage out of the chamber. The wall of the inlet port comprises a first aperture. The first aperture receives a first sealing member. The first sealing member pneumatically seals the first aperture that extends through the wall of the inlet port. The wall of the outlet port comprises a second aperture. The second aperture receives a second sealing member. The second sealing member pneumatically seals the second aperture that extends through the wall of the outlet port. A cartridge is removably attachable to the outer body of the chamber with an interlocking structure. The cartridge supports a first sensor that is receivable within the first seal and that extends through the first aperture. The cartridge supports a second sensor that is receivable within the second seal and that extends through the second aperture.

In some configurations, the first sensor comprises a first sensing component and a second sensing component. The first sealing member separates the first sensing component from the second sensing component.

In some configurations, the first sensing component is a first thermistor and the second sensing component is a second thermistor.

In some configurations, the first sealing member and the second sealing member are removable.

In some configurations, the first sealing member has a contact portion that is adapted to contact a sensing portion of the first sensor. The contact portion has a reduced thickness.

In some configurations, the first sealing member has a contact portion that is adapted to contact a sensing portion of the first sensor. The contact portion has a substantially contact thickness.

In some configurations, the cartridge comprises an electrical connector. The electrical connector is electrically connected to the first sensor and the second sensor.

In some configurations, the interlocking structure comprises a recess defined on the outer body of the chamber and a boss defined on the cartridge.

In some configurations, the chamber has a liquid level sensing system and is adapted to hold a conductive liquid. The chamber comprises a body including a non-conductive wall having an interior surface, an exterior surface and a conductive base affixed to the non-conductive wall to form a container adapted to hold liquids. A sensor electrode can be positioned on the exterior surface of the non-conducting wall. A base electrode can be electrically coupled to the conductive base and can be positioned on an exterior surface of the conductive base. A conductive bridge can be attached to the interior surface of the non-conducting wall. The conductive bridge can be capacitively coupled to the sensor electrode. The conductive bridge and the base electrode can be conductively coupled when the conductive liquid contacts both the bridge and the base electrode. A voltage source can be electrically coupled to the sensor electrode and can be configured to supply a varying voltage to the sensor electrode. A detection system can be electrically coupled to the sensor electrode and can be configured to determine a capacitance of the sensor electrode.

In some configurations, the sensor electrode is positioned further from the conductive base than the conductive bridge such that at least a portion of the sensor electrode extends beyond the conductive bridge in a direction away from the conductive base.

In some configurations, the detection system is configured to detect a change in the capacitance of the sensor electrode when a level of the conducting liquid is higher than the conducting bridge.

In some configurations, the detection system is configured to detect a change in the capacitance of the sensor electrode when a level of the conducting liquid is below the sensor electrode.

In some configurations, the sensor electrode is larger than the conductive base.

In some configurations, the base electrode is electrically coupled to an electrical ground.

In some configurations, the conductive base provides a virtual electrical ground to the liquid level sensing system.

In some configurations, the voltage source comprises an alternating current voltage source.

In some configurations, the capacitance of the sensor electrode increases by a discrete amount when the conducting liquid contacts the conducting bridge.

In some configurations, A humidification unit incorporates the chamber as discussed above.

In some configurations, a chamber has a liquid level sensing system and is adapted to hold a non-conductive liquid. The chamber comprises a body comprising a non-conductive wall having an interior surface and an exterior surface and a conductive base affixed to the non-conductive wall to form a container adapted to hold liquids. A sensor electrode can be positioned on the exterior surface of the non-conducting wall. A base electrode can be electrically coupled to the conductive base and can be positioned on an exterior surface of the conductive base. A conductive bridge can be attached to the interior surface of the non-conducting wall. A voltage source electrically can be coupled to the sensor electrode. A detection system can be electrically coupled to the sensor electrode. The conductive bridge and the sensor electrode can be capacitively coupled. The conductive bridge and the base electrode can be capacitively coupled. The voltage source can be configured to supply a varying voltage to the sensor electrode. The detection system can be configured to determine a capacitance of the sensor electrode.

In some configurations, the detection system is further configured to determine a liquid level corresponding to the capacitance of the sensor electrode.

In some configurations, the detection system is configured to determine at least one of an out-of-liquid condition or an overfill condition.

In some configurations, the detection system is further configured to provide a notification corresponding to the liquid level.

In some configurations, the sensor electrode is removably attached to the exterior surface of the non-conducting wall.

In some configurations, a humidification unit incorporates the chamber as described above.

In some configurations, a chamber has a liquid level sensing system and is adapted to hold a conductive liquid. The chamber comprises a body comprising a non-conductive wall having an interior surface and an exterior surface. A wicking material can be attached to the interior surface of the non-conducting wall. The wicking material can be configured to allow the conductive liquid to move up the non-conductive wall through the wicking material. A conductive base can be affixed to the non-conductive wall to form a container adapted to hold liquids. A sensor electrode can be positioned on the exterior surface of the non-conducting wall. A voltage source can be electrically coupled to the sensor electrode. A detection system can be electrically coupled to the sensor electrode. The sensor electrode and the conductive liquid can be capacitively coupled. The voltage source can be configured to supply a varying voltage to the sensor electrode. The detection system can be configured to determine a capacitance of the sensor electrode.

In some configurations, the detection system is configured to determine an out-of-liquid condition when no conducting liquid is in the chamber.

In some configurations, the detection system is configured to provide a notification when the out-of-liquid condition is determined.

In some configurations, a humidification unit can incorporating the chamber as described above.

In some configurations, a composite tube comprises a first elongate member comprising a hollow body spirally wound to form at least in part an elongate tube having a longitudinal axis. A lumen extends along the longitudinal axis. A hollow wall surrounds the lumen. A second elongate member is spirally wound and joined between adjacent turns of the first elongate member. The second elongate member forms at least a portion of the lumen of the elongate tube.

In some configurations, the first elongate member is a tube.

In some configurations, the first elongate member forms in longitudinal cross-section a plurality of bubbles with a flattened surface at the lumen.

In some configurations, adjacent bubbles are separated by a gap above the second elongate member.

In some configurations, adjacent bubbles are not directly connected to each other.

In some configurations, the bubbles have perforations.

In some configurations, the second elongate member has a longitudinal cross-section that is wider proximal the lumen and narrower at a radial distance from the lumen.

In some configurations, the second elongate member has a longitudinal cross-section that is generally triangular.

In some configurations, the second elongate member has a longitudinal cross-section that is generally T-shaped or Y-shaped.

In some configurations, one or more conductive filaments can be embedded or encapsulated in the second elongate member.

In some configurations, the conductive filament is heating filament.

In some configurations, the conductive filament is sensing filament.

In some configurations, two conductive filaments can be embedded or encapsulated in the second elongate member.

In some configurations, four conductive filaments can be embedded or encapsulated in the second elongate member.

In some configurations, pairs of conductive filaments are formed into a connecting loop at one end of the composite tube.

In some configurations, the second elongate member has a longitudinal cross-section that is generally triangular, generally T-shaped, or generally Y-shaped, and the one or more conductive filaments are embedded or encapsulated in the second elongate member on opposite sides of the triangle, T-shape, or Y-shape.

In some configurations, the one or more filaments are spaced from the lumen wall.

In some configurations, a medical circuit component comprises the composite tube described above.

In some configurations, an inspiratory tube comprises the composite tube described above.

In some configurations, an expiratory tube comprises the composite tube described above.

In some configurations, a PAP component comprises the composite tube described above.

In some configurations, an insufflation circuit component comprises the composite tube described above.

In some configurations, an exploratory component comprises the composite tube described above.

In some configurations, a surgical component comprises the composite tube described above.

In some configurations, a method of manufacturing a composite tube comprises: providing a first elongate member comprising a hollow body and a second elongate member configured to provide structural support for the first elongate member; spirally wrapping the second elongate member around a mandrel with opposite side edge portions of the second elongate member being spaced apart on adjacent wraps, thereby forming a second-elongate-member spiral; and spirally wrapping the first elongate member around the second-elongate-member spiral, such that portions of the first elongate member overlap adjacent wraps of the second-elongate-member spiral and a portion of the first elongate member is disposed adjacent the mandrel in the space between the wraps of the second-elongate-member spiral, thereby forming a first-elongate-member spiral.

In some configurations, the method further comprises supplying air at a pressure greater than atmospheric pressure to an end of the first elongate member.

In some configurations, the method further comprises cooling the second-elongate-member spiral and the first-elongate-member spiral to form a composite tube having a lumen extending along a longitudinal axis and a hollow space surrounding the lumen.

In some configurations, the method further comprises forming the second elongate member.

In some configurations, the method further comprises forming the second elongate member comprises extruding the second elongate member with a second extruder.

In some configurations, the method further comprises the second extruder is configured to encapsulate one or more conductive filaments in the second elongate member.

In some configurations, the method further comprises forming the second elongate member comprises embedding conductive filaments in the second elongate member.

In some configurations, the method further comprises the conductive filaments are non-reactive with the second elongate member.

In some configurations, the method further comprises the conductive filaments comprise aluminum or copper.

In some configurations, the method further comprises forming pairs of conductive filaments into a connecting loop at one end of the composite tube.

In some configurations, the method further comprises forming the first elongate member.

In some configurations, the method further comprises forming the first elongate member comprises extruding the first elongate member with a first extruder.

In some configurations, the method further comprises the first extruder is distinct from the second extruder.

In some configurations, a medical tube comprises an elongate hollow body spirally wound to form an elongate tube having a longitudinal axis. A lumen extends along the longitudinal axis. A hollow wall surrounds the lumen. The elongate hollow body has in transverse cross-section a wall defining at least a portion of the hollow body. A reinforcement portion extends along a length of the elongate hollow body and is spirally positioned between adjacent turns of the elongate hollow body. The reinforcement portion forms a portion of the lumen of the elongate tube. The reinforcement portion is relatively thicker or more rigid than the wall of the elongate hollow body.

In some configurations, the reinforcement portion is formed from the same piece of material as the elongate hollow body.

In some configurations, the elongate hollow body in transverse cross-section comprises two reinforcement portions on opposite sides of the elongate hollow body, wherein spiral winding of the elongate hollow body joins adjacent reinforcement portions to each other such that opposite edges of the reinforcement portions touch on adjacent turns of the elongate hollow body.

In some configurations, opposite side edges of the reinforcement portions overlap on adjacent turns of the elongate hollow body.

In some configurations, the reinforcement portion is made of a separate piece of material than the elongate hollow body.

In some configurations, the hollow body forms in longitudinal cross-section a plurality of bubbles with a flattened surface at the lumen.

In some configurations, the bubbles have perforations.

In some configurations, one or more conductive filaments embedded or encapsulated within the reinforcement portion.

In some configurations, the conductive filament is heating filament.

In some configurations, the conductive filament is sensing filament.

In some configurations, two conductive filaments are included, wherein one conductive filament is embedded or encapsulated in each of the reinforcement portions.

In some configurations, two conductive filaments are positioned on only one side of the elongate hollow body.

In some configurations, pairs of conductive filaments are formed into a connecting loop at one end of the elongate tube.

In some configurations, the one or more filaments are spaced from the lumen wall.

In some configurations, a medical circuit component comprises the medical tube described above.

In some configurations, an inspiratory tube comprises the medical tube described above.

In some configurations, an expiratory tube comprises the medical tube described above.

In some configurations, a PAP component comprises the medical tube described above.

In some configurations, an insufflation circuit component comprises the medical tube described above.

In some configurations, an exploratory component comprises the medical tube described above.

In some configurations, a surgical component comprises the medical tube described above.

In some configurations, a method of manufacturing a medical tube comprises: spirally winding an elongate hollow body around a mandrel to form an elongate tube having a longitudinal axis, a lumen extending along the longitudinal axis, and a hollow wall surrounding the lumen, wherein the elongate hollow body has in transverse cross-section a wall defining at least a portion of the hollow body and two reinforcement portions on opposite sides of the elongate body forming a portion of the wall of the lumen, the two reinforcement portions being relatively thicker or more rigid than the wall defining at least a portion of the hollow body; and joining adjacent reinforcement portions to each other such that opposite edges of the reinforcement portions touch on adjacent turns of the elongate hollow body.

In some configurations, the method further comprises joining adjacent reinforcement portions to each other causes edges of the reinforcement portions to overlap.

In some configurations, the method further comprises supplying air at a pressure greater than atmospheric pressure to an end of the elongate hollow body.

In some configurations, the method further comprises cooling the elongate hollow body to join the adjacent reinforcement portions to each other.

In some configurations, the method further comprises extruding the elongate hollow body.

In some configurations, the method further comprises embedding conductive filaments in the reinforcement portions.

In some configurations, the method further comprises forming pairs of conductive filaments into a connecting loop at one end of the elongate tube.

For purposes of summarizing the invention, certain aspects, advantages and novel features of the invention have been described herein. It is to be understood that not necessarily all such advantages may be achieved in accordance with any particular embodiment of the invention. Thus, the invention may be embodied or carried out in a manner that achieves or optimizes one advantage or group of advantages as taught herein without necessarily achieving other advantages as may be taught or suggested herein.

BRIEF DESCRIPTION OF THE DRAWINGS

These and other features, aspects and advantages of the present invention will be described with reference to the following drawings, which are illustrative but should not be limiting of the present invention.

FIG. 1 is a simplified view of a humidification system arranged and configured in accordance with certain features, aspects and advantages of the present invention.

FIG. 21 is a perspective view of a cartridge with the sensors attached.

FIG. 37F shows a tube with a portion exposed in longitudinal cross-section.

FIG. 37G shows a longitudinal cross-section of a portion of a tube similar to the example tube of FIG. 37F.

FIGS. 38C and 38E show a front-perspective view of samples under testing in the jig. FIGS. 38D and 38F show a rear-perspective view of samples under testing in the jig.

FIG. 41D shows another aspect in a method for forming the composite tube.

FIG. 41E shows another aspect in a method for forming the composite tube.

FIG. 41F shows another aspect in a method for forming the composite tube.

FIGS. 41J-41Q show an alternative method of forming a tube.

FIGS. 43A-43L show a general flow chart and more detailed schematics and photographs relating to a method for attaching a connector to the end of the tube that is configured in use to connect to a humidifier.

FIGS. 44A-44I show schematics relating to a connector suitable for attaching a tube to a patient interface.

DETAILED DESCRIPTION OF THE PREFERRED EMBODIMENT

Certain embodiments and examples of humidification systems and/or liquid level sensing systems are described herein. Those of skill in the art will appreciate that the disclosure extends beyond the specifically disclosed embodiments and/or uses and obvious modifications and equivalents thereof. Thus, it is intended that the scope of the disclosure herein disclosed should not be limited by any particular embodiments described herein.

Humidification System

Figure 1A:
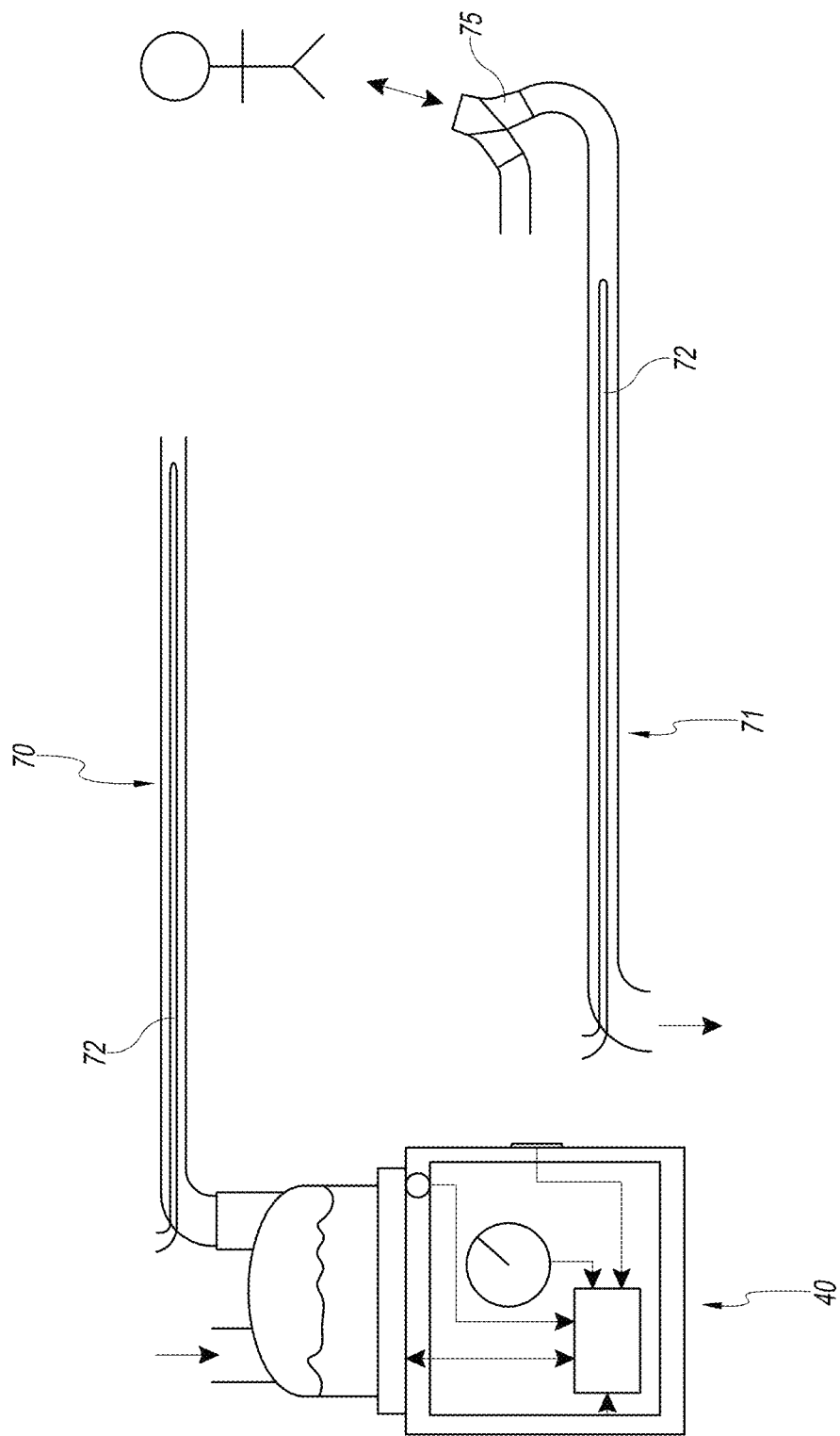
FIG. 1A is a simplified view of a humidification system.

FIGS. 1 and 1A illustrate a respiratory humidification system 20 that can include a sensing arrangement 22, liquid level sensing system 222, composite tubes, and/or other features arranged and configured in accordance with certain features, aspects and advantages of the present disclosure. The sensing arrangement 22, sensing system 222, composite tubes, and other features are illustrated and described herein in conjunction with the respiratory humidification system 20 but can find applicability in other applications involving the supply of a heated and humidified gas flow to a user or patient, including but not limited to laparoscopy, ventilation, and the like.

The illustrated respiratory humidification system 20 comprises a pressurized gas source 30. In some applications, the pressurized gas source 30 comprises a fan, blower or the like. In some applications, the pressurized gas source 30 comprises a ventilator or other positive pressure generating device. The pressurized gas source 30 comprises an inlet 32 and an outlet 34.

The pressurized gas source 30 provides a flow of fluid (e.g., oxygen, anesthetic gases, air or the like) to a humidification unit 40. The fluid flow passes from the outlet 34 of the pressurized gas source 30 to an inlet 42 of the humidification unit 40. In the illustrated configuration, the humidification unit 40 is shown separate of the pressurized gas source 30 with the inlet 42 of the humidification unit 40 connected to the outlet 34 of the pressurized gas source 30 with a conduit 44. In some applications, the pressurized gas source 30 and the humidification unit 40 can be integrated into a single housing.

While other types of humidification units can be used with certain features, aspects and advantages of the present invention, the illustrated humidification unit 40 is a pass over humidifier that comprises a humidification chamber 46 and the inlet 42 to the humidification unit 40 comprises an inlet to the humidification chamber 46. In some configurations, the humidification chamber 46 comprises a plastic formed body 50 with a heat conductive base 52 sealed thereto. A compartment can be defined within the humidification chamber 46. The compartment is adapted to hold a volume of water that can be heated by heat conducted through the base 52. In some applications, the base 52 is adapted to contact a heater plate 54. The heater plate 54 can be controlled through a controller 56 or other suitable component such that the heat transferred into the water can be varied.

Figure 2:
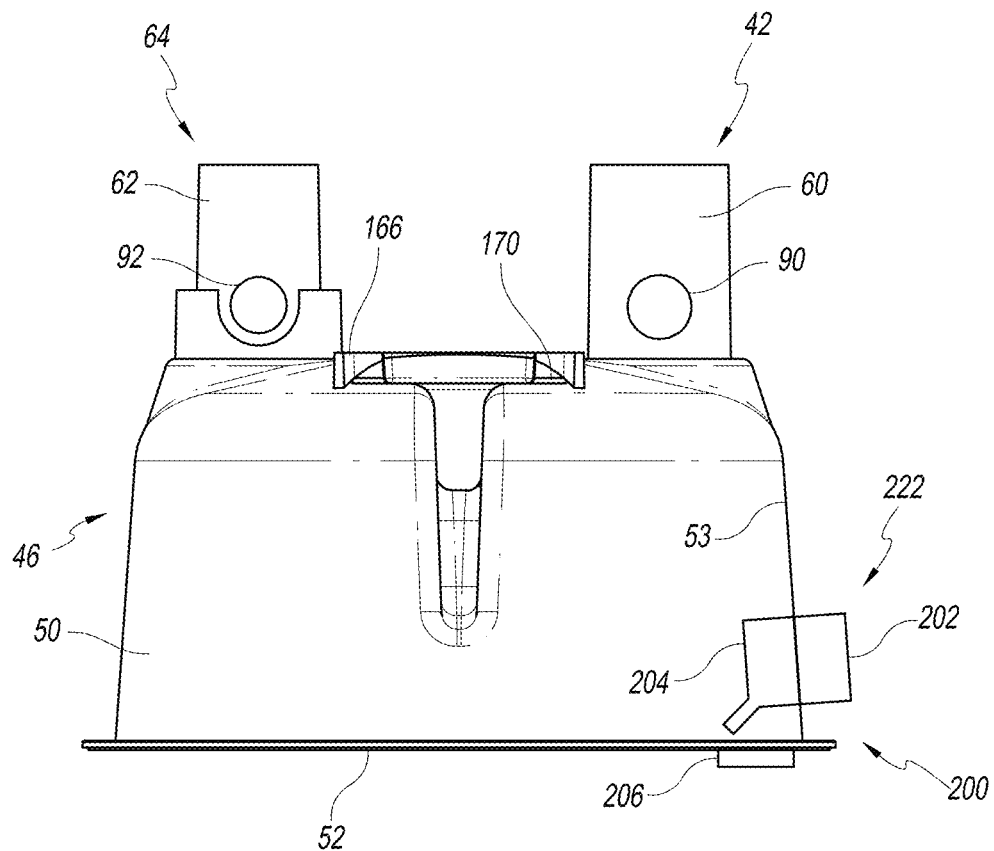
FIG. 2 is a side elevation view of a humidification chamber that is arranged and configured for use with certain features, aspects and advantages of the present invention.

With reference to FIG. 2, in the illustrated configuration, the body 50 of the humidification chamber 46 comprises a port 60 that defines the inlet 42 and the body 50 also comprises a port 62 that defines an outlet 64 of the humidification chamber 46. In some configurations, one or more of the ports 60, 62 can be formed on an end of a conduit or as a connector. In some configurations, the ports 60, 62 can have a portion that is received within an opening of the chamber. As water contained within the humidification chamber 46 is heated, water vapor is mixed with gases introduced into the humidification chamber 46 through the inlet port 60. The mixture of gases and water vapor exits the humidification chamber 46 through the outlet port 62.

With reference again to FIG. 1, an inspiratory conduit 70 or other suitable gases transportation pathway can be connected to the outlet 64 that defines the outlet port 62 of the humidification unit 40. The conduit 70 conveys toward a user the mixture of gases and water vapor that exits the humidification chamber 46. A condensation-reduction component may be positioned along at least a portion of the conduit 70. In the illustrated configuration, the condensation-reduction component comprises a heating element 72 that is positioned along at least a portion of the conduit 70. The heating element 72 can raise or maintain the temperature of the gases and water vapor mixture being conveyed by the conduit 70. In some configurations, the heating element 72 can be a wire that defines a resistance heater. Other configurations are possible. By increasing or maintaining the temperature of the gases and water vapor mixture, the water vapor is less likely to condensate out of the mixture.

A delivery component, such as an interface 74 for example but without limitation, can be provided to connect the conduit 70 to the user. In the illustrated configuration, the interface 74 comprises a mask. Moreover, in the illustrated configuration, the interface 74 comprises a mask that extends over the mouth and nose of the user. Any suitable interface 74 can be used. In some applications, certain features, aspects and advantages of the present invention can be used with intubation components, laparoscopy components, insufflators or the like. In some applications, such as those used with a ventilator, a suitable fitting (e.g., a Y-piece 75) can be positioned between the user and the conduit 70 such that an expiratory conduit 71 can be connected between the user and an inlet of the ventilator, for example but without limitation.

Figure 1B:
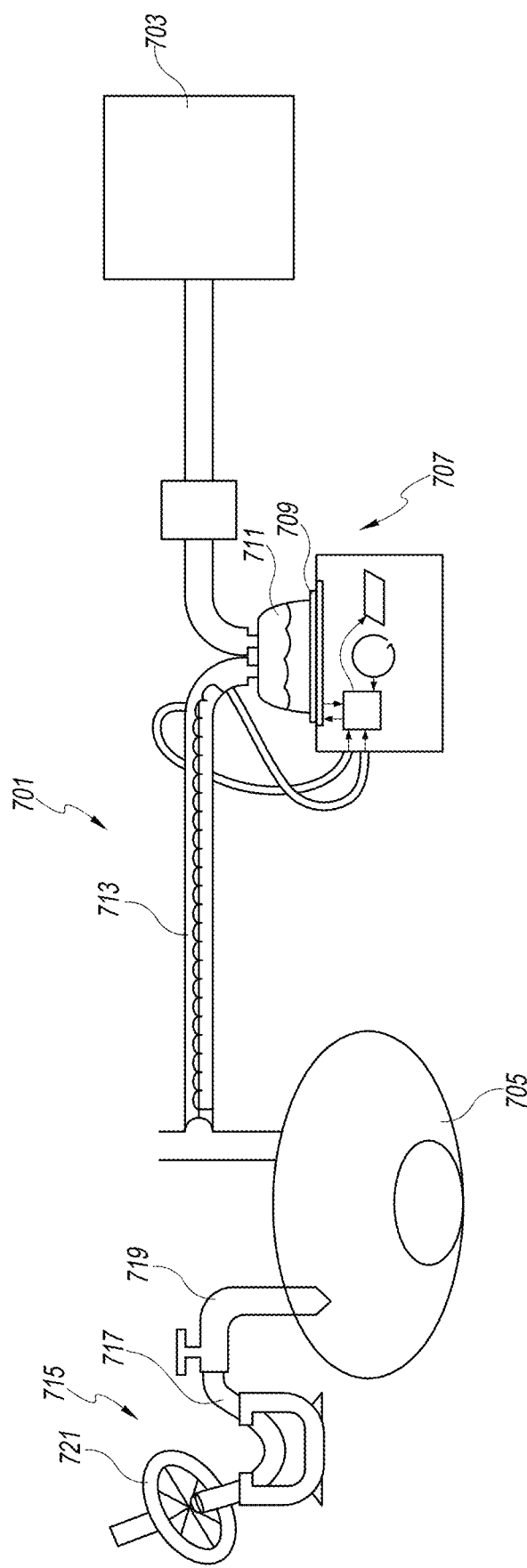
FIG. 1B is an insufflation system according to at least one embodiment.

As discussed above, the sensing arrangement 22, tubes, and other features illustrated and described herein can be used in conjunction with laparoscopic surgery, also called minimally invasive surgery or keyhole surgery. During laparoscopic surgery with insufflation, it may be desirable for the insufflation gas (commonly $CO_2$) to be humidified before being passed into the abdominal cavity. This can help reduce or eliminate the likelihood of "drying out" of the patient's internal organs, and can decrease the amount of time needed for recovery from surgery. FIG. 1B illustrates an example embodiment of an insufflation system 701, which includes an insufflator 703 that produces a stream of insufflation gases at a pressure above atmospheric for delivery into the patient 705 abdominal or peritoneal cavity. The gases pass into a humidification unit 707, including a heater base 709 and humidifier chamber 711, with the chamber 711 in use in contact with the heater base 709 so that the heater base 709 provides heat to the chamber 711. In the humidifier 707, the insufflation gases are passed through the chamber 711 so that they become humidified to an appropriate level of moisture. The system 701 includes a delivery conduit 713 that delivers humidified insufflation gases from the humidifier chamber 711 to the patient 705 peritoneal cavity or surgical site. A smoke evacuation system 715 leading out of the body cavity of the patient 705 comprises a discharge or exhaust limb 717, a discharge assembly 719, and a filter 721.

In some configurations, the delivery conduit 713 can also retain smoke rather than using (or in addition to) a smoke evacuation system. For example, in some configurations, rather than evacuating smoke from the patient's body cavity through an evacuation system, the smoke can sucked, withdrawn or guided into and back through the path of the conduit 713 (i.e. into and through the outer walls of the tube). The path 203 could include a filter/absorbent medium to receive the smoke. The conduit could be generally disposable after surgery so it does not need to be cleaned afterwards. A valve or other type of discharge assembly (e.g., discharge assembly 719) may be incorporated between the cavity and the path 203 to guide the smoke into the path after/during surgery.

Sensing and Control System

The controller 56 of the humidification unit 40 can control operation of various components of the respiratory humidification system 20. While the illustrated configuration is shown with a single controller 56, multiple controllers can be used in other configurations. The multiple controllers can communicate or can be provided separate functions and, therefore, the controllers need not communicate. In some configurations, the controller 56 may comprise a microprocessor, a processor or logic circuitry with associated memory or storage that contains software code for a computer program. In such configurations, the controller 56 can control operation of the humidification system 20 in accordance with instructions, such as contained within the computer program, and also in response to external inputs.

In some configurations, the controller 56 can receive input from a heater plate sensor 80. The heater plate sensor 80 can provide the controller 56 with information regarding the temperature and/or power usage of the heater plate 54. In some configurations, another input to the controller 56 can be a user input component 82. The user input component 82 can comprise a switch, dial, knob, or other suitable control input device, including but not limited to touch screens and the like. The user input component 82 can be operated by the user, a healthcare professional or other person to set a desired temperature of gases to be delivered to the user, a desired humidity level of gases to be delivered or both. In some configurations, the user input component 82 can be operated to control other operating characteristics of the humidification system 20. For example, the user input component 82 can control heating delivered by the heating element 72 or any desired characteristic of the air flow (e.g., pressure, flow rate, etc.).

Liquid Level Sensing System

The controller 56 also receives input from the liquid level sensing system 222. The liquid level sensing system 222 can comprise one or more sensors positioned on or near the chamber 46 or base 52. The liquid level sensing system 222 can include a voltage source and a detection system for determining liquid levels in the chamber 46, as described herein. The controller 56 can receive liquid level information from the liquid level sensing system 222 and adjust control properties in response to the liquid level information. In some embodiments, the controller 56 can notify a user through the user interface component 82 about liquid level conditions.

FIG. 2 illustrates an example humidification chamber 46 having a liquid level sensing system 222 according to some embodiments. The liquid level sensing system 222 can include one or more sensors 200. The sensors 200 can be positioned so that they are capacitively and/or conductively coupled to one another and/or to ground. The capacitance of one or more of the sensors 200 can change in response to changes in liquid levels. The liquid level sensing system 222 can detect these changes and determine a fluid level or a fluid level condition (e.g., out of water, chamber overfill, etc.) based at least in part on the change in capacitance of one or more sensors 200.

The humidification chamber 46 can comprise a body 50 having at least one non-conductive wall 53. The non-conductive wall 53 can be made of any suitable material that does not effectively conduct electricity, such as an insulating material. The humidification chamber 46 comprises a base 52 sealed to the body 50. The base 52 can be made of any suitable electrically conductive material, any suitable electrically non-conductive material, or a combination of electrically conductive and electrically non-conductive materials. For example, the base 52 can comprise a conductive material covered in a non-conductive material. In some embodiments, the base 52 is made of an electrically non-conductive material where a base electrode 206 is present.

The liquid sensing system 222 includes a sensor electrode 202 positioned on or near an exterior surface of the non-conductive wall 53. The sensor electrode 202 can be made of a conducting material, such as a metal. The sensor electrode 202 can be attached to the non-conducting wall 53 using any conventional means. In some embodiments, the sensor electrode 202 is removably attached to the non-conducting wall 53 to allow repositioning of the sensor electrode 202 or to allow it to be used with a different humidification chamber 46.

The liquid sensing system 222 can include a bridge 204 attached to an interior surface of the non-conducting wall 53. The bridge 204 is made of a conducting material and is positioned on or near the interior surface of the non-conducting wall 53. In some embodiments, the bridge 204 is affixed to the interior surface of the non-conducting wall 53 using any conventional means such that the bridge 204 remains substantially stationary in response to changes in a level of liquid in the chamber 46. The bridge 204 can be positioned relatively near a position of the sensor electrode 202 on the exterior surface of the non-conducting wall 53. The relative positions of the sensor electrode 202 and the bridge 204 can be configured to produce a discrete and measurable increase in the capacitance of the sensor electrode 202 when a liquid contacts the bridge 204. A measurable change can be any change in capacitance that is detected by the fluid level sensing system 222, as described more fully herein. By placing the bridge 204 in the chamber 46, a sudden and discrete increase in capacitance can be observed when a liquid contacts the bridge 204. It should be understood that the bridge 204 is not electrically coupled to the sensor electrode 202 through physical connections or wired means, but is capacitively coupled to the sensor electrode 202 based at least in part on the electrical properties of each and/or their physical proximity. Furthermore the bridge 204 is not electrically coupled to any other component of the liquid level sensing system 222 through wired means. Instead, the bridge 204 can be capacitively coupled to a base electrode 206 where the chamber 46 contains a non-conductive liquid or the bridge 204 can be conductively coupled to the base electrode 206 where the chamber 46 contains a conductive liquid that provides an electrically conductive path between the bridge 204 and the base 52. Thus, there are no wires or cables passing from outside of the chamber 46 to inside of the chamber 46 as with other systems having a sensor placed inside a chamber. This allows the structure of the humidification chamber 46 to remain free from pathways for cables or wires which pass from the exterior to the interior of the chamber 46 (which may require sealing to prevent losing fluids through the pathways) when using the liquid level sensing system 222 described herein.

The liquid level sensing system 222 can include a base electrode 206 positioned on the base 52 of the humidification chamber 46. In some embodiments, the base 52 acts as a virtual electrical ground for the fluid level sensing system 222 meaning that it is not electrically coupled to an electrical ground but provides a virtual electrical ground to the system 222. In some embodiments, the base electrode 206 is coupled to an electrical ground through the base 52 (e.g., the base 52 can provide a virtual ground or it can be electrically coupled to ground), through an electrical circuit, or through some other means.

In some embodiments, the sensor electrode 202 is not positioned opposite the bridge 204 as illustrated in FIG. 2. The sensor electrode 202 can be positioned in other locations and/or moved relative to the bridge 204 and still experience a discrete and measurable change in capacitance as described herein. This is due at least in part to the change in capacitance of the sensor electrode 202 when liquid contacts the bridge 204. This allows for flexible positioning of the sensor electrode 202. The sensor electrode 202 can be positioned to accommodate different designs of the body 50. For example, some humidification chambers may be shaped such that there are mechanical restrictions which prevent placing the sensor electrode 202 on an exterior surface opposite the bridge 204. It may be desirable to move the sensor electrode 202 farther from the base 52 as compared to the position of the bridge 204. This can increase the change in capacitance relative to ground by increasing a distance between the ground (e.g, the base 52) and the sensor electrode 202. Because the capacitance of the sensor electrode 202 changes when liquid contacts the bridge 204 even when the two are displaced from one another, the sensor electrode 202 can be vertically displaced from the bridge 204 (e.g., farther from the base 52 than the bridge 204). This allows the liquid level sensing system 222 to detect liquid levels below the position of the electrode sensor 202. Furthermore, the sensor electrode 202 can be bigger than the bridge 204. This can allow for overfill detection where there is a first discrete change in capacitance when the liquid level reaches the bridge 204 and a second discrete change in capacitance when the liquid level reaches the sensor electrode 202. Thus, by sizing and positioning the sensor electrode 202 such that the second discrete change in capacitance occurs when the liquid level nears the top of the chamber, the liquid level sensing system 222 can be configured to detect an overfill condition. The sensor electrode 202 can be sized and positioned such that the second discrete change in capacitance can occur at when the liquid level reaches any desired height.

In some embodiments, the humidification chamber 46 includes containers within the body 50 for holding a liquid such that the liquid does not contact the wall 53. Such containers can include, for example, tubes or other such structures within the body 50 of the humidification chamber 46. The liquid level sensing system 222 can be configured to determine liquid levels in such a humidification chamber by positioning the bridge 204 within the containers. The sensor electrode 202 can be positioned on the exterior of the body 50, as before. Thus, when the liquid reaches the bridge 204, there is a similar measurable change in capacitance of the system which can be detected by the liquid level sensing system 222.

Figure 2A:
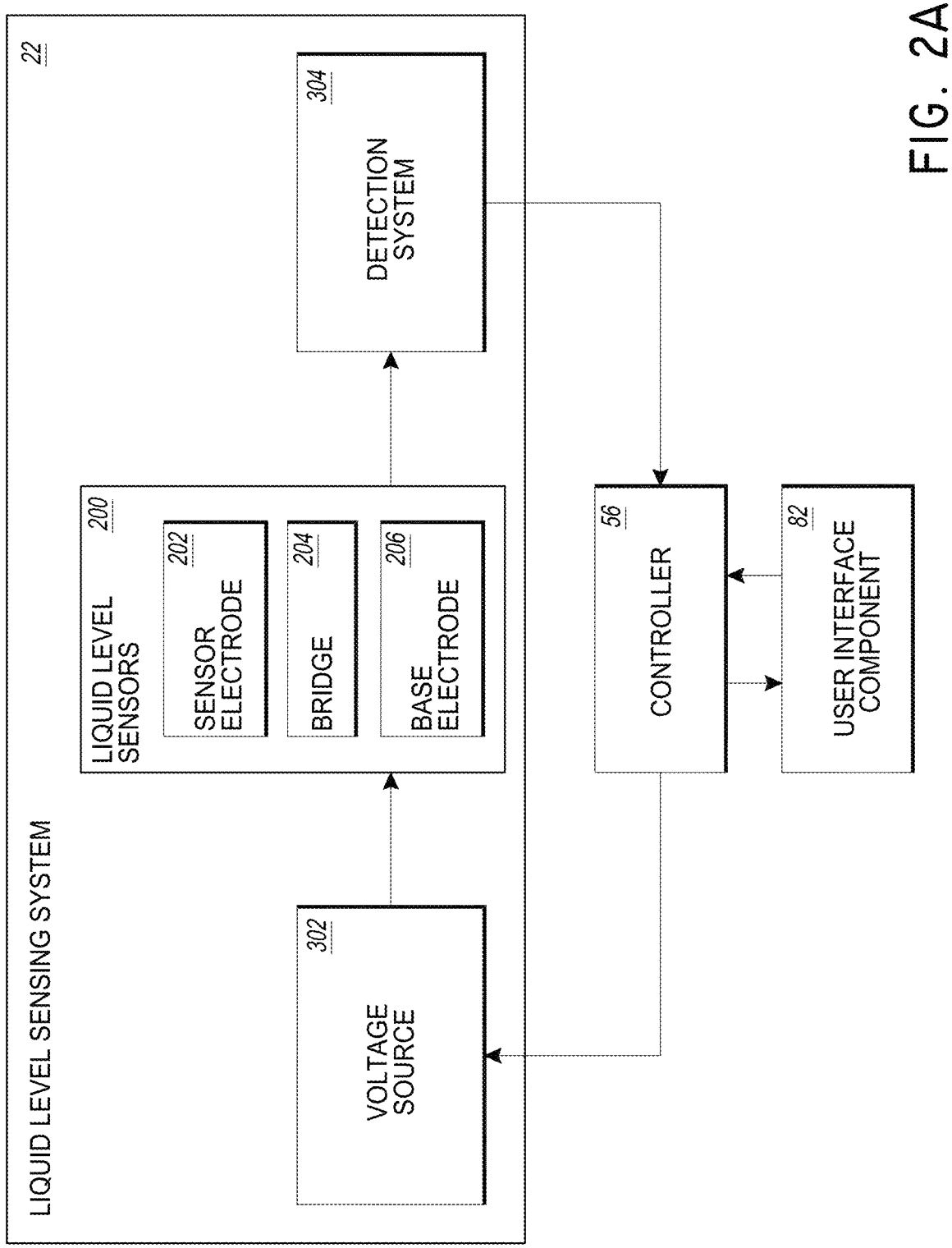
FIG. 2A illustrates a block diagram of a liquid level sensing system incorporated with a controller of a humidification system.

FIG. 2A illustrates a block diagram of a liquid level sensing system 222 incorporated with a controller 56 of a humidification unit 40. The liquid level sensing system 222 can include a voltage source 302, a detection system 304, and liquid level sensors 200 configured to detect a change in capacitance of the liquid level sensing system 222 corresponding to a liquid level condition, such as an out-of-liquid condition or a chamber overfill condition. The controller 56 can control the voltage source 302 and receive signals from the detection system 304 to determine the liquid level condition. The controller 56 can use the user interface component to control the determination of the liquid level condition or to notify a user of the liquid level condition.

The controller 56 can include hardware, software, and/or firmware components used to control the humidification unit 40. The controller 56 can be configured to control the voltage source 302, receive information from the detection system 304, receive user input from the user interface component 82, determine a level of liquid in a chamber 46, and determine a liquid level condition. The controller 56 can include modules configured to control the attached components and analyze received information. The controller 56 can include data storage for storing received information, control parameters, executable programs, and other such information.

The liquid level sensing system 222 includes a voltage source 302 coupled to the liquid level sensors 200, particularly the electrode sensor 202 described with reference to FIGS. 2, 2B, and 2C. The voltage source 302 can be a source of alternating current ("AC") and varying voltage. The voltage source 302 can be electrically coupled to the sensor electrode 202.

The liquid level sensing system 222 includes a detection system 304 coupled to the liquid level sensing sensors 200. The detection system 304 can be configured to measure a change in capacitance in the liquid level sensors 200. For example, the detection system 304 can include electronic circuitry configured to produce a voltage across the sensor electrode 202 which can be different from the supplied voltage from the voltage source 302. The difference between the supplied voltage and the voltage across the sensor electrode 202 can be related to the capacitance of the system 222. The detection system 304 can include data acquisition hardware configured to produce a signal corresponding to a measured voltage, capacitance, resistance, or some combination of these. The detection system 304 can include measurement tools configured to acquire and/or display a value corresponding to a capacitance, voltage, resistance or the like.

The liquid level sensing system 222 can be coupled to the controller 56 such that it can send information to and receive commands from the controller 56. For example, the liquid level sensing system 222 can receive a command from the controller 56 to vary a voltage supplied by the voltage source 302 to the sensor electrode 202. In some embodiments, the voltage source 302 produces a defined, known, or programmed voltage without input from the controller 56. The liquid level sensing system 222 can send information from the detection system 304 to the controller. The controller 56 can receive this information and analyze it to determine a liquid level condition. For example, the controller 56 can receive information that indicates that the chamber is out of liquid or nearly out of liquid. The controller 56 can then generate an out-of-liquid alert, notification, or signal. Similarly, the controller can receive information that indicates that the chamber has too much liquid. The controller 56 can then generate an overfill alert, notification, or signal. In some embodiments, the detection system 304 analyzes the information from the liquid level sensors 200 to determine the liquid level conditions. In some embodiments, the controller 56 receives information from the detection system 304 and can analyze this information to determine a liquid level condition. In some embodiments, the liquid level sensing system 222 and/or the controller 56 can be configured to determine a volume of liquid present in the humidification chamber 46 in addition to or instead of determining whether the chamber is out of liquid or has too much liquid. In some embodiments, the controller 56 can use the liquid level information as feedback in controlling other systems such as the heater plate 54.

The user interface component 82 can be coupled to the controller 56 to display information and/or receive input from a user. The user interface component 82 can display, for example, information about the liquid level condition, a voltage supplied by the voltage source 302, measurements acquired by the detection system 304, results of analysis by the controller 56, or any combination of these. The user interface component 82 can be used to enter control parameters such as a voltage to supply to the sensor electrode 202, characteristics of the supplied voltage (e.g., frequency, amplitude, shape, etc.), a frequency of measurements to be taken by the detection system 304, threshold values associated with measurements from the detection system 304 for use in determining out-of-liquid or overfill conditions, or any combination of these.

The controller 56 is configured to interact with the modules, data storage, and external systems of the humidification unit 40. The controller 56 can include one or more physical processors and can be used by any of the other components, such as the detection system 304, to process information. The controller 56 includes data storage. Data storage can include physical memory configured to store digital information and can be coupled to the other components of the humidifier unit 40, such as the liquid level sensing system and the user interface component 82.

Figure 2B:
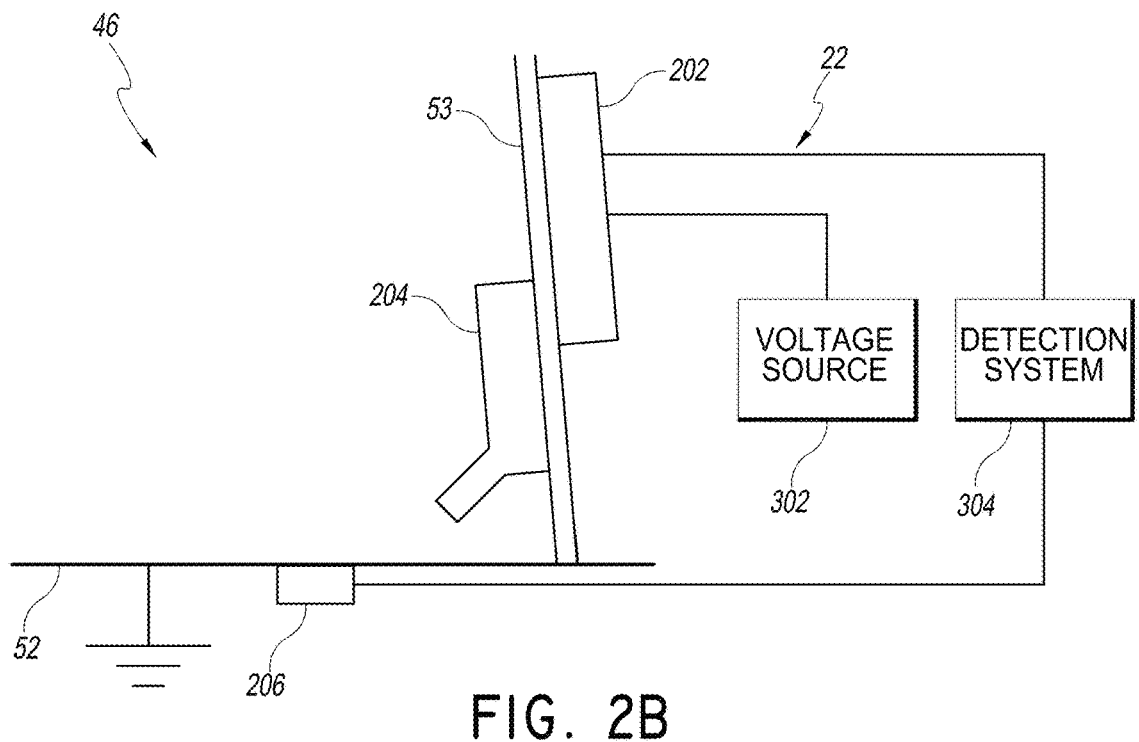
FIG. 2B illustrates an example liquid level sensing system in a humidification chamber with accompanying voltage source and detection system.

FIG. 2B illustrates an example liquid level sensing system 222 in a humidification chamber 46 with accompanying voltage source 302 and detection system 304. The humidification chamber 46 can include a non-conducting wall 53 to which is attached the sensor electrode 202 on an exterior side of the wall 53 and a conducting bridge 204 on the interior side of the wall 53. The humidification chamber includes a base 52 sealed to the non-conducting wall 53. A base electrode 206 can be attached to the base 52 which can act as a virtual ground for the base electrode 206, or the base electrode 206 can be coupled to ground through some other means. The voltage source 302 can supply a voltage which varies in current, voltage, or both to the sensor electrode 202. The detection system 304 can be coupled to the sensor electrode 202 and the base electrode to measure changes in capacitance. By determining a change in capacitance, the detection system can determine a liquid level condition in the humidification chamber 46.

When a conductive liquid in the humidification chamber 46 reaches the bridge 204, the bridge 204 is conductively coupled to the base electrode 206. This creates a virtual short to ground from the bridge 204, through the liquid, and to the ground. The bridge 204 is also capacitively coupled to the sensor electrode 202. Creating a virtual short from the bridge 204 to the base electrode 206 can change the capacitance of the system which can be measured as a discrete increase in capacitance of the sensor electrode 202 relative to ground. The liquid level sensing system 222 can detect this discrete increase in capacitance and determine a corresponding liquid level condition, as described more fully herein.

When a non-conductive liquid in the humidification chamber 46 reaches the bridge 204, the non-conductive liquid can act as a dielectric in a capacitive system. The bridge 204 in this scenario is capacitively coupled both to the sensor electrode 202 and to the base electrode 206. The presence of the non-conductive liquid at the bridge 204 causes a discrete change in the capacitance of the system which can be detected by measuring the capacitance of the sensor electrode 202 relative to ground. The liquid level sensing system 222 can detect this change in capacitance and determine a corresponding liquid level condition, as described more fully herein.

As illustrated in FIG. 2B, the sensor electrode 202 can be vertically offset relative to the bridge 204. As a result, the liquid level sensing system 222 can experience two discrete changes in capacitance. A first change occurs when the liquid reaches the bridge 204. A second change occurs when the liquid reaches the sensor electrode 202. The detection system can be configured to detect the two discrete changes and determine a corresponding liquid level condition. For example, the second discrete change can correspond to the chamber 46 having too much liquid, or an overfill condition.

In some embodiments, the sensor electrode 202 can be larger than the bridge 204. The increase in size can result in an increase in capacitance as capacitance is generally correlated to a physical size of an object. This increase in capacitance can increase the sensitivity of the system to changes in liquid levels. In some embodiments, the increase in size of the sensor electrode 202 can be used to detect an overfill condition due at least in part to a change in capacitance when liquid levels rise above the bridge 204. For example, the sensor electrode 202 and the bridge 204 can be positioned opposite one another. Because the sensor electrode 202 is larger than the bridge 204, it can extend vertically beyond the bridge 204. As a result, when the liquid level reaches the bridge 204 there will be a first discrete change in capacitance and when the liquid level is over the top of the bridge 204 there will be a second discrete change in capacitance as the liquid level will be of a height with the top of the sensor electrode 202. These changes in capacitance can be used to detect various liquid level conditions including an out-of-liquid condition or an overfill condition.

In some embodiments, the detection system 304 is configured to detect any change in capacitance in the liquid level sensing system 222. The detection system 304 can be configured to correlate these changes with volumes of liquid in the chamber 46. For example, as liquid levels increase, the capacitance of the sensor electrode 202 can change in relation to the level changes. The detection system 304 can determine an approximate liquid level value corresponding to a value of the capacitance. In this way, the liquid level sensing system 222 can estimate the water level in the humidification chamber 46.

Figure 2C:
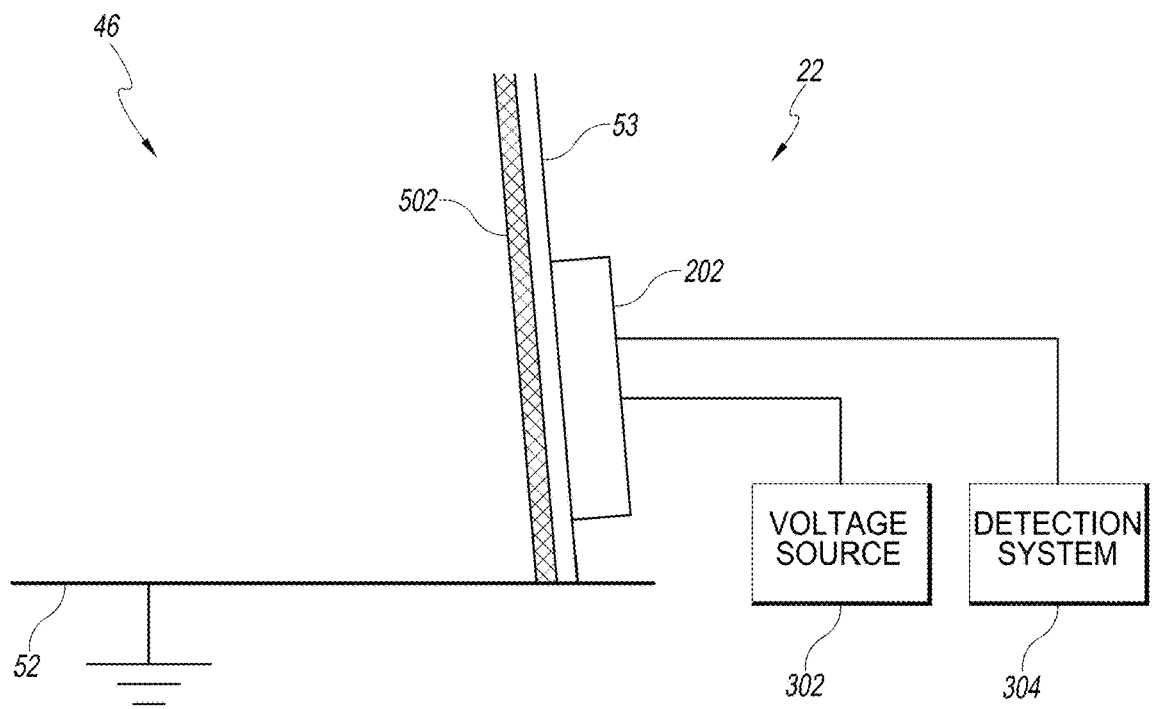
FIG. 2C illustrates an example liquid level sensing system in a humidification chamber having a wicking material along an interior wall.

FIG. 2C illustrates an example liquid level sensing system 222 in a humidification chamber 46 having a wicking material 502 along an interior of a non-conducting wall 53. The wicking material 502 is configured to provide a means for a liquid to move up the material through capillary action when there is any liquid in the chamber 46. This allows the liquid level sensing system 222 to detect a presence of a liquid in the chamber 46.

When the chamber 46 receives any conductive liquid, the conductive liquid will ascend the wicking material through capillary action. Once the conductive liquid arrives at a height that is level with the sensor electrode 202, the capacitance of the sensor electrode 202 changes as the conductive liquid is grounded due at least in part to the conductive connection with the base 52. The detection system 304 can detect this change in capacitance and signal the presence of liquid in the chamber 46. This can be used to determine whether there is liquid in the chamber 46 or if there is an out-of-liquid condition.

Figure 2D:
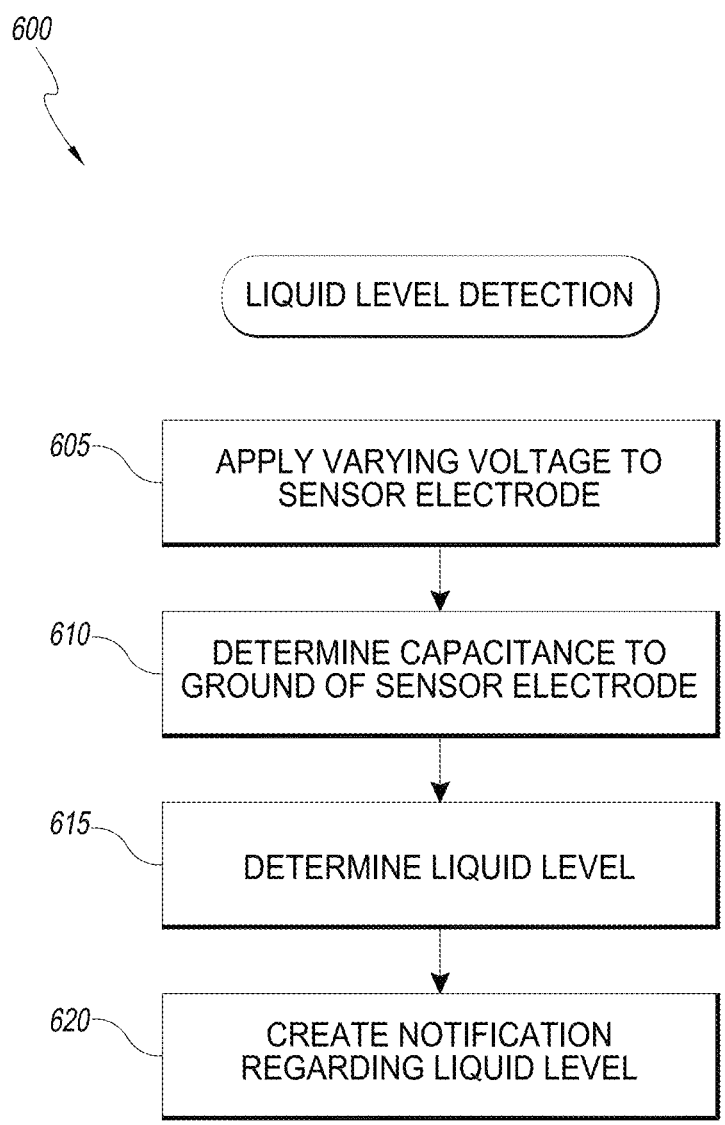
FIG. 2D illustrates a flow chart of an example method of detecting liquid levels in a humidification chamber.

FIG. 2D illustrates a flow chart of an example method 600 of detecting liquid levels in a humidification chamber 46 based at least in part on determining a change in capacitance of a sensor electrode 202. The example method 600 as described herein provides several advantageous features. One such feature is that the example method 600 can be used in a system where the humidification chamber 46 contains a conductive or non-conductive liquid without changing the manner in which the method functions. For example, determining a liquid level based at least in part on a change in capacitance between the sensor electrode 202 and ground works when the chamber 46 contains either conducting or non-conducting liquids, as described herein. For ease of description, the method will be described as being performed by the liquid level sensing system 222, but any individual step or combination of steps can be performed by any component of the liquid level sensing system 222 or the controller 56 of the humidification unit 40.

In block 605, the liquid level sensing system 222 uses a voltage source 302 to produce a varying electrical output that is coupled to a sensor electrode 202 attached to an exterior surface of a non-conducting wall 53 of a body 50 of the humidification chamber 46. The voltage source 302 can produce an electrical signal that varies in current, voltage, or both. For example, the voltage source 302 can be an AC voltage source. In some embodiments, the voltage source 302 is controlled by the controller 56. In some embodiments, the voltage source 302 is independently controlled or produces a selected, known, defined, or pre-determined electrical output.

In block 610, the liquid level sensing system 222 determines a capacitance of the sensor electrode 202 relative to ground. A detection system 304 can measure parameters of the liquid level sensing system 222 such as, for example, capacitance, resistance, voltage, or any combination of these. The detection system 304 can use this information to detect a change in the capacitance of the system 222.

The detection system 304 can include circuitry configured to produce measurable differences in parameters in response to a change in capacitance of the sensor electrode 202. For example, the detection system 304 can include circuit having a voltage divider having a resistor in series with the sensor electrode 202. The voltage source 302 can provide an AC voltage to the circuit. The detection system 304 can measure the voltage across the resistor and the sensor electrode 202. The capacitance of the sensor electrode 202 can be calculated based at least in part on the values of the measured voltages. As another example, the detection system 304 can include a circuit having a known capacitor in series with the sensor electrode 202. The voltage source can provide an AC voltage to the circuit. The detection system 304 can measure the voltage across the known capacitor and the sensor electrode 202 and calculate the capacitance of the sensor electrode 202. Other known methods of determining capacitance can be used by the detection system 304.

In some embodiments, the chamber 46 can be configured to hold conductive liquid. The sensor electrode 202 can be capacitively coupled to the bridge 204 and the bridge 204 can be conductively coupled to the base electrode 206, which is grounded. The conductive liquid turns the bridge 204 into a ground thereby creating a capacitance between the sensor electrode 202 and ground through the bridge 204. In some embodiments, the chamber 46 can be configured to hold non-conductive liquid. The sensor electrode 202 can be capacitively coupled to the bridge 204 and the bridge 204 can be capacitively coupled to the base electrode 206, which is grounded. This system creates a capacitive system having a dielectric that affects the capacitance between the sensor electrode 202 and the bridge 204, and between the bridge 204 and the base electrode 206, which is grounded. In some embodiments, the chamber 46 includes a wicking material on an interior surface of the non-conducting wall 53. The chamber 46 is configured to hold conductive liquid which moves up the wicking material when placed in the chamber 46. When the conductive material reaches the sensor electrode 202, the conducting liquid acts to change the capacitance of the sensor electrode 202 where the sensor electrode 202 is capacitively coupled to the conducting liquid in the wicking material, which is grounded.

In block 615, the liquid level sensing system 222 determines a liquid level based at least in part on the capacitance determined in block 610. According to the several embodiments described herein, the liquid level sensing system 222 can determine a volume of liquid in the chamber and/or it can determine a liquid level condition such as an out-of-liquid condition or an overfill condition.

In block 620, the liquid level sensing system 222 can create a notification related to the liquid level determined in block 615. For example, if an out-of-liquid condition is determined, the liquid level sensing system 222 can produce an audible or visible alert to a user or send a signal to the controller 56 of the humidification unit 40. The controller 56 can change control parameters based at least in part on the received notification regarding the liquid level, such as ceasing to energize a heater plate 54. The liquid level sensing system 222 can include its own notification system or use the user interface component 82 to notify operators or users of liquid level conditions.

Examples of liquid level sensing systems and associated components and methods have been described with reference to the figures. The figures show various systems and modules and connections between them. The various modules and systems can be combined in various configurations and connections between the various modules and systems can represent physical or logical links. The representations in the figures have been presented to clearly illustrate principles related to sensing liquid levels using capacitive and conductive techniques, and details regarding divisions of modules or systems have been provided for ease of description rather than attempting to delineate separate physical embodiments. The examples and figures are intended to illustrate and not to limit the scope of the inventions described herein. For example, the principles herein may be applied to a respiratory humidifier as well as other types of humidification systems, including surgical humidifiers. The principles herein may be applied in respiratory applications as well as in other scenarios where liquid level sensing is desirable.

As used herein, the term "processor" refers broadly to any suitable device, logical block, module, circuit, or combination of elements for executing instructions. For example, the controller 56 can include any conventional general purpose single- or multi-chip microprocessor such as a Pentium® processor, a MIPS® processor, a Power PC® processor, AMD® processor, or an ALPHA® processor. In addition, the controller 56 can include any conventional special purpose microprocessor such as a digital signal processor. The various illustrative logical blocks, modules, and circuits described in connection with the embodiments disclosed herein can be implemented or performed with a general purpose processor, a digital signal processor (DSP), an application specific integrated circuit (ASIC), a field programmable gate array (FPGA), or other programmable logic device, discrete gate or transistor logic, discrete hardware components, or any combination thereof designed to perform the functions described herein. Controller 56 can be implemented as a combination of computing devices, e.g., a combination of a DSP and a microprocessor, a plurality of microprocessors, one or more microprocessors in conjunction with a DSP core, or any other such configuration.

Data storage can refer to electronic circuitry that allows information, typically computer or digital data, to be stored and retrieved. Data storage can refer to external devices or systems, for example, disk drives or solid state drives. Data storage can also refer to fast semiconductor storage (chips), for example, Random Access Memory (RAM) or various forms of Read Only Memory (ROM), which are directly connected to the communication bus or the controller 56. Other types of memory include bubble memory and core memory. Data storage can be physical hardware configured to store information in a non-transitory medium.

Flow and Temperature Sensing System

With reference to FIG. 1, the controller 56 also receives input from a flow sensor 84 and at least one temperature sensor 86. Any suitable flow sensor 84 can be used and any suitable temperature sensor 86 can be used. In some configurations, the flow sensor 84 can include a temperature sensor 86.

Preferably, the flow sensor 84 is positioned between ambient air and the humidification chamber 46. More preferably, the flow sensor 84 is positioned between the pressurized gas source 30 and the humidification chamber 46. In the illustrated configurations, the flow sensor 84 is positioned on the inlet port 60 of the humidification chamber 46. In some configurations, the sensor 84 can be positioned on a connector used to couple a conduit to the inlet port 60. The sensor 84 also can be positioned in any suitable location.

Preferably, the temperature sensor 86 is positioned between the humidification chamber 46 and the user. More preferably, the temperature sensor 86 is positioned between the humidification chamber 46 and the interface 74. In the illustrated configurations, the temperature sensor 86 is positioned on the outlet port 62 of the humidification chamber 46. In some configurations, the sensor 86 can be positioned on a connector used to couple a conduit to the outlet port 62. The sensor 86 also can be positioned in any suitable location.

At least a portion of one or more of the sensors 84, 86 can be mounted outside of a flow path defined through the humidification system 20. In some configurations, one or more of the sensors 84, 86 is configured for removal from the flow path without directly accessing the flow path through the humidification system 20. Preferably, the one or more sensors 84, 86 is configured to sense one or more characteristic of flow through a portion of the flow path through the humidification system while remaining pneumatically sealed from the flow path.

With reference to FIG. 2, in the illustrated configuration, the inlet port 60 comprises an aperture 90. The aperture 90 extends through a wall of the inlet port 60 and provides a communication path through the wall of the inlet port 60. Similarly, in the illustrated configuration, the outlet port 62 comprises an aperture 92. The aperture 92 extends through a wall of the outlet port 62 and provides a communication path through the wall of the outlet port 62. In some configurations, the aperture 90 and the aperture 92 each is defined around a cylinder with an axis and the axes extend generally parallel with each other. Other configurations are possible. In addition, while the illustrated configurations position the apertures 90, 92 within portions of the humidification chamber 46, one or more of the apertures can be positioned in other locations on the humidification system 20.

Figure 3:
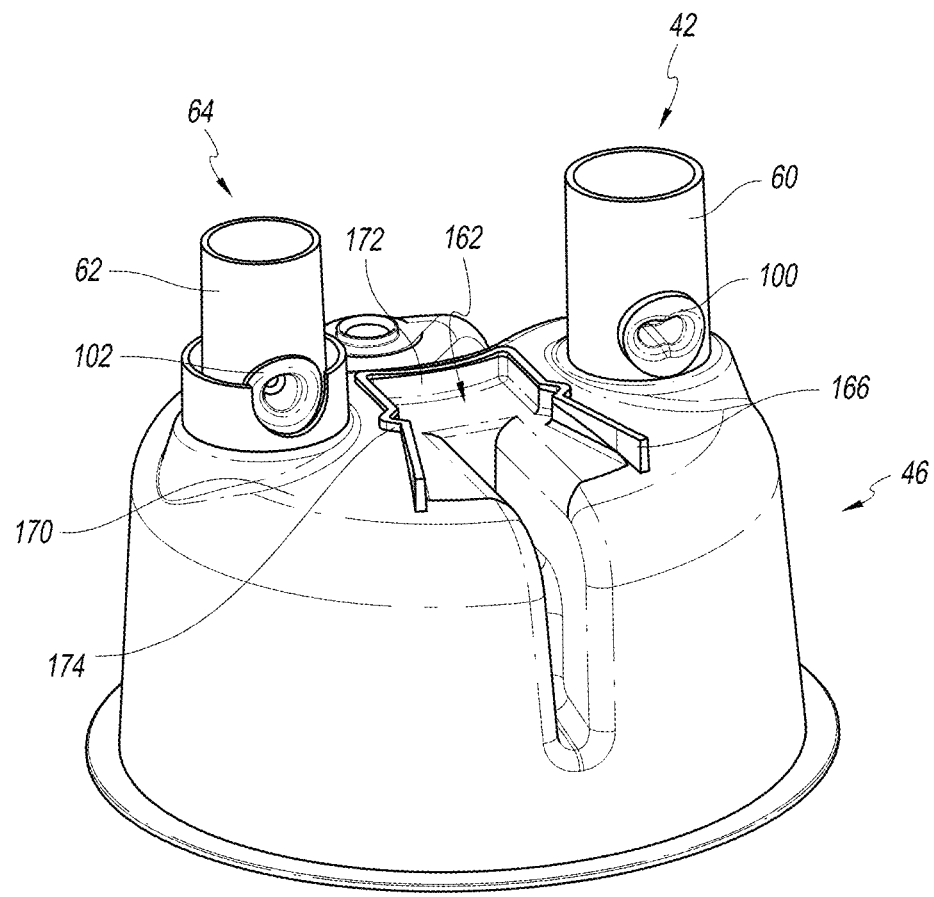
FIG. 3 is a perspective view of the humidification chamber of FIG. 2 with seals inserted into apertures formed in ports of the humidification chamber.

With reference now to FIG. 3, the humidification chamber 46 is shown with a first seal 100 positioned within the aperture 90 in the inlet port 60 and a second seal 102 positioned within the aperture 92 in the outlet port 62. The first seal 100 preferably pneumatically seals the aperture 90 and the second seal 102 preferably pneumatically seals the aperture 92 such that the gas path defined within the respective portions of the humidification system 20 is isolated from ambient by the seals 100, 102. In other words, the seals 100, 102 substantially close the apertures 90, 92. Accordingly, in the illustrated configuration, the seals 100, 102 define a barrier that reduces the likelihood of fluid or gas passing through the apertures 90, 92. In some applications, at least one of the seals 100, 102, and preferably both of the seals 100, 102, also is resistant to the passage of water vapor.

The first seal 100 and the second seal 102 can be formed from any suitable material. In some applications, the first seal 100 and the second seal 102 are formed from a resilient or flexible material. Preferably, at least one of the seals 100, 102 is formed entirely of a resilient or flexible material. In some applications, at least a portion of at least one of the seals 100, 102 is formed entirely of a resilient or flexible material. In some applications, one or more of the seals 100, 102 can be formed of a material with a Shore-A hardness of between about 20 and about 60, and more preferably between about 30 and about 40. In some applications, one or more of the seals 100, 102 can be formed of Silicone, polyethylene, or thermoplastic polyurethane.

Figure 17:
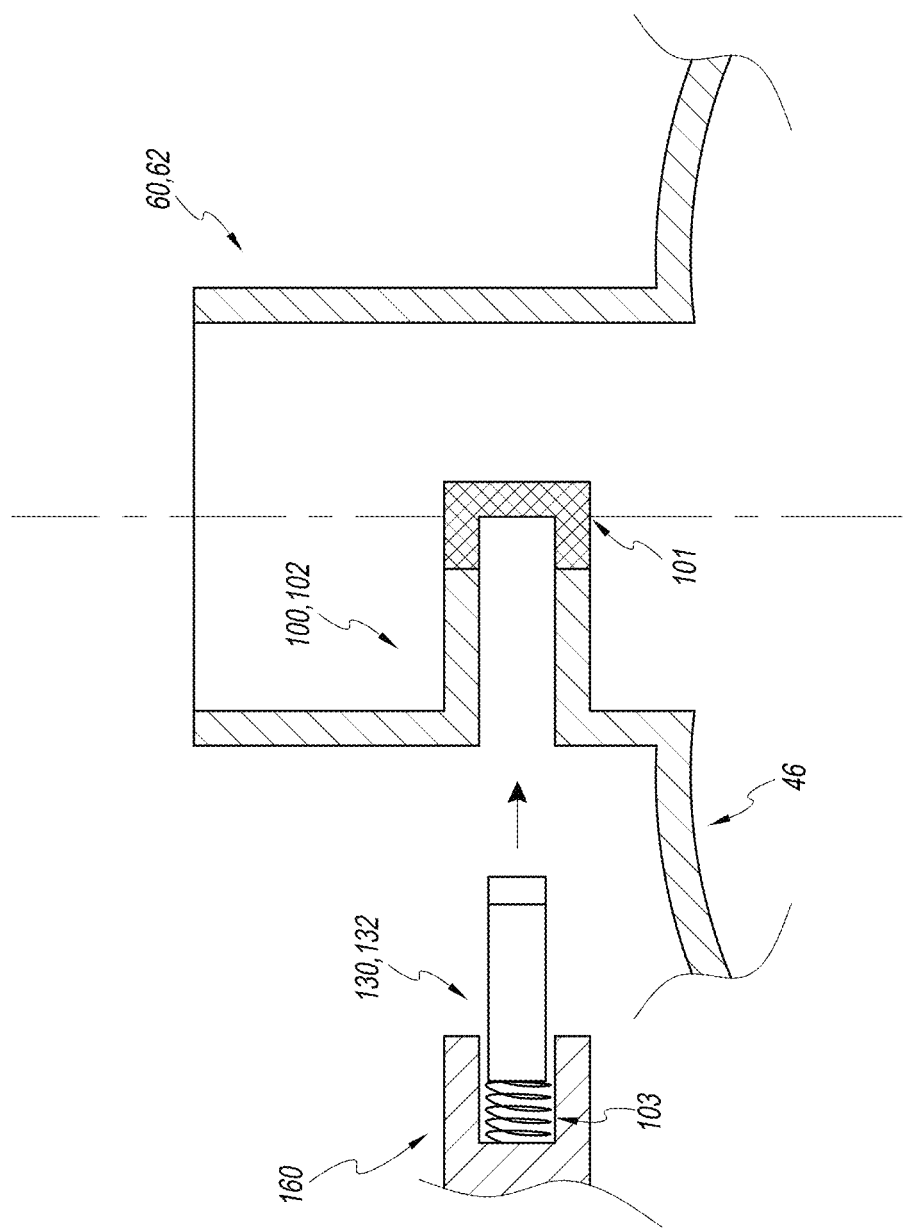
FIG. 17 is a partial sectioned view of a chamber having a port with a sleeve and a biased sensor.
Figure 18A:
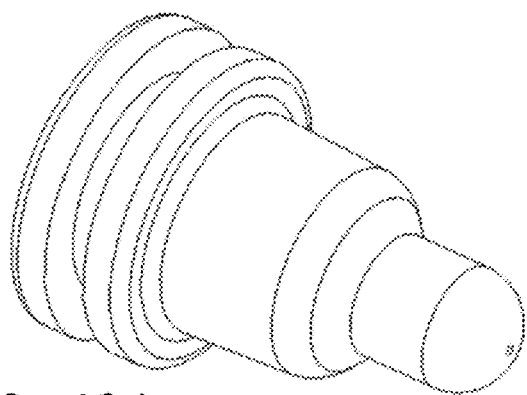
FIG. 18A is a perspective view of a seal.
Figure 18B:
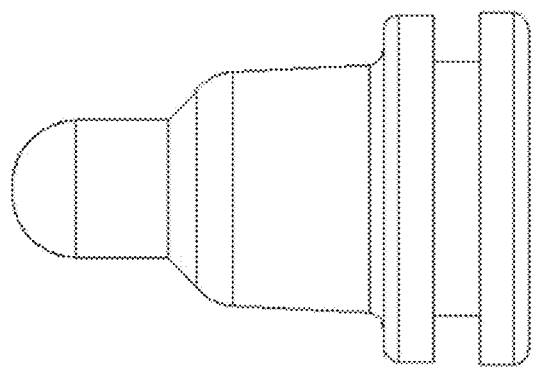
FIG. 18B is a side view of the seal of FIG. 18A.
Figure 18C:
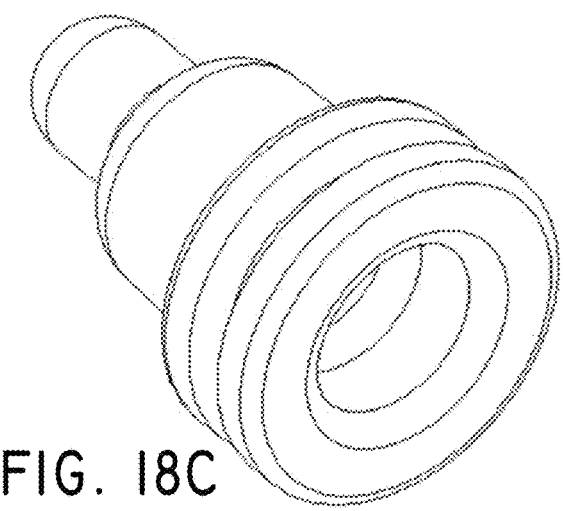
FIG. 18C is another perspective view of the seal of FIG. 18A.
Figure 18D:
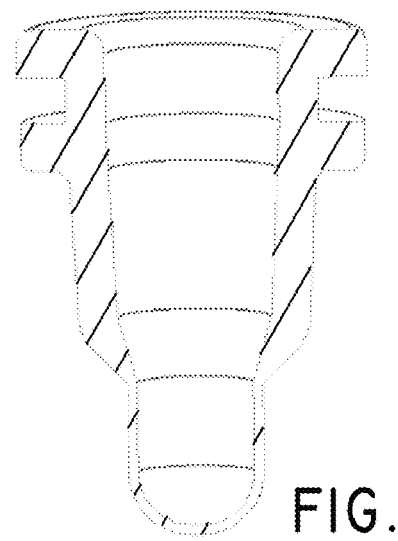
FIG. 18D is a sectioned view of the seal of FIG. 18A.
Figure 18E:
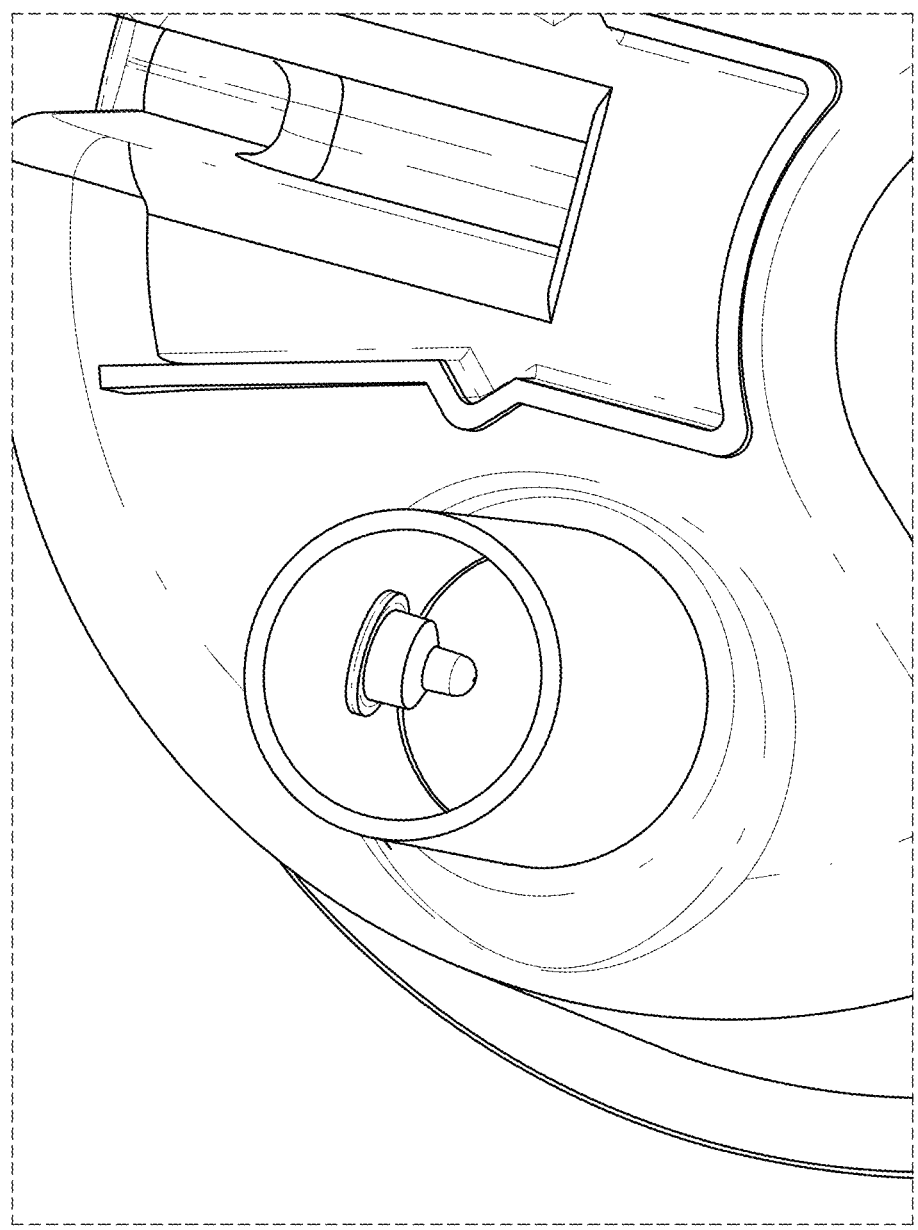
FIG. 18E is a perspective view of the seal of FIG. 18A shown on a port of a humidification chamber.
Figure 18F:
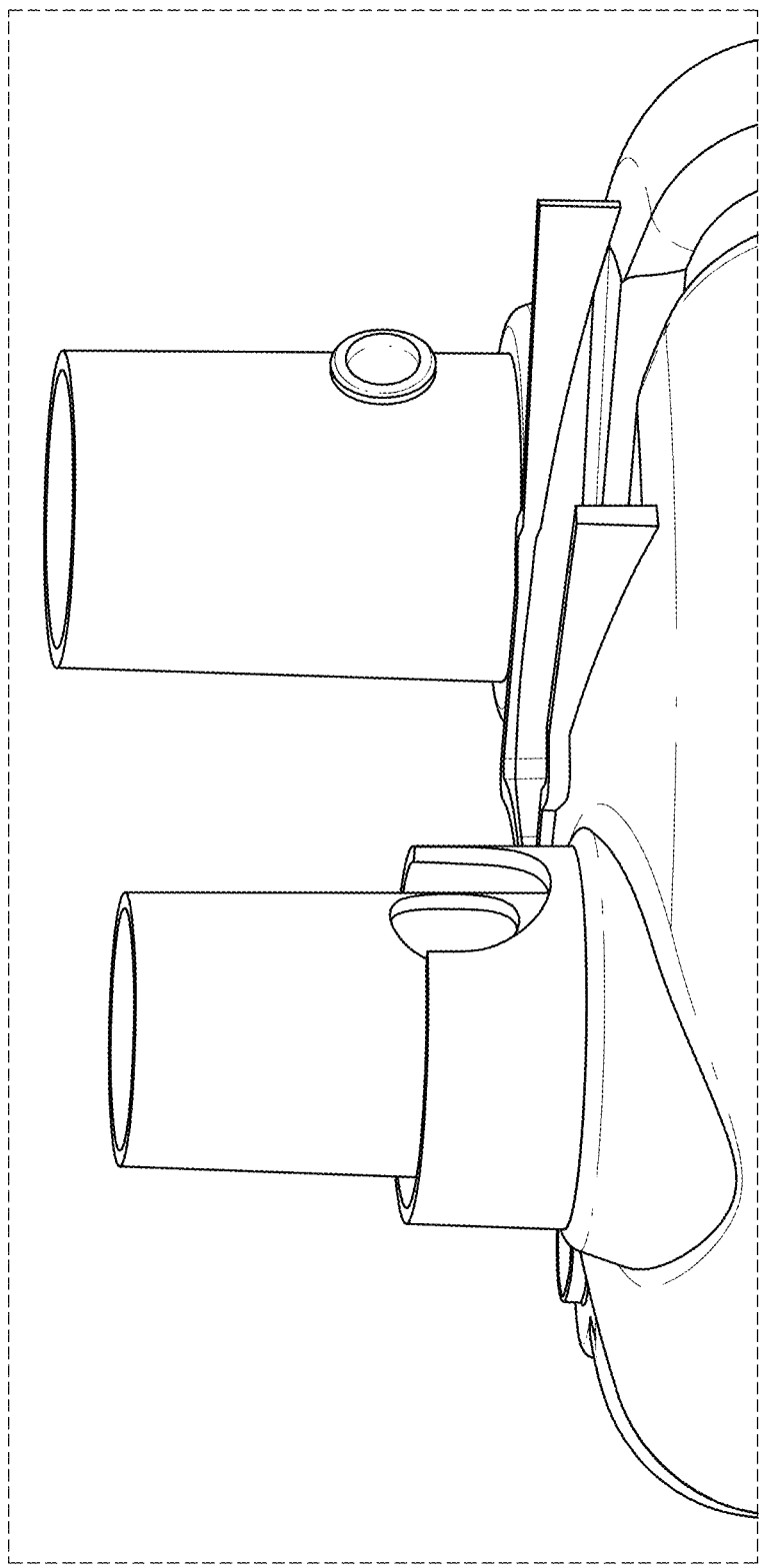
FIG. 18F is another perspective view of the seal and chamber of FIG. 18E.
Figure 18G:
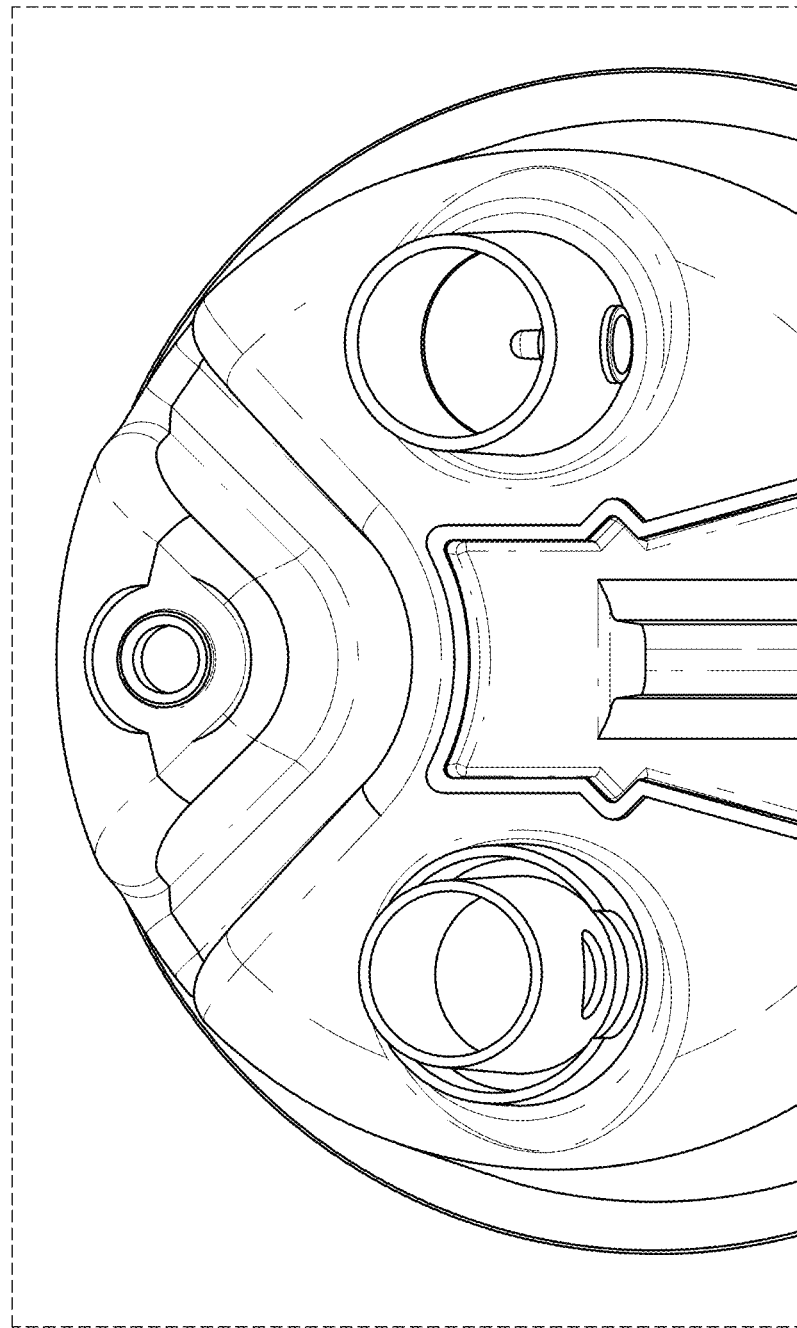
FIG. 18G is another perspective view of the seal and chamber of FIG. 18E.

In some applications, such as that shown in FIG. 17, at least a portion of at least one of the seals 100, 102 can be formed with a rigid material. For example but without limitation, at least a portion of at least one of the seals 100, 102 can be formed of a metal. When at least one of the seals 100, 102 is formed entirely of a rigid material, the seal preferably is configured to provide repeatable contact and thermal conduction between the barrier formed by the seal 100, 102 and an associated sensor. In some embodiments, the seals 100, 102 can be formed of the same material as the chamber 46, can be formed of a different material with a different (preferably higher) thermal conductivity, or a combination thereof. If a combination is used, preferably at least a portion of a tip 101, or at least a portion exposed to flow within the port, and in some configurations, the ultimate end of the tip 101, of the seal is formed of a material with a higher thermal conductivity (e.g., aluminum, copper). In some configurations, the tip 101 is positioned such that the seal 100, 102 extends to an axial center of the port. In some configurations, the tip 101 is positioned such that the seal 100, 102 traverses at least half of the transverse dimension of the port 60, 62. The seals 100, 102 can be formed integrally with the chamber 46 or, for example but without limitation, can be overmoulded, press-fit and glued, co-moulded, or welded thereto.

In some embodiments, at least one of the seals 100, 102 can be formed of a first, more thermally-conductive portion arranged to receive an end or a sensing portion of the associated sensor 130, 132 and a second, less thermally-conductive or thermally non-conductive portion. The second portion preferably is arranged to reduce or eliminate a conduction or other transmission of heat from the sensing element or tip of the sensor 130, 132 into the surrounding portions of the apparatus. For example, where the associated sensor 130, 132 comprises a thermistor, the second portion preferably generally or substantially thermally isolates the thermistor. In other words, the tip of the thermistor could be arranged in the more thermally-conductive first portion, which can be positioned within the flow of gases that the thermistor is measuring. In some configurations, the less thermally-conductive or thermally non-conductive portion may comprise a different material from the more thermally-conductive portion. In some configurations, a porous material or a foam material can be used in provide improved insulation. In such an arrangement, less heat is conducted from the first portion to the ambient environment through the second portion. The reduced conduction allows the thermistor to provide a more accurate reading of the gas by maximizing or increasing the heat transfer between the first portion and the tip of the thermistor.

In some embodiments, means may be provided to increase a reliability of a contact between the associated sensor and the tip portion of the seal. For example, in the arrangement of FIG. 17, a spring, or any other suitable biasing or cushioning member, may be interposed between a sensor 130, 132 and a cartridge 160 that carries or otherwise supports the sensor 130, 132. In such arrangements, the member 103 (e.g., spring, biasing member or cushioning member) compressed to provide a relatively repeatable force between the end of the sensor 130, 132 and the tip 101, for example but without limitation. In some applications, a flexible or elastic membrane can connect the tip 101 to the chamber 46. In such configurations, the tip 101 can be displaceable relative to at least some portion of the chamber 46 (including the port 60, 62). In other words, the flexible or elastic membrane can stretch with the insertion of the sensor 130, 132 due to contact of the sensor 130, 132 with the tip 101 to provide a generally repeatable force between the end of the sensor 130, 132 and the tip 101 while providing a generally contacting thermal mass at the tip 101.

Figure 4:
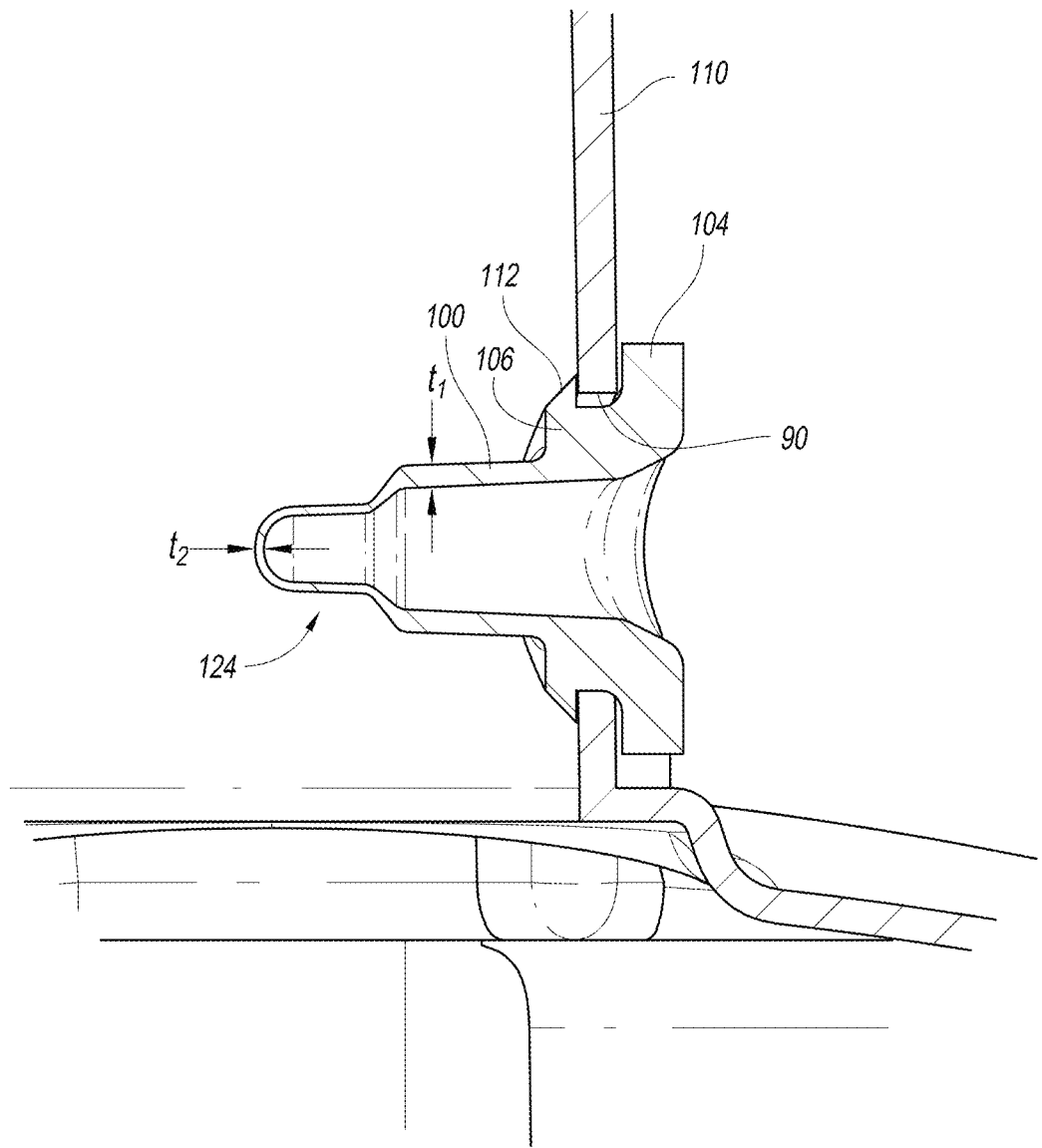
FIG. 4 is a sectioned view through one of the seals and an inlet port of the humidification chamber.
Figure 6:
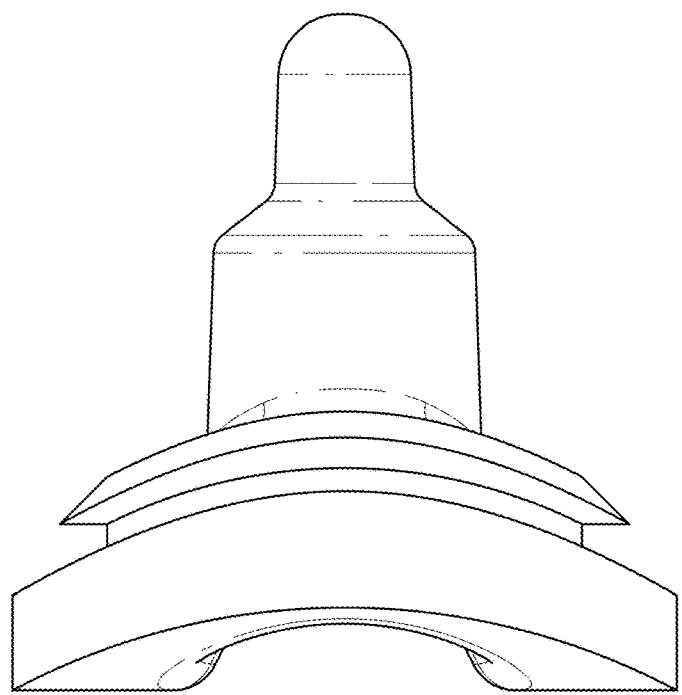
FIG. 6 is a side view of the seal of FIG. 4, which is substantially the same as the opposing side view of the seal.
Figure 5:
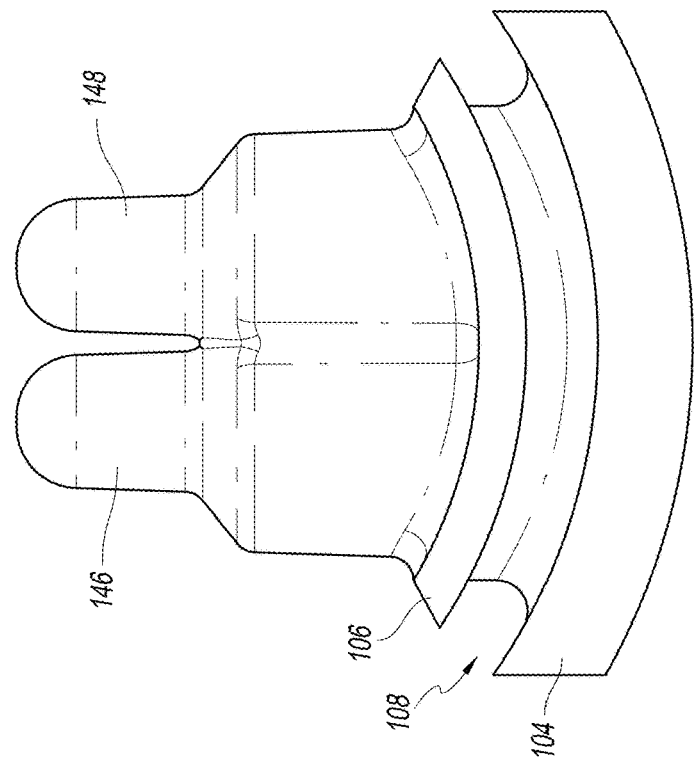
FIG. 5 is a top view of the seal of FIG. 4, which is substantially the same as the bottom view of the seal.
Figure 8:
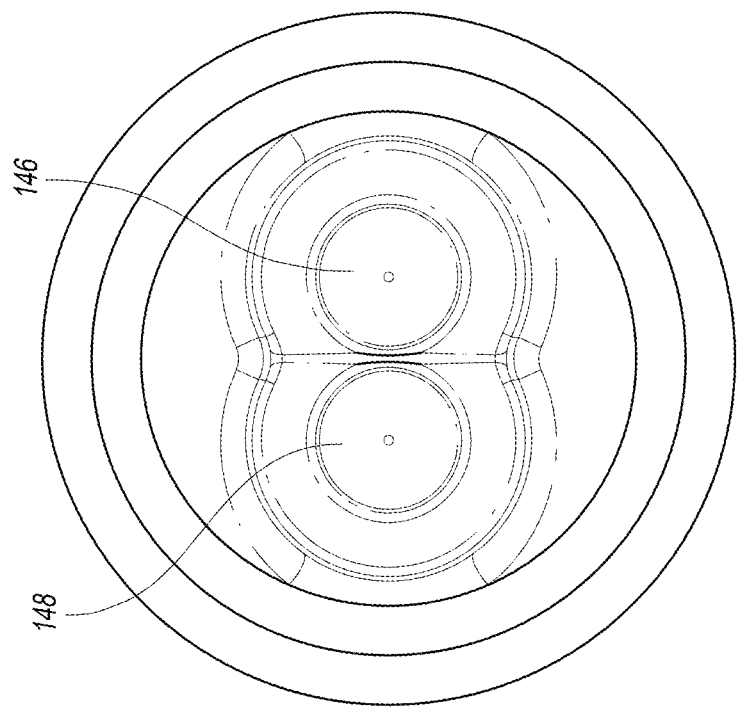
FIG. 8 is a rear view of the seal of FIG. 4.
Figure 7:
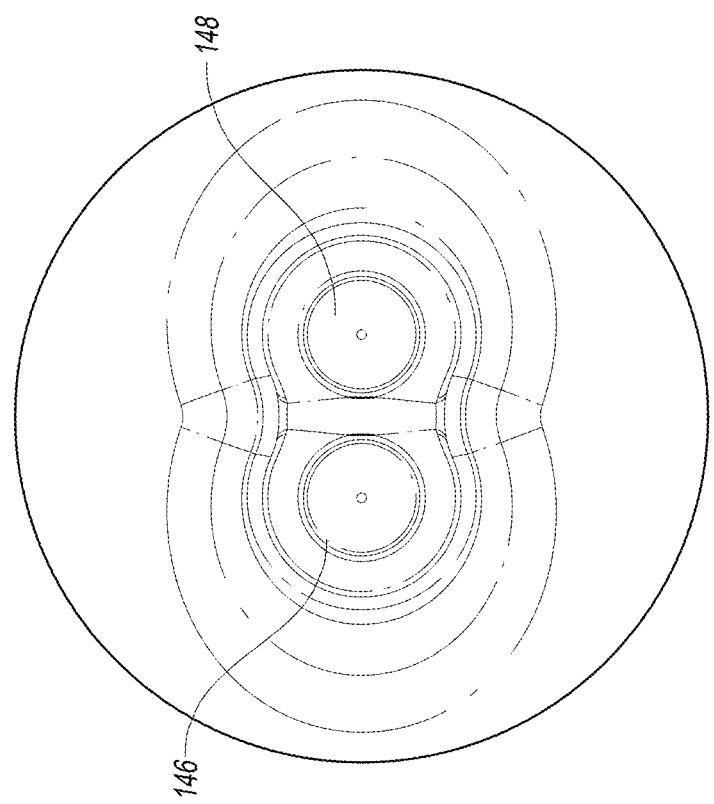
FIG. 7 is a front view of the seal of FIG. 4.
Figure 9:
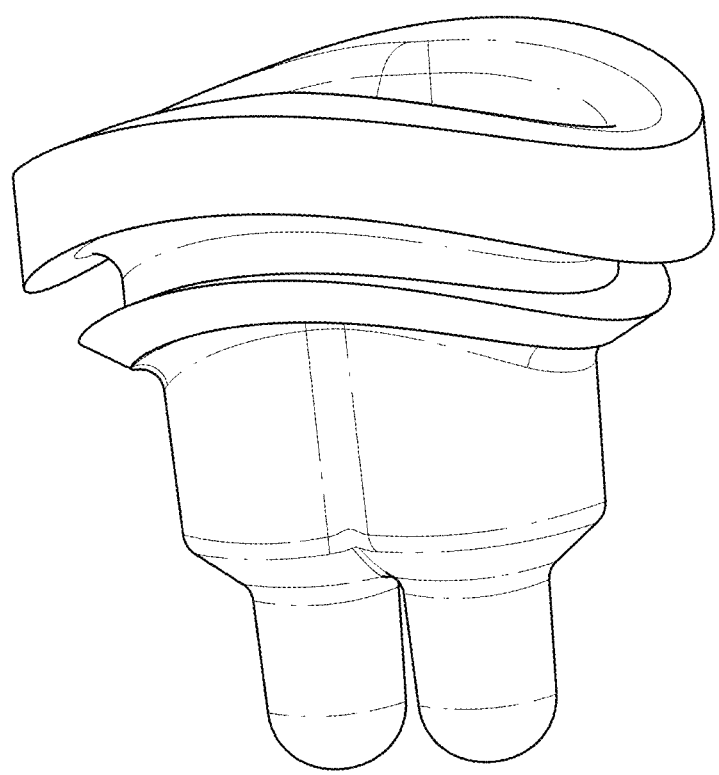
FIG. 9 is a perspective view of the seal of FIG. 4.

In some arrangements, at least one of the seals 100, 102, and preferably both, comprises a feature to retain the seal 100, 102 in position within the respective aperture 90, 92. With reference to FIG. 4, the illustrated first seal 100 comprises an outer flange 104 and an inner flange 106. As shown in FIG. 5, a channel 108 is defined between the outer flange 104 and the inner flange 106. The channel 108 preferably is sized to accommodate a wall 110 of the inlet port 60. More preferably, the channel 108 is sized to form a fluid and/or gas tight seal with the wall 110 that surrounds the aperture 90. In the configuration illustrated in FIGS. 3-9, a base surface of the channel 108 has a surface that is at least partially curved or sloping to improve the seal between the seal 100 and the wall defining the aperture 90. In some configurations, such as that shown in FIGS. 18A-18G, the base surface can be substantially planar instead of at least partially curved or sloping.

In some arrangements, at least one of the seals 100, 102 can be permanently or at least semi-permanently attached to the apertures 90, 92. In some arrangements, at least one of the seals 100, 102 can be removable and replaceable. The seals 100, 102 can be configured to have a useable life similar to that of one of the other components. For example, the seals 100, 102 preferably comprise a useable life similar to the chamber 46 such that the chamber 46 and the seals 100, 102 would be disposed of at the same time. In some configurations, especially where the seals 100, 102 are permanently attached to the chamber 46, the seals 100, 102 preferably have a longer life than the chamber 46 such that the seals 100, 102 are not the limiting component on a life span of the chamber 46.

In the illustrated configuration, the inner flange 106 has a smaller outer circumference than the outer flange 104. The smaller outer circumference of the inner flange 106 facilitates insertion of the seal 100 into the aperture 90. The inner flange 106 of the first seal 100 can comprise a sloped surface 112 to further assist with the installation of the first seal 100 into the aperture 90. While it is possible to slope or taper a surface of the outer flange 104 to facilitate installation, because the illustrated first seal 100 is designed to be pressed into the aperture 90 from the outside of the inlet port 60, the sloped or tapered surface 112 preferably is positioned on the inner flange 106.

Figure 10:
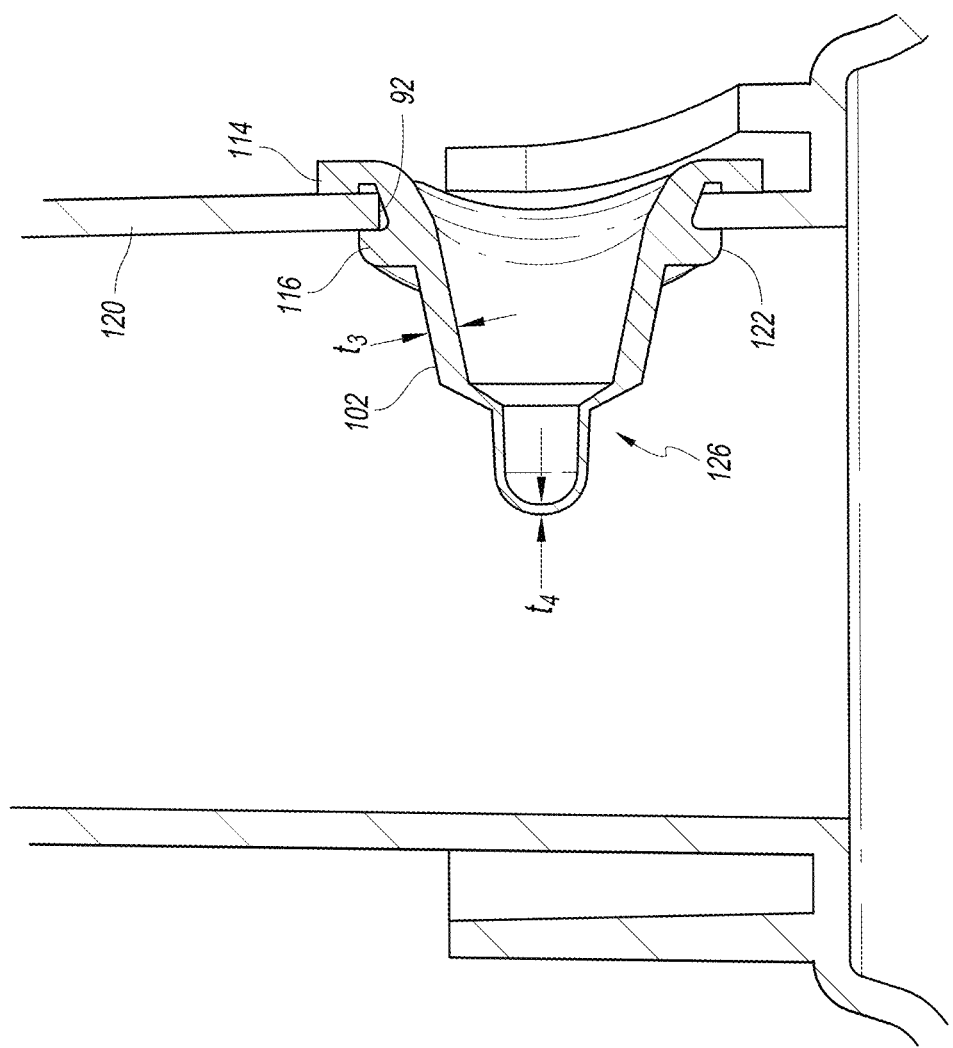
FIG. 10 is a sectioned view through one of the seals and an outlet port of the humidification chamber.
Figure 12:
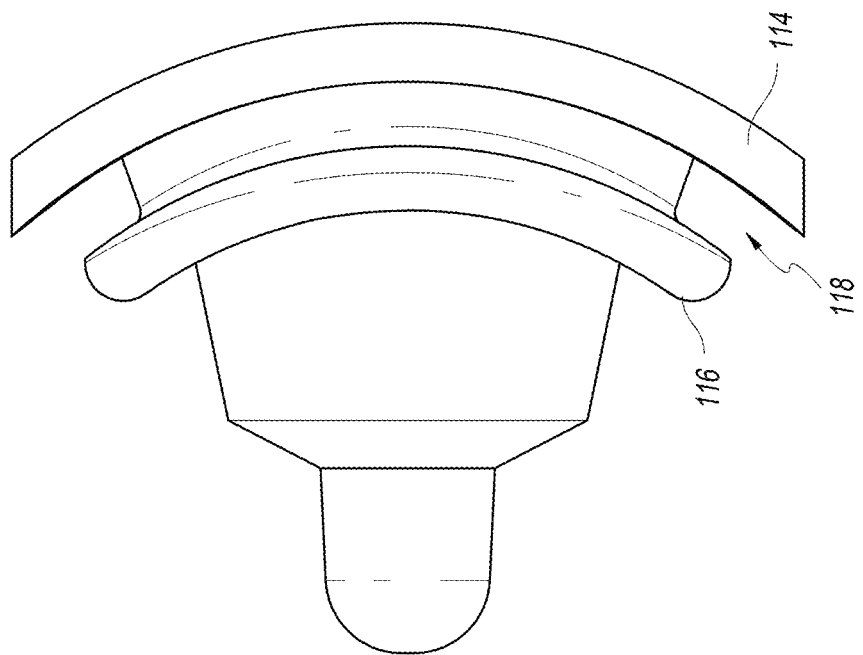
FIG. 12 is a top view of the seal of FIG. 10, which is substantially the same as the bottom view of the seal.
Figure 11:
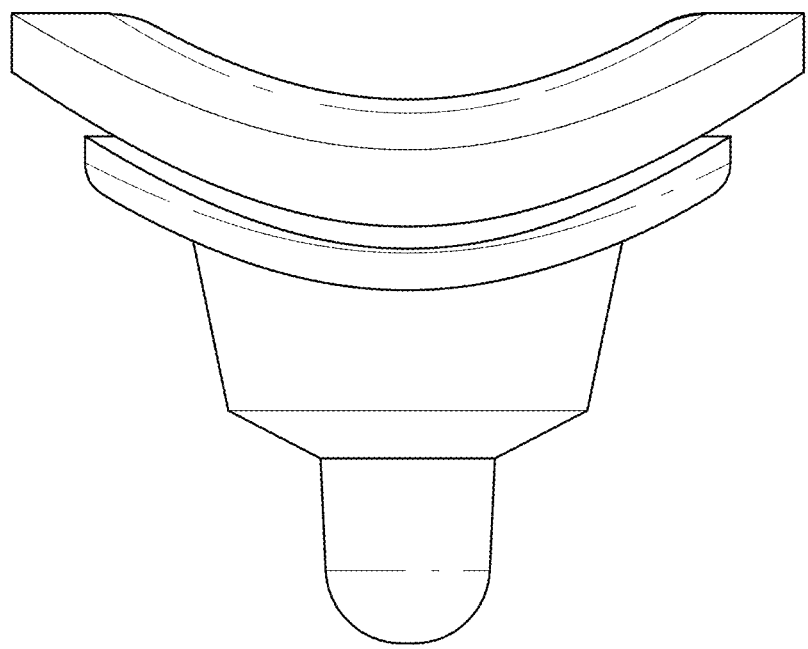
FIG. 11 is a side view of the seal of FIG. 10, which is substantially the same as the opposing side view of the seal.
Figure 14:
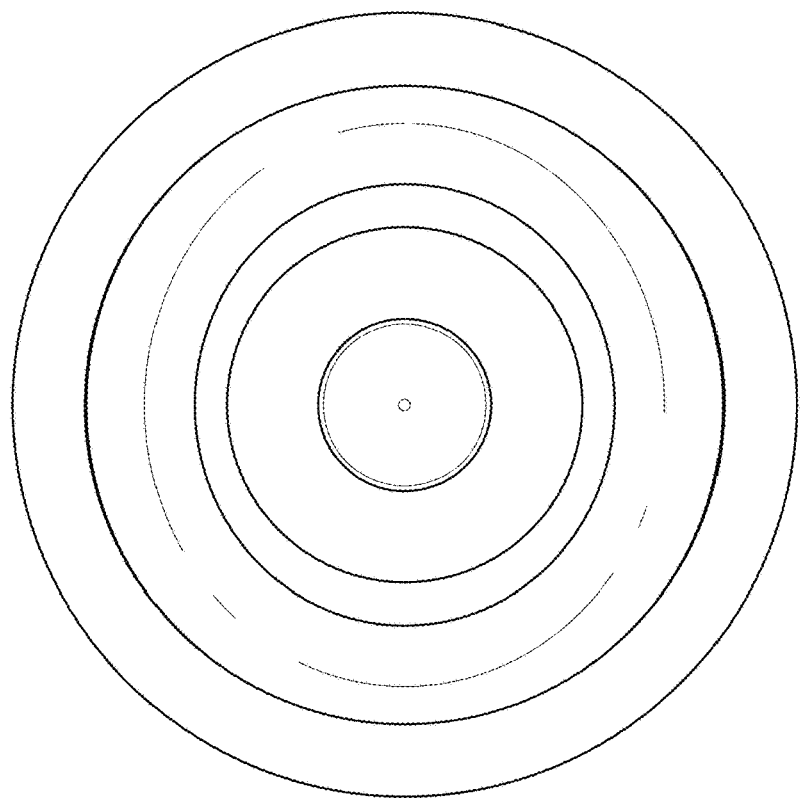
FIG. 14 is a rear view of the seal of FIG. 10.
Figure 13:
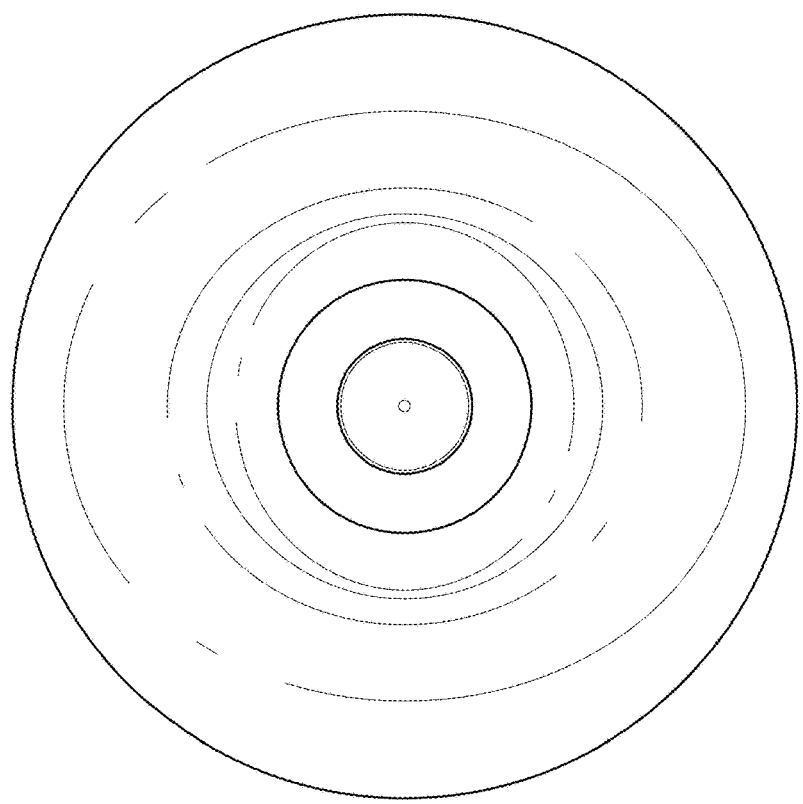
FIG. 13 is a front view of the seal of FIG. 10.
Figure 15:
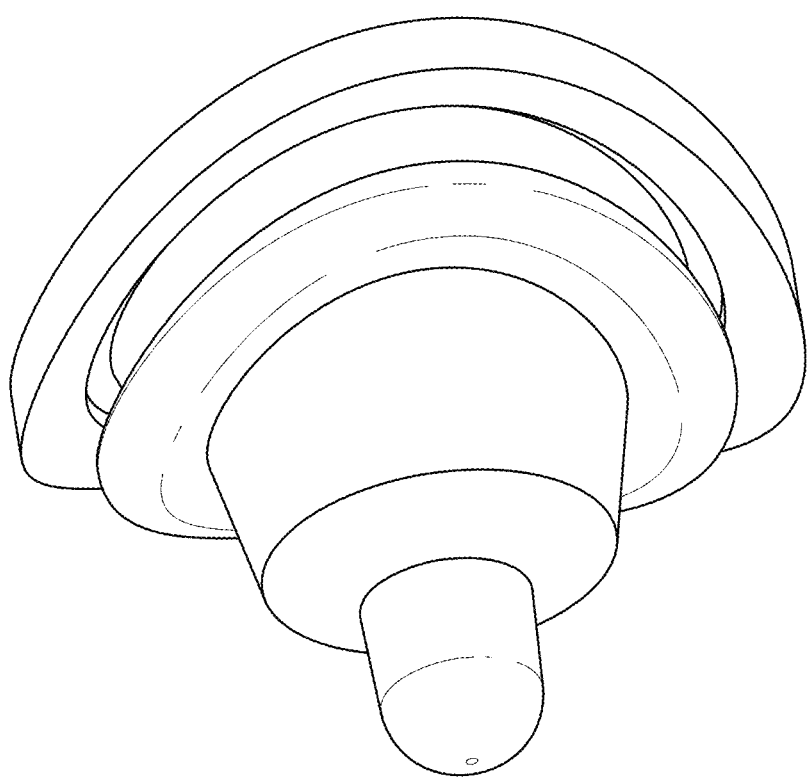
FIG. 15 is a perspective view of the seal of FIG. 10.

With reference to FIG. 10, the illustrated second seal 102, similar to the first seal 100, comprises an outer flange 114 and an inner flange 116. As best shown in FIG. 12, a channel 118 is defined between the outer flange 114 and the inner flange 116. As shown in FIG. 10, the channel 118 preferably is sized to accommodate a wall 120 of the outlet port 62. More preferably, the channel 118 is sized to form a fluid and/or gas tight seal with the portion of the wall 120 that generally surrounds the aperture. As with the seal 100, a base surface of the channel 118 has a surface that is at least partially curved or sloping to improve the seal between the seal 102 and the wall defining the aperture 92. In some configurations, the base surface can be substantially planar (see, e.g., FIGS. 18A-18G).

The inner flange 116 has a smaller outer circumference than the outer flange 104. The smaller outer circumference of the inner flange 116 facilitates insertion of the seal 102 into the aperture 92. The inner flange 116 of the second seal 102 can comprise a curved surface 122 to assist with the installation of the second seal 102 into the aperture 92. As with the first seal 100, it is possible to slope or taper a surface of the outer flange 114 to facilitate insertion but, because the illustrated second seal is designed to be pressed into the aperture 92 from the outside of the outlet port 62, the sloped or tapered surface preferably is positioned on the inner flange 116.

Figure 16:
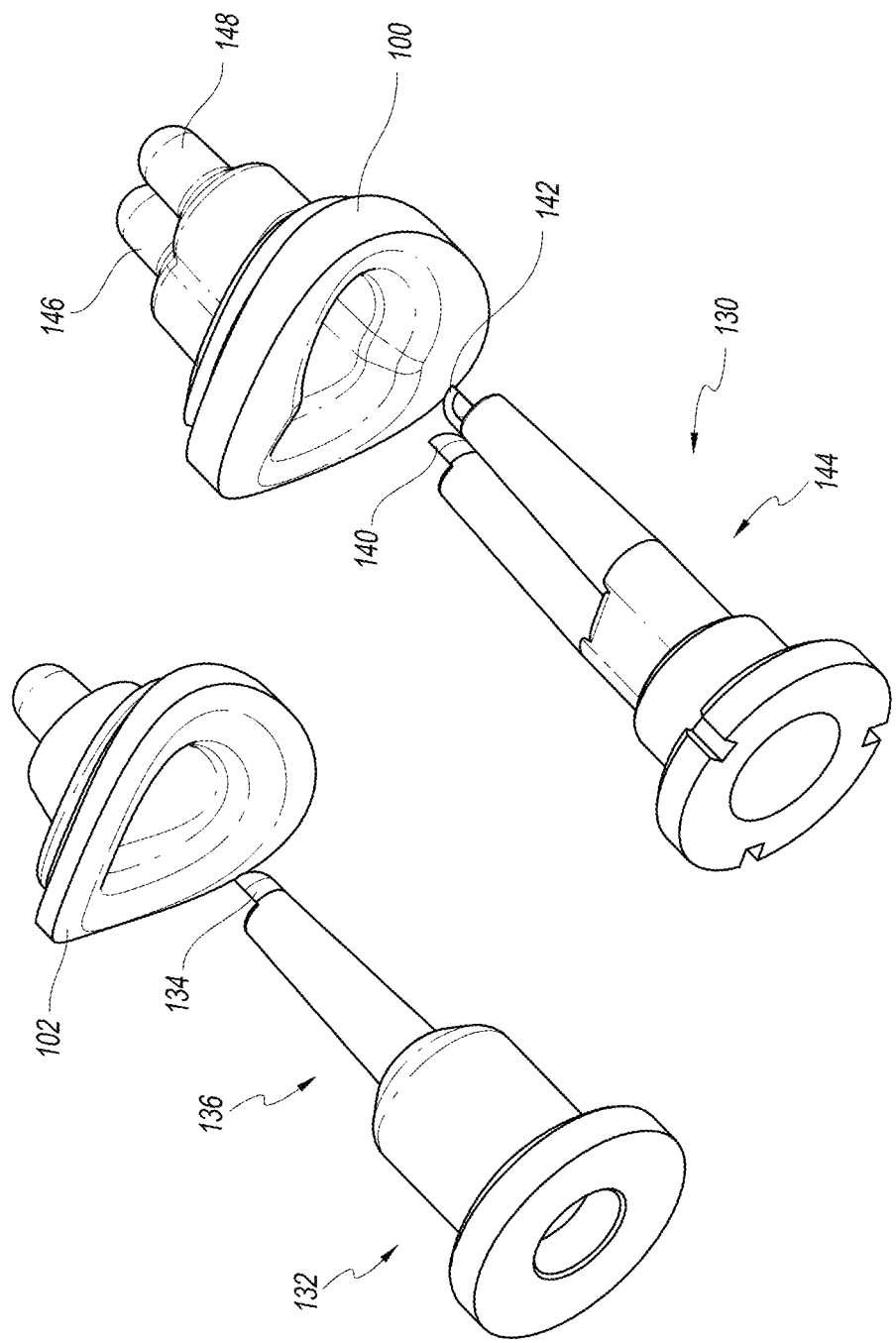
FIG. 16 is an exploded perspective view of the seals of FIGS. 4 and 10 together with corresponding sensors.

With reference to FIG. 16, a first sensor 130 is insertable into the first seal 100 and a second sensor 132 is insertable into the second seal 102. In some configurations, the sensors 130, 132 will not seal the apertures if the seals 100, 102 are not positioned within the apertures. The first seal 100 and the second seal 102 define a barrier that is positioned between the gas flow path and the first sensor 130 and the second sensor 132 respectively. With the first seal 100 and the second seal 102 defining the barrier, the sensors 130, 132 remain external to the flow path. Because the first and second sensors 130, 132 remain external to the flow path, the sensors 130, 132 can be reused and need not be cleaned before subsequent reuse. Even though the sensors 130, 132 remain external to the flow path, however, the sensors 130, 132 are able to provide measurements of flow characteristics. For instance, the first sensor 130 can be used to detect flow rate while the second sensor can be used to detect temperature.

Any suitable components can be used as the sensors. For example, thermocouples, resistance temperature detectors, fixed resistors and the like can be used as the sensors 130, 132. In the illustrated arrangement, the sensors 130, 132 comprise thermistors. The second sensor 132 uses a single thermistor 134 mounted to a body 136. The sensor 132 can be used to sense a temperature of the flow in the flow path. As shown in the illustrated arrangement, the temperature sensor 132 can be positioned to extend the thermistor 134 into the flow path on the outlet port 62. In some configurations, the temperature sensor can be positioned in other regions of the humidification system 20 (e.g., on the conduit 44, the conduit 70, or the like).

The illustrated first sensor 130 preferably comprises a first thermistor 140 and a second thermistor 142 mounted on a single body 144. In some configurations, the first thermistor 140 and the second thermistor 142 can be mounted on separate bodies; however, mounting the first and second thermistors 140, 142 on the single body 144 improves the accuracy in positioning of the first and second thermistors 140, 142 relative to each other. As shown in the illustrated arrangement, the first sensor 130 can be positioned to extend the two thermistors 140, 142 into the flow path on the inlet port 60. Positioning the first sensor 130 on the inlet is desired because the sensor is detecting flow rate and positioning the first sensor 130 in an region of relatively dry flow is desirable. In some configurations, the flow sensor 130 can be positioned in other regions of the humidification system 20 (e.g., on the conduit 44, the conduit 70, or the like).

Through the use of the first and second thermistors 140, 142, a constant temperature flow measurement approach can be used. In this approach, the first thermistor 140 functions as a reference sensor that measures the flow temperature at the sensing location and the second thermistor 142, which can be a heated thermistor, is heated to a preset temperature differential above the flow temperature. In some applications, a resistor can be used to heat the second thermistor 142 instead of using a heated thermistor. In some configurations, all of the thermistors can be both heated and non-heated thermistors. Flow velocity can be determined using the measured flow temperature, the known heat transfer characteristics of the heated second thermistor 142 and the power consumed to maintain the temperature difference between the two thermistors 140, 142. In other words, the power required to maintain the second thermistor 142 at the elevated temperature is processed to determine the flow rate. Thus, the first sensor 130 and the second sensor 132 preferably measure flow velocity within about 50% of the actual point velocity and temperature within about 0.3 degrees C. Other techniques also can be used. For example but without limitation, constant power can be provided to the thermistors and the heat conducted into a nearby thermistor can be used to determine the rate of flow.

As illustrated in FIG. 16, the first sensor 130 can be inserted into the first seal 100 and the second sensor 132 can be inserted into the second seal 102. The seals 100, 102 isolate the sensors 130, 132 from the flow such that the sensors 130, 132 are protected against contamination from the flow. As such, the sensors 130, 132 need not be cleaned and can be reused without cleaning.

With reference to FIGS. 4 and 10, one or more of the seals 100, 102 can decrease in thickness toward a respective distal end 124, 126. With particular reference to FIG. 4, the seal 100 has a first thickness t1 that is larger than a thickness t2 present at the distal end 124 of the seal 100. Preferably, a portion of the seal 100 that is adapted to be in contact with the sensing portion of the first sensor 130 has the reduced thickness t2 to improve sensitivity while improving robustness with the thicker portion. In some configurations, the portion of the seal 100 that is adapted to contact the sensing portion of the first sensor has a substantially constant thickness to improve performance. With reference to FIG. 10, the seal 102 is constructed similarly to the seal 100 with a first thickness t3 being larger than a second thickness t4. Other suitable configurations are possible. In some configurations, the sensor 103, 132 is inserted at such a depth into the seal 100, 102 that the tip of the seal 100, 102 will be stretched by the insertion. In some configurations, the tip of the seal 100, 102 will stretch before other regions of the seal 100, 102. The stretching of the tip can decrease the thickness of the seal 100, 102 towards the distal end when compared to the seal 100, 102 without the sensor 130, 132 inserted. The stretching of the tip also decreases the likelihood of an air bubble forming between the tip of the sensor 130, 132 and the tip of the seal 100, 102, which air bubble could reduce the thermal conduction between the seal 100, 102 and the sensor 130, 132.

With continued reference to FIGS. 4 and 10, the distal ends 124, 126 of the illustrated seals 100, 102 have a decreased diameter. In the illustrated configuration, the distal ends 124, 126 are necked down relative to the other end. In some configurations, a smooth taper or other suitable configuration can be used.

In the illustrated configuration, the first sensor 130 comprises the first and second thermistors 140, 142 on the single body 144. The first sensor 130 is received within the first seal 100. Desirably, thermal conduction is minimized between the first thermistor 140 (i.e., the reference temperature) and the second thermistor 142 (i.e., the heated thermistor for flow measurement). Heat conduction between the thermistors 140, 142 within single barrier has been discovered. The heat conduction can result in a circular reference: with flow temperature measured using the non-heated first thermistor 140, a constant temperature offset (e.g., approximately 60 degrees C.) is applied to the heated second thermistor 142 and the power required to achieve this temperature offset is measured; if the heated second thermistor 142 heats the non-heated first thermistor 140, the target temperature raises and the cycle repeats. Thus, the illustrated first seal 100 comprises two separate sleeves 146, 148 for the two thermistors 140, 142. By positioning the first thermistor 140 in the first sleeve 146 and the second thermistor 142 in the second sleeve 148, the first thermistor 140 and the second thermistor 142 are substantially isolated and the seal 100 provides independent barrier layers for each thermistor 140, 142. In some configurations, the first thermistor 140 and the second thermistor 142 may be substantially isolated by using baffles between the thermistors 140, 142, providing different orientations of the thermistors 140, 142, and/or using flow sensors, for example but without limitation.

Figure 19B:
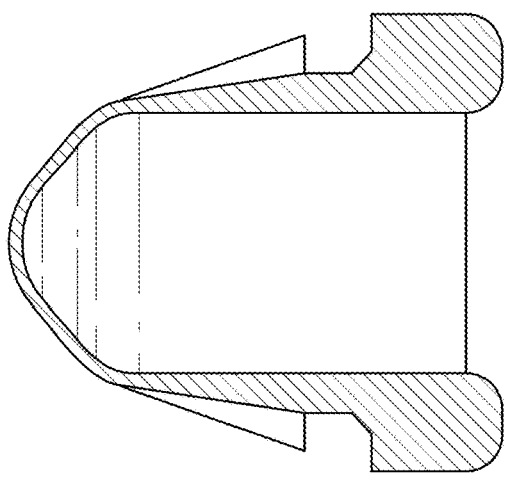
FIG. 19B is a section view of the seal of FIG. 19A.
Figure 19C:
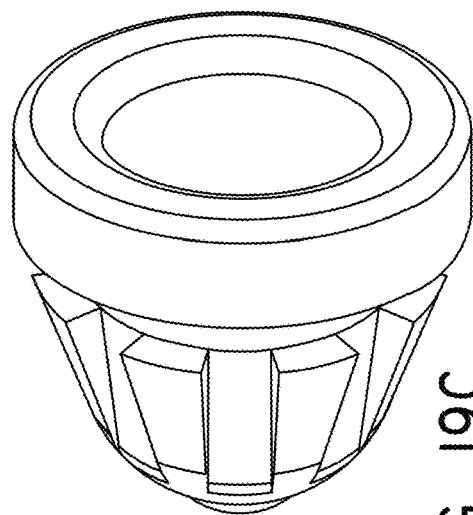
FIG. 19C is a perspective view of the seal of FIG. 19A.
Figure 19A:
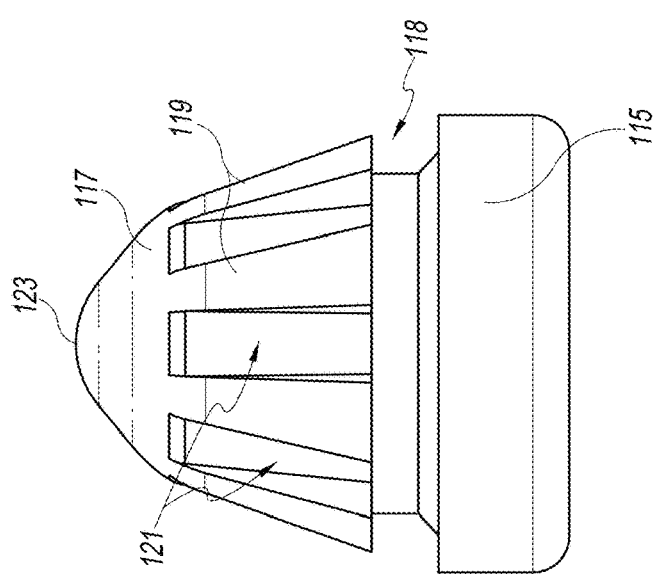
FIG. 19A is a side view of a seal.

An alternative seal configuration is shown in FIGS. 19A-19C. In the illustrated embodiment, the seal 102 includes a generally cylindrical base 115. The seal 102 also comprises a generally bell-shaped head 117. The illustrated bell-shaped head 117 comprises a plurality of triangular ribs 119 around its perimeter. In some embodiments, a channel 118 can be defined between the base 115 and the head 117 and sized to accommodate the wall 120 of the outlet port 62. The ribs 119 can deflect to allow the seal 102 to be inserted into the aperture 92 then return to an expanded state to help hold the seal 102 in place within the aperture 92. As the ribs 119 depress, they spread into spaces 121 between the ribs 119. In some embodiments, a radio of a width of the rib 119 to a width of the space 121 between ribs 119 is about 1:1. In some embodiments, the ratio is about 3:7. A ratio that is too high (i.e., the space 121 between ribs 119 is small compared to the ribs 119) may not allow the ribs 119 to depress sufficiently, resulting in greater difficulty installing the seal 102 in the aperture 92. A ratio that is too low (i.e., the space 121 is large compared to the ribs 119) may provide a reduced retention force so that the seal 102 is not held as securely in the aperture 92. In the illustrated embodiment, the seal includes eight ribs 119, but more or fewer ribs 119 are also possible. However, if too many ribs 119 are included, the ribs 119 would be made thinner and might be weaker. Alternatively, including too few ribs 119 might require making the ribs 119 larger, leaving less space to spread.

Figure 20B:
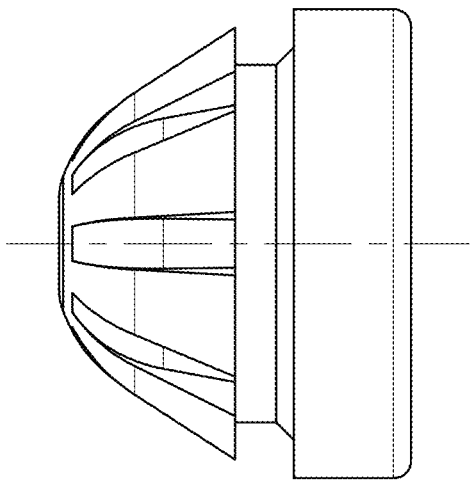
FIG. 20B is a side view of a seal.
Figure 20C:
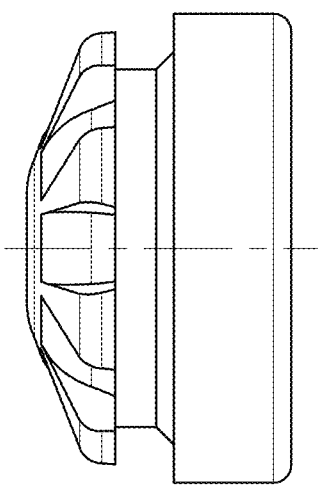
FIG. 20C is a side view of a seal.
Figure 20A:
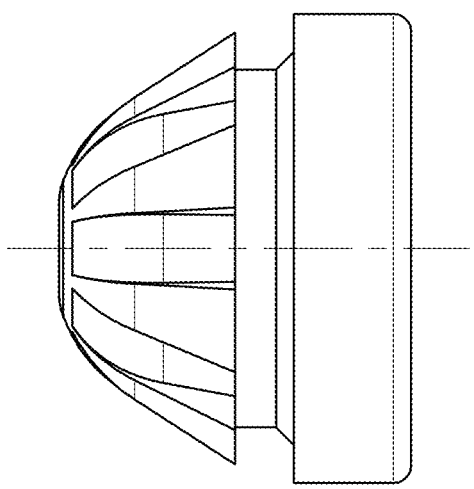
FIG. 20A is a side view of a seal.

When the sensor 132 is inserted into the seal 102 of FIGS. 19A-19C, a tip 123 of the seal 102 can stretch to conform to the shape of the sensor 132. As the amount of stretch to accommodate the sensor 132 increases, the seal material becomes thinner. This can advantageously improve the reactivity and accuracy of the sensor, increase the contact area between the sensor as seal as the seal stretches to match the shape of the sensor, and more securely hold the seal in the aperture 92. However, if the tip 123 of the seal is too flat and requires too great a degree of stretch to accommodate the sensor, it can be more difficult to insert the sensor in the seal and the seal material may degrade or break. In the illustrated embodiment, the seal can have a length of about 7.50 mm, a base 115 diameter of about 7 mm, a diameter measured at the widest portion of the ribs 119 of about 6.50 mm, and a tip 123 thickness of about 0.020 mm. Alternative configurations of seals having ribs 119 are shown in FIGS. 20A-20C. The seals of FIGS. 20A and 20B can both have lengths of about 6 mm, base 115 diameters of about 8 mm, diameters measured at the widest portion of the ribs 119 of about 7.50 mm, and tip thicknesses of about 0.20 mm. However, the seal of FIG. 20A can have ribs 119 sized so that the space 121 between ribs is about 1.4 mm, whereas the seal of FIG. 20B can have ribs 119 sized so that the space 121 is about 1.1 mm. The seal of FIG. 20C can have a length of about 4.50 mm, a base diameter of about 8 mm, a diameter measured at the widest portion of the ribs 119 of about 7.50 mm, and a tip thickness of about 0.20 mm. The ribs 119 of the seal of FIG. 20C can have slightly rounded or curved ends.

With reference again to FIG. 16, the sensors 130, 132, because they are removable and replaceable, preferably have a repeatable tip thermal mass. In some arrangements, the accuracy of the sensors 130, 132 can be improved if the thermal mass exposed inside of the flow passage is repeatable. For this reason, the depth of insertion of the sensors 130, 132 into the respective flow preferably is generally repeatable.

Figure 36:
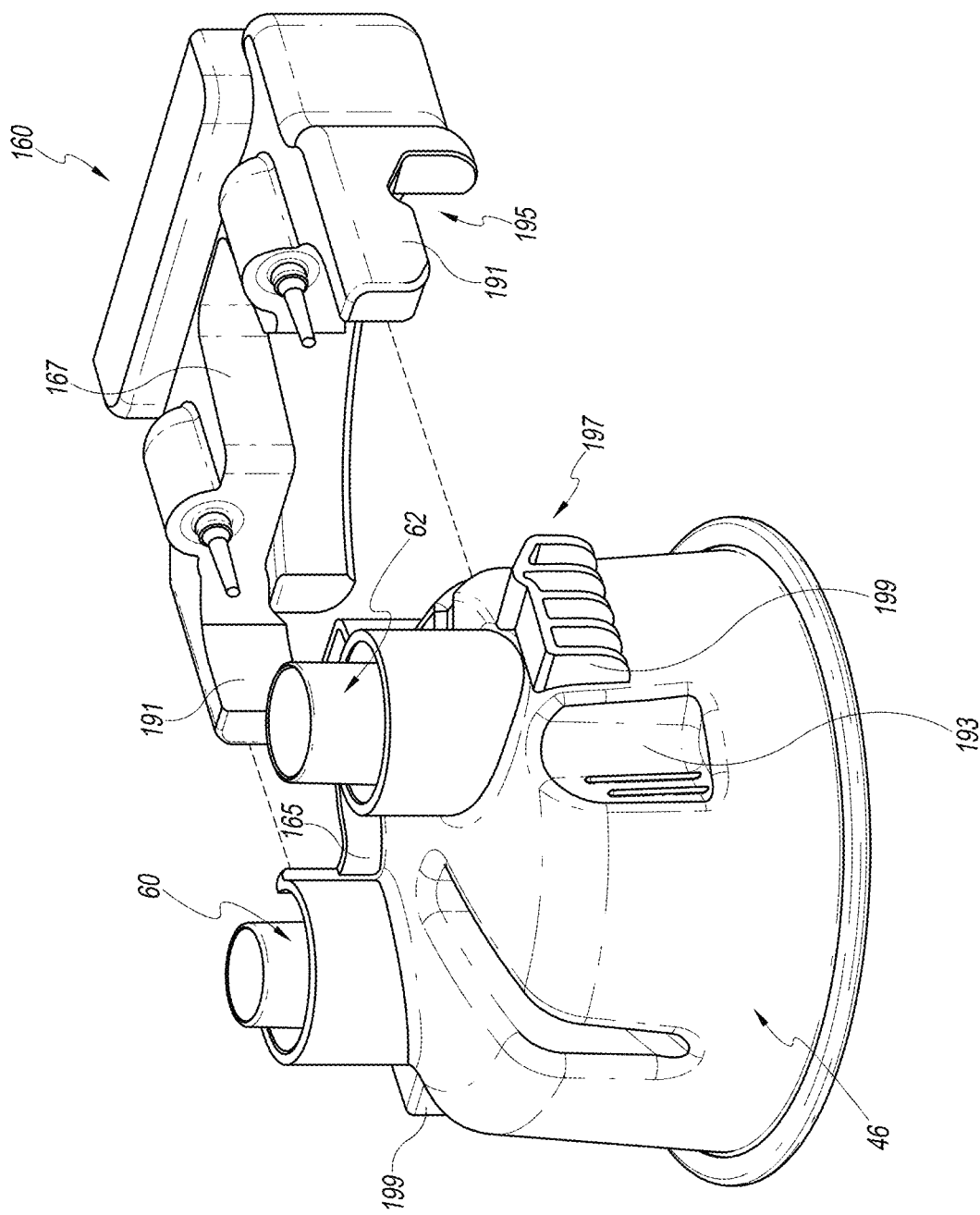
FIG. 36 is an exploded perspective view showing an alternative cartridge being assembled to an alternative humidification chamber.

To provide repeatable depth of insertion of the sensors 130, 132, and to simplify the mounting of the sensors 130, 132, the illustrated configuration comprises a cartridge 160. With reference to FIG. 3 and FIG. 21, the cartridge 160 and the top of the illustrated humidification chamber 46 comprise a coupling configuration. In the illustrated configuration, the top of the humidification chamber 46 comprises a recess structure 162 while the cartridge 160 comprises a corresponding boss structure 164. In some configurations, the top of the humidification chamber can comprise at least a portion of a boss structure while the bottom of the cartridge 160 comprises at least a portion of a corresponding recess structure. Another configuration is shown in FIG. 36, wherein an upwardly protruding member 165 is positioned on the top of the chamber 46 and a corresponding recess 167 is formed on the cartridge 160. In the configuration shown in FIG. 36, the cooperation of the protruding member 165 and the recess 167 can guide the connection between the cartridge 160 and the chamber 46. Any other suitable configuration can be used.

The sensor 130, 132 can include a shield configured to protect at least a tip or sensing component of the sensor 130, 132 from damage that might be caused by incidental or inadvertent contact, bumping or knocking, for example but without limitation. In some configurations, the shield can include one or more fingers 131 arranged around the tip or sensing element of the sensor 130, 132. In some configurations, one or more of the fingers can be curved such that a portion of the finger is located substantially above the tip or sensing element of the sensor 130, 132 and another portion of the finger is located substantially alongside of the tip or sensing element of the sensor 130, 132.

In the illustrated configuration shown in FIG. 3, a ridge 166 defines at least a portion of the recess structure 162. The ridge 166 extends upward from an upper surface 170. The ridge defines a stop 172 and a pair of snap recesses 174. As shown in FIG. 21, a pair of protrusions 180 extend downward from a lower surface 182 of the illustrated cartridge 160. Each of the protrusions 180 comprises a locking tab 184. Each locking tab 184 is at an end of a respective arm 186 in the illustrated configuration. The locking tabs 184 can deflect inward while the cartridge 160 is being slid into position on the chamber 46. The locking tabs 184 snap into position within the snap recesses 174 formed on the ridge 166. With the locking tabs 184 snapped into position within the snap recesses 174, the cartridge 160 is secured in position in the sliding direction. In addition, a stop 190 on the cartridge 160 moves into proximity with or contacts the stop 172 of the ridge 162. Because the sensors 130, 132 are slid into position within the ports 60, 62, the cartridge 160 also is generally secured against movement normal to the sliding direction.

In some configurations, such as that shown in FIG. 36, the cartridge 160 includes one or more arms 191. The arms 191 can be adapted to extend along outer sides of the ports 60, 62 of the chamber 46. The arms can assist with locating the cartridge 160 correctly with respect to the chamber 46. In addition, if the installed cartridge 160 is bumped or knocked, the force from the bump or knock can be transmitted to the one or more arms 191 and away from the more fragile sensors 130, 132.

In the illustrated configuration, the arms 191 comprise an interlock portion 195 while the chamber 46 comprises an interlock portion 197. In some configurations, the interlock portion 197 of the chamber is positioned laterally outward from the ports 60, 62. The lateral displacement provides for a stable connection. The interlock portion 197 can be positioned on bosses 199 or the like. In some configurations, gripping portions 193 can be defined in an outer surface or along an outer surface of the chamber 46. In one configuration, the gripping portion 193 can be defined on one side of the interlock portion 197 or boss 199 while the majority of the cartridge 160 will be positioned on another side of the interlock portion 197.

Any suitable shape can be used for the interlock portions 195, 197. In the illustrated configuration, the interlock portion 197 of the chamber 46 comprises a bump that extends upward while the interlock portion 195 of the chamber comprises a recess that corresponds to bump of the interlock portion 197. Preferably, when the chamber 46 and the cartridge 160 are fully mated, the two interlock portions 195, 197 hold the chamber 46 and the cartridge 160 together with at least a slight force that must be overcome for separation of the chamber 46 from the cartridge 160.

The cartridge 160 defines a chassis that carries the sensors 130, 132 and other desired electrical components. In the illustrated configuration, the cartridge comprises wings 192 that define sockets and the sensors 130, 132 plug into the sockets, as shown in FIG. 21. In some configurations, the sensors 130, 132 are designed for removal and replacement with the same cartridge 160. In some configurations, the cartridge 160 is designed for limited time use and will be disposed without allowing the sensors 130, 132 to be removed and replaced. In some configurations, the portions of the cartridge 160 carrying the sensors 130, 132 are separable from the central portion of the cartridge 160, which generally houses electronics or the like. Such configurations enable replacement of the sensors 130, 132 without replacing the portion of the cartridge 160 that contains the main portion of the housed electronics.

Figure 22:
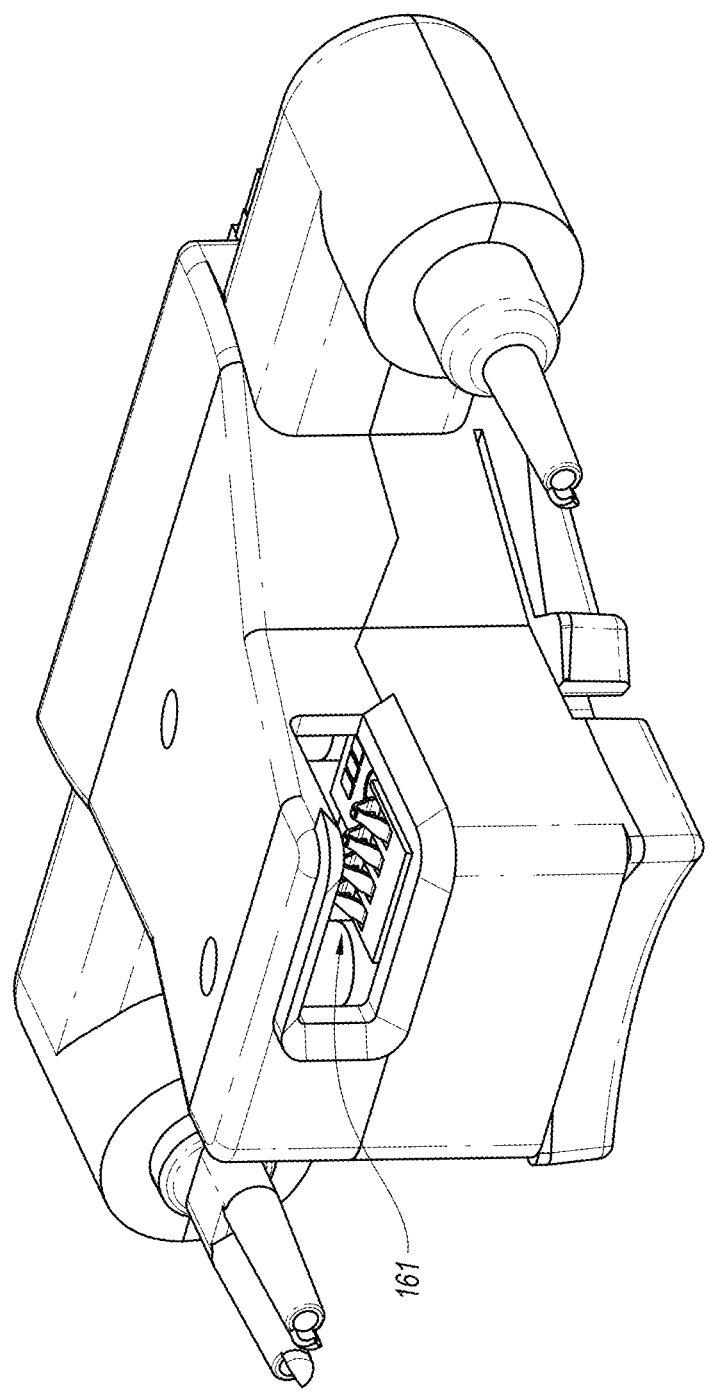
FIG. 22 is another perspective view of the cartridge and sensors.
Figure 24:
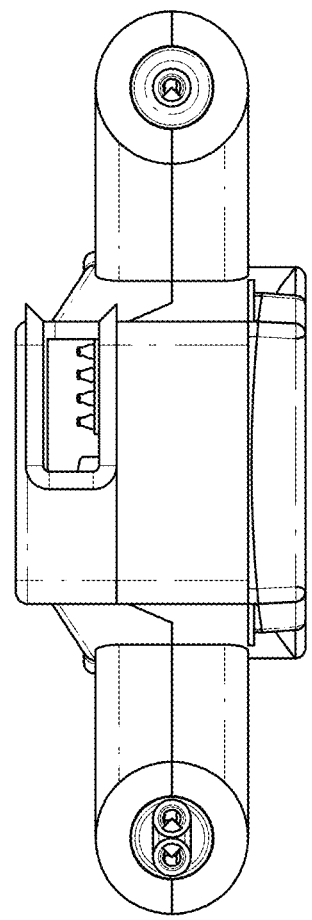
FIG. 24 is a rear view of the cartridge and sensors.
Figure 23:
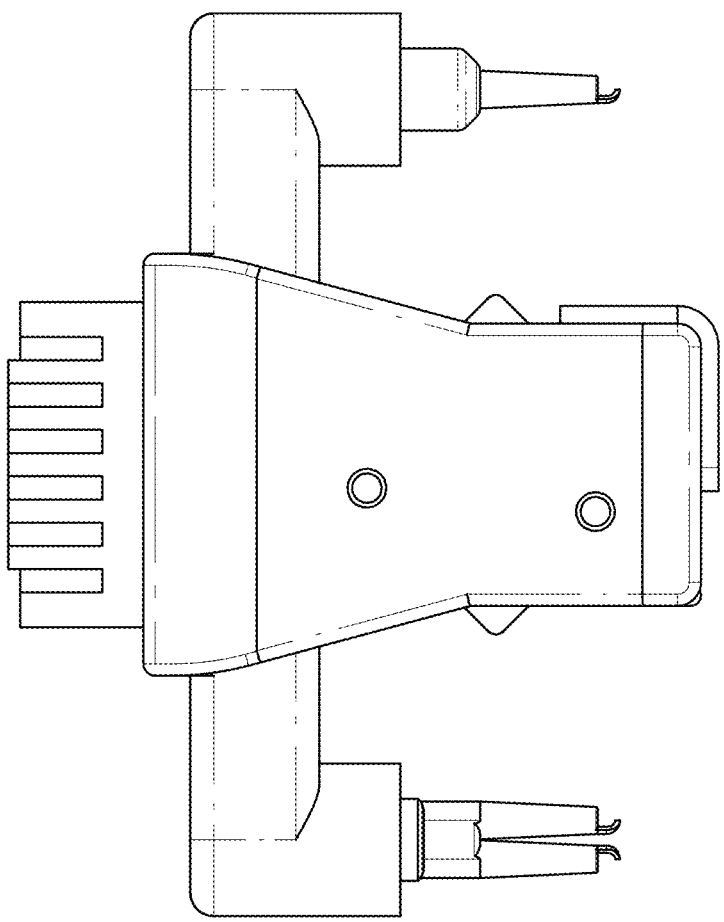
FIG. 23 is top view of the cartridge and sensors.
Figure 25:
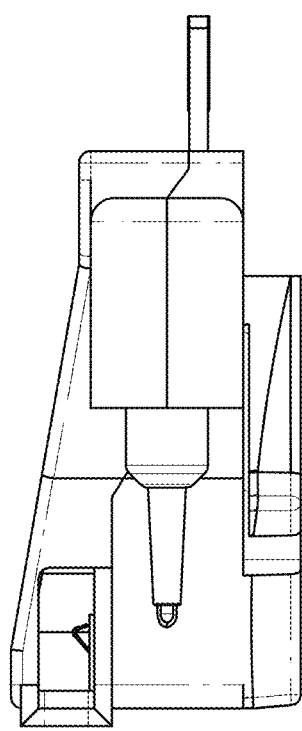
FIG. 25 is a left side view of the cartridge and sensors.
Figure 26:
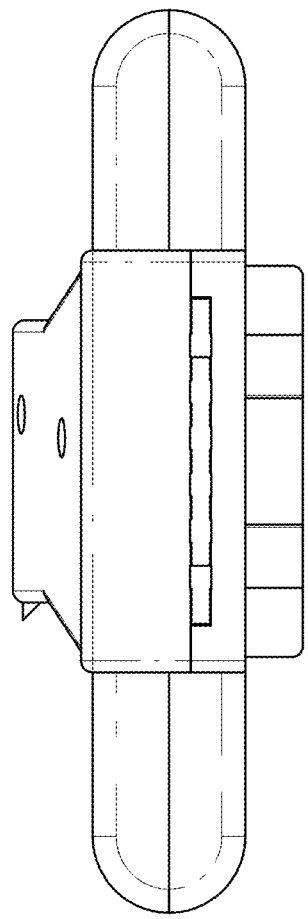
FIG. 26 is a front view of the cartridge.
Figure 27:
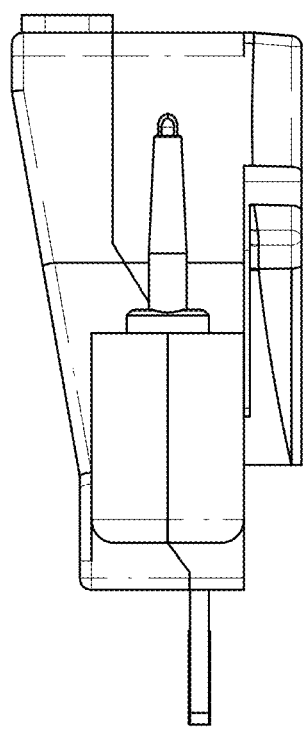
FIG. 27 is right side view of the cartridge and sensors.
Figure 28:
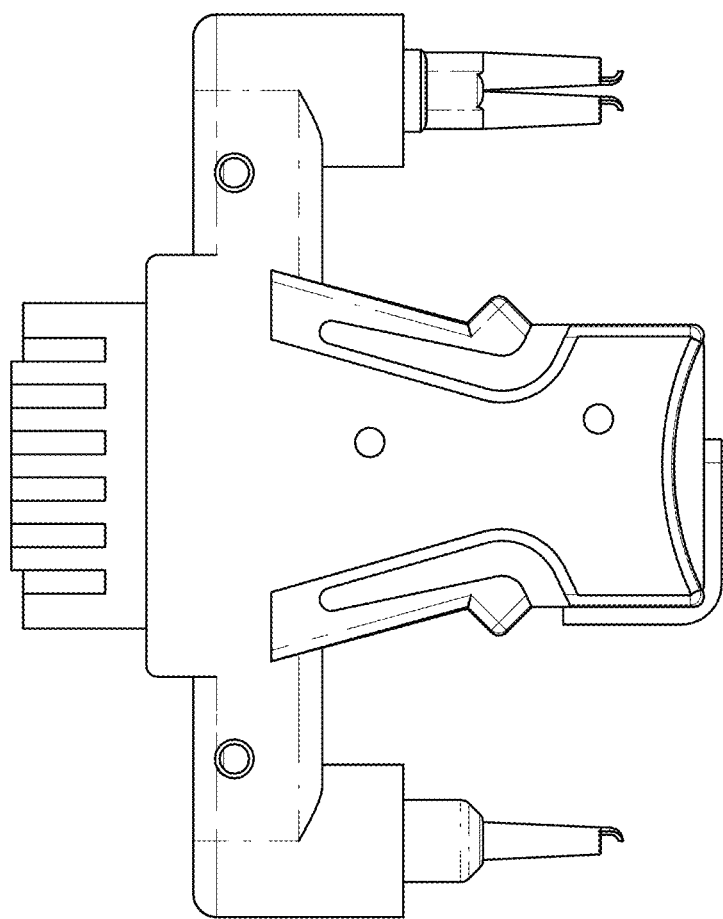
FIG. 28 is bottom view of the cartridge and sensors.
Figure 30:
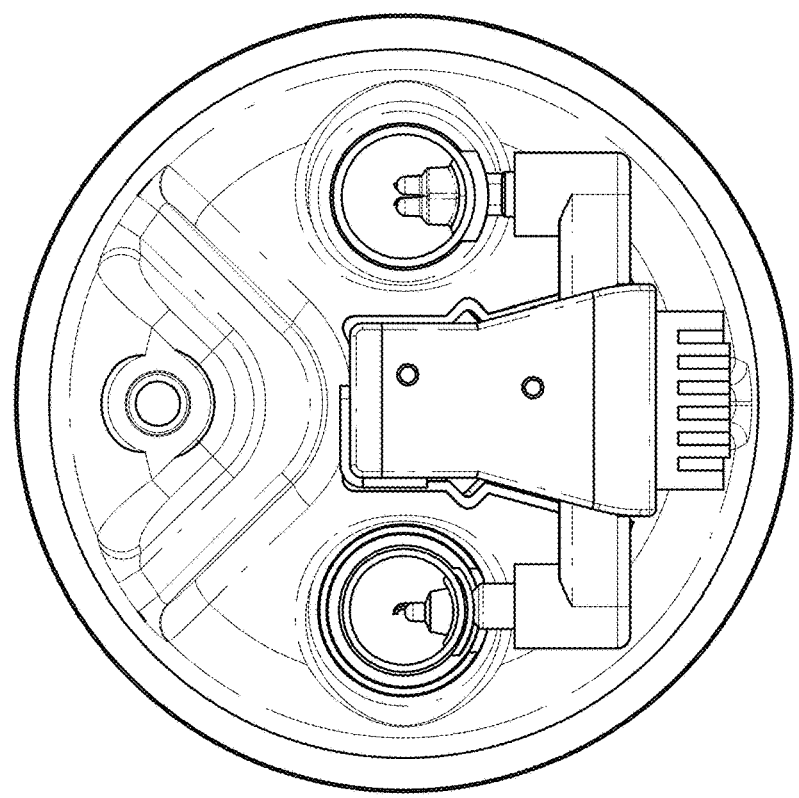
FIG. 30 is a top view of the cartridge assembled to the humidification chamber.
Figure 29:
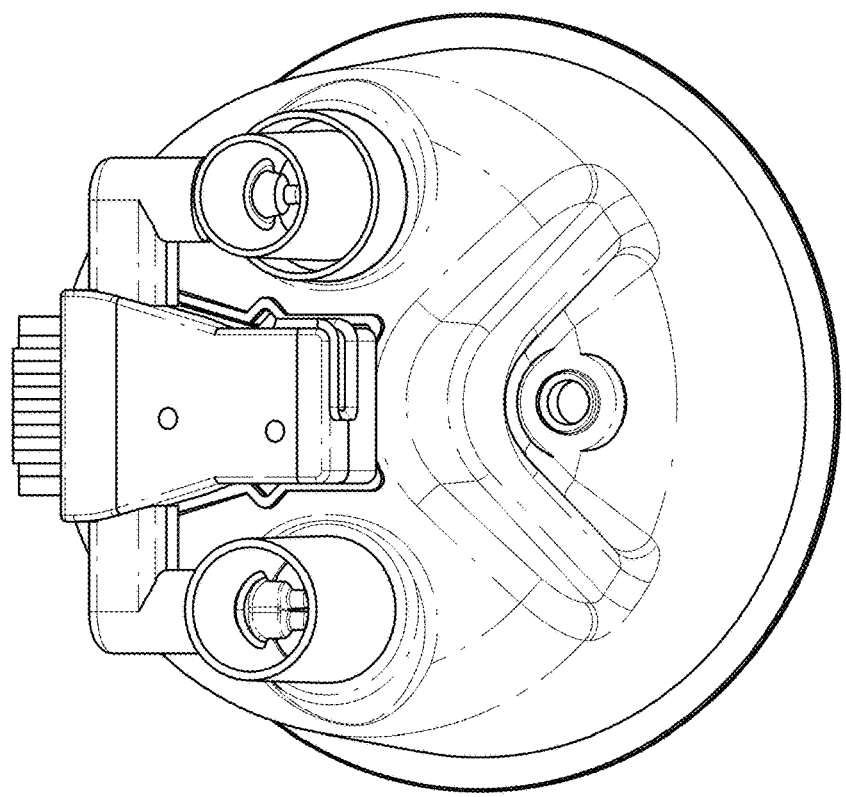
FIG. 29 is a perspective view of the cartridge assembled to the humidification chamber.
Figure 31:
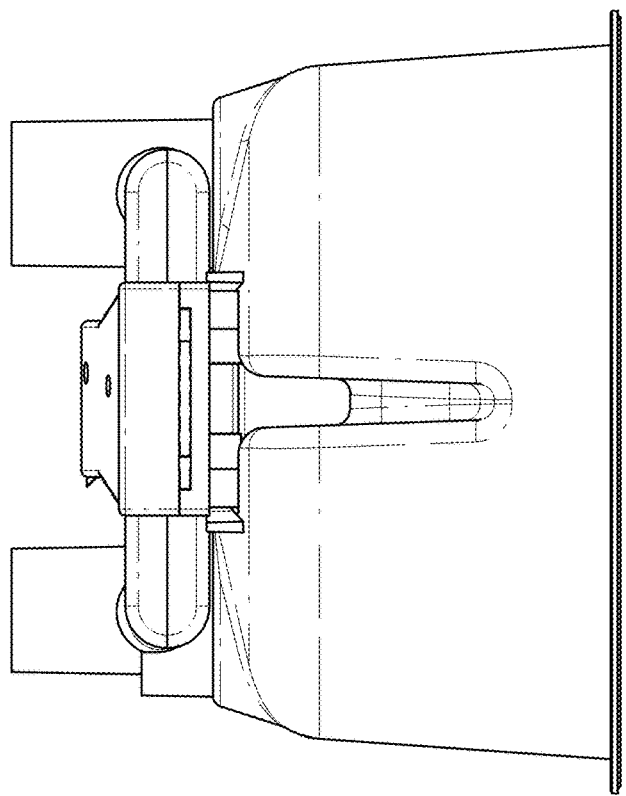
FIG. 31 is front view of the cartridge assembled to the humidification chamber.
Figure 32:
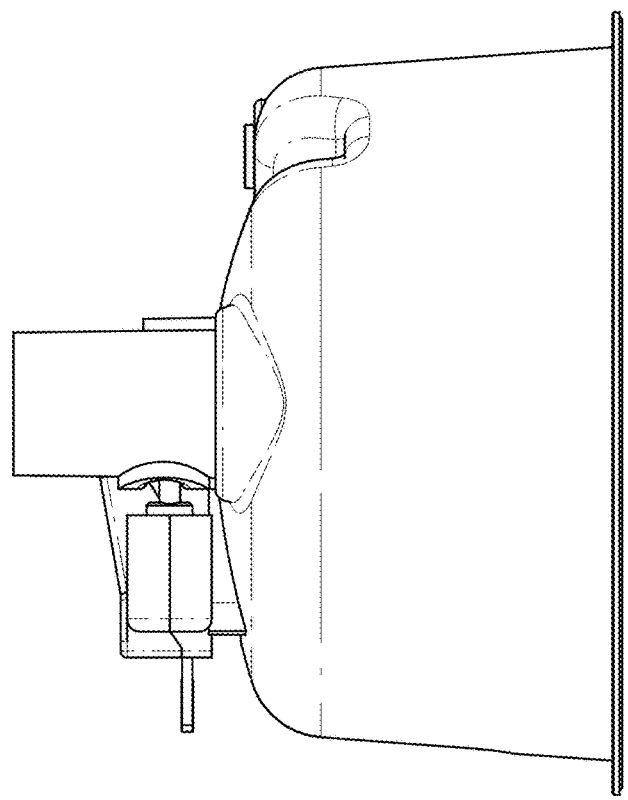
FIG. 32 is a right side view of the cartridge assembled to the humidification chamber.
Figure 34:
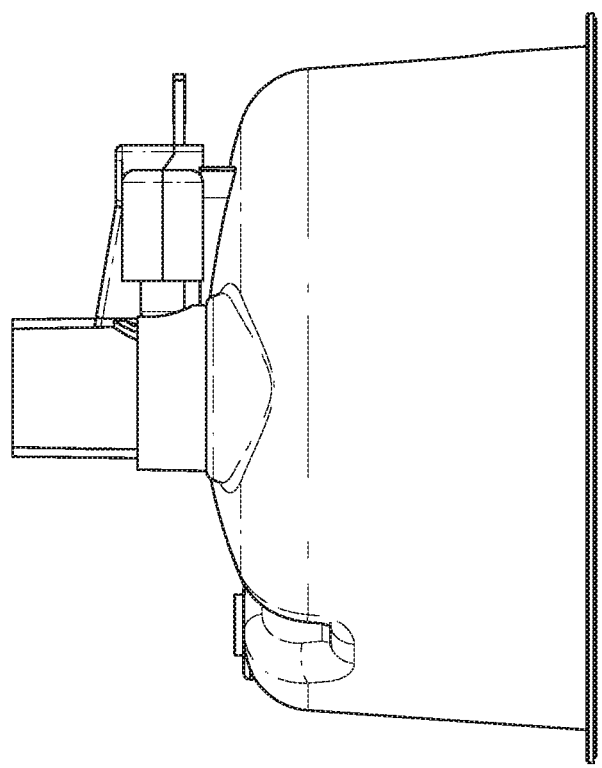
FIG. 34 is a left side view of the cartridge assembled to the humidification chamber.
Figure 33:
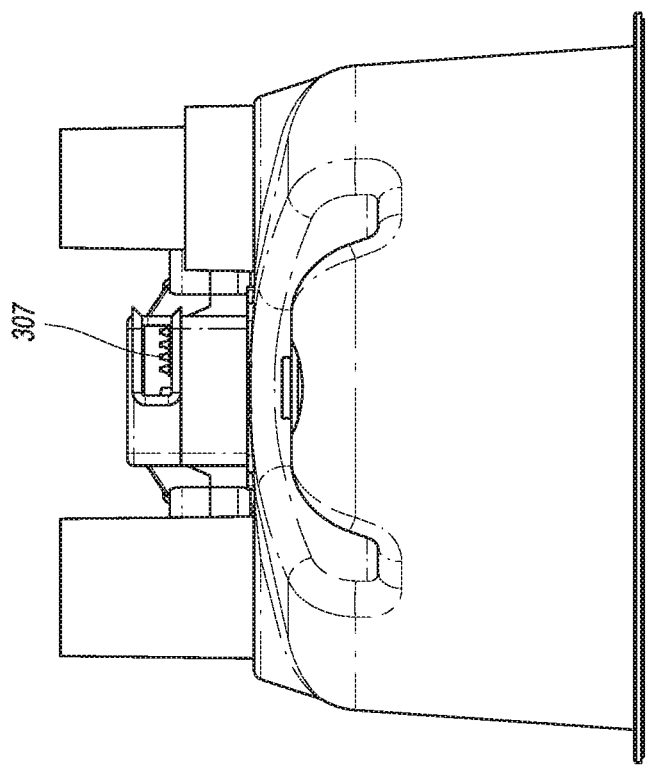
FIG. 33 is a rear view of the cartridge assembled to the humidification chamber.
Figure 35:
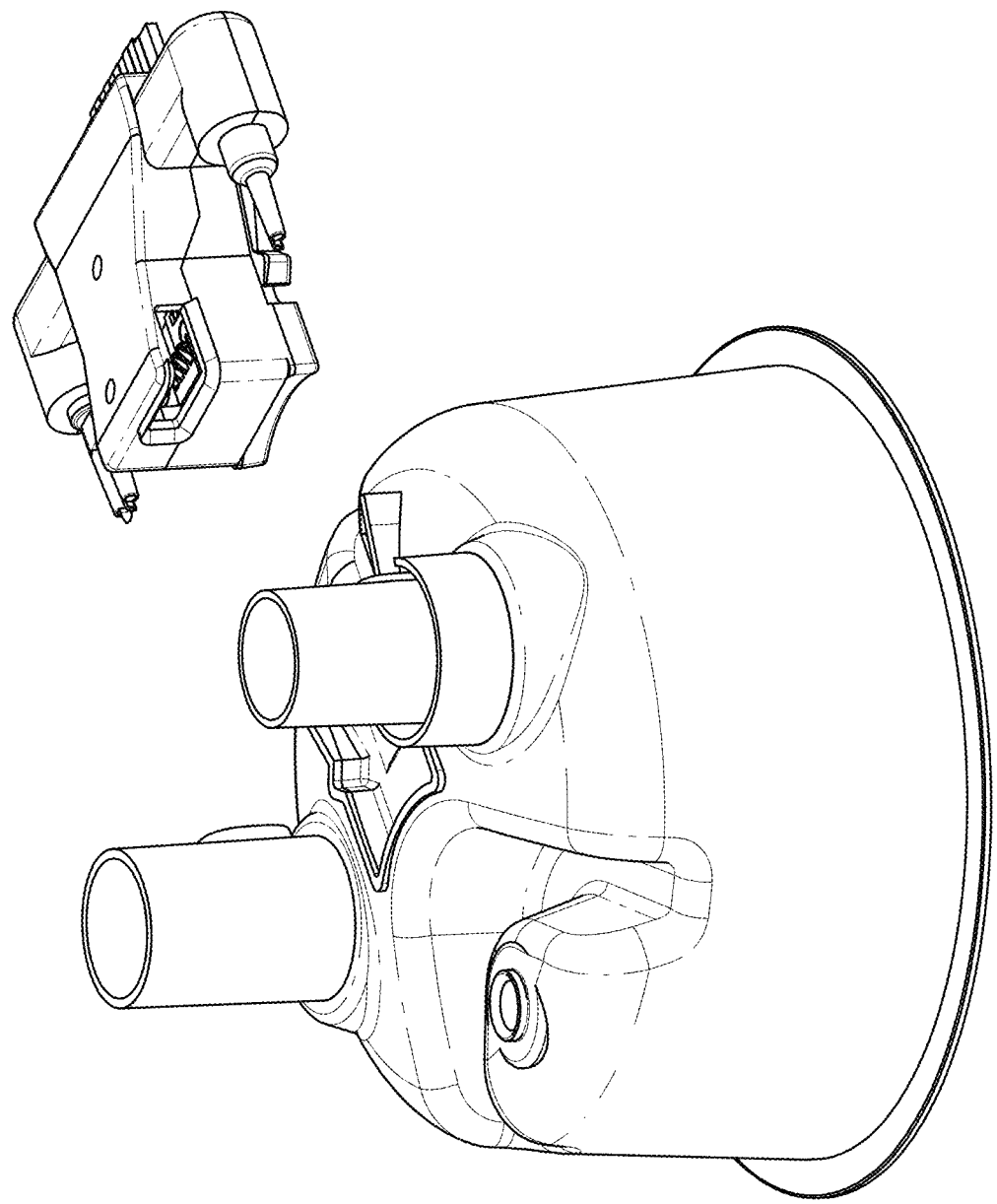
FIG. 35 is an exploded perspective view showing the cartridge being assembled to the humidification chamber.

With reference to FIG. 22, the cartridge comprises a recessed electrical connector 161. The electrical connector 161 is electrically connected to the sensors 130, 132 in any suitable manner. Preferably, the electrical connector 161 is a female USB connector. In addition, the electrical connector 161 is adapted to provide an electrical connection to the controller 56 or any other suitable component. Preferably, with the cartridge 160 mounted to the humidification chamber 46, when the humidification chamber 46 is installed into the humidification unit 40, a corresponding connector 307 (preferably, a male USB connector or the like) on the humidification unit 40 makes electrical connection with the connector 161. In this manner, connection of the sensors to the controller 56 is greatly simplified and the possibility of improper electrical connection is greatly reduced.

The wings 192 on the illustrated chassis provide mounting structures for the sensors 130, 132 and also position the sensors 130, 132 for repeatable depth of insertion of the sensing portions of the sensors 130, 132 into the flow path. Advantageously, when the sensors 130, 132 are mounted in the cartridge 160 and that cartridge 160 is snapped into position on the chamber 46, the sensing portions of the sensors 130, 132 are positioned in a desired location within the flow path.

Composite Tubes

As described above, the respiratory humidification system 20 can include a conduit 44 connecting the gas source 30 to the humidification unit 40, an inspiratory conduit 70, and/or an expiratory conduit. In some embodiments, portions or entireties of any or all of these conduits can be composite tubes, which can be tubes having two or more portions or components. Composite tubes as described herein can also be used other applications, for example but without limitation, in laparoscopic surgery. For example, the use of a composite tube as the conduit 713 in the example insufflation system 701 illustrated in FIG. 1B can help deliver humidified gases to the patient 705 surgical site with minimized heat loss. This can advantageously reduce overall energy consumption in the insufflation system, because less heat input is needed to compensate for heat loss With reference to FIG. 37A, an example composite tube comprises a first elongate member 203 and a second elongate member 205. In the illustrated embodiment, the first 203 and second 205 elongate members are distinct components; however, in other embodiments, the first and second elongate members can be regions of a tube formed from a single material. Thus, the first elongate member 203 can represent a hollow portion of a tube, while the second elongate member 205 represents a structural supporting or reinforcement portion of the tube which adds structural support to the hollow portion. The hollow portion and the structural supporting portion can have a spiral configuration, as described herein. The composite tube 201 may be used to form the inspiratory conduit 70 and/or the expiratory conduit as described above, a coaxial tube, or any other medical tube.

In this example, the first elongate member 203 comprises a hollow body spirally wound to form, at least in part, an elongate tube having a longitudinal axis LA-LA and a lumen 207 extending along the longitudinal axis LA-LA. In at least one embodiment, the first elongate member 203 is a tube. Preferably, the first elongate member 203 is flexible. Furthermore, the first elongate member 203 is preferably transparent or, at least, semi-transparent or semi-opaque. A degree of optical transparency allows a caregiver or user to inspect the lumen 207 for blockage or contaminants or to confirm the presence of moisture. A variety of plastics, including medical grade plastics, are suitable for the body of the first elongate member 203. Examples of suitable materials include Polyolefin elastomers, Polyether block amides, Thermoplastic co-polyester elastomers, EPDM-Polypropylene mixtures, and Thermoplastic polyurethanes.

In at least one embodiment, the extrudate used to form the first elongate member 203 further comprises an antiblocking additive. Antiblocking additives can reduce the adhesion of two adjacent layers of film. Antiblocking additives can include calcined kaolin (CaK), hydrous kaolin (HyK), calcium carbonate (CaC), talc (TaC), natural silica (NSi1), natural silica (NSi2), diatomaceous earth (DiE) and synthetic silica (SSi). In some configurations, the antiblocking additive is food-safe. In some embodiments, the antiblocking additive is talc. The addition of talc to the plastic extrudate advantageously reduces the stickiness of the resultant first elongate member 203. The addition of talc to the extrudate also reduces the noise made when the first elongate member 203 is dragged over an object, such as the edge of a desk or bedside table. In addition, the addition of talc reduces the noise the tube makes when it is moved, flexed, and so forth by reducing the extent to which adjacent bubbles stick (and unstick) to each other when bunched (and unbunched) around the vicinity of a bend. In certain embodiments, the talc is in the range of 1.5 to 10 (or about 1.5 to about 10) weight percent of the total extrudate. In certain embodiments, the talc is in the range of 1.5 to 5 (or about 1.5 to about 5) weight percent of the total extrudate. In certain embodiments, the talc is in the range of 10 (or about 10) weight percent or less of the total extrudate. In certain embodiments, the talc is in the range of 5 (or about 5) weight percent or less of the total extrudate. In certain embodiments, the talc is in the range of 1.5 (or about 1.5) weight percent or more of the total extrudate. Desirably, the amount of talc is low enough that the tube will be reasonably clear to allow inspection of the inside of the tube.

The hollow body structure of the first elongate member 203 contributes to the insulating properties to the composite tube 201. An insulating tube 201 is desirable because, as explained above, it prevents heat loss. This can allow the tube 201 to deliver gas from a heater-humidifier to a patient while maintaining the gas's conditioned state with minimal energy consumption.

In at least one embodiment, the hollow portion of the first elongate member 203 is filled with a gas. The gas can be air, which is desirable because of its low thermal conductivity ($2.62 \times 10^{-2}$ W/m·K at 300K) and very low cost. A gas that is more viscous than air may also advantageously be used, as higher viscosity reduces convective heat transfer. Thus, gases such as argon ($17.72 \times 10^{-3}$ W/m·K at 300K), krypton ($9.43 \times 10^{-3}$ W/m·K at 300K), and xenon ($5.65 \times 10^{-3}$ W/m·K at 300K) can increase insulating performance. Each of these gases is non-toxic, chemically inert, fire-inhibiting, and commercially available. The hollow portion of the first elongated member 203 can be sealed at both ends of the tube, causing the gas within to be substantially stagnant. Alternatively, the hollow portion can be a secondary pneumatic connection, such as a pressure sample line for conveying pressure feedback from the patient-end of the tube to a controller. The first elongate member 203 can be optionally perforated. For instance, the surface of the first elongate member 203 can be perforated on an outward-facing surface, opposite the lumen 207. In another embodiment, the hollow portion of the first elongate member 203 is filled with a liquid. Examples of liquids can include water or other biocompatible liquids with a high thermal capacity. For instance, nanofluids can be used. An example nanofluid with suitable thermal capacity comprises water and nanoparticles of substances such as aluminum.

The first elongate member 203 can contain a quantity of a fluid (such as air) and can be substantially sealed so as to prevent the quantity of fluid escaping. In use, the fluid can be configured to be used to measure one or more properties of the tube 201, the first elongate member 203, the second elongate member 205, and/or the gas traveling along the tube 201. In at least one embodiment, the pressure of gas passing along the tube can be measured. A reference measurement of the pressure of the fluid is made before gas begins to circulate. As gas begins to pass through the tube 201, the pressure of the gas will tend to cause a proportional rise in the pressure of the fluid within the first elongate member 203. By comparing a measurement taken in use with the reference measurement, the pressure of the gas within the tube 201 can be determined. In another embodiment, a fluid is chosen that changes one or more properties based on the operational heat range of the gas within the tube 201. In this manner, by measuring the property of the fluid, the temperature of the gas can be determined. For example, a fluid which expands with temperature can be used. In use, the temperature of the fluid will tend towards the temperature of the gas flow. By then measuring the pressure of the fluid, the temperature of the fluid can be determined. This may have particular benefit when the temperature of the gas flow is difficult or undesirable to measure directly.

In some embodiments, at least a portion of the first elongate member 203 is formed of a material that allows vapor to pass through, for example for example, an activated perfluorinated polymer material with extreme hydrophilic properties, such as NAFION, or a hydrophilic polyester block copolymer, such as SYMPATEX. Preferably, the portion of the first elongate member 203 that forms the lumen of the tube 201 will be formed of the material. In use, a quantity of humidification fluid (such as water) is passed through the space formed by the first elongate member. As the humidification fluid is heated (for example, by the heating filaments 215 disposed in the second elongate member 205), a portion of the humidification fluid will tend to evaporate. This can then pass through the breathable portion into the gas flow, thereby humidifying the gas flow. In such an embodiment, the tube 201 may provide sufficient humidification to the gas flow that a standalone humidifier can be omitted from the system.

In some embodiments, a gas flow can be passed along the space inside the first elongate member 203. For example, exhaled respiratory gases can be carried. In some embodiments, the first elongate member or at least a portion of the first elongate member (preferably the outer-facing side) can be made of a material that allows water vapor to pass therethrough, for example, an activated perfluorinated polymer material with extreme hydrophilic properties, such as NAFION, or a hydrophilic polyester block copolymer, such as SYMPATEX. In this manner, as the exhaled gas travels along the length of the first elongate member, it will tend to dry from about 100% relative humidity at the patient-end to reduced humidity level at the opposite end.

The second elongate member 205 is also spirally wound and joined to the first elongate member 203 between adjacent turns of the first elongate member 203. The second elongate member 205 forms at least a portion of the lumen 207 of the elongate tube. The second elongate member 205 acts as structural support for the first elongate member 203.

In at least one embodiment, the second elongate member 205 is wider at the base (proximal the lumen 207) and narrower at the top. For example, the second elongate member can be generally triangular in shape, generally T-shaped, or generally Y-shaped. However, any shape that meets the contours of the corresponding first elongate member 203 is suitable.

Preferably, the second elongate member 205 is flexible, to facilitate bending of the tube. Desirably, the second elongate member 205 is less flexible than the first elongate member 203. This improves the ability of the second elongate member 205 to structurally support the first elongate member 203. For example, the modulus of the second elongate member 205 is preferably 30-50 MPa (or about 30-50 MPa). The modulus of the first elongate member 203 is less than the modulus of the second elongate member 205. The second elongate member 205 can be solid or mostly solid. In addition, the second elongate member 205 can encapsulate or house conductive material, such as filaments, and specifically heating filaments or sensors (not shown). Heating filaments can minimize the cold surfaces onto which condensate from moisture-laden air can form. Heating filaments can also be used to alter the temperature profile of gases in the lumen 207 of composite tube 201. A variety of polymers and plastics, including medical grade plastics, are suitable for the body of the second elongate member 205. Examples of suitable materials include Polyolefin elastomers, Polyether block amides, Thermoplastic co-polyester elastomers, EPDM-Polypropylene mixtures and Thermoplastic polyurethanes. In certain embodiments, the first elongate member 203 and the second elongate member 205 may be made from the same material. The second elongate member 205 may also be made of a different color material from the first elongate member 203, and may be transparent, translucent or opaque. For example, in one embodiment the first elongate member 203 may be made from a clear plastic, and the second elongate member 205 may be made from an opaque blue (or other color) plastic.

In some embodiments, the second elongate member 205 can be made of a material that wicks water. For example, an absorbent sponge-like material can be used. Preferably, the second elongate member 205 is connected to a water source, such as a water bag. In use, water is conveyed along at least a portion of the length of the second elongate member 205 (preferably, substantially the whole length). As gas passes along the second elongate member 205, water vapor will tend to be picked up by the gases, thereby humidifying the gas flow. In some embodiments, the one or more heater filaments embedded in the second elongate member 205 can be controlled to alter the rate of evaporation and thereby alter the level of humidification provided to the gas flow.

This spirally-wound structure comprising a flexible, hollow body and an integral support can provide crush resistance, while leaving the tube wall flexible enough to permit short-radius bends without kinking, occluding or collapsing. Preferably, the tube can be bent around a 25 mm diameter metal cylinder without kinking, occluding, or collapsing, as defined in the test for increase in flow resistance with bending according to ISO 5367:2000(E). This structure also can provide a smooth lumen 207 surface (tube bore), which helps keep the tube free from deposits and improves gas flow. The hollow body has been found to improve the insulating properties of a tube, while allowing the tube to remain light weight.

As explained above, the composite tube 201 can be used as an expiratory tube and/or an inspiratory tube in a breathing circuit, or a portion of a breathing circuit. Preferably, the composite tube 201 is used at least as an inspiratory tube.

Figure 37A:
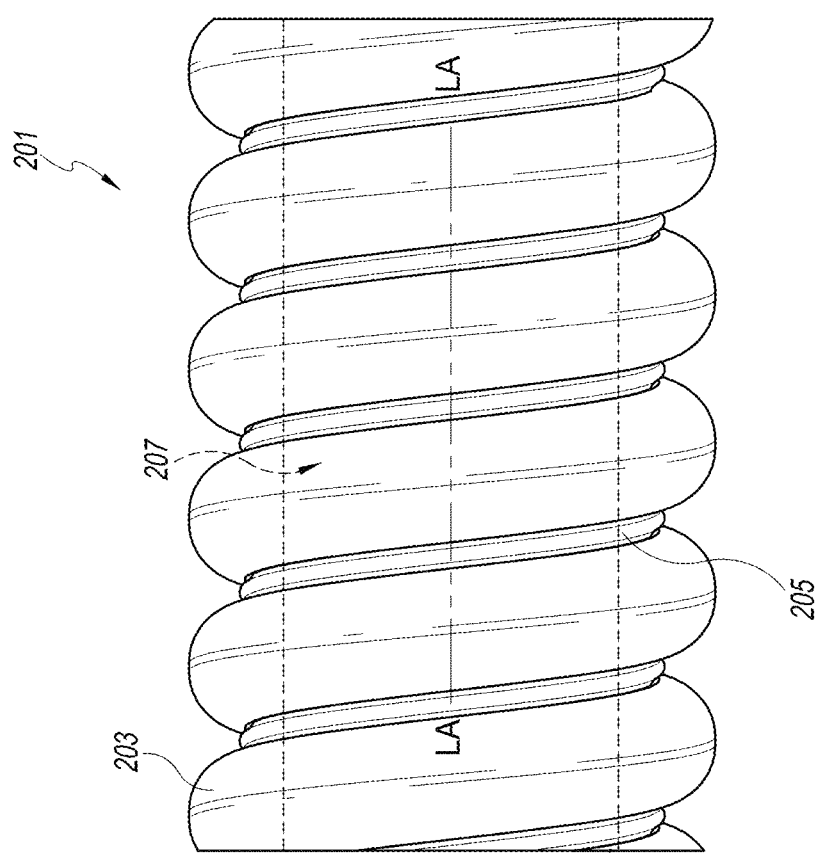
FIG. 37A shows a side-plan view of a section of an example composite tube.
Figure 37B:
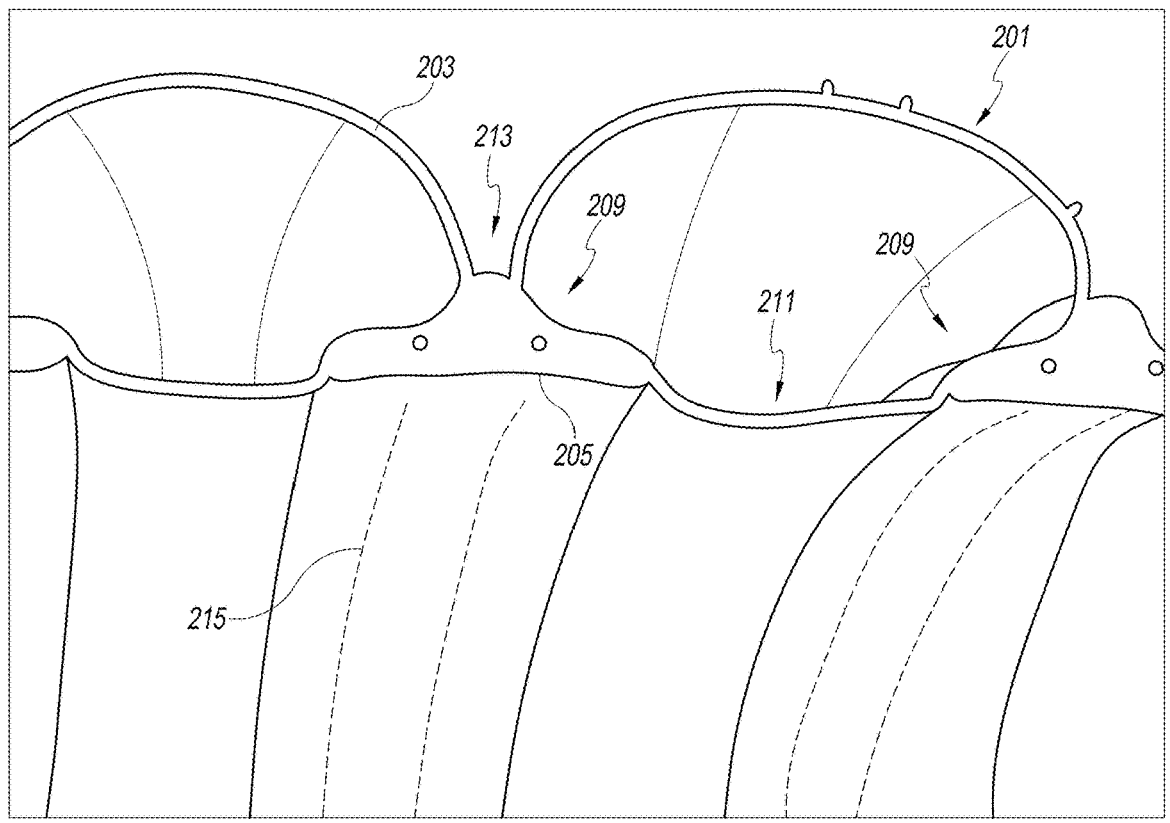
FIG. 37B shows a longitudinal cross-section of a top portion a tube similar to the example composite tube of FIG. 37A.

FIG. 37B shows a longitudinal cross-section of a top portion of the example composite tube 201 of FIG. 37A. FIG. 37B has the same orientation as FIG. 37A. This example further illustrates the hollow-body shape of the first elongate member 203. As seen in this example, the first elongate member 203 forms in longitudinal cross-section a plurality of hollow bubbles. Portions 209 of the first elongate member 203 overlap adjacent wraps of the second elongate member 205. A portion 211 of the first elongate member 203 forms the wall of the lumen (tube bore).

It was discovered that having a gap 213 between adjacent turns of the first elongate member 203, that is, between adjacent bubbles, unexpectedly improved the overall insulating properties of the composite tube 201. Thus, in certain embodiments, adjacent bubbles are separated by a gap 213. Furthermore, certain embodiments include the realization that providing a gap 213 between adjacent bubbles increases the heat transfer resistivity (the R value) and, accordingly, decreases the heat transfer conductivity of the composite tube 201. This gap configuration was also found to improve the flexibility of the composite tube 201 by permitting shorter-radius bends. A T-shaped second elongate member 205, as shown in FIG. 37B, can help maintain a gap 213 between adjacent bubbles. Nevertheless, in certain embodiments, adjacent bubbles are touching. For example, adjacent bubbles can be bonded together.

One or more conductive materials can be disposed in the second elongate member 205 for heating or sensing the gas flow. In this example, two heating filaments 215 are encapsulated in the second elongate member 205, one on either side of the vertical portion of the "T." The heating filaments 215 comprise conductive material, such as alloys of Aluminum (Al) and/or Copper (Cu), or conductive polymer. Preferably, the material forming the second elongate member 205 is selected to be non-reactive with the metal in the heating filaments 215 when the heating filaments 215 reach their operating temperature. The filaments 215 may be spaced away from lumen 207 so that the filaments are not exposed to the lumen 207. At one end of the composite tube, pairs of filaments can be formed into a connecting loop.

In at least one embodiment, a plurality of filaments are disposed in the second elongate member 205. The filaments can be electrically connected together to share a common rail. For example, a first filament, such as a heating filament, can be disposed on a first side of the second elongate member 205. A second filament, such as a sensing filament, can be disposed on a second side of the second elongate member 205. A third filament, such as a ground filament, can be disposed between the first and second filaments. The first, second, and/or third filaments can be connected together at one end of the second elongate member 205.

Figure 37C:
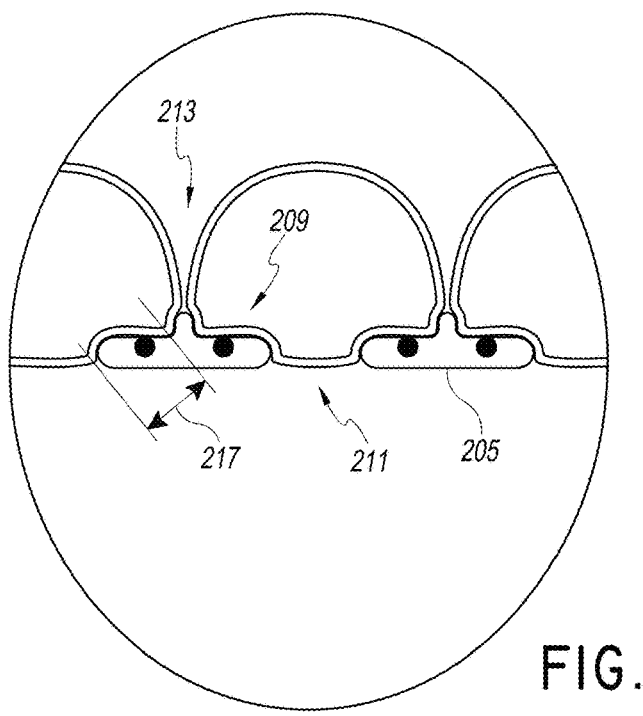
FIG. 37C shows another longitudinal cross-section illustrating a first elongate member in the composite tube.
Figure 37D:
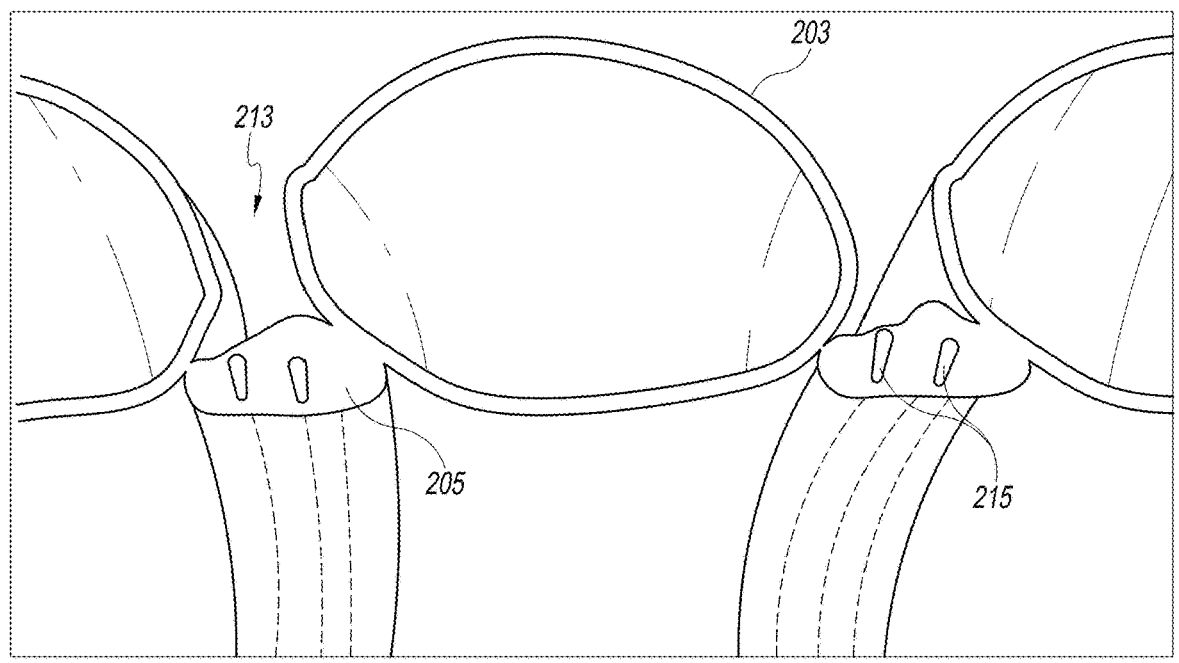
FIG. 37D shows another longitudinal cross-section of a top portion of a tube.
Figure 48A:
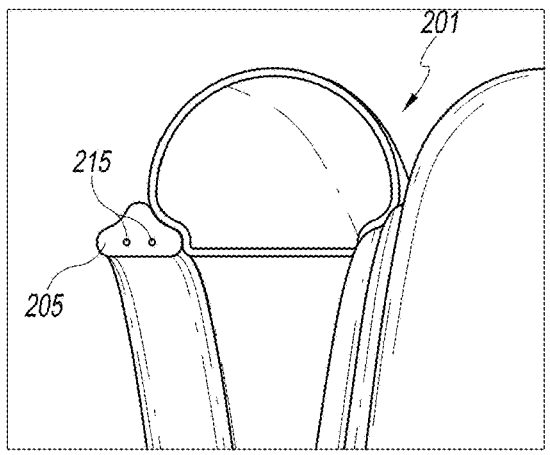
FIGS. 48A-48C show examples of first elongate member shapes configured to improve thermal efficiency.
Figure 48B:
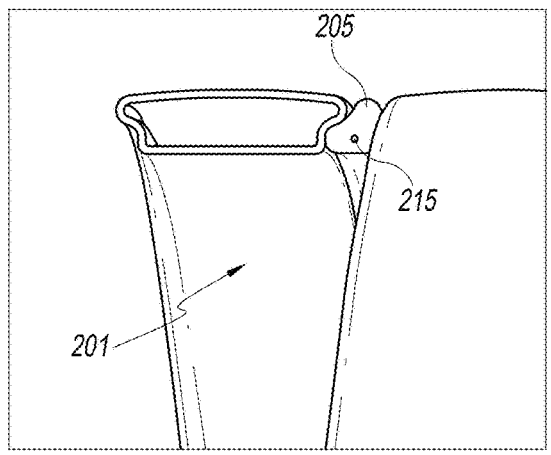
Figure 48C:
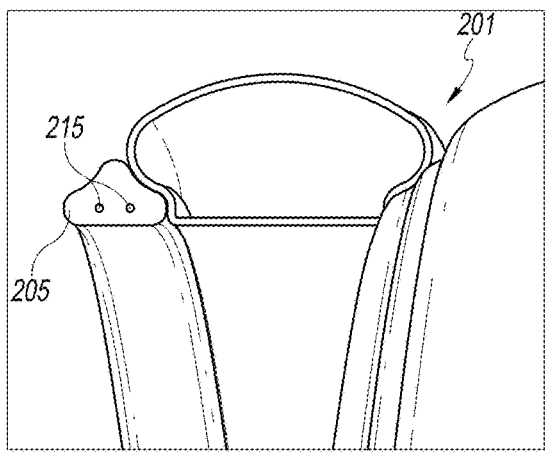

FIG. 37C shows a longitudinal cross-section of the bubbles in FIG. 37B. As shown, the portions 209 of the first elongate member 203 overlapping adjacent wraps of the second elongate member 205 are characterized by a degree of bond region 217. A larger bond region improves the tubes resistance to delamination at the interface of the first and second elongate members. Additionally or alternatively, the shape of the bead and/or the bubble can be adapted to increase the bond region 217. For example, FIG. 37D shows a relatively small bonding area on the left-hand side. FIG. 48B, discussed in greater detail herein, also demonstrates a smaller bonding region. In contrast, FIG. 37E has a much larger bonding region than that shown in FIG. 37D, because of the size and shape of the bead. FIGS. 48A and 48C, discussed in greater detail herein, also illustrate a larger bonding region. It should be appreciated that, although the configurations in FIGS. 37E, 48A, and 48C may be preferred in certain embodiments, other configurations, including those of FIGS. 37D, 48B, and other variations, may be utilized in other embodiments as may be desired.

FIG. 37D shows a longitudinal cross-section of a top portion of another composite tube. FIG. 37D has the same orientation as FIG. 37B. This example further illustrates the hollow-body shape of the first elongate member 203 and demonstrates how the first elongate member 203 forms in longitudinal cross-section a plurality of hollow bubbles. In this example, the bubbles are completely separated from each other by a gap 213. A generally triangular second elongate member 205 supports the first elongate member 203.

Figure 37E:
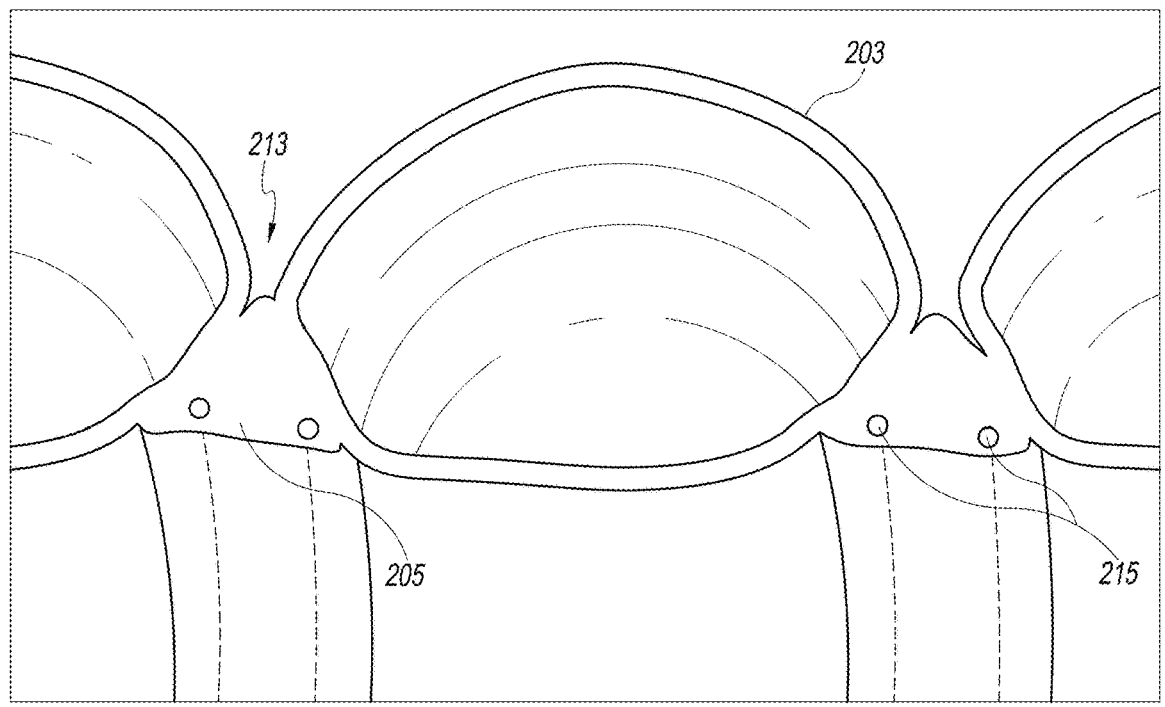
FIG. 37E shows another longitudinal cross-section of a top portion of a tube.

FIG. 37E shows a longitudinal cross-section of a top portion of another composite tube. FIG. 37E has the same orientation as FIG. 37B. In the example of FIG. 37E, the heating filaments 215 are spaced farther apart from each other than the filaments 215 in FIG. 37B. It was discovered that increasing the space between heating filaments can improve heating efficiency, and certain embodiments include this realization. Heating efficiency refers to the ratio of the amount of heat input to the tube to the amount of energy output or recoverable from the tube. Generally speaking, the greater the energy (or heat) that is dissipated from the tube, the lower the heating efficiency. For improved heating performance, the heating filaments 215 can be equally (or about equally) spaced along the bore of the tube. Alternatively, the filaments 215 can be positioned at extremities of the second elongate member 205, which may provide simpler manufacturing.

In FIG. 37F, the first elongate member 203 forms in longitudinal cross-section a plurality of hollow bubbles. In this example, there are a plurality of bubbles, and more specifically, two adjacent wraps of the first elongate member 203, between wraps of the second elongate member 205. This configuration is shown in greater detail in FIG. 37G. As described and shown elsewhere in this disclosure, certain configurations can implement greater than two, for example, three, wraps of the first elongate member 203 between wraps of the second elongate member 205.

Embodiments comprising a plurality of adjacent wraps of the first elongate member 203 between wraps of the second elongate member 205 can be advantageous because of improvements in overall tube flexibility. The substantially solid second elongate member 205 is generally less flexible than the hollow first elongate member 203. Accordingly, certain embodiments include the realization that overall tube flexibility can be improved by increasing the number of bubbles of first elongate member 203 between wraps of the second elongate member 205.

Figure 38A:
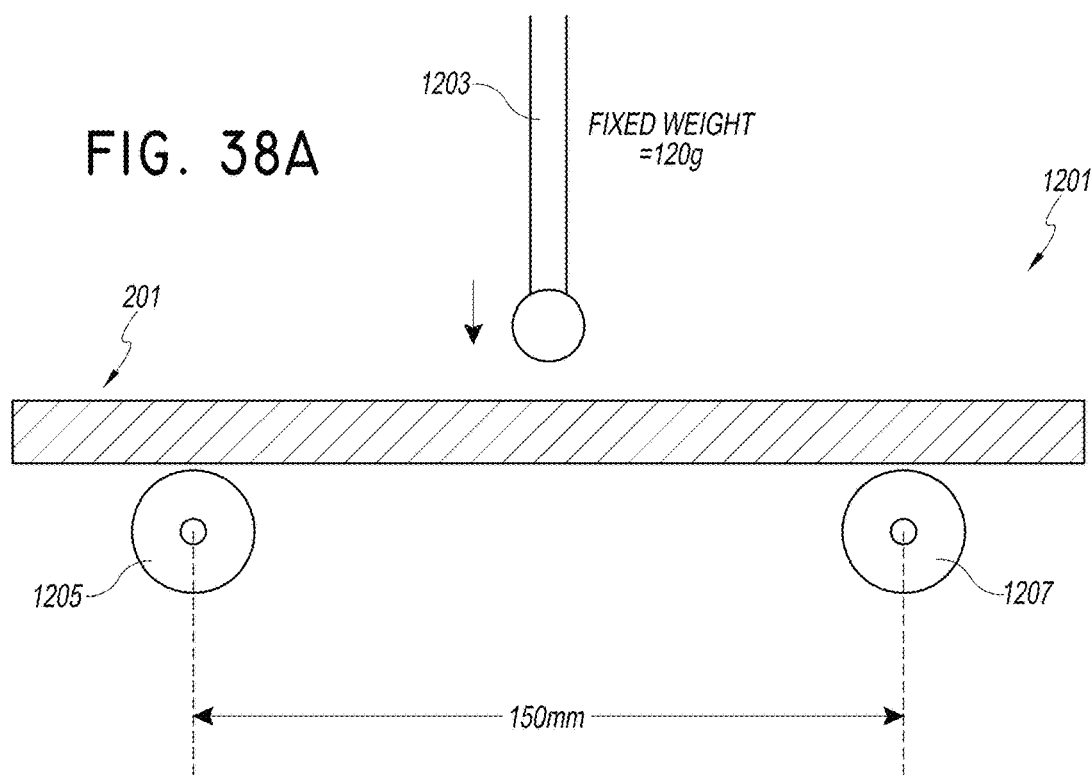
FIG. 38A shows a front-plan cross-sectional schematic of a flexibility jig.
Figure 38B:
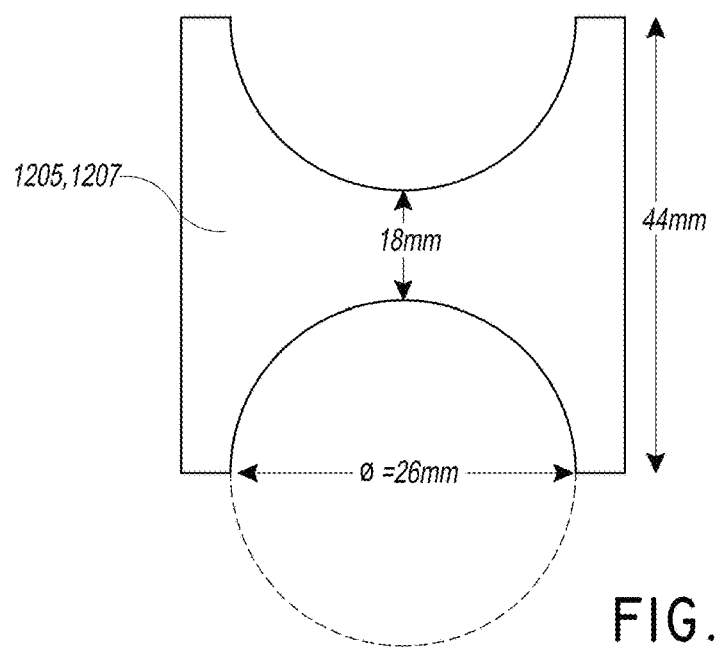
FIG. 38B shows a detailed front-plan cross-sectional schematic of rollers on the flexibility jig of FIG. 38A.

A first 300 mm-length sample of tube comprising two bubbles between wraps of the second elongate member 205 and a second 300 mm-length sample of tube comprising one bubble between wraps of the second elongate member 205 were each tested on a flexibility jig. A front-plan cross-sectional schematic of the flexibility jig is shown in FIG. 38A. The jig 1201 used a rod 1203 with a fixed mass of 120 g to apply a force to each tube 201, which was positioned between two rollers 1205 and 1207. The force exerted by the rod 1203 was about 1.2 N (0.12 kg*9.81 m/s$^2$). A detailed front-plan cross-sectional schematic of rollers 1205 and 1207 is shown in FIG. 38B. Both rollers 1205 and 1207 had the same dimensions. The vertical deflection was measured using the position of the fixed weight with respect to a vertical support 1209 of the flexibility jig, shown in the photographs of FIGS. 38C through 38F.

Figure 38C:
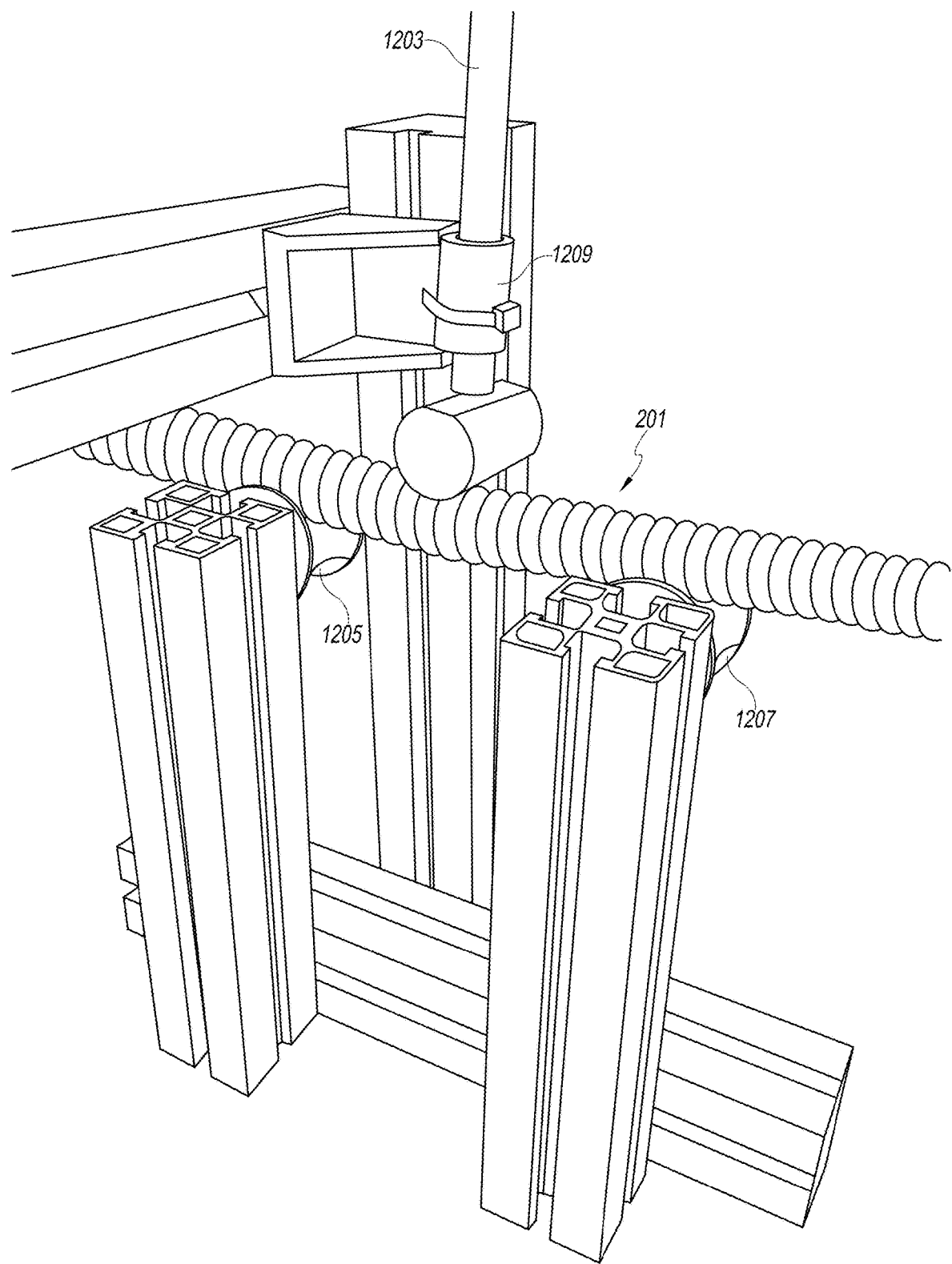
FIGS. 38C-38F show a flexibility jig in use.
Figure 38D:
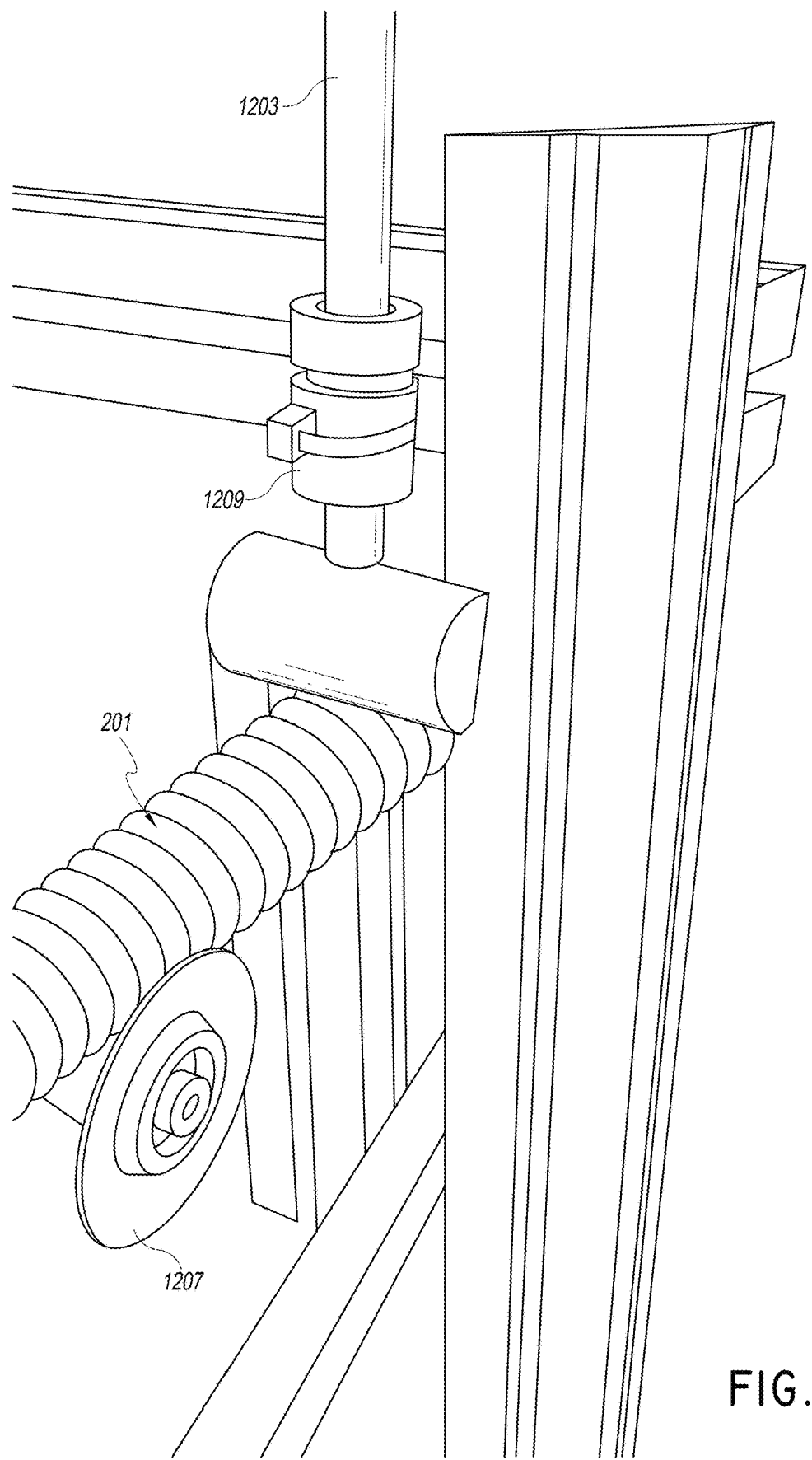
Figure 38E:
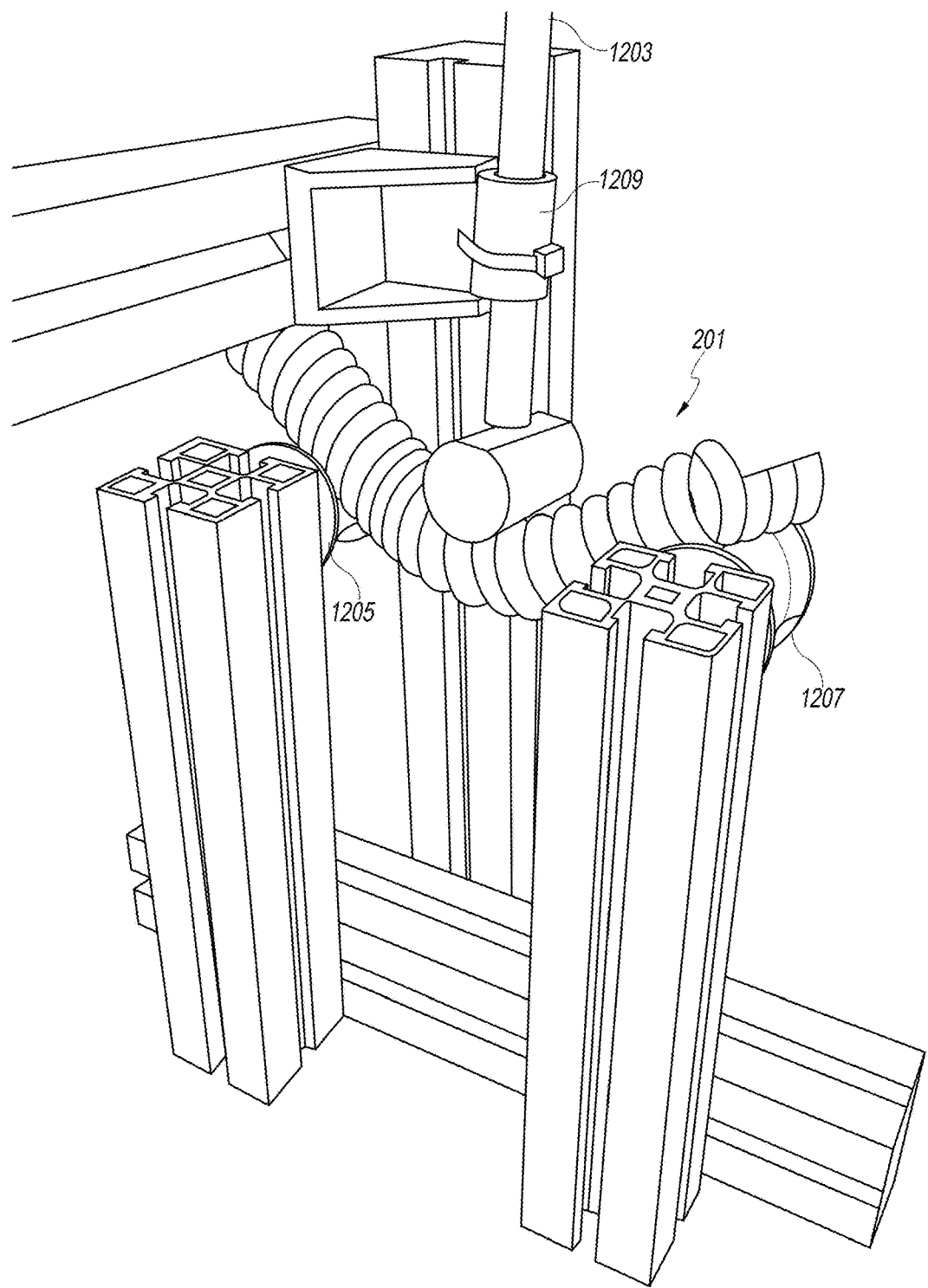
Figure 38F:
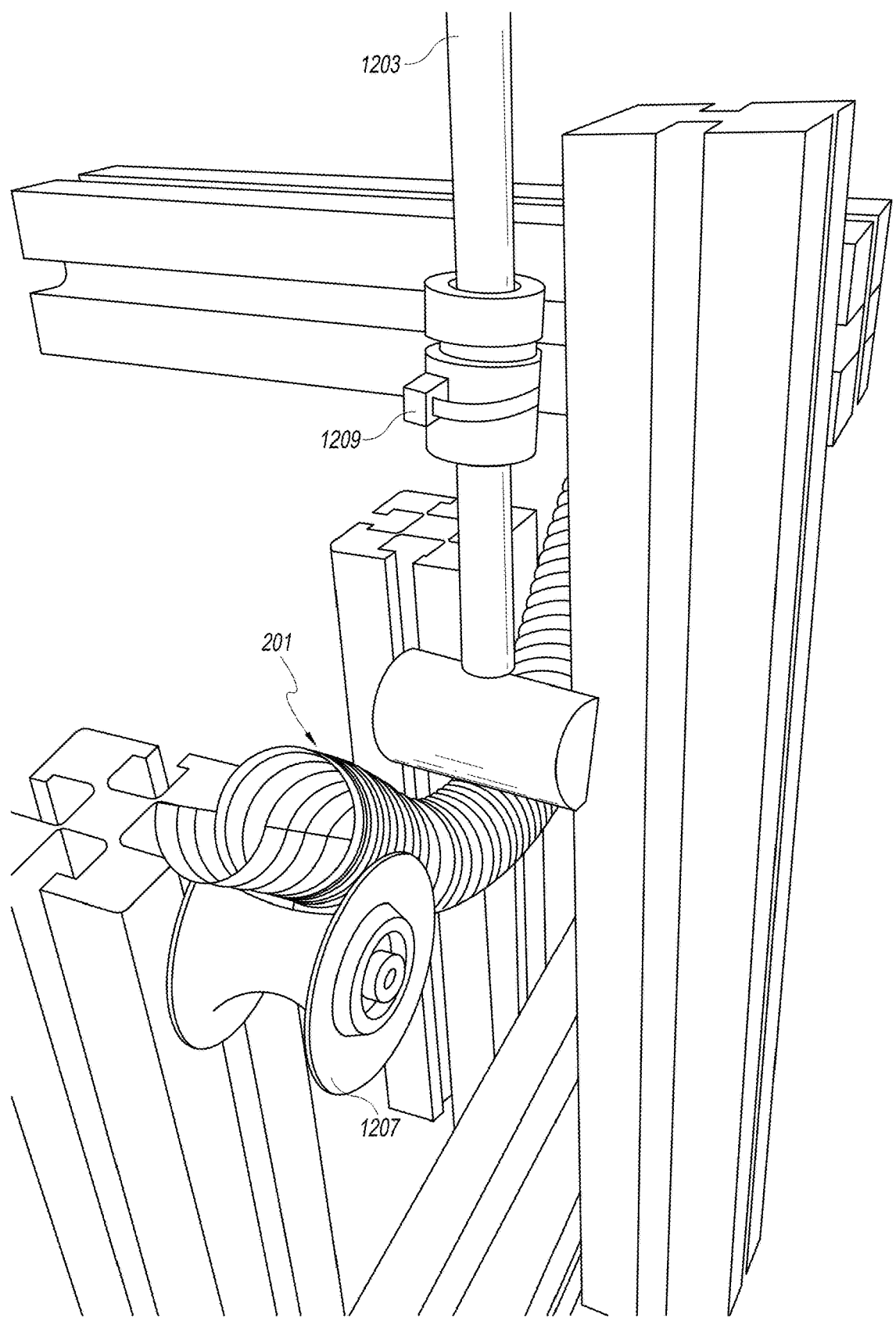

FIG. 38C shows a front-perspective view of the second sample under testing in the jig 1201. FIG. 38D shows a rear-perspective view of the second sample under testing in the jig 1201. FIG. 38E shows a front-perspective view of the first sample under testing in the jig 1201. FIG. 38F shows a rear-perspective view of the first sample under testing in the jig 1201. As shown in FIGS. 38C through 38F, the second sample shown in FIGS. 38E and 38F had substantially greater vertical deflection than the first sample shown in FIGS. 38C and 38D. Specifically, the second sample had a vertical deflection of 3 mm, while the first sample was much more flexible, having a vertical deflection of 42 mm.

Another advantage of embodiments comprising a plurality of adjacent wraps of the first elongate member 203 between wraps of the second elongate member 205 is improved recovery from crushing. It was observed that, after crushing, samples having multiple bubbles between wraps of the first elongate member 203 recovered their shape more quickly than samples having a single bubble between wraps of the first elongate member 203.

Yet another advantage of embodiments comprising a plurality of adjacent wraps of the first elongate member 203 between wraps of the second elongate member 205 is improved resistance to crushing. Crush resistance is a mechanical property that plays an important role in the resilience of the tube while in service. The hospital environment can be harsh, as the tube can be subjected to crushing by a patient's arm or leg, bed frames, and other equipment.

Figure 39A:
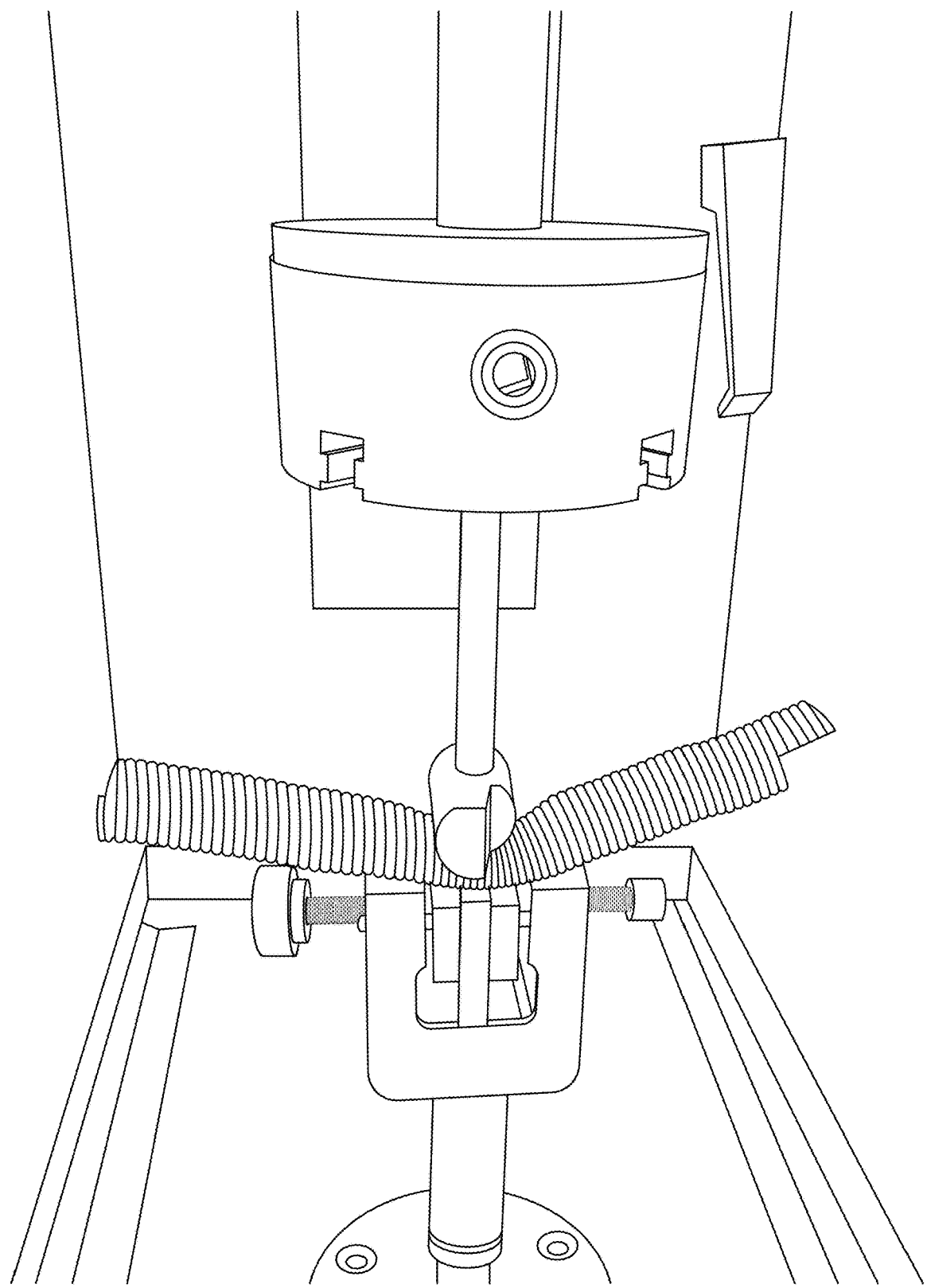
FIG. 39A shows a crush resistance testing jig.

Crush resistance testing was performed on four tube samples using an Instron machine set up as shown in the photograph in FIG. 39A. The cylinder 1301 was plunged downwards 16 mm from the top of the tube at a rate of 60 mm/min. The Instron machine has a load cell to accurately measure force exerted on a component versus extension. The load vs. extension was plotted, as shown in FIG. 39B.

Figure 39B:
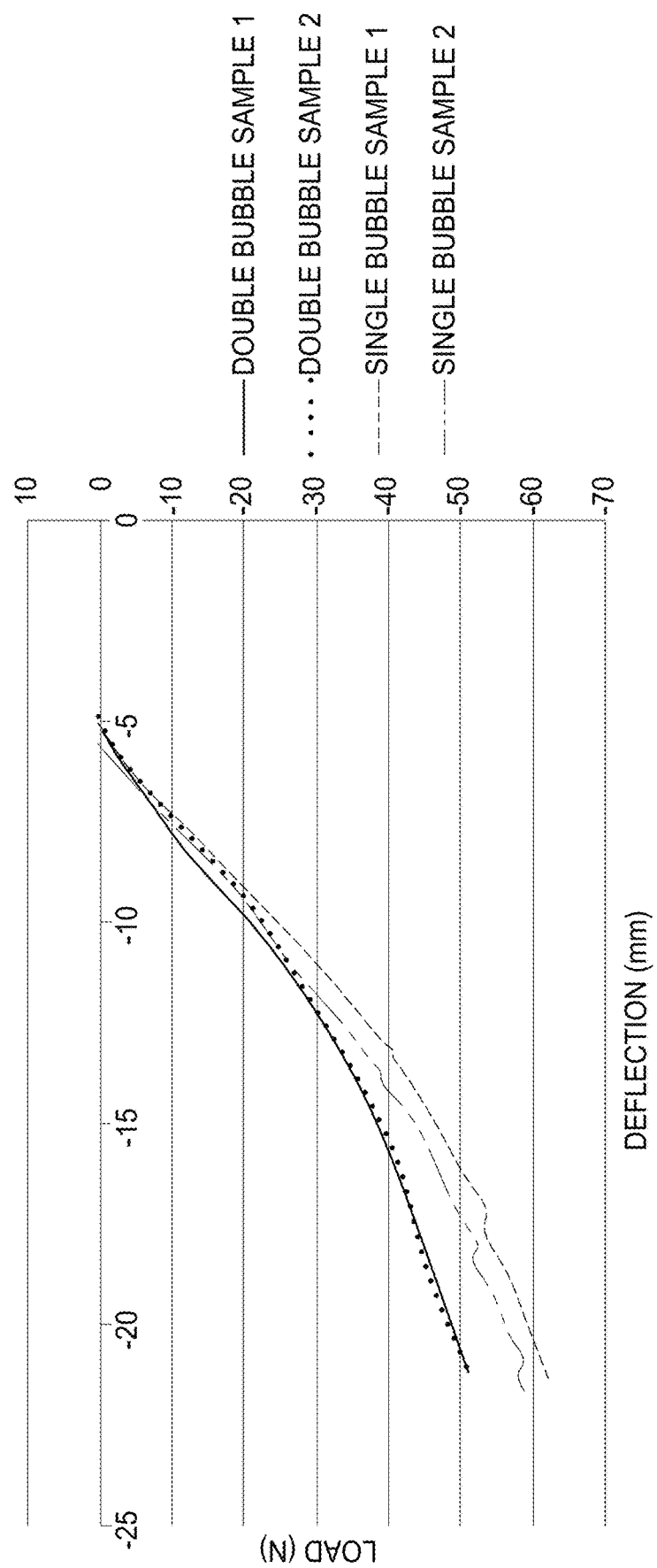
FIG. 39B shows a plot of load vs. extension, used for determining crush stiffness.

The crush stiffness for each sample was found by fitting a line of best fit to the data of FIG. 39B and calculating its gradient. The calculated crush stiffness for each sample is shown in TABLE 1A. In TABLE 1A (and elsewhere in this disclosure), the designation "double bubble" refers to a sample of tube comprising two bubbles between wraps of the second elongate member 205, when the sample is viewed in longitudinal cross section. The designation "single bubble" refers to a sample of tube comprising a single bubble between wraps of the second elongate member 205, when the sample is viewed in longitudinal cross section. The average crush stiffness (measured in N/mm) represents the average maximum force per unit width which produces no crush.

TABLE 1A

| Sample | Crush Stiffness (N/mm) | Average |
| --- | --- | --- |
| Double Bubble, Sample 1 | 3.26 | 3.21 |
| Double Bubble, Sample 2 | 3.15 | |
| Single Bubble, Sample 1 | 3.98 | 3.86 |
| Single Bubble, Sample 2 | 3.74 | |

As shown in the foregoing table, single bubble tubes had an average crush stiffness of 3.86 N/mm, while double bubble tubes had an average crush stiffness of 3.21 N/mm. In other words, the double bubble tubes had an approximately 16.8% lower resistance to crush than the single bubble tubes. Nevertheless, crush stiffness per unit thickness for the double bubble tubes was observed to be approximately 165% of the value for the single bubble tubes, as shown below in TABLE 1B.

TABLE 1B

| | Bubble Thickness (mm) | Crush Stiffness (N/mm) | Stiffness/Bubble Thickness (N/mm$^2$) |
| --- | --- | --- | --- |
| Double Bubble | 0.22 | 3.21 | 14.32 |
| Single Bubble | 0.43 | 3.86 | 8.70 |

Stated another way, when outer bubble thickness is taken into account, the double bubble tube is around 65% more resistant to crush than the single bubble tube variant. As shown in FIGS. 37F and 37G, the bubbles in the double bubble configuration are taller than they are wide, which results in more material in the vertical plane. Thus, it is believed that the unexpected improvement in crush resistance per unit thickness of the bubble may be attributed to the additional vertical web between beads working in the direction of crush.

Tensile testing was also performed on the single and double bubble tube samples. Both samples were 230 mm in length and were elongated by 15 mm at a rate of 10 mm/min. The force required to elongate the samples was measured. The results are shown in TABLE 1C.

TABLE 1C

| Sample | Peak Force at 15 mm extension (N) |
| --- | --- |
| Double Bubble | 17.60 |
| Single Bubble | 54.65 |

As shown in TABLE 1C, the double bubble tube was significantly stretchier in the axial (longitudinal) plane. This increase in longitudinal stretchiness is believed to be due to the single bubble tube having more material in between the beads that are working in the axial plane.

Yet another advantage to the multiple-bubble configuration described above is that the configuration imparts the ability to hold or transport additional fluids. As explained above, the hollow portion of the first elongate member 203 can be filled with a gas. The multiple discrete bubbles or hollow portions can be filled with multiple discrete gases. For example, one hollow portion can hold or transport a first gas and a second hollow portion can be used as a secondary pneumatic connection, such as a pressure sample line for conveying pressure feedback from the patient-end of the tube to a controller. As another example, multiple discrete bubbles or hollow portions can be filled with a combination of liquids, or a combination of liquids and gases. A first bubble can hold or transport a gas, and a second bubble can hold or transport a liquid, for instance. Suitable liquids and gases are described above.

It should be appreciated that, although the configurations in FIGS. 37F and 37G may be preferred in certain embodiments, other configurations, may be utilized in other embodiments as may be desired.

Referring now to FIGS. 37H-37L and 37V-37Z, some variations of the tube 201 are shown which are adapted to provide increased lateral stretch in the tube. FIGS. 37V-37Z show a stretched state of the tubes shown in FIGS. 37H-37L, respectively.

Figure 37H:
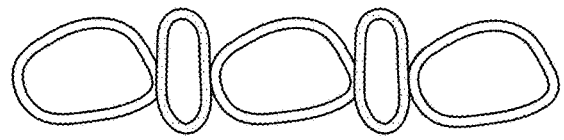
FIGS. 37H-L show variations of a tube adapted to provide increased lateral stretch in the tube.
Figure 37I:
Figure 37J:
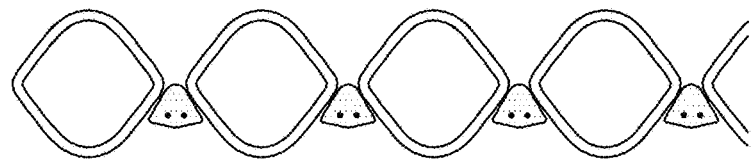
Figure 37K:
Figure 37L:
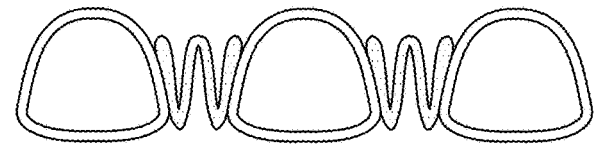
Figure 37V:
FIGS. 37V-Z show a stretched state of the tubes shown in FIGS. 37H-L, respectively.

Certain embodiments include the realization that the tubes shown in FIGS. 37H, 37I, and 37L comprise a second elongate member 205 having a shape that increases stretch capability. For example, in FIG. 37H, the second elongate member 205 is substantially oblate having a profile substantially the same height as the first elongate member 203. As shown in FIG. 37V, this allows the second elongate member 205 to deform outwards to at least twice the width compared to the second elongate member 205 at rest.

Figure 37W:

In FIGS. 37I and 37L, the second elongate member 205 is shaped so as to have an accordion-like shape. On stretching, the second elongate member 205 can therefore accommodate an increase amount of stretching by flattening (as shown in FIGS. 37W and 37Z, respectively).

Figure 37X:
Figure 37Y:
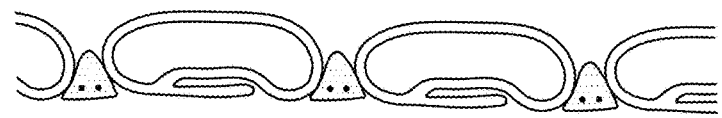
Figure 37Z:
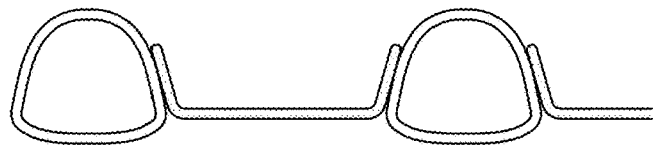

In FIGS. 37J and 37K, the first elongate member 203 is given a shape that allows it to deform outward, thereby allowing an increased lateral stretch (as shown in FIGS. 37X and 37Y, respectively).

Figure 40A:
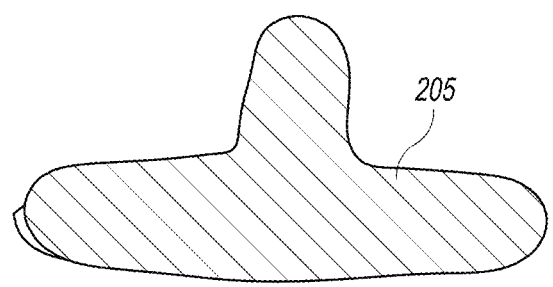
FIG. 40A shows a transverse cross-section of a second elongate member in the composite tube.

Reference is next made to FIGS. 40A through 40H which demonstrate example configurations for the second elongate member 205. FIG. 40A shows a cross-section of a second elongate member 205 having a shape similar to the T-shape shown in FIG. 37B. In this example embodiment, the second elongate member 205 does not have heating filaments. Other shapes for the second elongate member 205 may also be utilized, including variations of the T-shape as described below and triangular shapes.

Figure 40B:
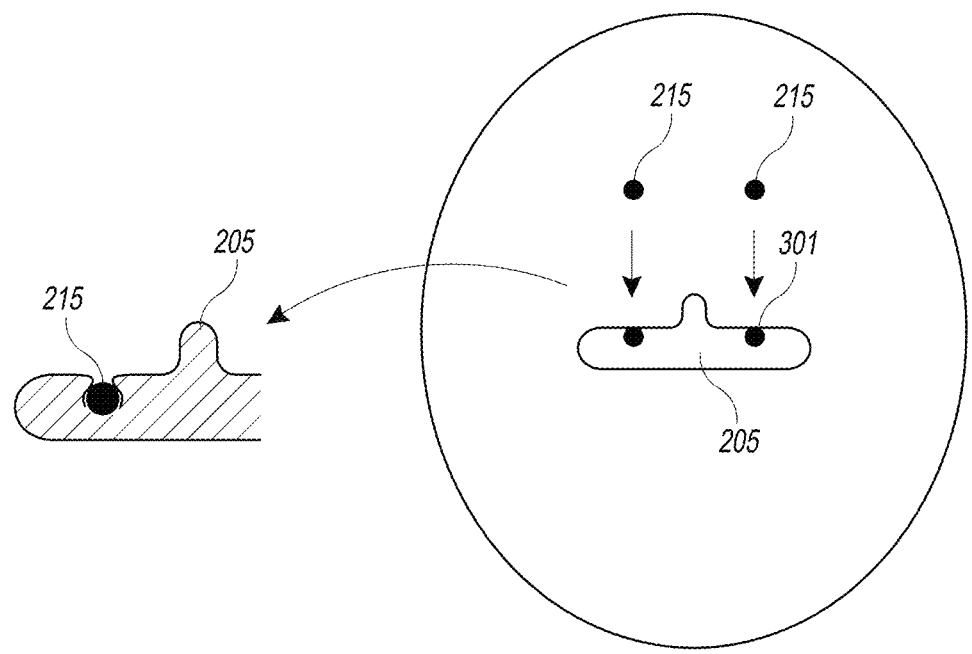
FIG. 40B shows another transverse cross-section of a second elongate member.

FIG. 40B shows another example second elongate member 205 having a T-shape cross-section. In this example, heating filaments 215 are embedded in cuts 301 in the second elongate member 205 on either side of the vertical portion of the "T." In some embodiments, the cuts 301 can be formed in the second elongate member 205 during extrusion. The cuts 301 can alternatively be formed in the second elongate member 205 after extrusion. For example, a cutting tool can form the cuts in the second elongate member 205. Preferably, the cuts are formed by the heating filaments 215 as they are pressed or pulled (mechanically fixed) into the second elongate member 205 shortly after extrusion, while the second elongate member 205 is relatively soft. Alternatively, one or more heating filaments can be mounted (e.g., adhered, bonded, or partially embedded) on the base of the elongate member, such that the filament(s) are exposed to the tube lumen. In such embodiments, it can be desirable to contain the filament(s) in insulation to reduce the risk of fire when a flammable gas such as oxygen is passed through the tube lumen.

Figure 40C:
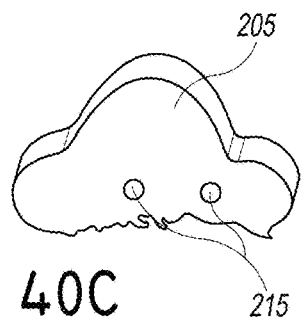
FIG. 40C shows another example second elongate member.

FIG. 40C shows yet another example second elongate member 205 in cross-section. The second elongate member 205 has a generally triangular shape. In this example, heating filaments 215 are embedded on opposite sides of the triangle.

Figure 40D:
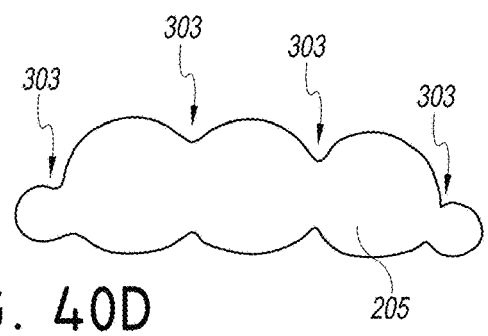
FIG. 40D shows another example second elongate member.

FIG. 40D shows yet another example second elongate member 205 in cross-section. The second elongate member 205 comprises four grooves 303. The grooves 303 are indentations or furrows in the cross-sectional profile. In some embodiments, the grooves 303 can facilitate the formation of cuts (not shown) for embedding filaments (not shown). In some embodiments, the grooves 303 facilitate the positioning of filaments (not shown), which are pressed or pulled into, and thereby embedded in, the second elongate member 205. In this example, the four initiation grooves 303 facilitate placement of up to four filaments, e.g., four heating filaments, four sensing filaments, two heating filaments and two sensing filaments, three heating filaments and one sensing filament, or one heating filament and three sensing filaments. In some embodiments, heating filaments can be located on the outside of the second elongate member 205. Sensing filaments can be located on the inside.

Figure 40E:
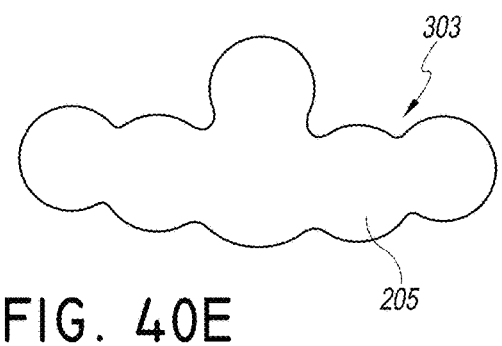
FIG. 40E shows another example second elongate member.

FIG. 40E shows still another example second elongate member 205 in cross-section. The second elongate member 205 has a T-shape profile and a plurality of grooves 303 for placing heating filaments.

Figure 40F:
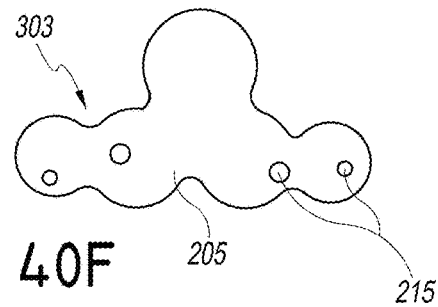
FIG. 40F shows another example second elongate member.

FIG. 40F shows yet another example second elongate member 205 in cross-section. Four filaments 215 are encapsulated in the second elongate member 205, two on either side of the vertical portion of the "T." As explained in more detail below, the filaments are encapsulated in the second elongate member 205 because the second elongate member 205 was extruded around the filaments. No cuts were formed to embed the heating filaments 215. In this example, the second elongate member 205 also comprises a plurality of grooves 303. Because the heating filaments 215 are encapsulated in the second elongate member 205, the grooves 303 are not used to facilitate formation of cuts for embedding heating filaments. In this example, the grooves 303 can facilitate separation of the embedded heating filaments, which makes stripping of individual cores easier when, for example, terminating the heating filaments.

Figure 40G:
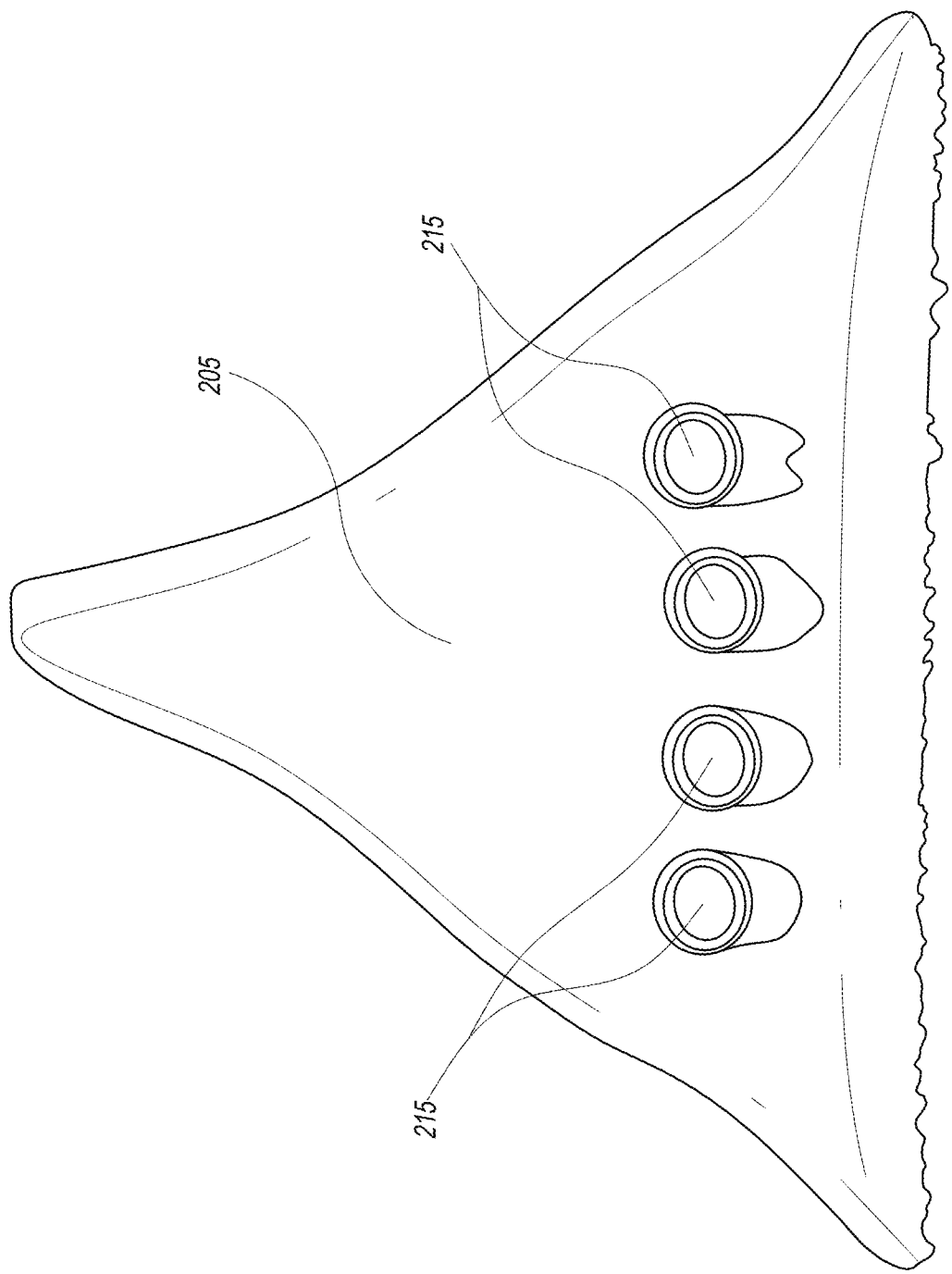
FIG. 40G shows another example second elongate member.

FIG. 40G shows yet another example second elongate member 205 in cross-section. The second elongate member 205 has a generally triangular shape. In this example, the shape of the second elongate member 205 is similar to that of FIG. 40C, but four filaments 215 are encapsulated in the second elongate member 205, all of which are central in the bottom third of the second elongate member 205 and disposed along a generally horizontal axis.

As explained above, it can be desirable to increase the distance between filaments to improve heating efficiency. In some embodiments, however, when heating filaments 215 are incorporated into the composite tube 201, the filaments 215 can be positioned relatively central in the second elongate member 205. A centralized position promotes robustness of the composite tubing for reuse, due in part to the position reducing the likelihood of the filament breaking upon repeating flexing of the composite tube 201. Centralizing the filaments 215 can also reduce the risk of an ignition hazard because the filaments 215 are coated in layers of insulation and removed from the gas path.

As explained above, some of the examples illustrate suitable placements of filaments 215 in the second elongate member 205. In the foregoing examples comprising more than one filament 215, the filaments 215 are generally aligned along a horizontal axis. Alternative configurations are also suitable. For example, two filaments can be aligned along a vertical axis or along a diagonal axis. Four filaments can be aligned along a vertical axis or a diagonal axis. Four filaments can be aligned in a cross-shaped configuration, with one filament disposed at the top of the second elongate member, one filament disposed at the bottom of the second elongate member (near the tube lumen), and two filaments disposed on opposite arms of a "T," "Y," or triangle base.

Figure 40H:
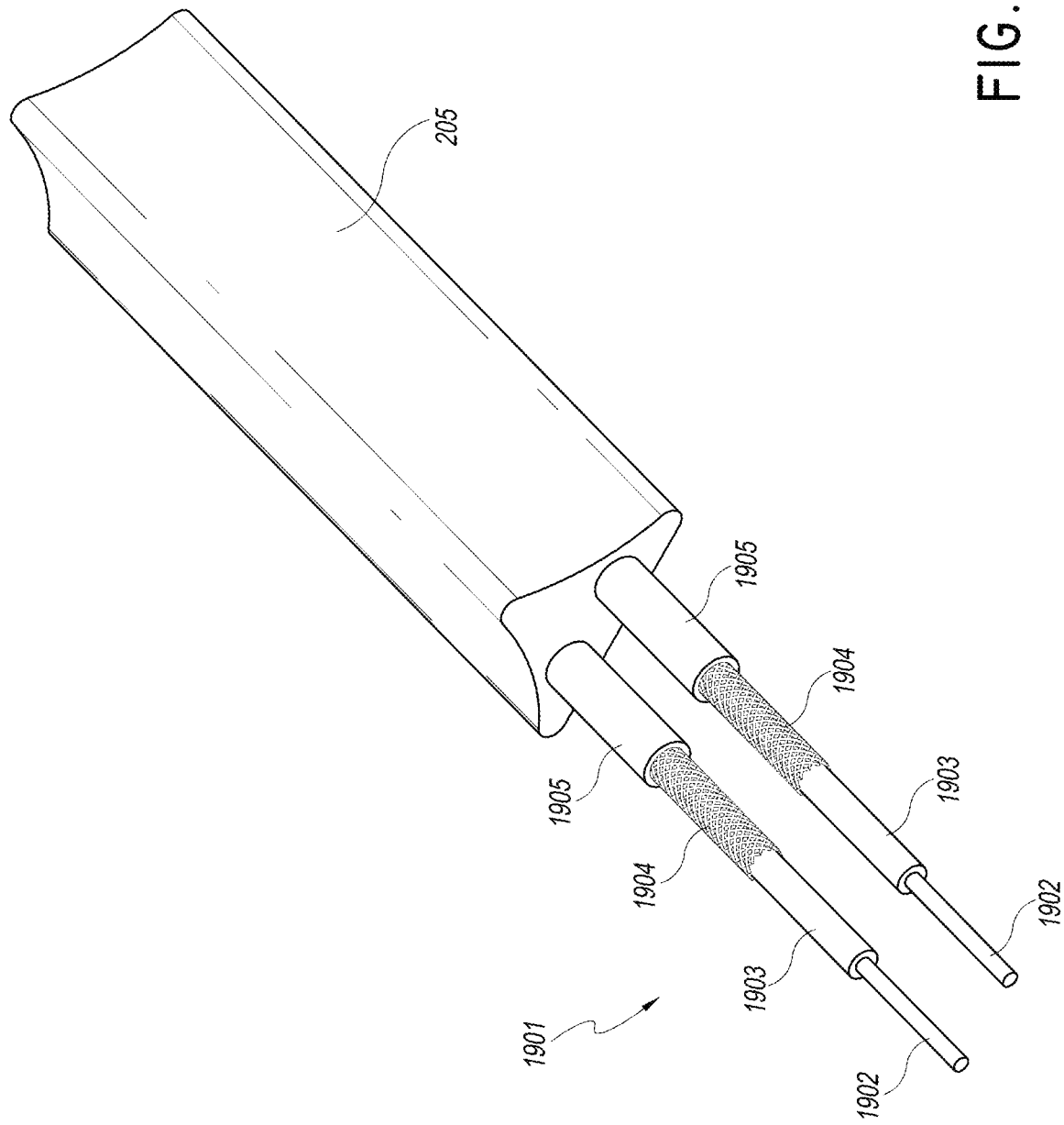
FIG. 40H shows an alternative embodiment of the second elongate member.

Referring now to FIG. 40H, an alternative embodiment of the second elongate member 205 is shown. The second elongate member 205 comprises one or more coaxial cables 1901 having a conductor 1902 surrounded by an insulation layer 1903, a shield layer 1904, and a sheath layer 1905. In certain embodiments, one or more of cables 1901 can be a multi-axial cable, that is, have multiple conductors 1902 arranged within the insulation layer 1903. In this manner, a single assembly containing multiple wires (including heater wires and/or sensor wires) can be used in the second elongate member 205, thereby simplifying assembly and providing some shielding (via the shield layer 1904) from RF interference and the like.

In some embodiments, one or more data transmission cables can be included in the second elongate member 205. The data transmission cables can comprise fiber optic cables. In at least one embodiment, a single fiber optic cable is included in the second elongate member 205 and used in a passive mode. In a passive mode, at a first end of the cable, a light source and a light sensor are provided. At a second end, a reflector is provided. In use, the light source provides a quantity of light having certain properties towards the reflector. The reflector then reflects the light towards the light sensor, which can analyze the reflected light to determine the properties of the light. The reflector can be adapted to change the property of the reflected light depending on a property of the system. For example, the reflector can be used to monitor condensation within the interface. The reflector can comprise a material which, for example, changes color depending on the presence of condensation at the second end. The reflector can alternatively or additionally include a material which changes color or the like depending on the level of humidity (either relative humidity or absolute humidity) and/or the temperature of gas at the second end.

TABLES 2A and 2B show some example dimensions of medical tubes described herein, as well as some ranges for these dimensions. The dimensions refer to a transverse cross-section of a tube. In these tables, lumen diameter represents the inner diameter of a tube. Pitch represents the distance between two repeating points measured axially along the tube, namely, the distance between the tip of the vertical portions of adjacent "T"s of the second elongate member. Bubble width represents the width (maximum outer diameter) of a bubble. Bubble height represents the height of a bubble from the tube lumen. Bead height represents the maximum height of the second elongate member from the tube lumen (e.g., the height of the vertical portion of the "T"). Bead width represents the maximum width of the second elongate member (e.g., the width of the horizontal portion of the "T"). Bubble thickness represents the thickness of the bubble wall.

TABLE 2A

| Feature | Infant Dimension (mm) | Infant Range (±) | Adult Dimension (mm) | Adult Range (±) |
|---|---|---|---|---|
| Lumen diameter | 11 | 1 | 18 | 5 |
| Pitch | 4.8 | 1 | 7.5 | 2 |
| Bubble width | 4.2 | 1 | 7 | 1 |
| Bead width | 2.15 | 1 | 2.4 | 1 |
| Bubble height | 2.8 | 1 | 3.5 | 0.5 |
| Bead height | 0.9 | 0.5 | 1.5 | 0.5 |
| Bubble thickness | 0.4 | 0.35 | 0.2 | 0.15 |

TABLE 2B

| Feature | Infant Dimension (mm) | Infant Range (±) | Adult Dimension (mm) | Adult Range (±) |
|---|---|---|---|---|
| Lumen diameter | 11 | 1 | 18 | 5 |
| Pitch | 4.8 | 1 | 7.5 | 2 |
| Bubble width | 4.2 | 1 | 7 | 1 |
| Bead width | 2.15 | 1 | 3.4 | 1 |
| Bubble height | 2.8 | 1 | 4.0 | 0.5 |
| Bead height | 0.9 | 0.5 | 1.7 | 0.5 |
| Bubble thickness | 0.4 | 0.35 | 0.2 | 0.15 |

In another example embodiment, a medical tube has the approximate dimensions shown in TABLE 2C.

TABLE 2C

| Feature | Dimension (mm) | Range (+/−) |
|---|---|---|
| Pitch | 5.1 | 3.0 |
| Bubble width | 5.5 | 2.0 |
| Bubble height | 3.2 | 2.0 |
| Bubble thickness on top, farthest from lumen (outer wall thickness) | 0.24 | +0.20/−0.10 |
| Bubble thickness adjacent lumen (inner wall thickness) | 0.10 | +0.20/−0.05 |
| Outer diameter of tube | 22.5 | 3.0 |
| Inner diameter of tube | 17.2 | 4.0 |

The dimensions shown in TABLE 2C can be particularly advantageous for obstructive sleep apnea (OSA) applications. Compared to conduits used in respiratory care, conduits used in OSA applications desirably are more flexible, have a smaller outer diameter, have less weight, and are quieter and less tacky to the touch.

In order to improve flexibility, the conduit can be formed to have a reduced pitch. In some configurations, the first elongate member can be formed into a conduit having a pitch of between about 2 mm and about 8 mm. In some configurations, the conduit can have a pitch of between about 4.5 mm to about 5.6 mm. In some configurations, the conduit can have a pitch of about 5.1 mm. In some configurations, the conduit can incorporate a heater, have an internal diameter of about 17 mm and have a length of about 72 inches (183 cm) while including a pitch of between about 5 and 5.1 mm. In such configurations, the resistance of the heater, which is a function of the length of the first elongate member (and the second elongate member that contains the heater and that is positioned alongside the first elongate member), can have an acceptable level of resistance for use with a CPAP or otherwise within the OSA field. In some configurations, the first elongate member can be formed into a conduit and, as such, the first elongate member has a portion having a first thickness that defines a lumen within the conduit and a second portion having a second thickness that defines at least a portion of the outer surface of the conduit. In some such configurations, the first thickness is less than the second thickness. Surprisingly, when the first thickness is less than the second thickness, the conduit exhibits more flexibility as compared to simply reducing the thickness throughout the first elongate member. In some such configurations, the first thickness is about 0.16 mm and the second thickness is about 0.22 mm. In some configurations, the conduit can incorporate a heater, have an internal diameter of about 17 mm and have a length of about 72 inches (183 cm) while having a weight of between about 85 grams and about 90 grams.

In order to make the conduit quieter as it is moved or dragged along a surface, the first elongate member can be formed to have a reduced wall thickness and the wall can be soft and deformable. In some configurations, the first elongate member can be formed to have a wall thickness of between about 0.05 mm and about 44 mm. In some configurations, the first elongate member can be formed to have a wall thickness of between about 0.13 mm and about 0.44 mm. In some configurations, the first elongate member can be formed to have a wall thickness of between about 0.13 mm and about 0.26 mm. In some configurations, the first elongate member can be formed to have a wall thickness of between about 0.16 mm and about 0.24 mm. In some configurations, the first elongate member can be formed to have a wall thickness of between about 0.17 mm and about 0.225 mm. Forming the elongate member with a reduced thickness also has the effect of reducing the overall weight of the conduit.

In order to reduce the size of the conduit, the diameter can be reduced while maintaining a sufficient diameter to reduce the likelihood of an unacceptable pressure drop. In some configurations, the internal diameter can be between about 13 mm and about 22 mm. In some configurations, the internal diameter can be between about 16 mm and about 19 mm. In some configurations, the conduit can have an outer diameter of about 22.5 mm. In some configurations, the conduit can have an outer diameter of about 22.5 mm, an internal diameter of about 17.2 mm and a length of about 72 inches (183 cm). Such a configuration results in a suitable pressure drop of the length of the conduit while providing a desired reduction in size to the conduit while having a conduit with a bubble extending around an outer periphery of the conduit, which otherwise would result in an undesired increase in size when compared to standard corrugated tubing.

In order to provide a desired tactile experience, the conduit desirably has an improved surface texture. Surprisingly, the improvement to the surface texture also has resulted in a quieter conduit in use. In some configurations, the first elongate member can be formed from an extrudate that includes an antiblocking additive. The antiblocking additive, as discussed above, can reduce sticking between layers of the conduit, which has been discovered to help in reducing noise levels associated with the conduit (e.g., when dragging the conduit over a corner of furniture or the like). In some configurations, the first elongate member can be formed from an extrudate that includes talc. In some configurations, the first elongate member can be formed from an extrudate that includes between about 1.5 weight percent and about 10 weight percent talc. In some configurations, the first elongate member can be formed from an extrudate that includes between about 1.5 weight percent and about 3 weight percent talc. In some configurations, the first elongate member can be formed from an extrude that includes about 1.5 weight percent talc.

TABLES 3A and 3B provide example ratios between the dimensions of tube features for the tubes described in TABLES 2A and 2B respectively.

TABLE 3A

| Ratios | Infant | Adult |
| --- | --- | --- |
| Lumen diameter:Pitch | 2.3:1 | 2.4:1 |
| Pitch:Bubble width | 1.1:1 | 1.1:1 |
| Pitch:Bead width | 2.2:1 | 3.1:1 |
| Bubble width:Bead width | 2.0:1 | 2.9:1 |
| Lumen diameter:Bubble height | 3.9:1 | 5.1:1 |
| Lumen diameter:Bead height | 12.2:1 | 12.0:1 |

TABLE 3A-continued

| Ratios | Infant | Adult |
| --- | --- | --- |
| Bubble height:Bead height | 3.1:1 | 2.3:1 |
| Lumen diameter:Bubble thickness | 27.5:1 | 90.0:1 |

TABLE 3B

| Ratios | Infant | Adult |
| --- | --- | --- |
| Lumen diameter:Pitch | 2.3:1 | 2.4:1 |
| Pitch:Bubble width | 1.1:1 | 1.1:1 |
| Pitch:Bead width | 2.2:1 | 2.2:1 |
| Bubble width:Bead width | 2.0:1 | 2.1:1 |
| Lumen diameter:Bubble height | 3.9:1 | 4.5:1 |
| Lumen diameter:Bead height | 12.2:1 | 10.6:1 |
| Bubble height:Bead height | 3.1:1 | 2.4:1 |
| Lumen diameter:Bubble thickness | 27.5:1 | 90.0:1 |

The following tables show some example properties of a composite tube (labeled "A"), described herein, having a heating filament integrated inside the second elongate member. For comparison, properties of a Fisher & Paykel model RT100 disposable corrugated tube (labeled "B") having a heating filament helically wound inside the bore of the tube are also presented.

Measurement of resistance to flow (RTF) was carried out according to Annex A of ISO 5367:2000(E). The results are summarized in TABLE 4. As seen below, the RTF for the composite tube is lower than the RTF for the model RT100 tube.

TABLE 4

| | RTF (cm H$_2$O) | | | |
| --- | --- | --- | --- | --- |
| Flow rate (L/min) | 3 | 20 | 40 | 60 |
| A | 0 | 0.05 | 0.18 | 0.38 |
| B | 0 | 0.28 | 0.93 | 1.99 |

Condensate or "rainout" within the tube refers to the weight of condensate collected per day at 20 L/min gas flow rate and room temperature of 18° C. Humidified air is flowed through the tube continuously from a chamber. The tube weights are recorded before and after each day of testing. Three consecutive tests are carried out with the tube being dried in between each test. The results are shown below in TABLE 5. The results showed that rainout is significantly lower in the composite tube than in the model RT100 tube.

TABLE 5

| | Tube | | | | | |
| --- | --- | --- | --- | --- | --- | --- |
| | A (Day 1) | A (Day 2) | A (Day 3) | B (Day 1) | B (Day 2) | B (day 3) |
| Weight before (g) | 136.20 | 136.70 | 136.70 | 111.00 | 111.10 | 111.10 |
| Weight after (g) | 139.90 | 140.00 | 139.20 | 190.20 | 178.80 | 167.10 |
| Condensate weight (g) | 3.7 | 3.3 | 2.5 | 79.20 | 67.70 | 56.00 |

The power requirement refers to the power consumed during the condensate test. In this test, the ambient air was held at 18° C. Humidification chambers, such as humidification chamber 46 in FIG. 1, were powered by MR850 heater bases. The heating filaments in the tubes were powered independently from a DC power supply. Different flow rates were set and the chamber was left to settle to 37° C. at the chamber output. Then, the DC voltage to the circuits was altered to produce a temperature of 40° C. at the circuit output. The voltage required to maintain the output temperature was recorded and the resulting power calculated. The results are shown in TABLE 6. The results show that composite Tube A uses significantly more power than Tube B. This is because Tube B uses a helical heating filament in the tube bore to heat the gas from 37° C. to 40° C. The composite tube does not tend to heat gas quickly because the heating filament is in the wall of the tube (embedded in the second elongate member). Instead, the composite tube is designed to maintain the gas temperature and prevent rainout by maintaining the tube bore at a temperature above the dew point of the humidified gas.

TABLE 6

| Flow rate (L/min) | 40 | 30 | 20 |
| --- | --- | --- | --- |
| Tube A, power required (W) | 46.8 | 38.5 | 37.8 |
| Tube B, power required (W) | 28.0 | 27.5 | 26.8 |

Tube flexibility was tested by using a three-point bend test. Tubes were placed in a three point bend test jig and used along with an Instron 5560 Test System instrument, to measure load and extension. Each tube sample was tested three times; measuring the extension of the tube against the applied load, to obtain average respective stiffness constants. The average stiffness constants for Tube A and Tube B are reproduced in TABLE 7.

TABLE 7

| Tube | Stiffness (N/mm) |
| --- | --- |
| A | 0.028 |
| B | 0.088 |

Methods of Manufacture

Reference is next made to FIGS. 41A through 41F which demonstrate example methods for manufacturing composite tubes.

Figure 41A:
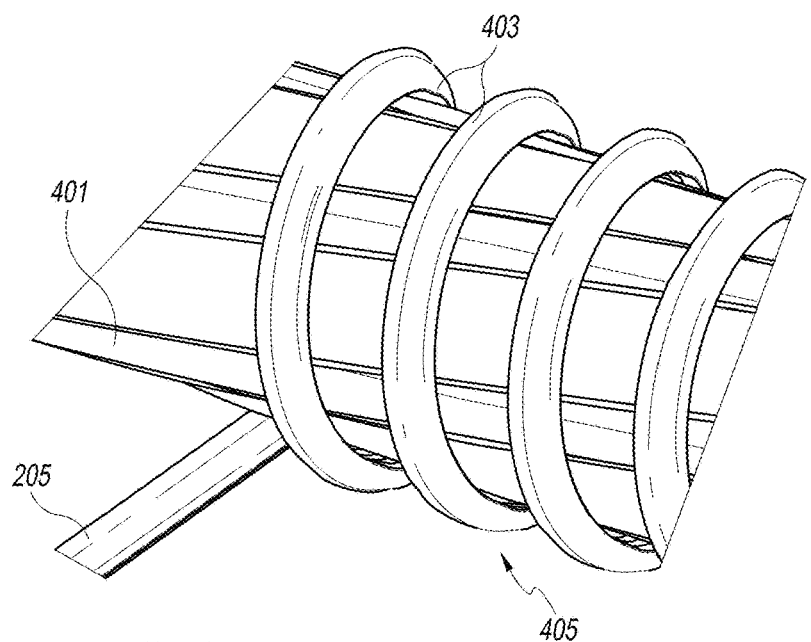
FIG. 41A shows an aspect in a method for forming the composite tube.

Turning first to FIG. 41A, in at least one embodiment, a method of manufacturing a composite tube comprises providing the second elongate member 205 and spirally wrapping the second elongate member 205 around a mandrel 401 with opposite side edge portions 403 of the second elongate member 205 being spaced apart on adjacent wraps, thereby forming a second-elongate-member spiral 405. The second elongate member 205 may be directly wrapped around the mandrel in certain embodiments. In other embodiments, a sacrificial layer may be provided over the mandrel.

In at least one embodiment, the method further comprises forming the second elongate member 205. Extrusion is a suitable method for forming the second elongate member 205. The second extruder can be configured to extrude the second elongate member 205 with a specified bead height. Thus, in at least one embodiment, the method comprises extruding the second elongate member 205.

Figure 41B:
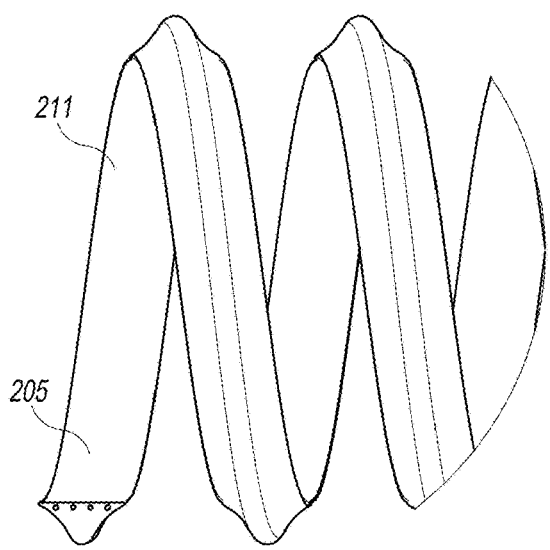
FIG. 41B shows a spiral-wound second elongate member.

As shown in FIG. 41B, extrusion can be advantageous because it can allow heating filaments 215 to be encapsulated in the second elongate member 205 as the second elongate member is formed 205, for example, using an extruder having a cross-head extrusion die. Thus, in certain embodiments, the method comprises providing one or more heating filaments 215 and encapsulated the heating filaments 215 to form the second elongate member 205. The method can also comprise providing a second elongate member 205 having one or more heating filaments 215 embedded or encapsulated in the second elongate member 205.

Figure 41C:
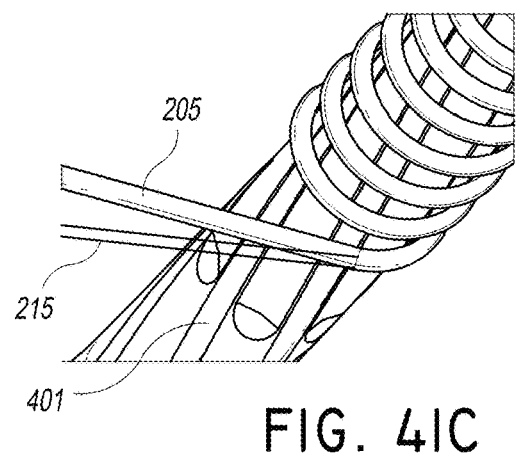
FIG. 41C shows another aspect in a method for forming the composite tube.
Figure 4I:
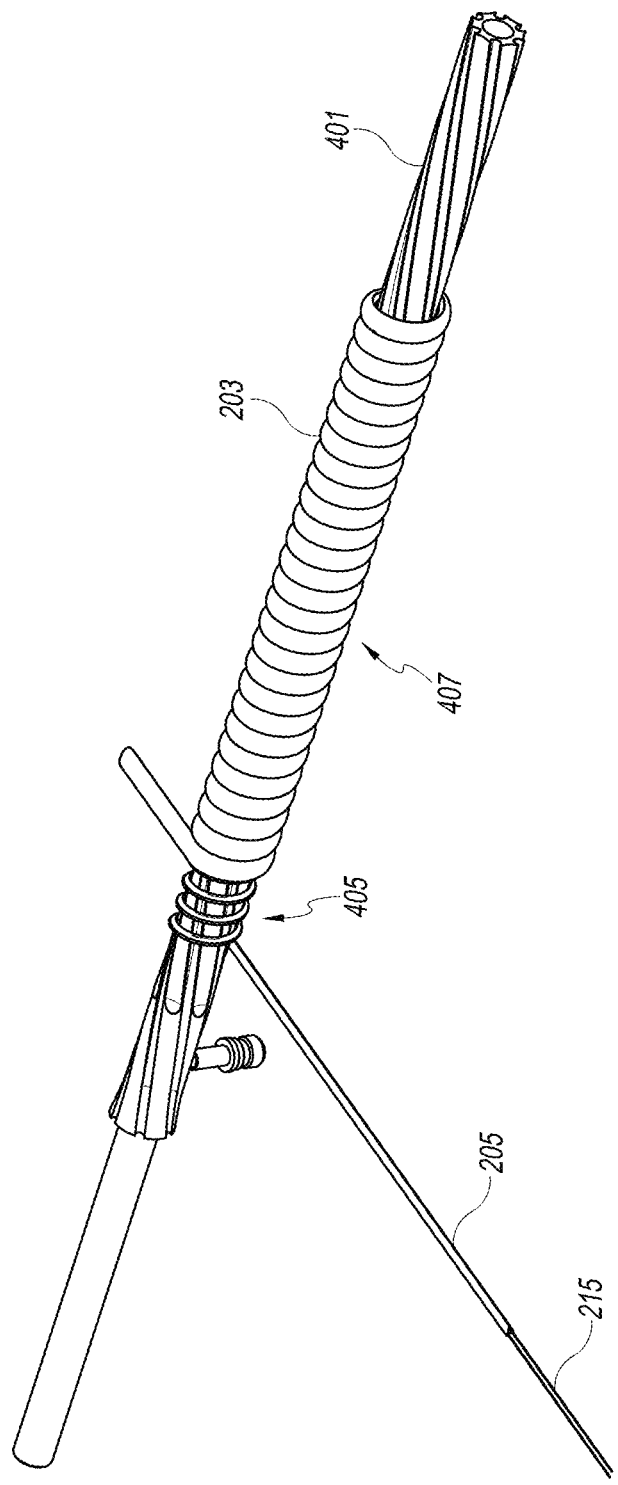
Figure 4I:
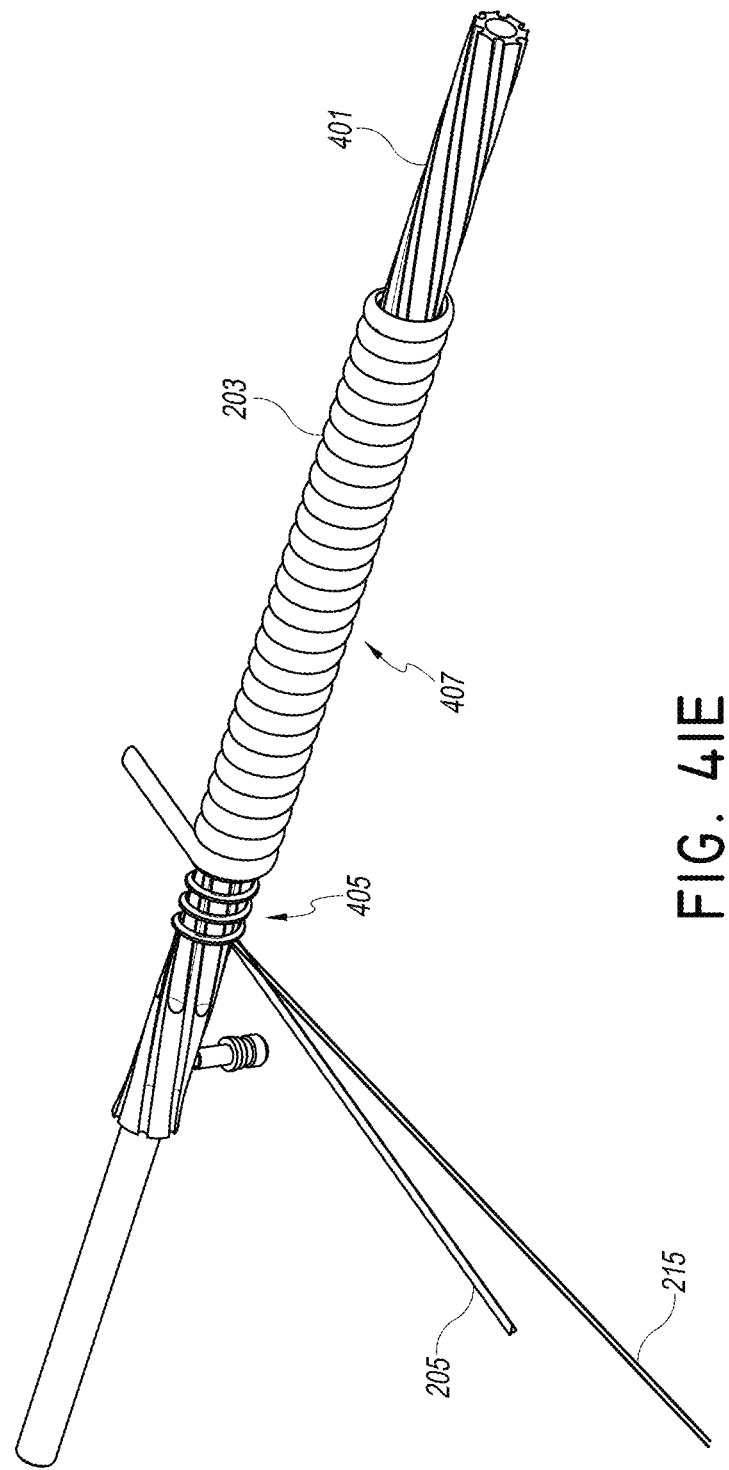
Figure 4I:
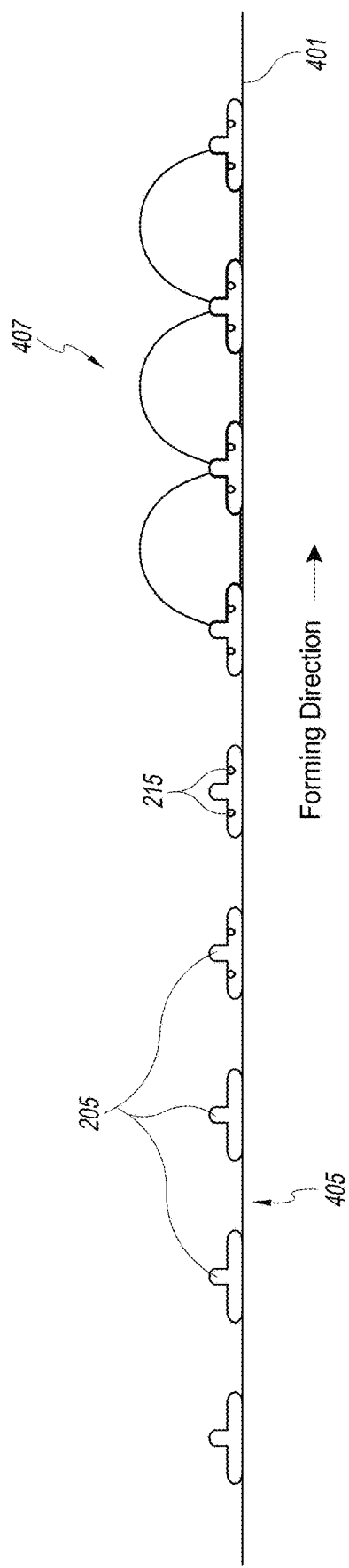

In at least one embodiment, the method comprises embedding one or more filaments 215 in the second elongate member 205. For example, as shown in FIG. 41C, filaments 215 can be pressed (pulled or mechanically positioned) into the second elongate member 205 to a specified depth. Alternatively, cuts can be made in the second elongate member 205 to a specified depth, and the filaments 215 can be placed into the cuts. Preferably, pressing or cutting is done shortly after the second elongate member 205 is extruded and the second elongate member 205 is soft.

As shown in FIGS. 41D and 41E, in at least one embodiment, the method comprises providing the first elongate member 203 and spirally wrapping the first elongate member 203 around the second-elongate-member spiral 405, such that portions of the first elongate member 203 overlap adjacent wraps of the second-elongate-member spiral 405 and a portion of the first elongate member 203 is disposed adjacent the mandrel 401 in the space between the wraps of the second-elongate-member spiral 405, thereby forming a first-elongate-member spiral 407. FIG. 41D shows such an example method, in which heating filaments 215 are encapsulated in the second elongate member 205, prior to forming the second-elongate-member spiral. FIG. 41E shows such an example method, in which heating filaments 215 are embedded in the second elongate member 205, as the second-elongate-member spiral is formed. An alternative method of incorporating filaments 215 into the composite tube comprises encapsulating one or more filaments 215 between the first elongate member 203 and the second elongate member 205 at a region where the first elongate member 203 overlaps the second elongate member 205.

As discussed above, at least one embodiment comprises a tube having multiple wraps of the first elongate member 203 between wraps of the second elongate member 205. Accordingly, in certain embodiments, the method comprises providing the first elongate member 203 and spirally wrapping the first elongate member 203 around the second-elongate-member spiral 405, such that a first side portion of the first elongate member 203 overlaps a wrap of the second-elongate-member spiral 405 and a second side portion of the first elongate member 203 contacts an adjacent side portion of the first elongate member 203. A portion of the first elongate member 203 is disposed adjacent the mandrel 401 in the space between the wraps of the second-elongate-member spiral 405, thereby forming a first-elongate-member spiral 407 comprising multiple wraps of the first elongate member 203 between wraps of the second elongate member 205.

Figure 41G:
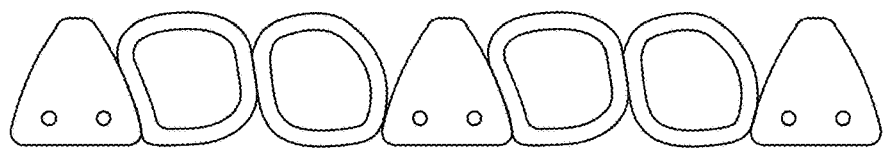
FIGS. 41G-41I show example configurations of longitudinal cross sections of tubes.

In at least one embodiment, the first elongate member 203 is wrapped multiple times between winds of the second elongate member 205. An example schematic of the resulting longitudinal cross-section is shown in FIG. 41G. Adjacent wraps of the first elongate member 203 can be fused using any suitable technique, such as heat fusing, adhesive, or other attachment mechanism. In at least one embodiment, adjacent molten or softened bubbles can be touched together and thereby bonded while hot and subsequently cooled with an air jet. Adjacent wraps of the first elongate member 203 can also be joined by winding them on the mandrel in a softened state and allowing them to cool.

Figure 41H:
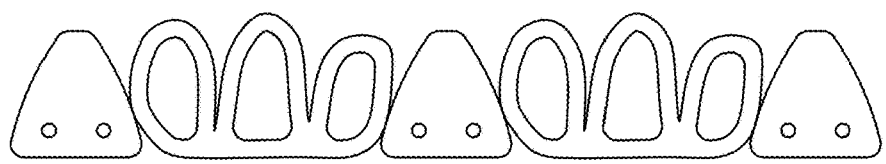
Figure 41I:
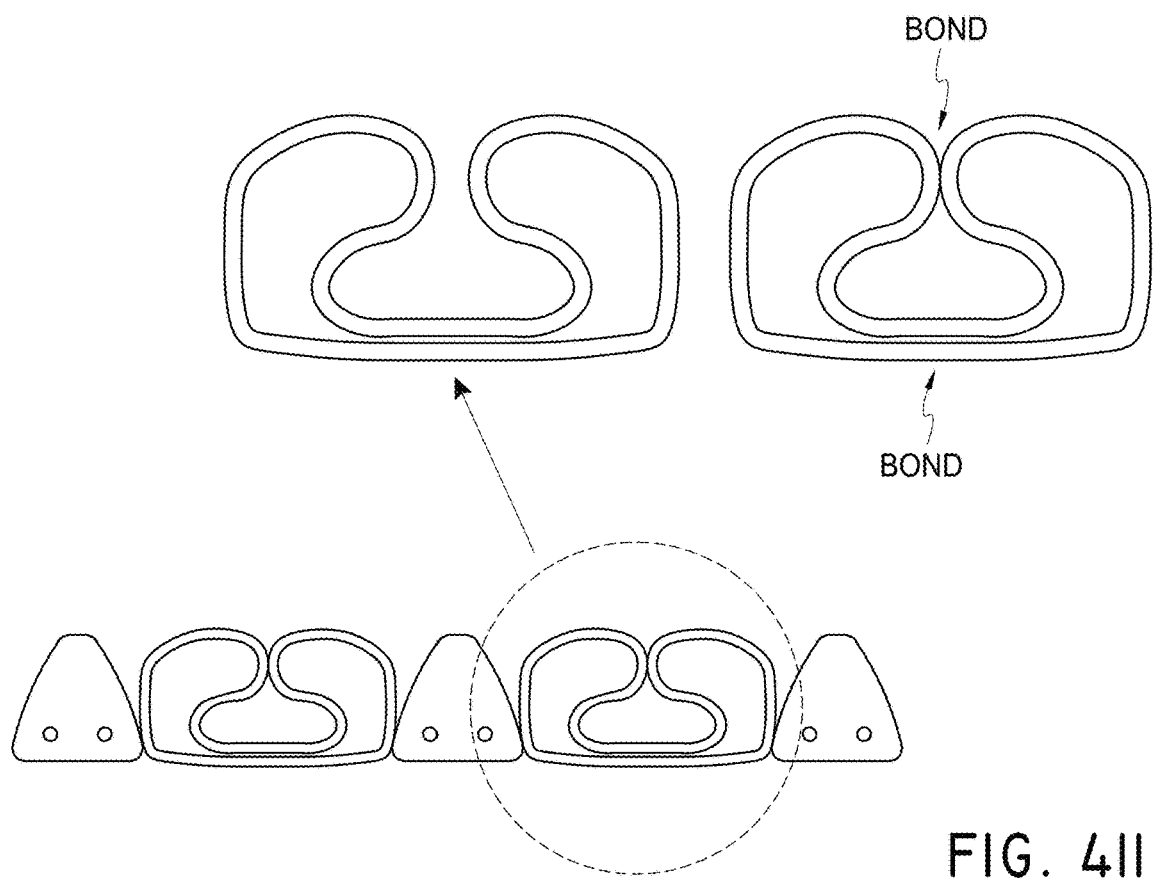

In at least one embodiment, the first elongate member 203 is wrapped a single time or multiple times between winds of the second elongate member 205, and the bubble or bubbles between winds of the second elongate member 205 are further collapsed into additional discrete bubbles using an appropriate technique such as a heat treatment. An example schematic of the resulting longitudinal cross-section is shown in FIG. 41H. As shown in FIG. 41H, one bubble of the first elongate member 203 can be collapsed into two or three or more discrete bubbles using any suitable technique, such as application of a mechanical force with an object or application of a force with a directed air jet. Another example schematic of a resulting longitudinal cross-section is shown in FIG. 41I. In this example, a center portion of a bubble is collapsed such that the top of the bubble is bonded to the bottom of the bubble to form two discrete bubbles separated by a flat bottom portion. Then, adjacent side portions of the two discrete bubbles are bonded to form a structure comprising three discrete bubbles.

The above-described alternatives for incorporating one or more heating filaments 215 into a composite tube have advantages over the alternative of having heating filaments in the gas path. Having the heating filament(s) 215 out of the gas path improves performance because the filaments heat the tube wall where the condensation is most likely to form. This configuration reduces fire risk in high oxygen environments by moving the heating filament out of the gas path. This feature also reduces performance as it reduces the heating wires effectiveness at heating the gases that are passing through the tube. Nevertheless, in certain embodiments, a composite tube 201 comprises one or more heating filaments 215 placed within the gas path. For example, heating filaments can be emplaced on the lumen wall (tube bore), for example, in a spiral configuration. An example method for disposing one or more heating filaments 215 on the lumen wall comprises bonding, embedding, or otherwise forming a heating filament on a surface of the second elongate member 205 that, when assembled, forms the lumen wall. Thus, in certain embodiments, the method comprises disposing one or more heating filaments 215 on the lumen wall.

Regardless of whether the heating filaments 215 are embedded or encapsulated on the second elongate member 205 or disposed on the second elongate member 205, or otherwise placed in or on the tube, in at least one embodiment, pairs of filaments can be formed into a connecting loop at one end of the composite tube to form a circuit.

FIG. 41F shows a longitudinal cross-section of the assembly shown in FIG. 41E, focusing on a top portion of the mandrel 401 and a top portion of the first-elongate-member spiral 407 and second-elongate-member spiral 405. This example shows the second-elongate-member spiral 405 having a T-shaped second elongate member 205. As the second-elongate member is formed, heating filaments 215 are embedded in the second elongate member 205. The right side of FIG. 41F shows the bubble-shaped profile of the first-elongate-member spiral, as described above.

The method can also comprise forming the first elongate member 203. Extrusion is a suitable method for forming the first elongate member 203. Thus, in at least one embodiment, the method comprises extruding the first elongate member 203. The first elongate member 203 can also be manufactured by extruding two or more portions and joining them to form a single piece. As another alternative, the first elongate member 203 can also be manufactured by extruding sections that produce a hollow shape when formed or bonded adjacently on a spiral-tube forming process.

The method can also comprise supplying a gas at a pressure greater than atmospheric pressure to an end of the first elongate member 203. The gas can be air, for example. Other gases can also be used, as explained above. Supplying a gas to an end of the first elongate member 203 can help maintain an open, hollow body shape as the first elongate member 203 is wrapped around the mandrel 401. The gas can be supplied before the first elongate member 203 is wrapped around the mandrel 401, while the first elongate member 203 is wrapped around the mandrel 401, or after the first elongate member 203 is wrapped around the mandrel 401. For instance, an extruder with an extrusion die head/tip combination can supply or feed air into the hollow cavity of the first elongate member 203 as the first elongate member 203 is extruded. Thus, in at least one embodiment, the method comprises extruding the first elongate member 203 and supplying a gas at a pressure greater than atmospheric pressure to an end of the first elongate member 203 after extrusion. A pressure of 15 to 30 cm $H_2O$—(or about 15 to 30 cm $H_2O$) has been found to be suitable.

In at least one embodiment, the first elongate member 203 and the second elongate member 205 are spirally wound about the mandrel 401. For example, the first elongate member 203 and second elongate member 205 may come out of an extrusion die at an elevated temperature of 200° C. (or about 200° C.) or more and then be applied to the mandrel after a short distance. Preferably, the mandrel is cooled using a water jacket, chiller, and/or other suitable cooling method to a temperature of 20° C. (or about 20° C.) or less, e.g., approaching 0° C. (or about 0° C.). After 5 (or about 5) spiral wraps, the first elongate member 203 and second elongate member 205 are further cooled by a cooling fluid (liquid or gas). In one embodiment, the cooling fluid is air emitted from a ring with jets encircling the mandrel. After cooling and removing the components from the mandrel, a composite tube is formed having a lumen extending along a longitudinal axis and a hollow space surrounding the lumen. In such an embodiment, no adhesive or other attachment mechanism is needed to connect the first and second elongate members. Other embodiments may utilize an adhesive or other attachment mechanism to bond or otherwise connect the two members. In another embodiment, the second elongate member 205 after extrusion and placement of the heating filaments may be cooled to freeze the location of the heating filaments. The second elongate member 205 may then be re-heated when applied to the mandrel to improve bonding. Example methods for re-heating include using spot-heating devices, heated rollers, etc.

The method can also comprise formed pairs of heating or sensing filaments into a connecting loop at one end of the composite tube. For example, end sections of two heating or sensing filaments can be extricated from the second elongate member 205 and then formed into a connecting loop e.g., by tying, bonding, adhering, fusing, etc the two filaments together. As another example, end sections of the heating filaments can be left free from the second elongate member 205 during the manufacturing process and then formed into a connecting loop when the composite tube is assembled.

Figure 41J:
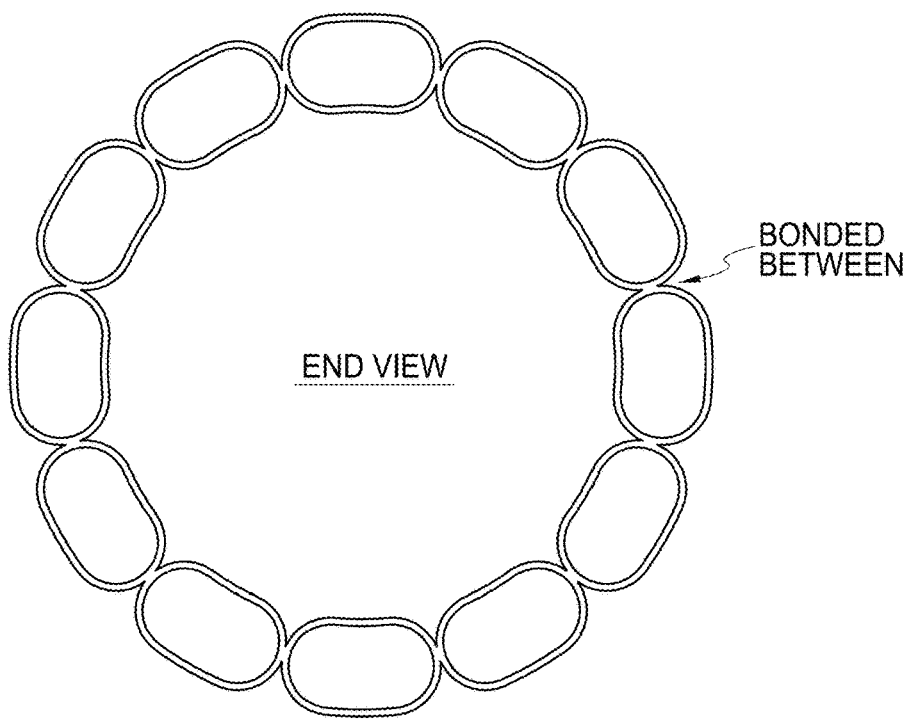
Figure 41K:
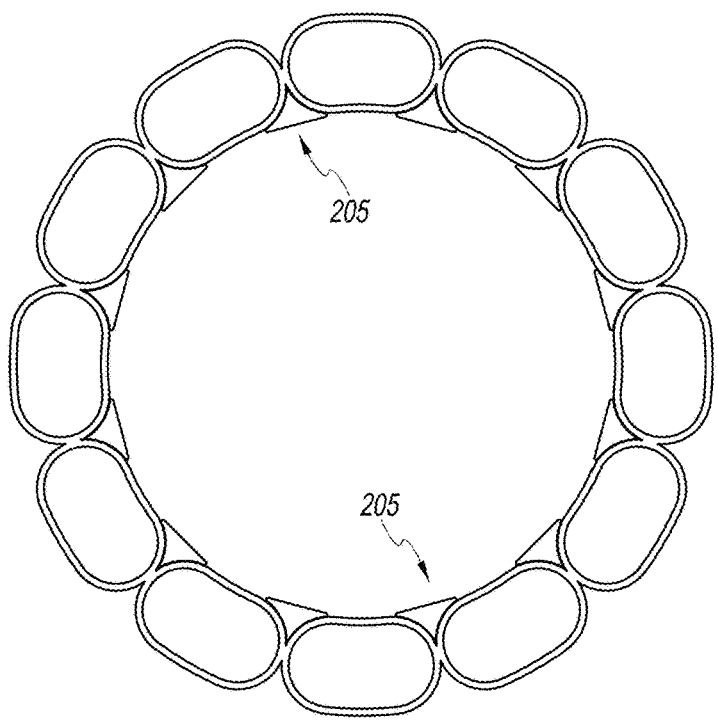
Figure 41L:
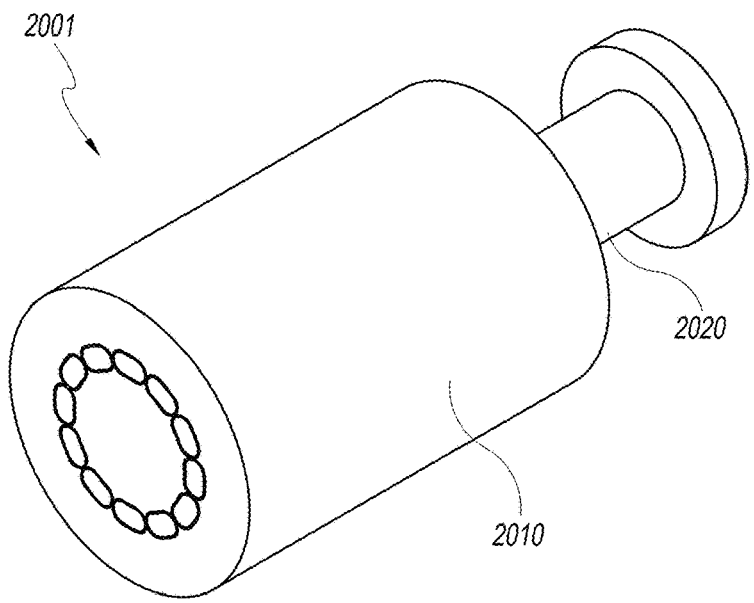
Figure 41M:
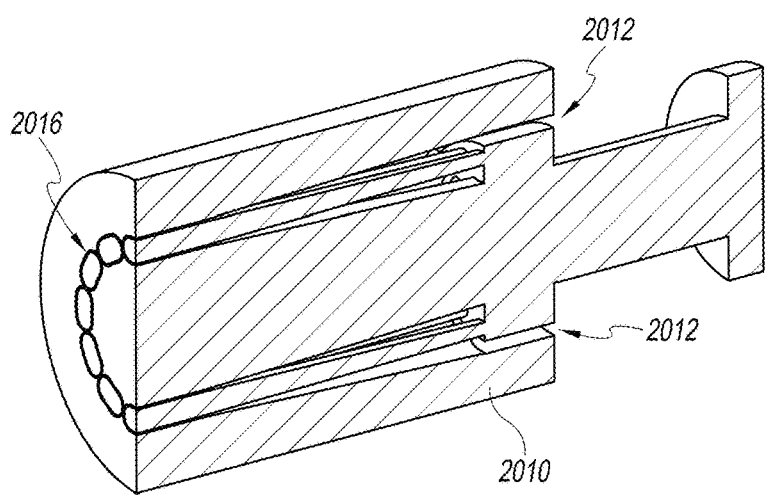
Figure 41N:
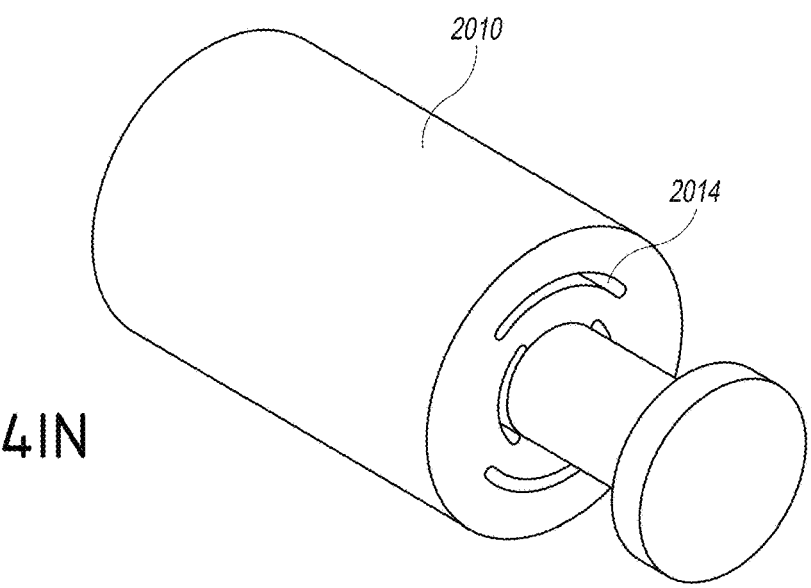
Figure 410:
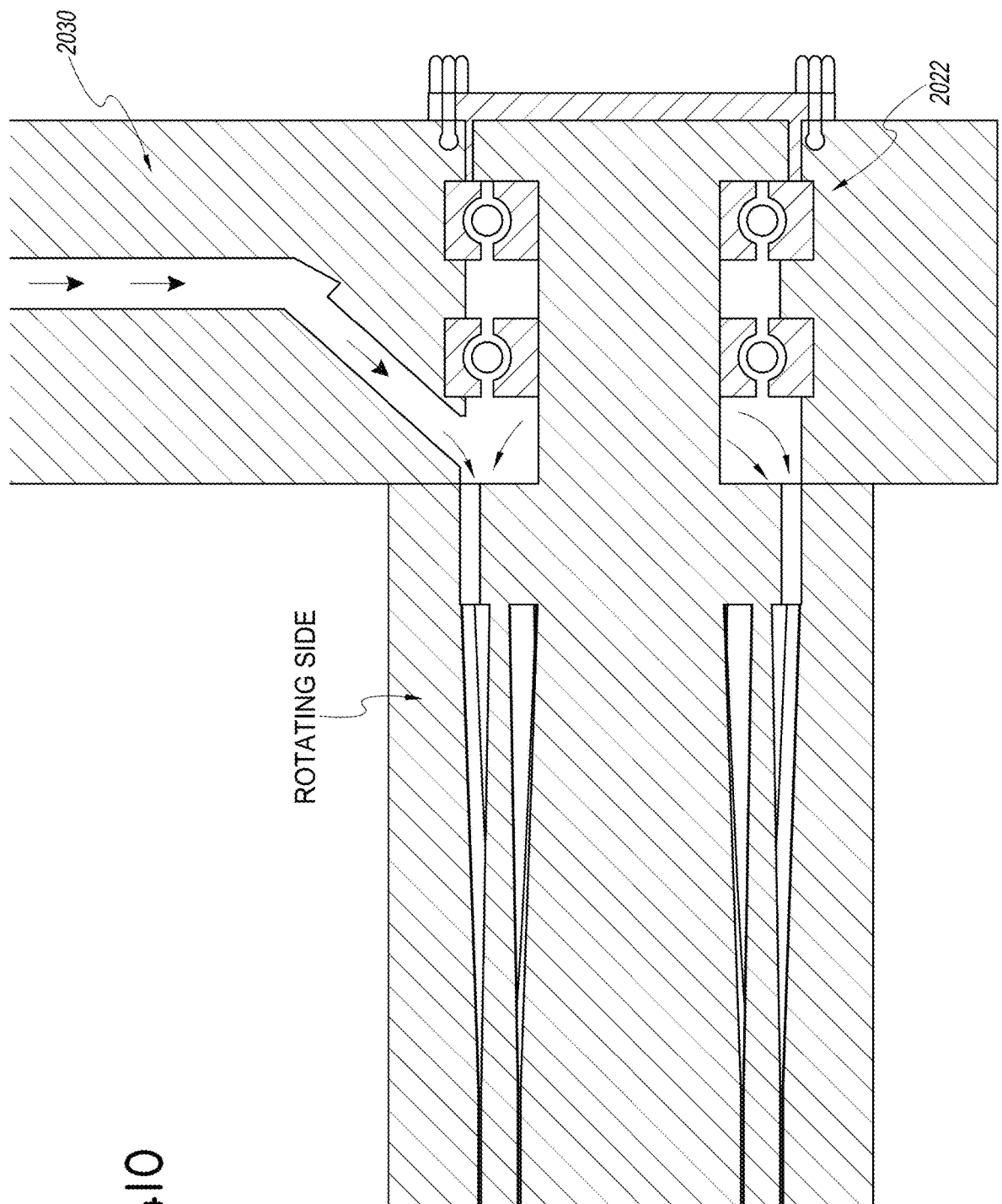
Figure 41P:
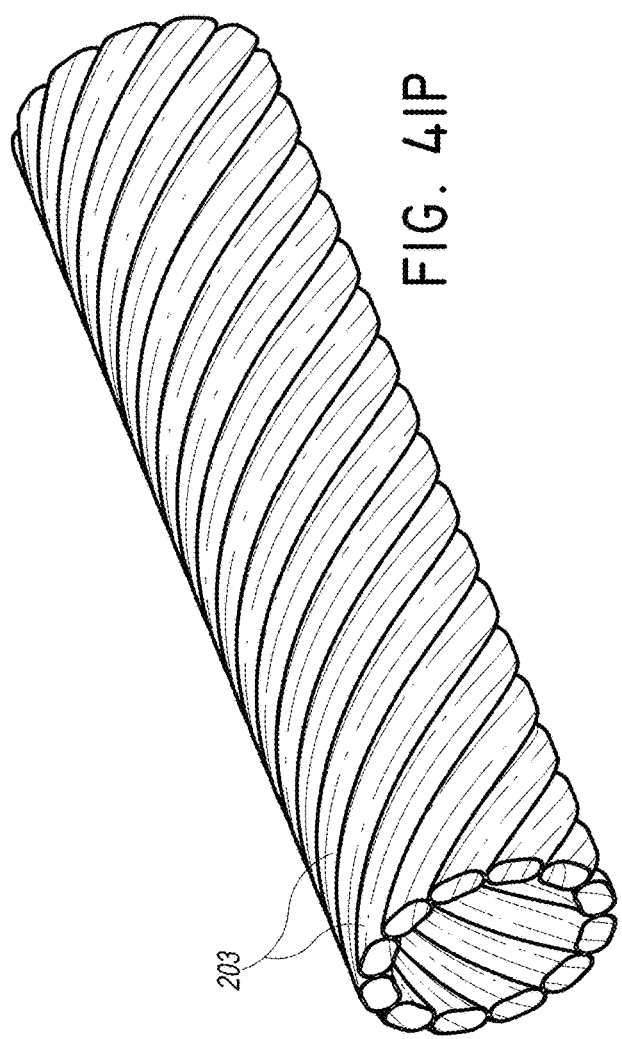
Figure 41Q:
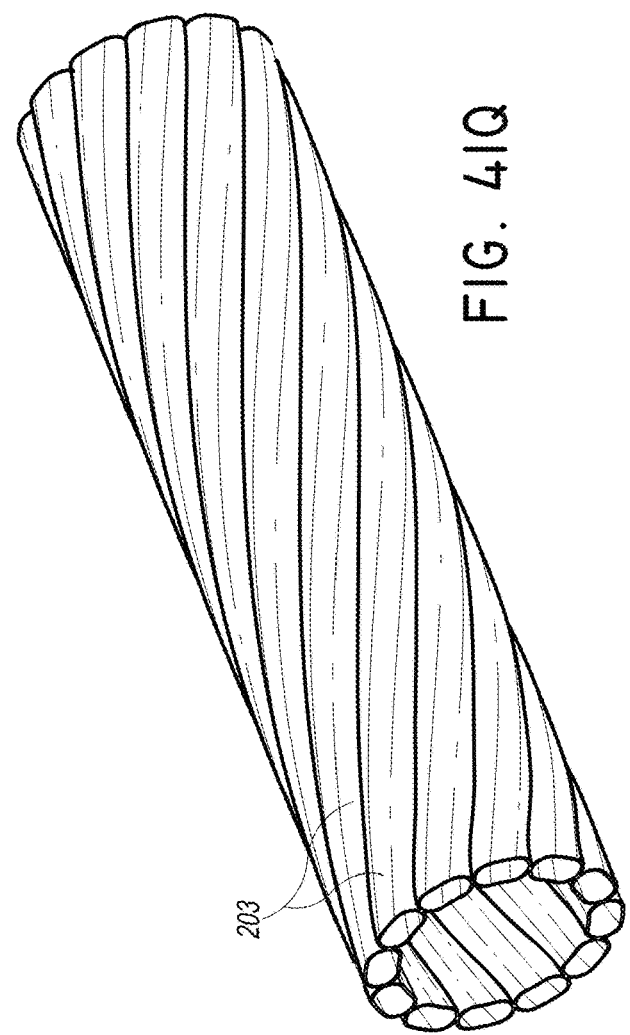

With reference now to FIGS. 41J-41Q, an alternative method of forming a tube 201 involves an extrusion tool 2001 having a series of flow paths running therealong. The extrusion tool 2001 can be used to form tubes such as the example tubes shown in FIGS. 41P and 41Q. As shown, tubes produced using the extrusion tool 2001 can include a plurality of first elongate members 203 extending generally along the longitudinal axis of the tube. In some embodiments, the extrusion tool 2001 includes a body 2010 and a central extension 2020. In some embodiments, the body 2010 and extension 2020 are generally cylindrical. The body 2010 can include one or more flow paths 2012 that allow for the passage of a molten plastic or another material through the body 2010 from an input end 2014 to an output or extrusion end 2016. In some embodiments, the flow paths have a substantially conical longitudinal cross-section (that is, are wider where the molten plastic first enters at the input 2014 and narrower near the extrusion end 2016). The flow paths can have various configurations to produce tubes 201 having various profiles. For example, the flow path configuration shown at the output or extrusion end 2016 in FIGS. 41L and 41M can produce a tube 201 having an end view profile as shown in FIG. 41J. FIG. 41K shows an end view of the tube of FIG. 41J including second elongate members 205, which may include heating filaments 215, disposed between adjacent bubbles or first elongate members 203. In use, the tool 2001 is adapted to rotate so as to induce the tube 201 to be helically formed. As shown in FIG. 41O, the central extension 2020 can couple the extrusion tool 2001 to an extruder 2030. Bearings 2022 disposed between the central extension 2020 and the extruder 2030 can allow the central extension 2020 and body 2010 to rotate relative to the extruder 2030. The rate of rotation of the tool 2001 can be adjusted to change the pitch or helix angle of the first elongate members 203. For example, a faster rate of rotation can produce a smaller helix angle, as shown in FIG. 41P. A slower rate of rotation can produce a larger helix angle, as shown in FIG. 41Q.

Medical Tubes Having a Single Spirally Wound Tube

FIGS. 42A-42F show transverse cross-sections of example embodiments of tubes comprising a single tube-shaped element having a first elongate member or portion 203 and a second elongate member or portion 205. As illustrated, the second elongate portions 205 are integral with the first elongate portions 203, and extend along the entire length of the single tube-shaped element. In the embodiments illustrated, the single tube-shaped element is an elongate hollow body having in transverse cross-section a relatively thin wall defining in part the hollow portion 501, with two reinforcement portions 205 with a relatively greater thickness or relatively greater rigidity on opposite sides of the elongate hollow body adjacent the relatively thin wall. These reinforcement portions form a portion of the inner wall of the lumen 207 after the elongate hollow body is spirally wound, such that these reinforcement portions are also spirally positioned between adjacent turns of the elongate hollow body.

In at least one embodiment, the method comprises forming an elongate hollow body comprising the first elongate portion 203 and the reinforcement portion 205. Extrusion is a suitable method for forming the elongate hollow body. Suitable cross-sectional shapes for the tube-shaped element are shown in FIGS. 42A-42F.

Figure 42A:
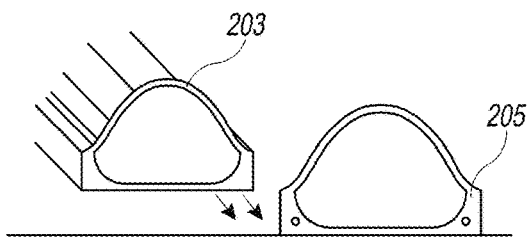
FIGS. 42A-42B show another example illustrating a single elongate hollow body being spirally wound to form a medical tube.
Figure 42B:
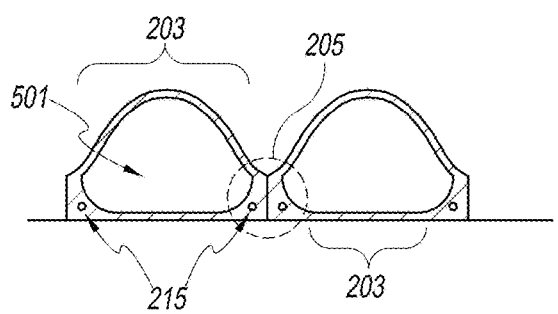
Figure 42C:
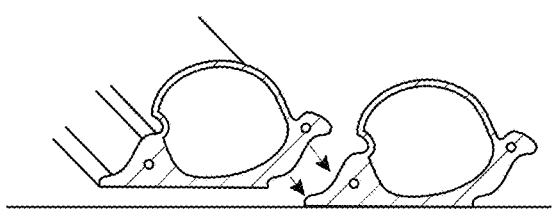
FIGS. 42C-42F show examples of other single elongate hollow bodies being spirally wound to form a medical tube.
Figure 42D:
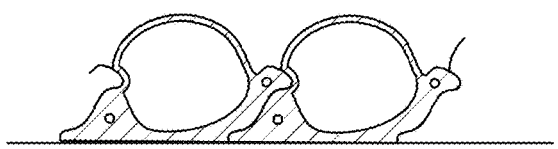
Figure 42E:
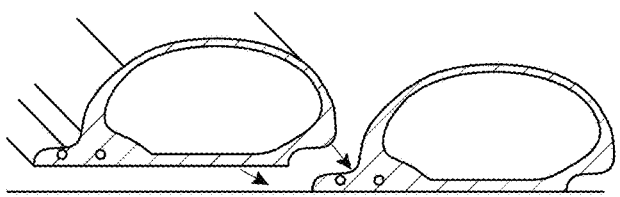
Figure 42F:
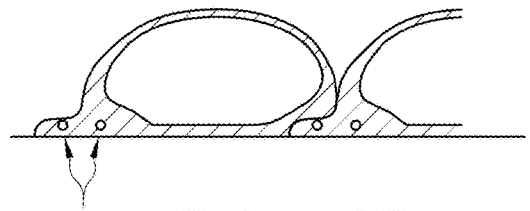

The elongate hollow body can be formed into a medical tube, as explained above, and the foregoing discussion is incorporated by this reference. For example, in at least one embodiment, a method of manufacturing a medical tube comprises spirally wrapping or winding the elongate hollow body around a mandrel. This may be done at an elevated temperature, such that the elongate hollow body is cooled after being spirally wound to join adjacent turns together As shown in FIG. 42B, opposite side edge portions of the reinforcement portions 205 can touch on adjacent turns. In other embodiments, opposite side edge portions of the second elongate member 205 can overlap on adjacent turns, as shown in FIGS. 42D and 42E. Heating filaments 215 can be incorporated into the second elongate member as explained above and as shown in FIGS. 42A through 42F. For example, heating filaments may be provided on opposite sides of the elongate hollow body such as shown in FIGS. 42A-42D. Alternatively, heating filaments may be provided on only one side of the elongate hollow body, such as shown in FIGS. 42E-42F. Any of these embodiments could also incorporate the presence of sensing filaments.

Placement of Chamber-End Connector with Electrical Connectivity

Figure 43A:
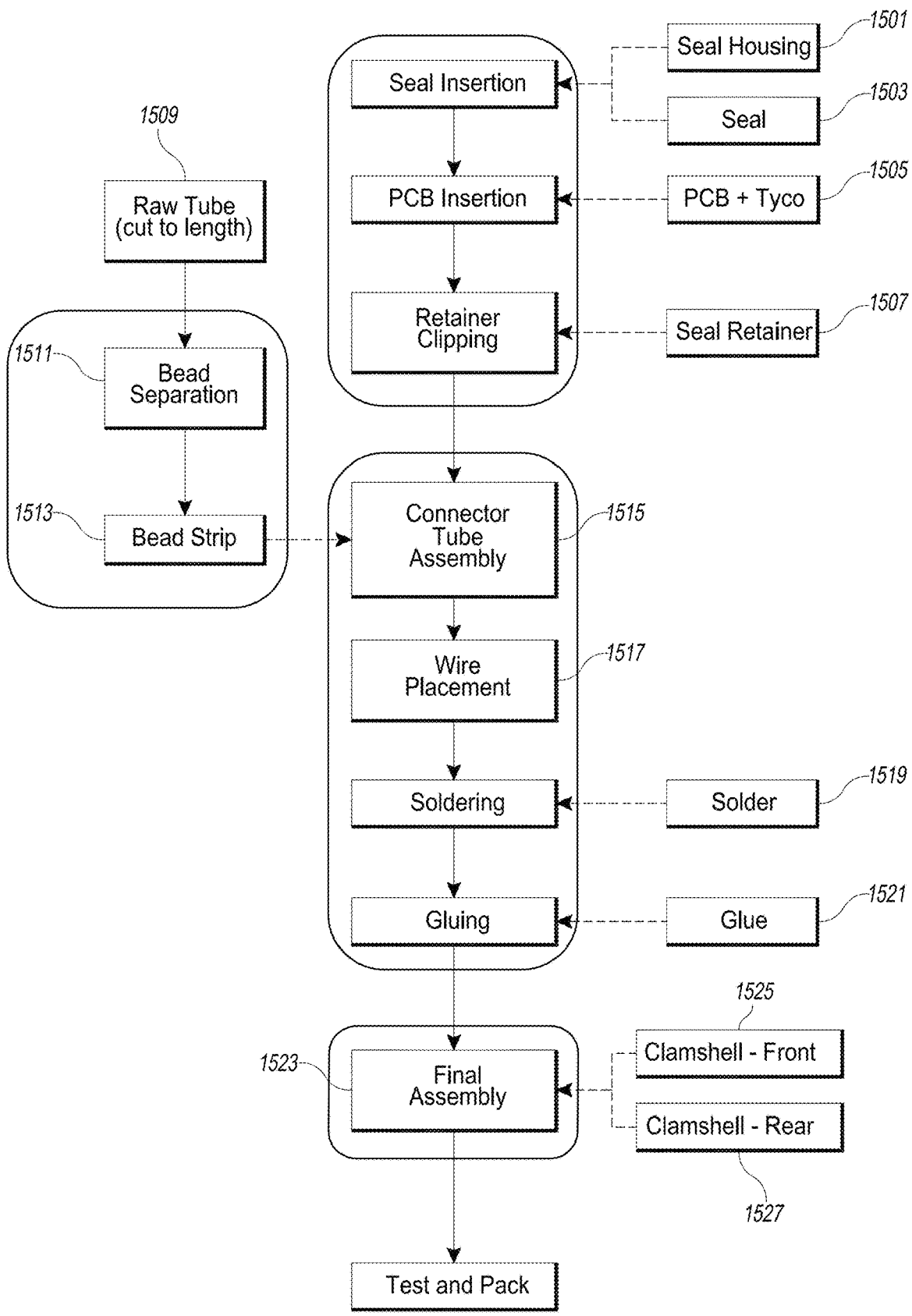

Reference is next made to FIG. 43A, which shows an example flow chart for attaching a connector to the end of the tube that is configured in use to connect to a humidifier. For example, as described above with reference to FIG. 1, the inspiratory conduit 70 connects to the humidification unit 40 via inlet 42. The example flow chart of FIG. 43A can make the inspiratory conduit 70 capable of physically and electrically connecting to the humidification unit 40.

In the example of FIG. 43A, a seal 1503 is inserted into a seal housing 1501. The act of seal insertion is also shown in greater detail in FIG. 43B. The seal housing 1501 is made of a molded plastic. One open end is sized and configured for connecting to a humidifier. The seal 1503 can be an o-ring, as shown in FIG. 43B. A suitable configuration for the o-ring can be a double-toric configuration comprising thicker concentric toruses connected by a thinner web. In this example, the o-ring is molded from a single elastomeric material, such as rubber. The seal 1503 is seated in a compliant ridge in the seal housing 1501. The seal 1503 is designed to seal against an outer surface of the port of the humidifier chamber. The seal 1503 can deflect to extend along the outer surface of the port. In other words, the double o-ring configuration includes an inner O-ring and an outer O-ring connected by a flange. The outer O-ring will be sealed within the connector while the inner O-ring can deflect along the flange portion and squeeze against the outer surface of the port. In such a position, a horizontal plane extending through a center axis of the inner O-ring may be in a different plane than a horizontal plane extending through a center axis of the outer O-ring.

Turning again to the example of FIG. 43A, a printed circuit board (PCB) is inserted into a compliant dock on the seal housing 1501. The act of PCB insertion is shown in greater detail in FIG. 43C. In FIG. 43C, an assembly 1505 comprising a PCB and a PCB connector is inserted into a compliant dock on the seal housing 1501. In this example, the PCB connector is an off-the-shelf connector sold by Tyco Electronics Corp. (Berwyn, Pa.). The PCB comprises four terminals suitable for receiving four conductive filaments encased in the second elongate member of the tube. However, the PCB can be configured to receive a suitable number of conductive filaments, if the second elongate member contains more or fewer than four conductive filaments.

Turning again to the example of FIG. 43A, a seal retainer 1507 is clipped onto one open end of the seal housing 1501 with the seal 1503 seated on the compliant ridge. Clipping the seal retainer 1507 in place compresses the seal 1503 and thereby forms a liquid- and gas-resistant connection between the seal housing 1501 and the seal retainer 1507. In this example, the seal retainer is made from a molded plastic and comprises a protruding portion sized and shaped to fit around the PCB. The protruding portion serves to support and protect the more flexible and fragile PCB. The resulting assembly comprising the seal housing 1501, seal 1503, PCB and PCB connector assembly 1505, and the seal retainer 1507 is referred to herein as a connector tube assembly 1515.

Turning again to the example of FIG. 43A, the tube is prepared for connection to the connector tube assembly 1515. As shown FIG. 43A and in greater detail in FIG. 43E, in step 1511, a portion of the second elongate member at one end of the tube is separated from the first elongate member. Then, in step 1513, a length of the separated second elongate member is stripped away to reveal four conductive filaments (or the number of conductive filaments contained in the second elongate member). Step 1513 is shown in greater detail in FIG. 43F.

As explained in FIG. 43A and as shown in greater detail in FIG. 43G, the portion of the tube with the stripped length of the second elongate member is inserted in the connector tube assembly 1515. As shown in step 1517 of FIG. 43A and FIG. 43H, the four conductive filaments are inserted in the four terminals of the PCB. Then, as shown in FIGS. 43A and 43I, a bead of solder 1519 is placed over each filament-terminal connection to secure the filament to the terminal and ensure a good electrical connection between each filament and its corresponding terminal.

To ensure that all pieces of the connector tube assembly 1515 are securely fixed to each other, a layer of glue 1521 is then applied. Glue is a broad term and refers to a material for joining, fixing, or attaching other materials. A glue can be adhesive or sticky to the touch when it is in a liquid or semi-solid state. When the glue has dried or otherwise cured into a solid state, the glue can be adhesive or non-adhesive or non-sticky to the touch. The glue can be a resin, such as an epoxy resin, or a thermoplastic elastomer (TPE). Use of TPE materials can be advantageous because they are generally flexible and can accommodate twisting, bending, or pressure without shattering.

Figure 43J:
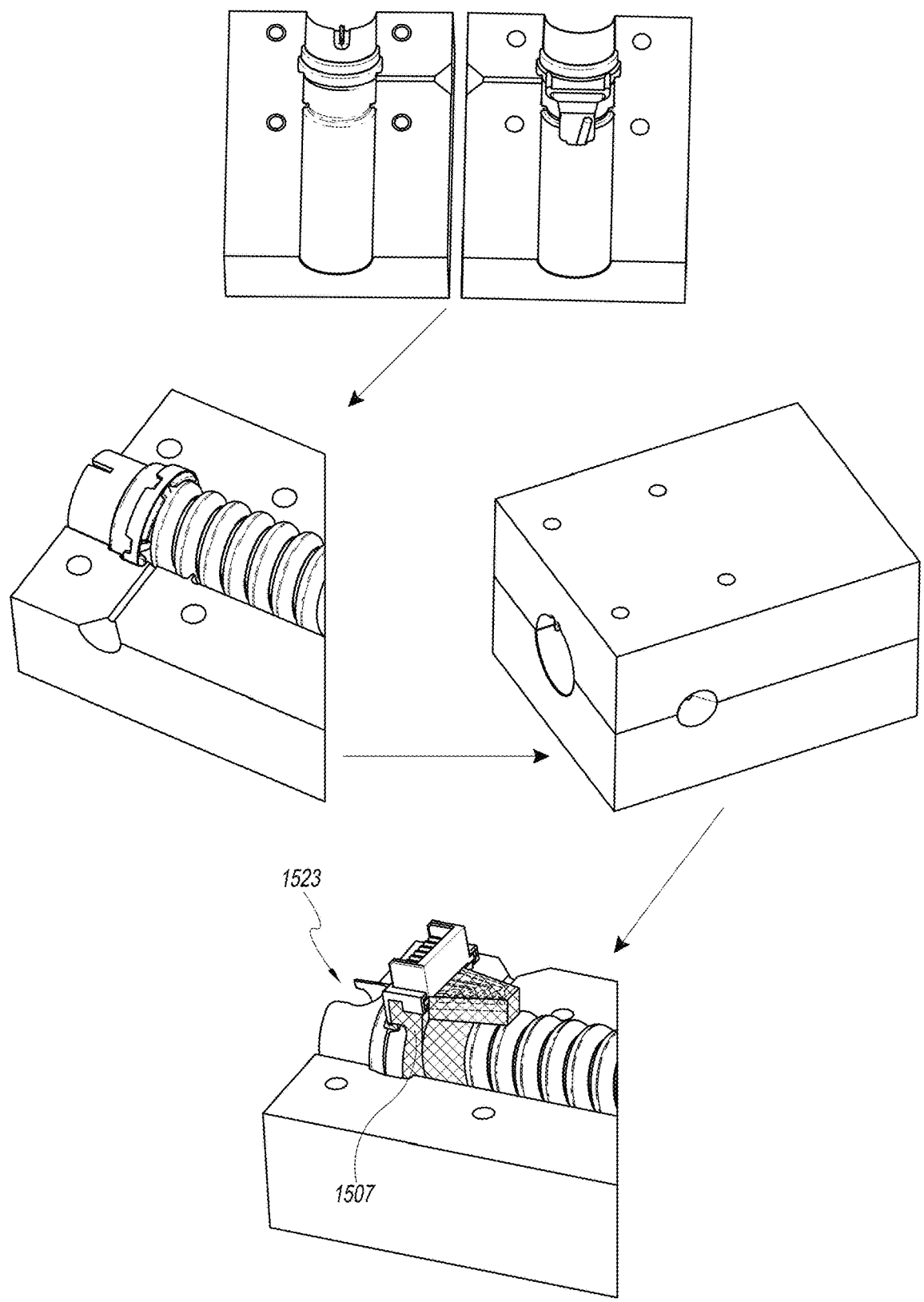

An example method for applying the glue 1521 is shown in FIG. 43J. In this method, a two-block mold is provided. In this example, the mold is stainless steel, however any suitable material can be used. For instance, the mold can be made from Teflon® PTFE blocks. One block is configured to accommodate the protruding PCB and PCB connector assembly 1505 of the connector tube assembly 1515 and the adjacent tube, and the other block is configured to accommodate the opposite portion of the tube and connector tube assembly 1515. The tube is placed in the compliant mold portions such that the blocks stack one on top of the other. A liquid glue is introduced into an inlet hole in the mold, and the glue is allowed to harden. Then, the mold is removed to expose the glued tube-and-connector assembly 1523, which includes a layer of hardened glue 1507 covering the PCB and the joint between the tube and the connector tube assembly 1515. The glue layer can cover the PCB and all of the soldered connections on the PCB. In this manner, the layer of glue can protect the PCB and the connections from corrosion. In other words, the glue serves three functions: sealing the connector and the conduit, holding the PCB in place and potting the PCB; the glue layer forms a pneumatic seal, a mechanical bond and a PCB pot.

Figure 43L:
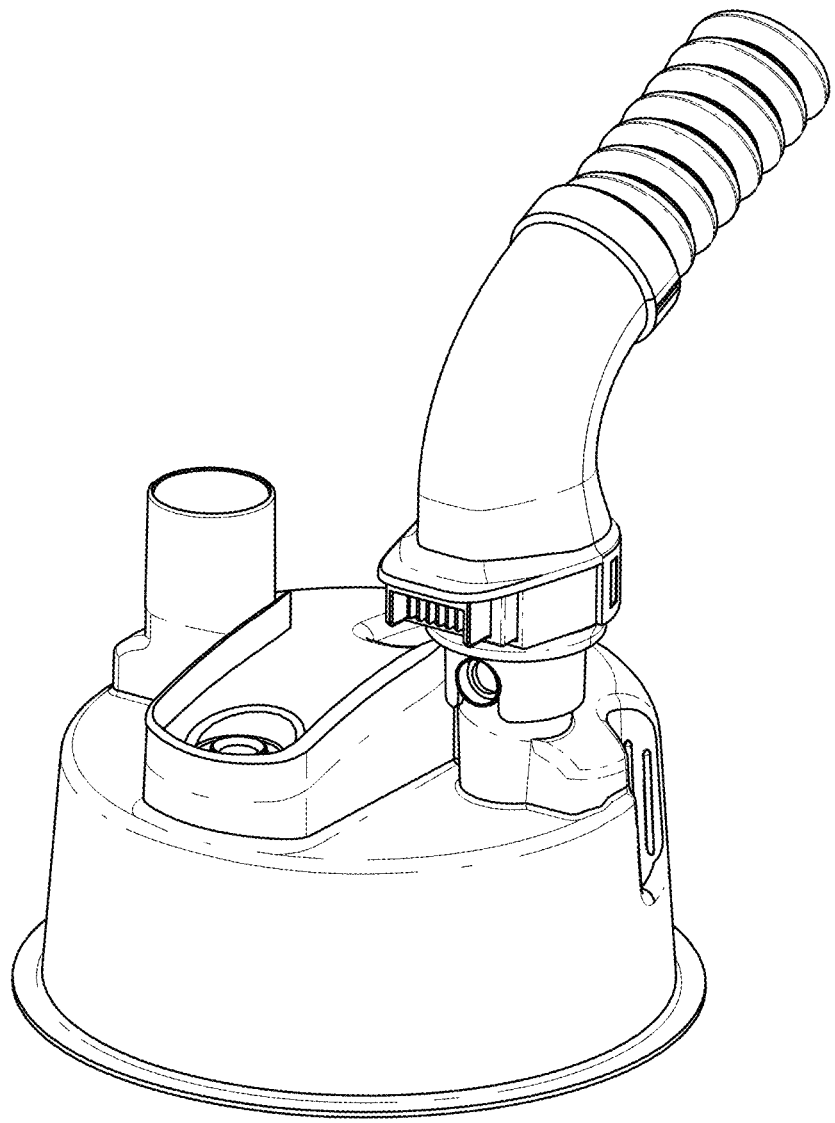

Returning again to FIG. 43A, the tube-and-connector assembly 1523 is then in condition for final assembly. As shown in greater detail in FIG. 43K, a front clamshell 1525 and a rear clamshell 1527 are snapped together around the tube-and-connector assembly 1523 such that a portion of the PCB connector is left exposed. The clamshell 1525, 1527 portions can be made of molded plastic or any other suitable material. The clamshell 1525, 1527 portions serve to further protect the tube-and-connector assembly 1523 and to maintain the tube-and-connector assembly in a bent position that promotes the return of condensate to the humidifier unit when in use. As shown in FIG. 43L, the final assembly can readily snap into a humidifier with a compliant electrical connector near the connection port.

Figure 44A:
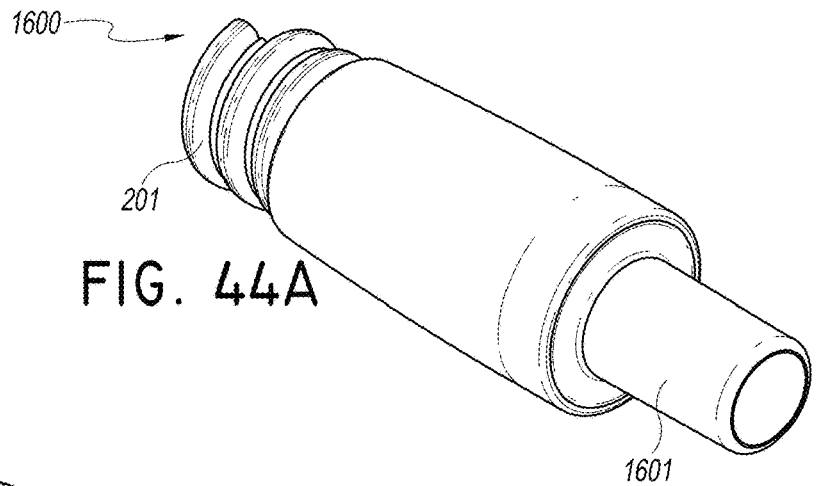
Figure 44B:
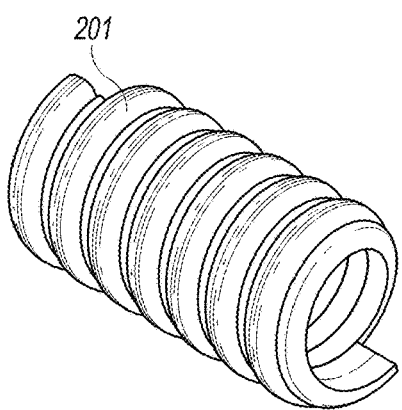

Although the foregoing manufacturing method has been described with reference to a flow chart, the flow chart merely provides an example method for attaching a connector to the end of the tube that is configured in use to connect to a humidifier. The method described herein does not imply a fixed order to the steps. Nor does it imply that any one step is required to practice the method. Embodiments may be practiced in any order and combination that is practicable.
Placement of Patient-End Connector with Electrical Connectivity Reference is next made to FIGS. 44A-44H, which show an example connector 1600 connecting one end of the tube 201 to a patient interface (not shown). The portion of the connector 1600 that connects to the patient interface is indicated by reference 1601. FIG. 44A shows a side perspective view of the connector 1600. As shown in FIG. 44B-44E, the connector 1600 comprises a tube 201, a PCB 1603 and an insert 1605, designated together as a computational fluid dynamics (CFD) assembly 1607 when assembled together, and a cover 1609. Each of FIGS. 44B-44E shows a side-perspective view that generally corresponds with the view of FIG. 44A.

Figure 44D:
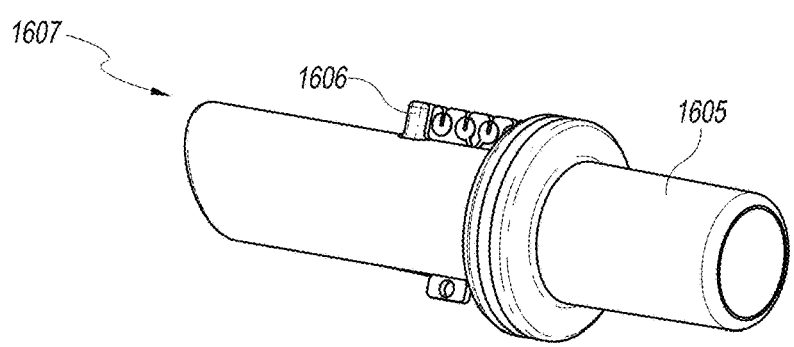
Figure 44C:
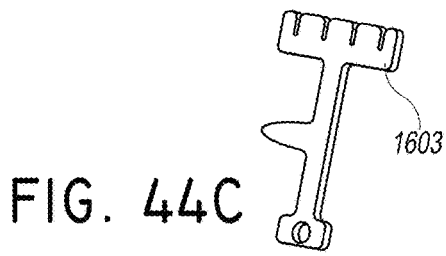
Figure 44E:
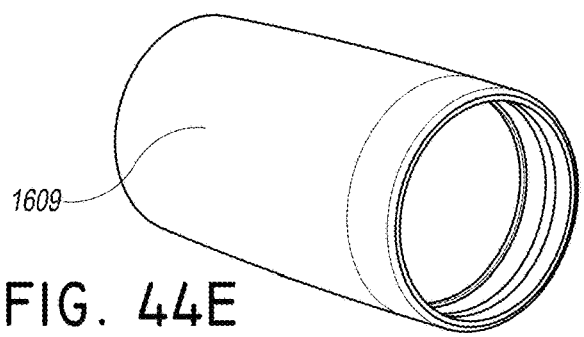

The insert 1605 and cover 1609 are preferably molded plastic components. The insert 1605 can serve one or more of a number of purposes, including providing a receptor for the tube, providing a suitable conduit for the gas flow path, providing a housing for the PCB, and providing a housing for a thermistor (discussed below). The cover 1609 protects and covers the relatively fragile PCB and protects the connection between the tube and the insert. As shown in FIG. 44A, the end of the insert 1605 that is inserted in the tube 201 is preferably angled to aid insertion into the tube 201. In addition, as shown in FIG. 44D, the insert desirably includes a stop portion 1606 that promotes correct placement of the tube 201 with respect to the insert 1605 and also serves to protects the PCB 1603.

To electrically connect the conductive filaments in the second elongate member of the tube 201 to the terminals of the PCB 1603, a procedure similar to that shown and described above with respect to FIGS. 43E-43I can be used.

Figure 44H:
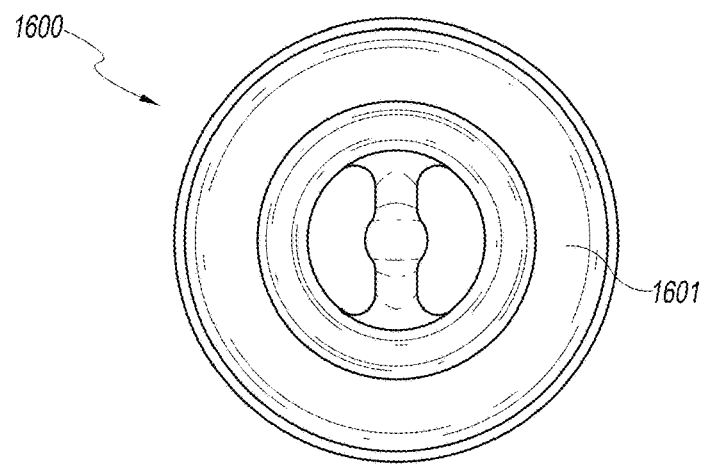

FIG. 44F shows a cross section of the connector 1600 and generally corresponds with the same side perspective view as FIG. 44A. FIG. 44H shows a cross section of the CFD assembly 1607 and generally corresponds with the side perspective view of FIG. 44D. These figures show greater details regarding the relative placement of the tube 201, CFD assembly 1607, and cover 1609.

Figure 44I:
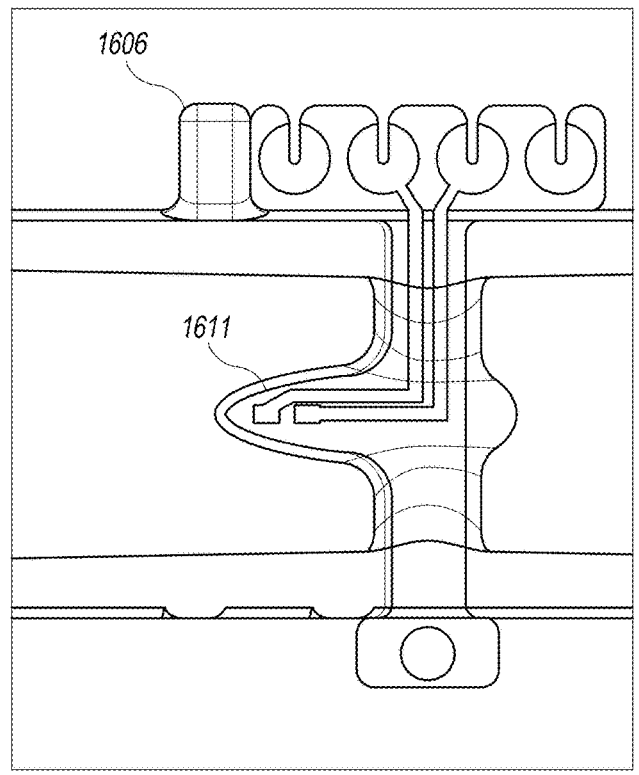

FIG. 44H shows a cross section of the connector 1600 taken along the width of the connector, as seen from the patient interface end 1601 of the connector, looking toward the tube (not shown). FIG. 44I shows a slide-plan cross section of the CFD assembly 1607 showing additional details of the PCB and thermistor 1611. As shown in FIGS. 44H and 44I, the thermistor 1611 is placed into the flow path. The thermistor 1611 can provide temperature and gas flow information to allow assessment of thermal conditions near the patient interface.
Placement of Spiral-Style Connector Reference is next made to FIGS. 45A-45E which show a connector without electrical connectivity to a PCB. However, in some configurations, the connector could be equally adapted to have electrical connectivity to a PCB. The connector is suitable for connecting to a patient interface or a humidifier. It is particularly suited for use as a patient-end connector and/or device-end connector in an obstructive-sleep apnea environment.

A spiral-ended molded insert 1701 is provided. The end of the insert 1701 opposite the spiral end is molded for insertion on or attachment to a humidifier port, and/or a patient interface port, and/or any other desired component.

Figure 45A:
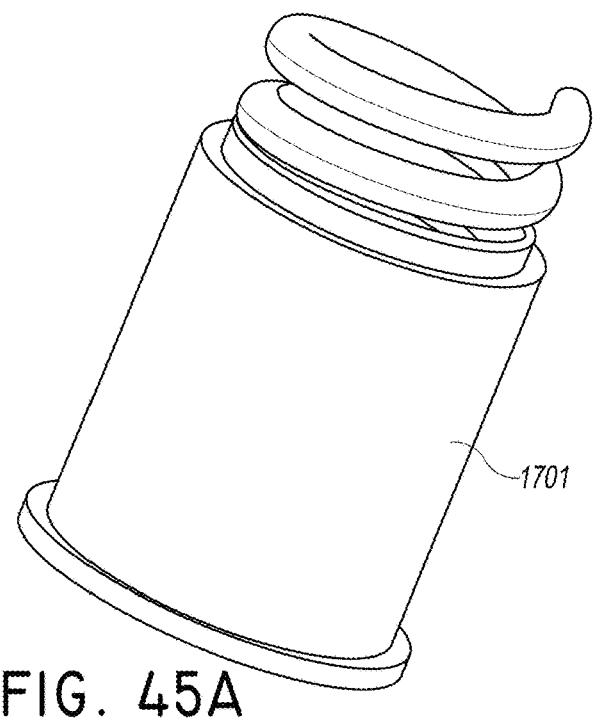
FIGS. 45A-45E show schematics relating to a connector suitable for attaching a tube to a humidifier port, patient interface, or any other suitable component.
Figure 45B:
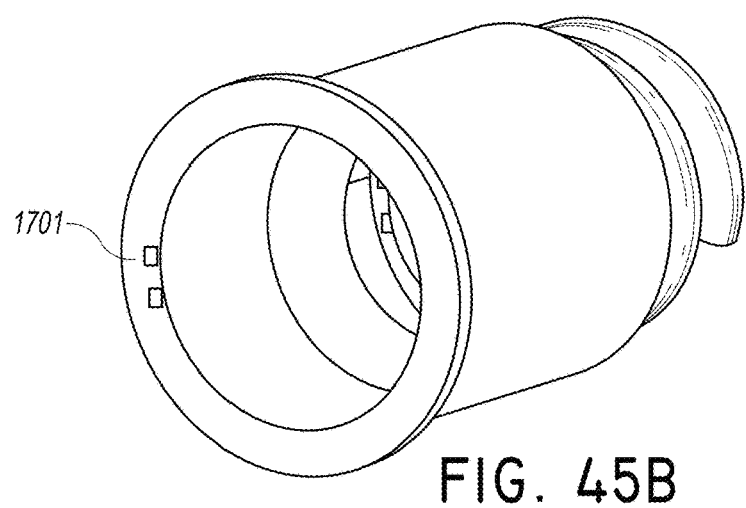
Figure 45C:
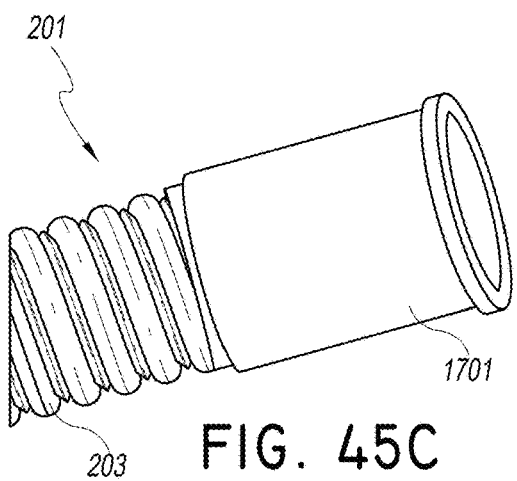
Figure 45D:
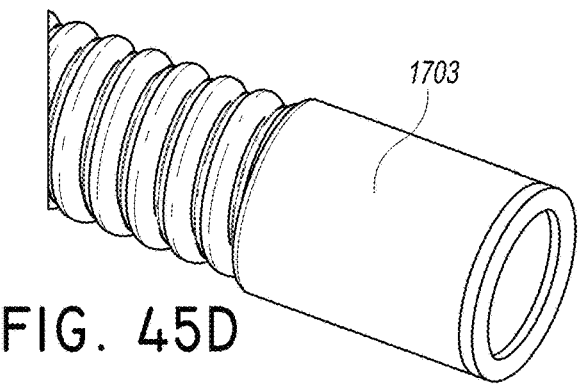
Figure 45E:
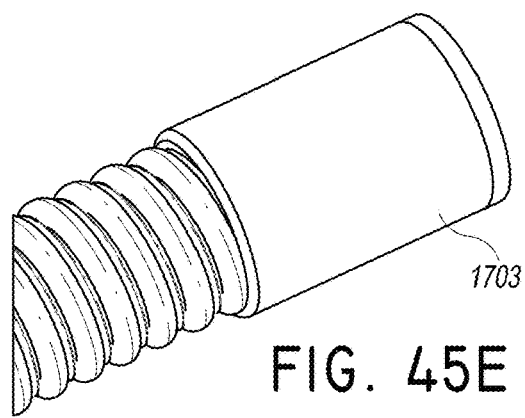
Figure 46A:
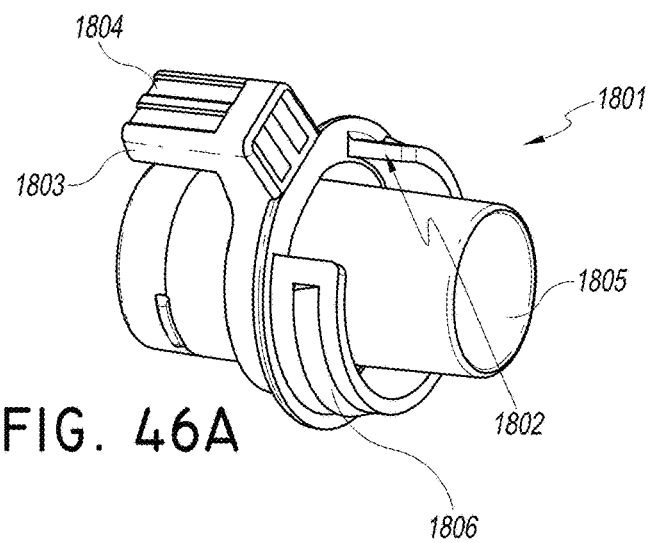
FIGS. 46A-46F show a connector which can be used for medical circuits having electrical wires running therethrough.
Figure 46B:
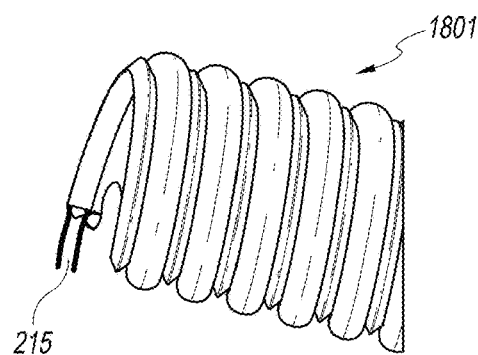
Figure 46C:
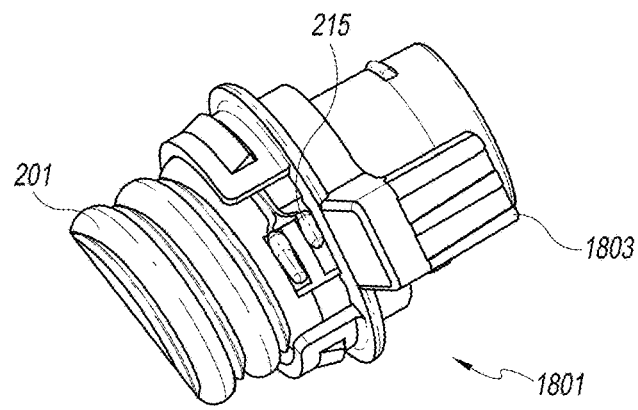
Figure 46D:
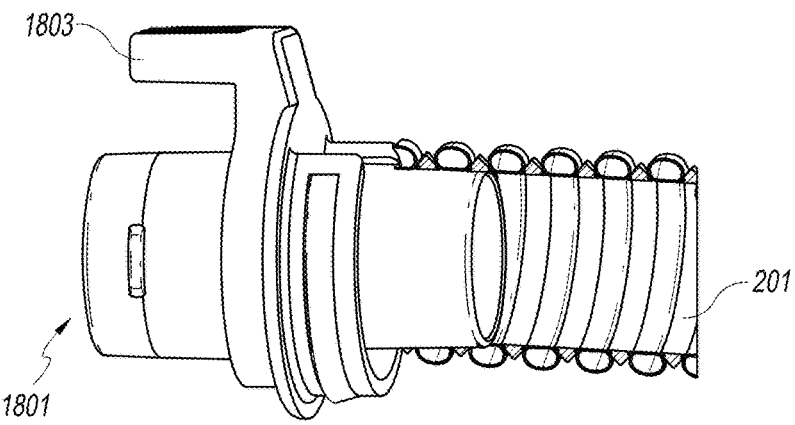
Figure 46E:
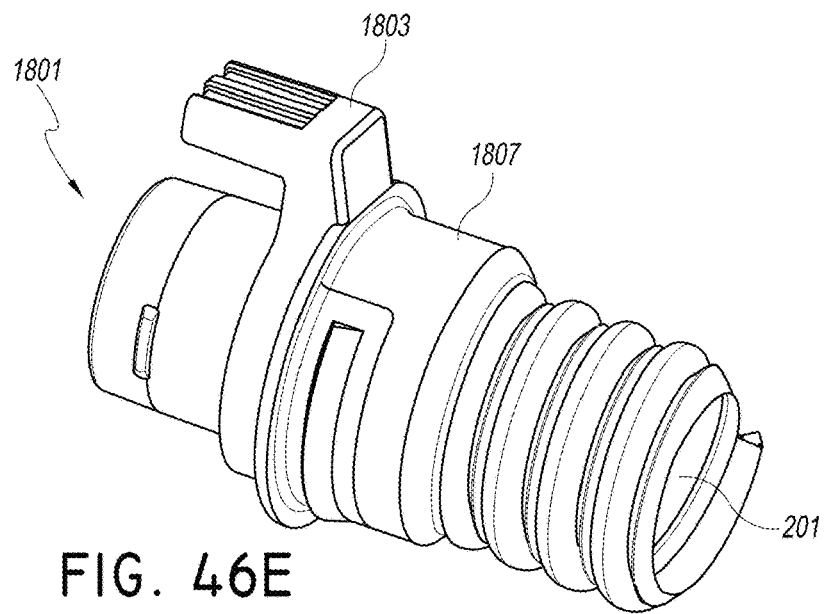
Figure 46F:
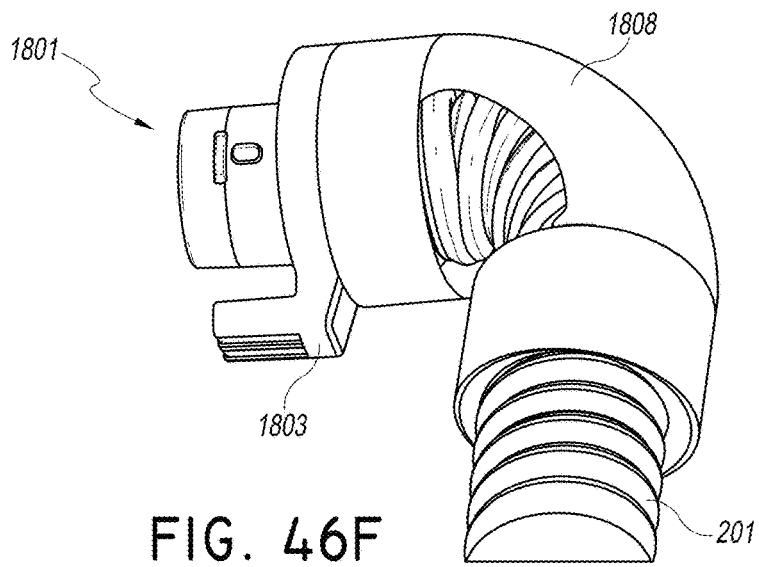

As shown in FIG. 45C, the spiral end of the insert 1701 is screwed onto the compliant turns of the tube 201. In this example, the spiral turns of the insert 1701 are sized and configured to fit over and around the turns of the first elongate member 203 of the tube 201.

It should be noted that, in the case of a tube having one or more electrically powered wires therein, an electrical connection can be provided on at least a portion of the insert 1701. When the insert 1701 is installed, the electrical connector will preferably align with the wires, thereby facilitating electrical connection. Solder or the like can then be used to secure the connection.

A soft rubber or TPE member 1703 can be inserted or molded on top of at least a portion of insert 1701 and, optionally, tube 201 to promote the attachment between the insert 1701 and the tube 201. In some cases, the insert 1701 (or at least the spiral end of the insert 1701) provides sufficient lateral crush resistance to enable high-pressure molding techniques to be used, where the pressure can exceed the lateral crush resistance of the tube 201 without the insert 1701. Member 1703 can also advantageously provide a soft surface to grip on when inserting and removing tube from a component.

The foregoing method of attaching a connector to a spiral-wound tube is provided by way of example. The method described herein does not imply a fixed order to the steps. Nor does it imply that any one step is required to practice the method. Embodiments may be practiced in any order and combination that is practicable.

Placement of Alternative Device-End Connector

Reference is next made to FIGS. 46A to 46F which show a connector which can be used for medical circuits having electrical wires running therethrough. The connector 1801 comprises a cut-out 1802, which in certain embodiments is 30 mm (or about 30 mm) across. In certain embodiments, on one end of the cut-out 1802 is a L-shaped arm 1803 which extends in part outward from the connector 1801 and in part parallel to the longitudinal axis of the connector 1801.

The arm 1803 can have one or more electrical conductors 1804 embedded therein. The conductors 1804 can be made of copper or brass or another suitably conductive material and can be formed as flat L-shaped pieces running substantially along the length of the arm 1803.

The connector 1801 can further comprise an inner portion 1805 adapted to sit substantially inside a portion of the tube 201 and an outer portion 1806 adapted to substantially surround a portion of the tube 201.

A portion of the second elongate member 205 is stripped away to reveal the one or more filaments 215 embedded therein. Preferably about 5 mm of the filaments 215 are revealed. The connector 1801 is then attached to the tube 215 such that the inner portion 1805 sits within tube 201 and the outer portion 1806 sits around the tube 201. Preferably the connector 1801 is oriented such that the revealed ends of the filaments 215 are located at or near the cut-out 1802.

The revealed ends of the filaments 215 are then electrically and/or physically connected to the conduct ors 1804. This can be done by soldering the ends to the conductors 1804, or any other method known in the art.

A soft rubber or TPE member 1807 can be inserted or molded on top of at least a portion of connector 1801 and, optionally, tube 201 to promote the attachment between the connector 1801 and the tube 201.

In some embodiments, a substantially L-shaped elbow 1808 can be placed over the assembly. The elbow 1808 can provide some additional strength to the connection and can provide a predetermined bend in the tube 201 (such that the connector 1701 can tend to sit at an angle of about 90° from the body of the tube 201).

Coaxial Tube

A coaxial breathing tube can also comprise a composite tube as described above. In a coaxial breathing tube, a first gas space is an inspiratory limb or an expiratory limb, and the second gas space is the other of the inspiratory limb or expiratory limb. One gas passageway is provided between the inlet of said inspiratory limb and the outlet of said inspiratory limb, and one gas passageway is provided between the inlet of said expiratory limb and the outlet of said expiratory limb. In one embodiment, the first gas space is said inspiratory limb, and the second gas space is said expiratory limb. Alternatively, the first gas space can be the expiratory limb, and the second gas space can be the inspiratory limb.

Figure 47:
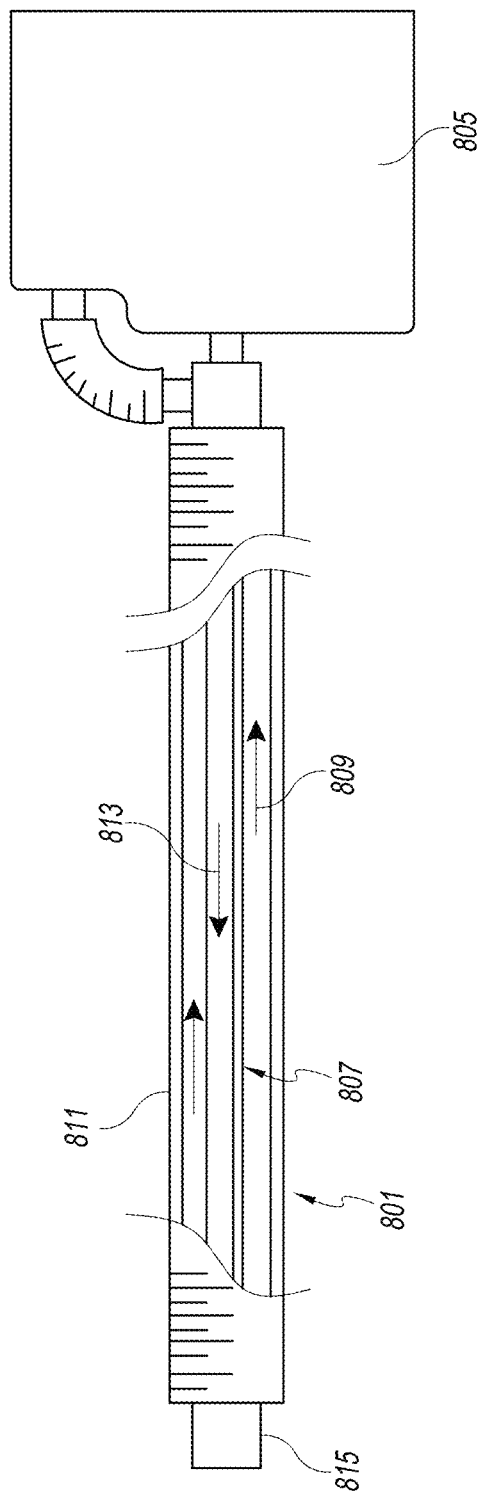
FIG. 47 is a schematic illustration of a coaxial tube, according to at least one embodiment.

Reference is next made to FIG. 47, which shows a coaxial tube 801 according to at least one embodiment. In this example, the coaxial tube 801 is provided between a patient and a ventilator 805. Expiratory gases and inspiratory gases each flow in one of the inner tube 807 or the space 809 between the inner tube 807 and the outer tube 811. It will be appreciated that the outer tube 811 may not be exactly aligned with the inner tube 807. Rather, "coaxial" refers to a tube situated inside another tube.

For heat transfer reasons, the inner tube 807 can carry the inspiratory gases in the space 813 therewithin, while the expiratory gases are carried in the space 809 between the inner tube 807 and the outer tube 811. This airflow configuration is indicated by arrows. However, a reverse configuration is also possible, in which the outer tube 811 carries inspiratory gases and the inner tube 807 carries expiratory gases.

In at least one embodiment, the inner tube 807 is formed from a corrugated tube, such as a Fisher & Paykel model RT100 disposable tube. The outer tube 811 can be formed from a composite tube, as described above.

With a coaxial tube 801, the ventilator 805 may not become aware of a leak in the inner tube 807. Such a leak may short circuit the patient, meaning that the patient will not be supplied with sufficient oxygen. Such a short circuit may be detected by placement of a sensor at the patient end of the coaxial tube 801. This sensor may be located in the patient end connector 815. A short circuit closer to the ventilator 805 will lead to continued patient re-breathing of the air volume close to the patient. This will lead to a rise in the concentration of carbon dioxide in the inspiratory flow space 813 close to the patient, which can be detected directly by a $CO_2$ sensor. Such a sensor may comprise any one of a number of such sensors as is currently commercially available. Alternatively, this re-breathing may be detected by monitoring the temperature of the gases at the patient end connector 815, wherein a rise in temperature above a predetermined level indicates that re-breathing is occurring.

In addition to the above to reduce or eliminate the formation of condensation within either the inner tube 807 or outer tube 811, and to maintain a substantially uniform temperature in the gases flow through the coaxial tube 801, a heater, such as a resistance heater filament, may be provided within either the inner tube 807 or outer tube 811, disposed within the gases spaces 809 or 813, or within the inner tube 807 or outer tube 811 walls themselves.

Thermal Properties

In embodiments of a composite tube 201 incorporating a heating filament 215, heat can be lost through the walls of the first elongate member 203, resulting in uneven heating. As explained above, one way to compensate for these heat losses is to apply an external heating source at the first elongate member 203 walls, which helps to regulate the temperature and counter the heat loss. Other methods for optimizing thermal properties can also be used, however.

Reference is next made to FIGS. 48A through 48C, which demonstrate example configurations for bubble height (that is, the cross-sectional height of the first elongate member 203 measured from the surface facing the inner lumen to the surface forming the maximum outer diameter) to improve thermal properties.

The dimensions of the bubble can be selected to reduce heat loss from the composite tube 201. Generally, increasing the height of the bubble increases the effective thermal resistance of the tube 201, because a larger bubble height permits the first elongate member 203 to hold more insulating air. However, it was discovered that, at a certain bubble height, changes in air density cause convection inside the tube 201, thereby increasing heat loss. Also, at a certain bubble height the surface area becomes so large that the heat lost through surface outweighs the benefits of the increased height of the bubble. Certain embodiments include these realizations.

The radius of curvature and the curvature of the bubble can be useful for determining a desirable bubble height. The curvature of an object is defined as the inverse of the radius of curvature of that object. Therefore, the larger a radius of curvature an object has, the less curved the object is. For example, a flat surface would have a radius of curvature of ∞, and therefore a curvature of 0.

FIG. 48A shows a longitudinal cross-section of a top portion of a composite tube. FIG. 48A shows an embodiment of a composite tube 201 where the bubble has a large height. In this example, the bubble has a relatively small radius of curvature and therefore a large curvature. Also, the bubble is approximately three to four times greater in height than the height of the second elongate member 205.

FIG. 48B shows a longitudinal cross-section of a top portion of another composite tube. FIG. 48B shows an embodiment of a composite tube 201 where the bubble is flattened on top. In this example, the bubble has a very large radius of curvature but a small curvature. Also, the bubble is approximately the same height as the second elongate member 205.

FIG. 48C shows a longitudinal cross-section of a top portion of another composite tube. FIG. 48C shows an embodiment of a composite tube 201 where the width of the bubble is greater than the height of the bubble. In this example, the bubble has a radius of curvature between that of FIG. 48A and FIG. 48B, and the center of the radius for the upper portion of the bubble is outside of the bubble (as compared to FIG. 48A). The inflection points on the left and right sides of the bubble are about at the middle (heightwise) of the bubble (as opposed to in the lower portion of the bubble, as in FIG. 48A). Also, the height of the bubble is approximately double that of the second elongate member 205, resulting in a bubble height between that of FIGS. 48A and 48B.

The configuration of FIG. 48A resulted in the lowest heat loss from the tube. The configuration of FIG. 48B resulted in the highest heat loss from the tube. The configuration of FIG. 48C had intermediate heat loss between the configurations of FIGS. 48A and 48B. However, the large external surface area and convective heat transfer in the configuration of FIG. 48A led to inefficient heating. Thus, of the three bubble arrangements of FIGS. 48A-48C, FIG. 48C was determined to have the best overall thermal properties. When the same thermal energy was input to the three tubes, the configuration of FIG. 48C allowed for the largest temperature rise along the length of the tube. The bubble of FIG. 48C is sufficiently large to increase the insulating air volume, but not large enough to cause a significant convective heat loss. The configuration of FIG. 48C was determined to have the poorest thermal properties, namely that the configuration of FIG. 48B allowed for the smallest temperature rise along the length of the tube. The configuration of FIG. 48A had intermediate thermal properties and allowed for a lower temperature rise than the configuration of FIG. 48C.

It should be appreciated that although the FIG. 48C configuration may be preferred in certain embodiments, other configurations, including those of FIGS. 48A, 48B, and other variations, may be utilized in other embodiments as may be desired.

TABLE 8 shows the height of the bubble, the outer diameter of the tube, and the radius of curvature of the configurations shown in each of FIGS. 48A, 48B, and 48C.

TABLE 8

| Tube (FIG.) | 48A | 48B | 48C |
|---|---|---|---|
| Bubble height (mm) | 3.5 | 5.25 | 1.75 |
| Outer diameter (mm) | 21.5 | 23.25 | 19.75 |
| Radius of curvature (mm) | 5.4 | 3.3 | 24.3 |

Figure 50A:
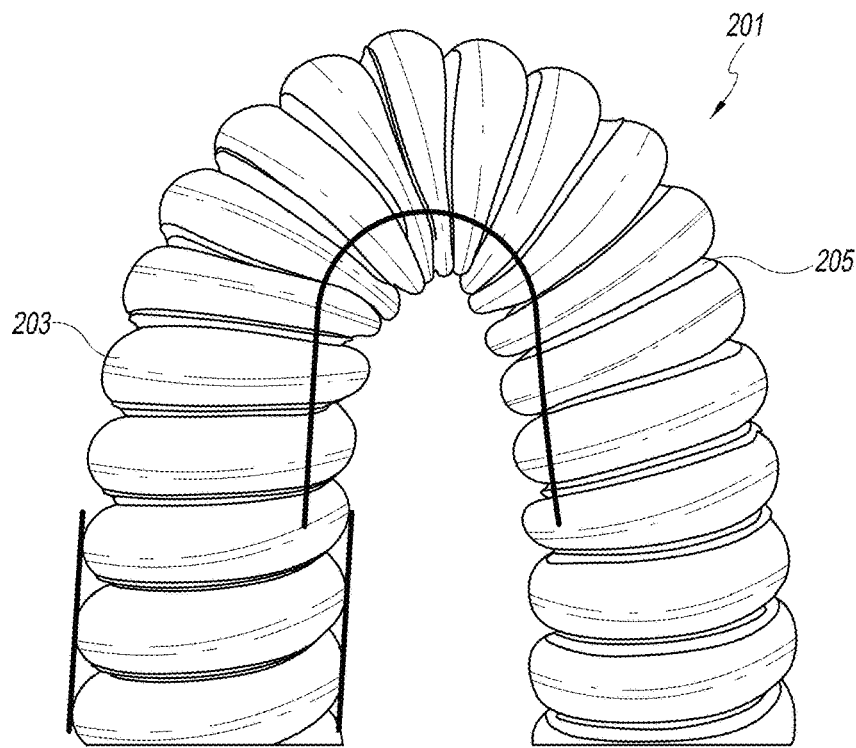
FIGS. 50A-50D demonstrate radius of curvature properties of tubes according to various embodiments.
Figure 50B:
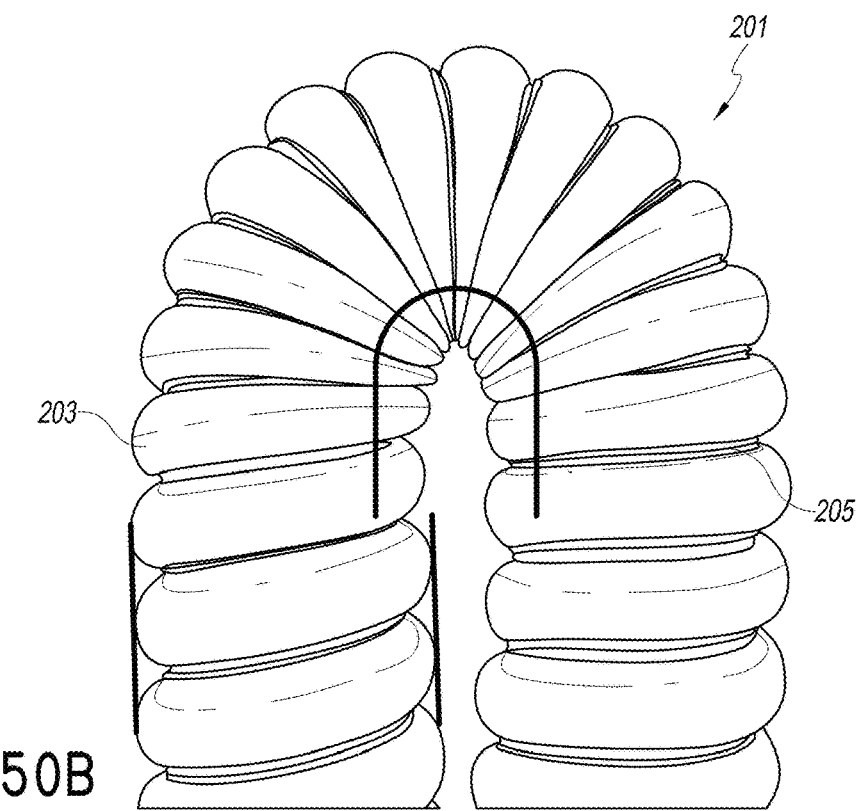
Figure 50C:
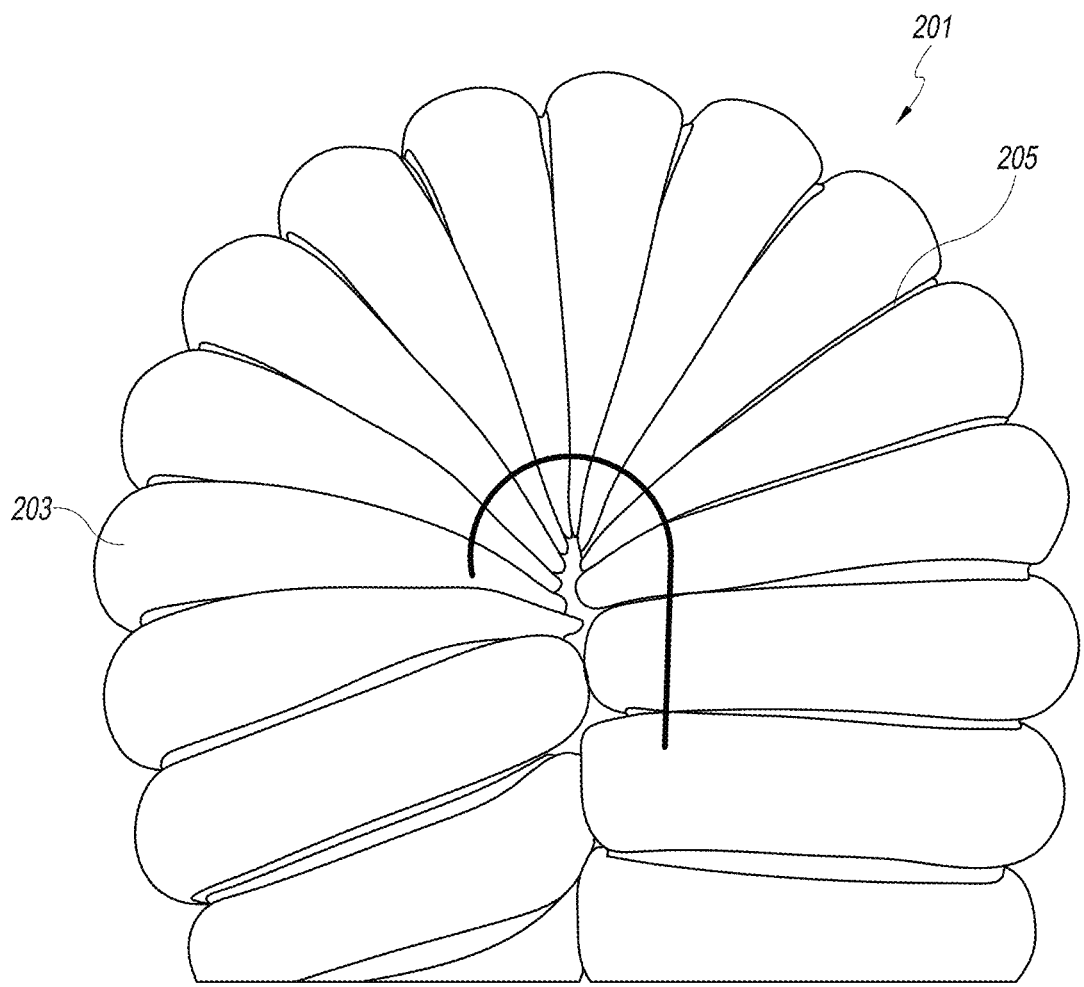

TABLE 8A shows the height of the bubble, the outer diameter, and the radius of curvature of further configurations as shown in FIGS. 50A-50C.

TABLE 8A

| Tube (FIG.) | 50A | 50B | 50C |
|---|---|---|---|
| Bubble height (mm) | 6.6 | 8.4 | 9.3 |
| Outer diameter (mm) | 24.6 | 26.4 | 27.3 |
| Radius of curvature (mm) | 10 | 8.7 | 5.7 |

Figure 50D:
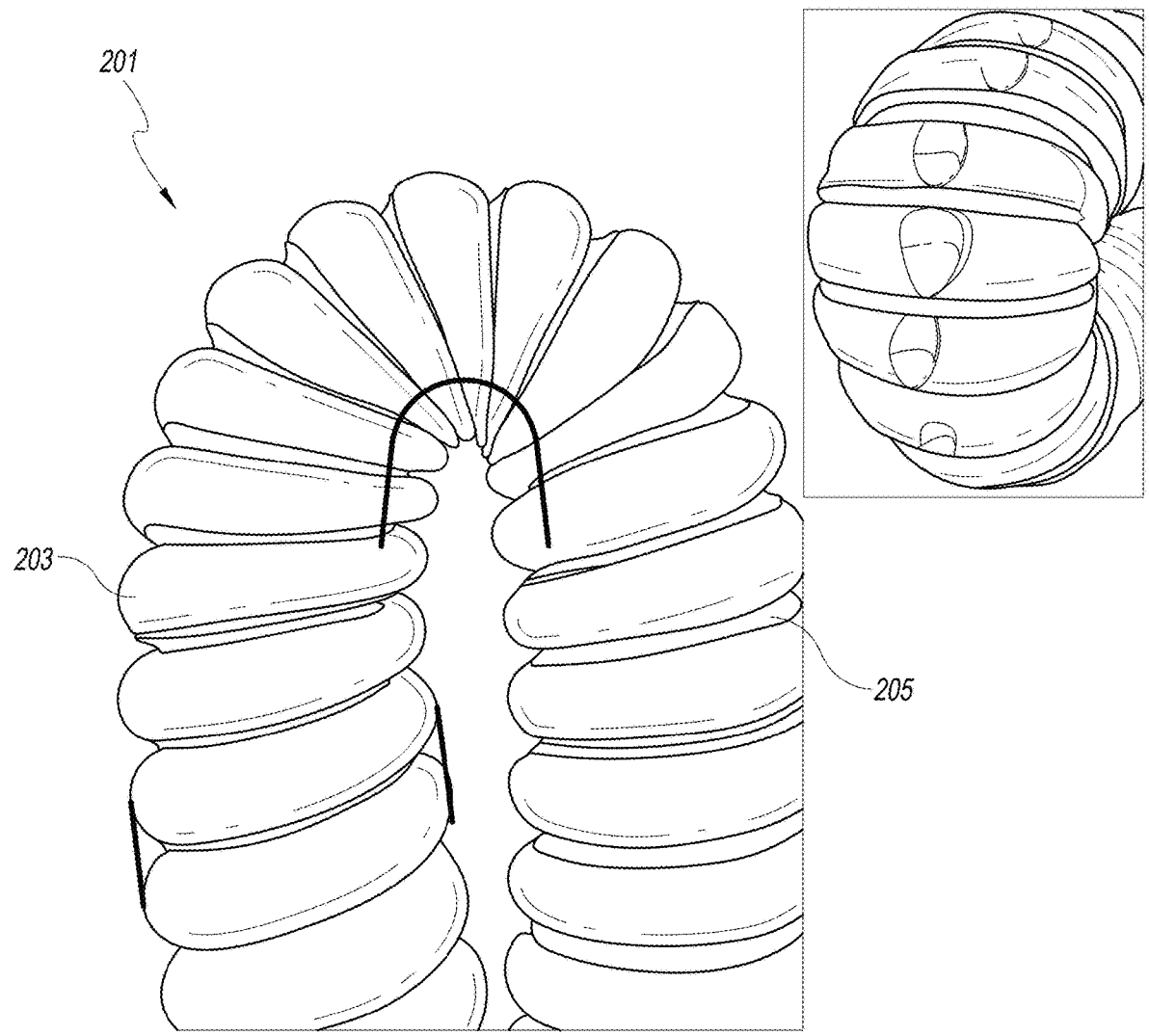

It should be noted that, in general, the smaller the radius of curvature, the tighter the tube can be bent around itself without the bubble collapsing or "kinking." For example, FIG. 50D shows a tube that has been bent beyond its radius of curvature (specifically, it shows the tube of FIG. 50A bent around a radius of curvature of 5.7 mm), thereby causing kinking in the walls of the bubble. Kinking is generally undesirable, as it can detract from the appearance of the tube, and can impair the thermal properties of the tube.

Accordingly, in some applications, the configurations with increased bending properties (such as those shown in FIG. 48A or 48B) can be desirable despite having less efficient thermal properties. In some applications, it has been found that a tube with an outer diameter of 25 mm to 26 mm (or about 25 mm to about 25 mm) provides a good balance between thermal efficiency, flexibility, and bending performance. It should be appreciated that although the configurations of FIGS. 48A and 48B may be preferred in certain embodiments, other configurations, including those of FIGS. 50A-50D and other variations, may be utilized in other embodiments as may be desired.

Reference is next made to FIGS. 48C through 48F which demonstrate example positioning of heating element 215 with similar bubble shapes to improve thermal properties. The location of the heating element 215 can change the thermal properties within the composite tube 201.

FIG. 48C shows a longitudinal cross-section of a top portion of another composite tube. FIG. 48C shows an embodiment of a composite tube 201 where the heating elements 215 are centrally located in the second elongate member 205. This example shows the heating elements 215 close to one another and not close to the bubble wall.

Figure 48D:
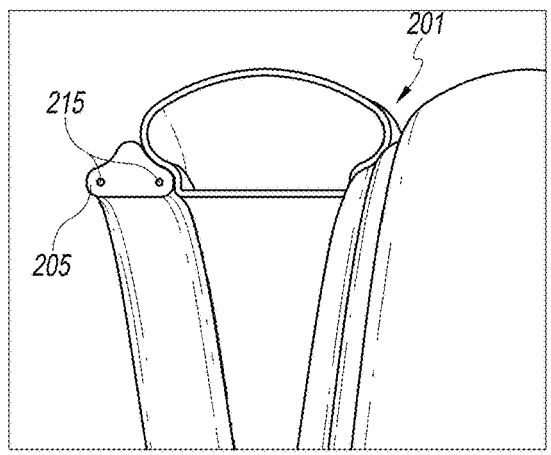
FIGS. 48D-48F show examples of filament arrangements configured to improve thermal efficiency.

FIG. 48D shows a longitudinal cross-section of a top portion of another composite tube. FIG. 48D shows an embodiment of a composite tube 201 in which the heating elements 215 are spaced farther apart, as compared to FIG. 48C, in the second elongate member 205. These heating elements are closer to the bubble wall and provide for better regulation of heat within the composite tube 201.

Figure 48E:
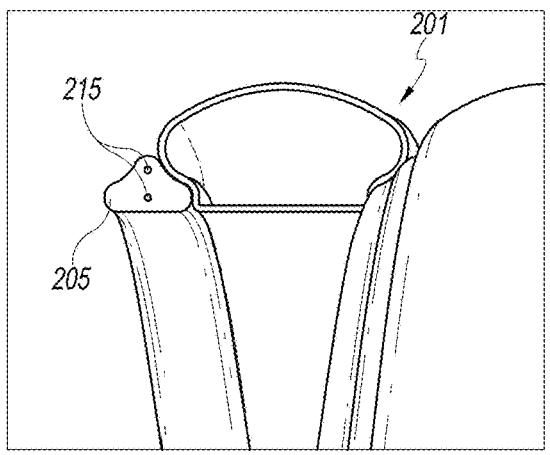

FIG. 48E shows a longitudinal cross-section of a top portion of another composite tube. FIG. 48E shows an embodiment of a composite tube 201 wherein the heating elements 215 are spaced on top of each other in the vertical axis of the second elongate member 205. In this example, the heating elements 215 are equally close to each bubble wall.

Figure 48F:
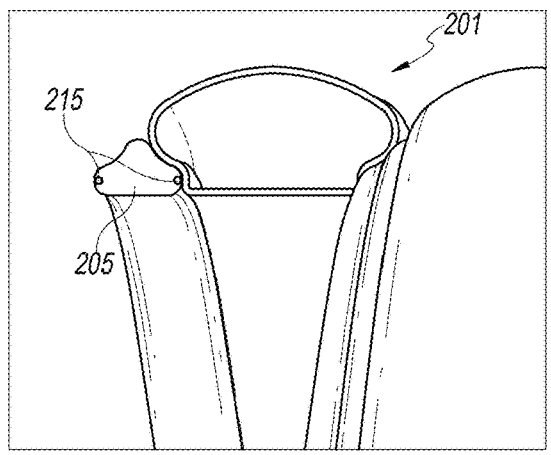

FIG. 48F shows a longitudinal cross-section of a top portion of another composite tube. FIG. 48F shows an embodiment of a composite tube 201 where the heating elements 215 are spaced at opposite ends of the second elongate member 205. The heating elements 215 are close to the bubble wall, especially as compared to FIGS. 48C-48E.

Of the four filament arrangements of FIGS. 48C-48F, FIG. 48F was determined to have the best thermal properties. Because of their similar bubble shapes, all of the configurations experienced similar heat loss from the tube.

However, when the same thermal energy was input to the tubes, the filament configuration of FIG. 48F allowed for the largest temperature rise along the length of the tube. The configuration of FIG. 48D was determined to have the next best thermal properties and allowed for the next largest temperature rise along the length of tube. The configuration of FIG. 48C performed next best. The configuration of FIG. 48E had the poorest performance and allowed for the smallest temperature rise along the length of the tube, when the same amount of heat was input.

It should be appreciated that although the FIG. 48F configuration may be preferred in certain embodiments, other configurations, including those of FIGS. 48C, 48D, 48E, and other variations, may be utilized in other embodiments as may be desired.

Figure 49A:
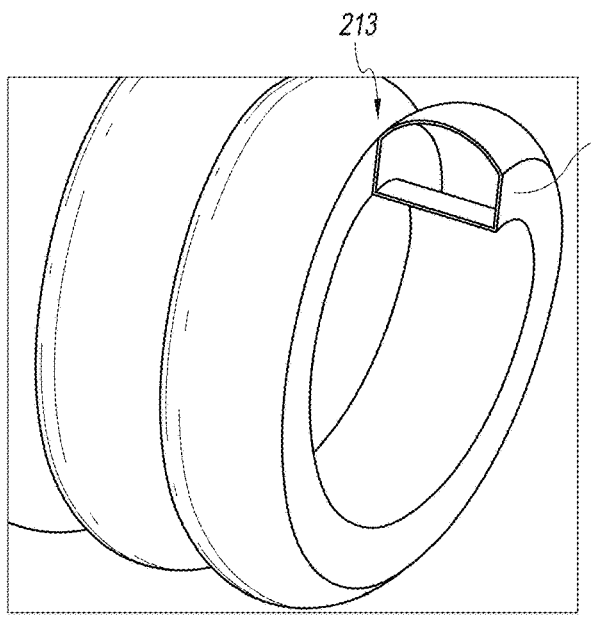
FIGS. 49A-49C show examples of first elongate member stacking.
Figure 49B:
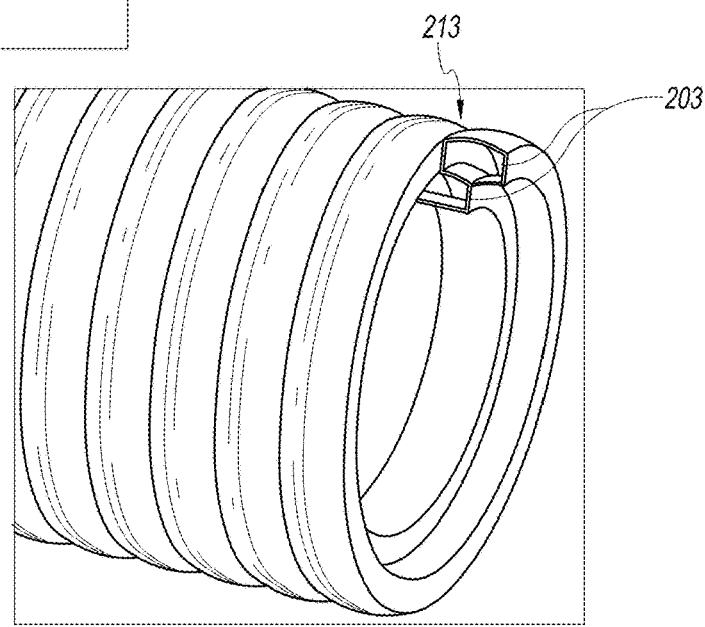
Figure 49C:
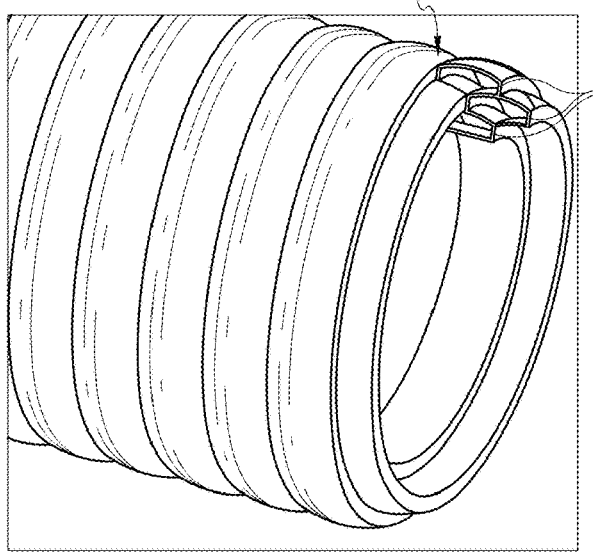

Reference is next made to FIGS. 49A through 49C, which demonstrate example configurations for stacking of the first elongate member 203. It was discovered that heat distribution can be improved in certain embodiments by stacking multiple bubbles. These embodiments can be more beneficial when using an internal heating filament 215. FIG. 49A shows a longitudinal cross-section of a top portion of another composite tube. FIG. 49A shows a cross section of a composite tube 201 without any stacking.

FIG. 49B shows a longitudinal cross-section of a top portion of another composite tube. FIG. 49B shows another example composite tube 201 with stacked bubbles. In this example, two bubbles are stacked on top of each other to form the first elongate member 203. As compared to FIG. 49A, the total bubble height is maintained, but the bubble pitch is half of FIG. 49A. Also, the embodiment in FIG. 49B has only a slight reduction in air volume. The stacking of the bubbles reduces natural convection and heat transfer in the gap between bubbles 213 and lowers the overall thermal resistance. The heat flow path increases in the stacked bubbles allowing heat to more easily distribute through the composite tube 201.

FIG. 49C shows a longitudinal cross-section of a top portion of another composite tube. FIG. 49C shows another example of a composite tube 201 with stacked bubbles. In this example, three bubbles are stacked on top of each other to form the first elongate member 203. As compared to FIG. 49A, the total bubble height is maintained, but the bubble pitch is a third of FIG. 49A. Also, the embodiment in FIG. 49A has only a slight reduction in air volume. The stacking of the bubbles reduces natural convection and heat transfer in the gap between bubbles 213.

Cleaning

In at least one embodiment, materials for a composite tube can be selected to handle various methods of cleaning. In some embodiments, high level disinfection (around 20 cleaning cycles) can be used to clean the composite tube 201. During high level disinfection, the composite tube 201 is subject to pasteurization at about 75° C. for about 30 minutes. Next, the composite tube 201 is bathed in 2% glutaraldehyde for about 20 minutes. The composite tube 201 is removed from the glutaraldehyde and submerged in 6% hydrogen peroxide for about 30 minutes. Finally, the composite tube 201 is removed from the hydrogen peroxide and bathed in 0.55% orthophthalaldehyde (OPA) for about 10 minutes.

In other embodiments, sterilization (around 20 cycles) can be used to clean the composite tube 201. First, the composite tube 201 is placed within autoclave steam at about 121° C. for about 30 minutes. Next, the temperature of the autoclave steam is increased to about 134° C. for about 3 minutes. After autoclaving, the composite tube 201 is surrounded by 100% ethylene oxide (ETO) gas. Finally, the composite tube 201 is removed from the ETO gas and submerged in about 2.5% glutaraldehyde for about 10 hours.

The composite tube 201 may be made of materials to withstand the repeated cleaning process. In some embodiments, part or all of the composite tube 201 can be made of, but is not limited to, styrene-ethylene-butene-styrene block thermo plastic elastomers, for example Kraiburg TF6STE. In other embodiments, the composite tube 201 can be made of, but is not limited to, hytrel, urethanes, or silicones.

Although certain preferred embodiments and examples are disclosed herein, inventive subject matter extends beyond the specifically disclosed embodiments to other alternative embodiments and/or uses, and to modifications and equivalents thereof. Thus, the scope of the claims or embodiments appended hereto is not limited by any of the particular embodiments described herein. For example, in any method or process disclosed herein, the acts or operations of the method or process can be performed in any suitable sequence and are not necessarily limited to any particular disclosed sequence. Various operations can be described as multiple discrete operations in turn, in a manner that can be helpful in understanding certain embodiments; however, the order of description should not be construed to imply that these operations are order dependent. Additionally, the structures described herein can be embodied as integrated components or as separate components. For purposes of comparing various embodiments, certain aspects and advantages of these embodiments are described. Not necessarily all such aspects or advantages are achieved by any particular embodiment. Thus, for example, various embodiments can be carried out in a manner that achieves or optimizes one advantage or group of advantages as taught herein without necessarily achieving other aspects or advantages as can also be taught or suggested herein.

Methods and processes described herein may be embodied in, and partially or fully automated via, software code modules executed by one or more general and/or special purpose computers. The word "module" refers to logic embodied in hardware and/or firmware, or to a collection of software instructions, possibly having entry and exit points, written in a programming language, such as, for example, C or C++. A software module may be compiled and linked into an executable program, installed in a dynamically linked library, or may be written in an interpreted programming language such as, for example, BASIC, Perl, or Python. It will be appreciated that software modules may be callable from other modules or from themselves, and/or may be invoked in response to detected events or interrupts. Software instructions may be embedded in firmware, such as an erasable programmable read-only memory (EPROM). It will be further appreciated that hardware modules may comprise connected logic units, such as gates and flip-flops, and/or may comprised programmable units, such as programmable gate arrays, application specific integrated circuits, and/or processors. The modules described herein can be implemented as software modules, but also may be represented in hardware and/or firmware. Moreover, although in some embodiments a module may be separately compiled, in other embodiments a module may represent a subset of instructions of a separately compiled program, and may not have an interface available to other logical program units.

In certain embodiments, code modules may be implemented and/or stored in any type of computer-readable medium or other computer storage device. In some systems, data (and/or metadata) input to the system, data generated by the system, and/or data used by the system can be stored in any type of computer data repository, such as a relational database and/or flat file system. Any of the systems, methods, and processes described herein may include an interface configured to permit interaction with users, operators, other systems, components, programs, and so forth.

It should be emphasized that many variations and modifications may be made to the embodiments described herein, the elements of which are to be understood as being among other acceptable examples. All such modifications and variations are intended to be included herein within the scope of this disclosure and protected by the following claims. Further, nothing in the foregoing disclosure is intended to imply that any particular component, characteristic or process step is necessary or essential.

What is claimed is:

1. A cartridge for use with a humidification apparatus, the cartridge comprising a chassis comprising mounting structures, one of the mounting structures at a first end for a single sensor coupled thereto and another one of the mounting structures at a second end for two sensors coupled thereto, the cartridge further comprising an electrical connector connected to the single sensor and the two sensors and adapted to provide an electrical and/or a communicative connection to a controller for the humidification apparatus, the electrical connector configured to be electrically connectable to a corresponding humidification unit connector, wherein each of the single sensor and the two sensors is configured to be removably mounted to a humidification chamber.

2. The cartridge of claim 1, wherein the electrical connector comprises a USB connector.

3. The cartridge of claim 1, wherein the first end and the second end are located at two opposing lateral ends of the cartridge.

4. The cartridge of claim 1, wherein each sensor of the single sensor and the two sensors comprises a sensing portion adapted to sense one or more gas properties.

5. The cartridge of claim 1, wherein one or more sensors of the single sensor and the two sensors comprises a thermistor.

6. The cartridge of claim 1, wherein each sensor of the single sensor and the two sensors comprises a thermistor.

7. The cartridge of claim 1, wherein the single sensor at the first end is a temperature sensor, and wherein one of the two sensors at the second end comprises a temperature sensor and the other sensor at the second end comprises a flow sensor.

8. The cartridge of claim 7, wherein the sensor comprising the flow sensor is a heated thermistor.

9. The cartridge of claim 1, wherein the single sensor at the first end is a temperature sensor.

10. The cartridge of claim 1, wherein said first end comprises a first wing defining first socket into which the single sensor is mounted, and wherein said second end comprises a second wing defining a second socket into which the two sensors are mounted.

11. The cartridge of claim 1, wherein each of the single sensor and the two sensors is removably coupled to the first end or the second end to allow replacement of the single sensor and the two sensors.

12. The cartridge of claim 1, wherein the chassis is a unitary chassis.

13. The cartridge of claim 12, wherein the chassis comprises a locking tab, the locking tab being deflectable when the cartridge is slid into position with respect to the humidification apparatus.

14. The cartridge of claim 1, wherein the cartridge comprises a boss structure configured to engage a corresponding recess in the humidification chamber.

15. The cartridge of claim 14, wherein the boss structure of the cartridge further comprises a pair of protrusions, each protrusion having a locking tab; and wherein when the boss structure of the cartridge is engaged into the recess of the humidification chamber, the locking tabs deflect inward and snap into the humidification chamber.

16. The cartridge of claim 1, further comprising one or more arms adapted to extend along outer sides of the humidification chamber to position the cartridge for connection to the humidification chamber.

17. The cartridge of claim 16, wherein the one or more arms are configured to absorb or bear any loads from the cartridge being bumped or knocked, the force being transmitted through the arms and not through the single sensor or the two sensors.

18. The cartridge of claim 16, wherein the one or more arms includes an interlock portion to engage with a complementary interlock portion on the humidification chamber to connect the humidification chamber and cartridge in use.

19. The cartridge of claim 18, wherein the interlock portion is positioned laterally spaced from a port of the humidification chamber.

20. A humidification apparatus comprising:
a humidification unit;
the cartridge of claim 1; and
a humidification chamber removably connectable to the humidification unit, the humidification chamber comprising two ports, the two ports defining first and second gas flow paths.

21. The humidification apparatus of claim 20, wherein each of the two ports comprises an aperture, each aperture corresponding to one of the single sensor or the two sensors of the cartridge and adapted to receive the single sensor or the two sensors.

22. The humidification apparatus of claim 21, wherein the single sensor and the two sensors are positioned on the cartridge such that the single sensor and the two sensors are consistently positioned within the gas flow paths with repeated removal and replacement of the cartridge and the humidification chamber from the humidification unit.

23. The humidification apparatus of claim 22, wherein each aperture comprises a barrier secured to a wall of the respective port, the barrier pneumatically sealing the aperture, and wherein at least a portion of the corresponding single sensor or two sensors is removably disposed within the barrier such that the barrier isolates the corresponding single sensor or two sensors from the gas flow paths.

24. The humidification apparatus of claim 23, wherein the barrier is adapted to stretch as the corresponding single sensor or two sensors is inserted through the aperture.

* * * * *